(12) United States Patent
Batt et al.

(10) Patent No.: US 9,415,118 B2
(45) Date of Patent: Aug. 16, 2016

(54) ANTIBODY DRUG CONJUGATES

(71) Applicant: Julie Lynn Batt, Wayland, MA (US)

(72) Inventors: David Bryant Batt, Wayland, MA (US);
Seth Alexander Ettenberg, Melrose, MA (US); Nicole Haubst, Munich (DE);
Tiancen Hu, Cambridge, MA (US);
David Jenkins, Carlisle, MA (US);
Engin Toksoz, Munich (DE);
Konstantin Petropoulos, Munich (DE);
Matthew John Meyer, Framingham, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/204,023

(22) Filed: Mar. 11, 2014

(65) Prior Publication Data

US 2014/0308201 A1    Oct. 16, 2014

Related U.S. Application Data

(60) Provisional application No. 61/780,368, filed on Mar. 13, 2013.

(51) Int. Cl.
| | | |
|---|---|---|
| *C07K 16/00* | (2006.01) | |
| *A61K 47/48* | (2006.01) | |
| *A61K 45/06* | (2006.01) | |
| *A61K 31/496* | (2006.01) | |
| *A61K 31/5025* | (2006.01) | |
| *A61K 31/662* | (2006.01) | |

(52) U.S. Cl.
CPC ......... *A61K 47/48384* (2013.01); *A61K 31/496* (2013.01); *A61K 31/5025* (2013.01); *A61K 31/662* (2013.01); *A61K 45/06* (2013.01); *A61K 47/48561* (2013.01)

(58) Field of Classification Search
None
See application file for complete search history.

(56) References Cited

U.S. PATENT DOCUMENTS

| | | |
|---|---|---|
| 2009/0274713 A1 | 11/2009 | Chari et al. |
| 2010/0260748 A1 | 10/2010 | Elkins et al. |
| 2012/0039915 A1 | 2/2012 | Liu et al. |
| 2014/0301946 A1 | 10/2014 | Batt et al. |

FOREIGN PATENT DOCUMENTS

| | | |
|---|---|---|
| WO | 2005/037992 A2 | 4/2005 |
| WO | 2005/066211 A2 | 7/2005 |
| WO | 2006/113623 A2 | 10/2006 |
| WO | 2006/124451 A2 | 11/2006 |
| WO | 2007/008547 A2 | 1/2007 |
| WO | 2007/134210 A2 | 11/2007 |
| WO | 2009/100105 A2 | 8/2009 |
| WO | 2009/148928 A1 | 12/2009 |
| WO | 2010/126551 A2 | 11/2010 |
| WO | 2011/066503 A2 | 6/2011 |
| WO | 2012/021841 A2 | 2/2012 |
| WO | 2012/074757 A1 | 6/2012 |
| WO | 2014/089193 A1 | 6/2014 |

OTHER PUBLICATIONS

Paul, W.E. Fundamental Immunology, 3rd Edition, 1993, pp. 292-295.*
MacCallum R.M. et al, Antibody-antigen interactions: Contact analysis and binding site topography. J. Mol. Biol., 1998, vol. 262, p. 732-745.*
Casset F, et al. A peptide mimetic of an anti-CD4 monoclonal antibody by rational design. Biochemical and Biophysical Research Communications, 2003, vol. 307, p. 198-205.*
Bendig, M.M. Humanization of rodent monoclonal antibodies by CDR grafting. Methods: A Companion to Methods in Enzymology, 1995; vol. 8, p. 83-93.*
Abusedra, A, et al. Selective Usage of IGLV Segments (IgV-Lambda) in CLL igl Rearrangements. NCBI GenBank Accession No. AAD29349.1, immunoglobulin lambda light chain variable region, partial [*Homo sapiens*]. May 9, 1999; downloaded from the internet <http://www.ncbi.nlm.nih.gov/protein/4761418?report=genbank&log$=protalign.
Baxendale et al., Immunogenetic analysis of the immune response to pneumococcal polysaccharide. Eur J Immunol. Apr. 2000;30(4):1214-23.
Bridges, SL. Immunoglobulin Lambda Light Chain Expression in Normal Individuals and Rheumatoid Arthritis Patients: Frequent N Region Addition, Oligoclonal B Lymphocyte Expansion, and Evidence of Polymorphism of the Lambda Locus. NCB I GenBank Accession No. AAC16822, Immunoglobulin Lambda Light Chain Variable Region, Partial [*Homo sapiens*]. May 20, 1998. Submitted May 5, 1998; downloaded from the internet <http://www.ncbi.nlm.nih.gov/protein/3142546?report=genbank&log$=protalign&blast_rank=3&RID=558YZEGP013> on Oct. 30, 2014, p. 1.
Giomarelli et al., Inhibition of thrombin-induced platelet aggregation using human single-chain Fv antibodies specific for TREM-like transcript-1. Thromb Haemost. Jun. 2007;97(6):955-63.
Hunt, et al. A Humanized Murine Monoclonal Antibody Protects Mice Either Before or After Challenge With Virulent Venezuelan Equine Encephalomyelitis Virus. NCBI GenBank Accession No. ABH10632.1, Humanized Murine Anti-VEEV Antibody Hy4-26C Heavy Chain, Partial [synthetic construct]. Aug. 14, 2006. Submitted Oct. 6, 2010; downloaded from the internet <http://www.ncbi.nlm.nih.gov/protein/111606535?report=genbank&log$=genbank&blast_rank=2&RID=5688JA97013 >on Oct. 30, 2014, p. 1.
Jacob IN, MJ et al. Human IgG Monoclonal Anti-Aipha(I lb)-Beta(3)-Binding Fragments Derived From Immunized Donors Using Phage Display. NCB I GenBank Accession No. CAC28922.1, < Immunoglobulin Lambda Light Chain Variable Region, Partial [*Homo sapiens*]. Feb. 6, 2002. Submitted Feb. 6, 2001; downloaded from the internet < http://www.ncbi.nlm.nih.gov/protein/12734074 ?report=genbank&log$=protalign&blast_rank=5&RID=558YZEGP013> on Oct. 30, 2014, p. 1.

(Continued)

*Primary Examiner* — Michael Pak

(57) ABSTRACT

The present invention relates to anti-FGFR2 antibodies, antibody fragments, antibody drug conjugates, and their uses for the treatment of cancer.

24 Claims, 32 Drawing Sheets

(56) References Cited

OTHER PUBLICATIONS

Johnston et al., Fibroblast growth factor receptors (FGFRs) localize in different cellular compartments. A splice variant of FGFR-3 localizes to the nucleus. J Biol Chem. Dec. 22, 1995;270(51):30643-50.
Kramer et al., The human antibody repertoire specific for rabies virus glycoprotein as selected from immune libraries. Eur J Immunol. Jul. 2005;35(7):2131-45.
Lantto et al., Capturing the natural diversity of the human antibody response against vaccinia virus. J. Virol. Feb. 2011;85(4):1820-33. Epub Dec. 8, 2010.
Lantto, et al. Capturing the natural diversity of the human antibody response against vaccinia virus. NCB I GenBank Accession No. ADU57665.1, anti-vaccinia virus immunoglobulin heavy chain variable region, partial [*Homo sapiens*]. Feb. 14, 2011. Submitted Oct. 6, 2010; downloaded from the internet< http://www.ncbi.nlm.nih.gov/protein/316925257?report=genbank&log$=protalign&blast_rank=99&RID=562BJHG2015> on Oct. 30, 2014, p. 1.
Lantto, et al. Capturing the Natural Diversity of the Human Antibody Response Against Vaccinia Virus. NCB I GenBank Accession No. ADU5781 0.1, Anti-Vaccinia Virus . . . . Immunoglobulin Light Chain Variable Region, Partial [*Homo sapiens*]. Feb. 14, 2011. Submitted Oct. 6, 2010; downloaded from the internet <http://www.ncbi.nlm.nih.gov/protein/316925547?report=genbank&log$=protalign&blast_rank=7&RID=565WER54013 > on Oct. 30, 2014, p. 1.
Luo et al. Co-Evolution of Antibody Stability and Vk Cdr-L3 Ca Structure. NCBI PDB Accession No. 3NCJ_L, Chain L, Crystal Structure of Fab15 Mut8. Oct. 10, 2012. Submitted Jun. 4, 2010; downloaded from the internet <http://www.ncbi.nlm.nih.gov/protein/303325094?report=genbank&log$=protalign&blast_rank=4&RID=568P9JTD013> on Oct. 30, 2014; pp. 1-2.
Mouquet et al. Complex-Type N-Giycan Recognition by Potent Broadly Neutralizing HIV Antibodies. NCBI PDB Accession No. 4FQQ_L, Chain L, Crystal Structure of Germ line Antibody Pgt121-Gl Fab. Dec. 13, 2012. Submitted Jun. 25, 2012; downloaded from the internet <http://www.ncbi.nlm.nih.gov/protein/414145741?report=genbank&log$=protalign&blast_rank=5&RID=5714KG5B013> on Oct. 31, 2014; pp. 1-2.
Prosniak et al., Development of a Cocktail of Recombinant-Expressed Human Rabies Virus-Neutralizing Monoclonal Antibodies for Postexposure Prophylaxis of Rabies. NCBI GenBank Accession No. AA017821 .1, Anti-Rabies S057 Immunoglobulin Heavy Chain [*Homo sapiens*]. Jun. 26, 2003. Submitted Oct. 31, 2002; downloaded from the internet <http://www.ncbi.nlm.nih.gov/protein/27728677?report=genbank&log$=protalign&blast_rank=5&RID=5688JA97013 >on Oct. 30, 2014, p. 1.
Takekoshi et al., Human Monoclonal Anti-HBs Antibody. NCBI GenBank Accession No. BAD08204.1, Anti-HBs Antibody Heavy Chain, Partial [*Homo sapiens*]. Jan. 22, 2004. Submitted Jan. 20, 2004; downloaded from the internet <http://www.ncbi.nlm.nih.gov/protein/41 059927?report=genbank&log$=protalign&blast_rank=28&RID=570E23F9015> on Oct. 31, 2014, p. 1.
Wu et al., An approach to the proteomic analysis of a breast cancer cell line (SKBR-3). Proteomics. Jun. 2003;3(6):1037-46.

\* cited by examiner (A)

(B)

(A)

(B)

(A)

(B)

(C)

(D)

(E)

(F)

(A)

(B)

(C)

(A)

(B)

(C)

(D)

(B)

(A)

(B)

(C)

(A)

(B)

(C)

(D)

(B)

(D)

(A)

(B)

(D)

(A)

(B)

FGFR2 : FGF1 : Heparin (2:2:1)

SEQUENCE LISTING

```
<160> NUMBER OF SEQ ID NOS: 262

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asn Tyr Tyr Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Ile Tyr Pro Asp Asn Ser Asp Thr Thr Tyr Ser Pro Ser Phe Gln
1               5                   10                  15

Gly

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Ala Asp Ile
1
```

```
<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Tyr Ser Phe Thr Asn Tyr
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Pro Asp Asn Ser Asp
1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Ala Asp Ile
1

<210> SEQ ID NO 7
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Tyr Ile His Trp Val Arg Gln Met Pro Gly Lys Gly Leu Glu Trp Met
            35                  40                  45

Gly Ala Ile Tyr Pro Asp Asn Ser Asp Thr Thr Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Ala Asp Ile Trp Gly Gln Gly Thr Leu Val Thr Val Ser
            100                 105                 110

Ser

<210> SEQ ID NO 8
<211> LENGTH: 339
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 8

```
caggtgcagc tggtgcagtc aggcgccgaa gtgaagaagc ccggcgagtc actgaagatt      60
agctgtaaag ctccggcta tagcttcact aactactata ttcactgggt ccgacagatg     120
cccggcaagg gcctggaatg gatgggcgct atctaccccg ataatagcga cactacctac     180
tcacctagct ttcagggcca ggtcacaatt agcgccgata agtctattag caccgcctac     240
ctgcagtggt ctagcctgaa ggcctcagac accgctatgt actactgcgc tagaggcgcc     300
gacatctggg gccagggcac cctggtcacc gtgtcttca                            339
```

<210> SEQ ID NO 9
<211> LENGTH: 443
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile His Trp Val Arg Gln Met Pro Gly Lys Gly Leu Glu Trp Met
        35                  40                  45

Gly Ala Ile Tyr Pro Asp Asn Ser Asp Thr Thr Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Ala Asp Ile Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Arg Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
```

```
                260             265             270
Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
                340                 345                 350

Glu Met Thr Lys Asn Gln Val Ser Leu Thr Cys Leu Val Lys Gly Phe
                355                 360                 365

Tyr Pro Ser Asp Ile Ala Val Glu Trp Glu Ser Asn Gly Gln Pro Glu
                370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys
                435                 440

<210> SEQ ID NO 10
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
caggtgcagc tggtgcagtc aggcgccgaa gtgaagaagc cggcgagtc actgaagatt       60 agctgtaaag ctccggcta tagcttcact aactactata ttcactgggt ccgacagatg     120
cccggcaagg gcctggaatg gatgggcgct atctaccccg ataatagcga cactacctac     180
tcacctagct ttcagggcca ggtcacaatt agcgccgata gtctattag caccgcctac     240 ctgcagtggt ctagcctgaa ggcctcagac accgctatgt actactgcgc tagaggcgcc     300
gacatctggg gccagggcac cctggtcacc gtgtcttcag ctagcactaa gggcccaagt     360
gtgtttcccc tggcccccag cagcaagtct acttccggcg gaactgctgc cctgggttgc     420
ctggtgaagg actacttccc cgagcccgtg acagtgtcct ggaactctgg ggctctgact     480
tccggcgtgc acaccttccc cgccgtgctg cagagcagcg gcctgtacag cctgagcagc     540
gtggtgacag tgccctccag ctctctggga acccagacct atatctgcaa cgtgaaccac     600
aagcccagca caccaaggt ggacaagaga gtggagccca gagctgcga caagacccac     660 acctgccccc cctgcccagc tccagaactg ctgggagggc cttccgtgtt cctgttcccc     720
cccaagccca aggacaccct gatgatcagc aggaccccg aggtgacctg cgtggtggtg     780
gacgtgtccc acgaggaccc agaggtgaag ttcaactggt acgtggacgg cgtggaggtg     840
cacaacgcca agaccaagcc cagagaggag cagtacaaca gcacctacag ggtggtgtcc     900
gtgctgaccg tgctgcacca ggactggctg aacggcaaag aatacaagtg caaagtctcc     960
aacaaggccc tgccagcccc aatcgaaaag acaatcagca aggccaaggg ccagccacgg    1020
```

```
gagccccagg tgtacaccct gcccccccagc cgggaggaga tgaccaagaa ccaggtgtcc    1080
ctgacctgtc tggtgaaggg cttctacccc agcgatatcg ccgtggagtg ggagagcaac    1140
ggccagcccg agaacaacta caagaccacc cccccagtgc tggacagcga cggcagcttc    1200
ttcctgtaca gcaagctgac cgtggacaag tccaggtggc agcagggcaa cgtgttcagc    1260
tgcagcgtga tgcacgaggc cctgcacaac cactacaccc agaagtccct gagcctgagc    1320
cccggcaag                                                            1329
```

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Ala Ser Gln Asp Ile Asp Pro Tyr Leu Ser Asn
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Ala Ser Asn Leu Gln Ser
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Gln Thr Thr Ser His Pro Tyr Thr
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Gln Asp Ile Asp Pro Tyr Leu
1               5

<210> SEQ ID NO 15
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Ala Ser
1

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Thr Ser His Pro Tyr
1               5

<210> SEQ ID NO 17
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asp Pro Tyr
            20                  25                  30

Leu Ser Asn Trp Tyr Gln Gln Lys Pro Gly Lys Ala Pro Lys Leu Leu
        35                  40                  45

Ile Tyr Asp Ala Ser Asn Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Thr Thr Ser His Pro
                85                  90                  95

Tyr Thr Phe Gly Gln Gly Thr Lys Val Glu Ile Lys
                100                 105

<210> SEQ ID NO 18
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gacattcaga tgactcagtc acctagtagc ctgagcgcct cagtgggcga tagagtgact      60
atcacctgta gagcctctca ggacatcgac ccctacctgt ctaactggta tcagcagaag     120
cccggcaagg cccctaagct gctgatctac gacgcctcta acctgcagtc aggcgtgccc     180
tctaggttta gcggtagcgg ctcaggcacc gacttcaccc tgactatctc tagcctgcag     240
cccgaggact tcgctaccta ctactgtcag cagactacta gtcaccccta caccttcggc     300
cagggcacta aggtcgagat taag                                            324

<210> SEQ ID NO 19
<211> LENGTH: 215
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asp Pro Tyr
            20                  25                  30

Leu Ser Asn Trp Tyr Gln Gln Lys Pro Gly Lys Ala Pro Lys Leu Leu
        35                  40                  45

Ile Tyr Asp Ala Ser Asn Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Thr Ser His Pro
                85                  90                  95

Tyr Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
        210                 215

<210> SEQ ID NO 20
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gacattcaga tgactcagtc acctagtagc ctgagcgcct cagtgggcga tagagtgact      60
atcacctgta gagcctctca ggacatcgac ccctacctgt ctaactggta tcagcagaag     120
cccggcaagg cccctaagct gctgatctac gacgcctcta acctgcagtc aggcgtgccc     180
tctaggttta gcggtagcgg ctcaggcacc gacttcaccc tgactatctc tagcctgcag     240
cccgaggact tcgctaccta ctactgtcag cagactacta gtcaccccta cacctttcggc    300 cagggcacta aggtcgagat taagcgtacg gtggccgctc ccagcgtgtt catcttcccc     360
cccagcgacg agcagctgaa gagcggcacc gccagcgtgg tgtgcctgct gaacaacttc     420 taccccccggg aggccaaggt gcagtggaag gtggacaacg ccctgcagag cggcaacagc    480
caggagagcg tcaccgagca ggacagcaag gactccacct acagcctgag cagcaccctg     540
accctgagca aggccgacta cgagaagcat aaggtgtacg cctgcgaggt gacccaccag     600
ggcctgtcca gccccgtgac caagagcttc aacagggggcg agtgc                    645

```
<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Tyr Ala Leu Ser
1               5

<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ile Arg Ser Lys Ile Asp Gly Gly Thr Thr Asp Tyr Ala Ala Pro
1               5                   10                  15

Val Lys Gly

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Arg Ser Pro Ser Asp Ser Ser Ala Phe Ala Ile
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Phe Thr Phe Ser Ser Tyr
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ser Lys Ile Asp Gly Gly Thr
1               5

<210> SEQ ID NO 26
<211> LENGTH: 12
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 26

Asp Arg Ser Pro Ser Asp Ser Ser Ala Phe Ala Ile
1               5                   10

<210> SEQ ID NO 27
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Leu Ser Trp Val Arg Gln Ala Pro Gly Lys Gly Leu Glu Trp Val
        35                  40                  45

Gly Arg Ile Arg Ser Lys Ile Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Arg Ser Pro Ser Asp Ser Ser Ala Phe Ala Ile
            100                 105                 110

Trp Gly Gln Gly Thr Leu Val Thr Val Ser Ser
        115                 120

<210> SEQ ID NO 28
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
caggtgcagc tggtggaatc aggcggcgga ctggtcaagc ctggcggtag cctgagactg      60
agctgcgccg cctccggctt caccttctct agctacgccc tgagctgggt ccgacaggct    120
cctggcaagg gcctggaatg ggtcggacgg attagatcta agatcgacgg cggcactacc    180
gactacgccg ctcctgtgaa gggacggttc actatctcta gggacgactc taagaacacc    240
ctgtacctgc agatgaatag cctgaaaacc gaggacaccg ccgtctacta ctgcgctaga    300
gatagatcac tagcgactc tagcgccttc gctatctggg gccagggcac cctggtcacc    360
gtgagttca                                                             369

<210> SEQ ID NO 29
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Leu Ser Trp Val Arg Gln Ala Pro Gly Lys Gly Leu Glu Trp Val
        35                  40                  45

Gly Arg Ile Arg Ser Lys Ile Asp Gly Gly Thr Thr Asp Tyr Ala Ala
50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Arg Ser Pro Ser Asp Ser Ser Ala Phe Ala Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser

```
                420                 425                 430
Val Met His Glu Ala Leu His Asn His Tyr Thr Gln Lys Ser Leu Ser
        435                 440                 445

Leu Ser Pro Gly Lys
    450

<210> SEQ ID NO 30
<211> LENGTH: 1359
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
caggtgcagc tggtggaatc aggcggcgga ctggtcaagc ctggcggtag cctgagactg      60
agctgcgccg cctccggctt caccttctct agctacgccc tgagctgggt ccgacaggct     120
cctggcaagg gcctggaatg gtcggacgg attagatcta agatcgacgg cggcactacc      180
gactacgccg ctcctgtgaa gggacggttc actatctcta gggacgactc taagaacacc     240
ctgtacctgc agatgaatag cctgaaaacc gaggacaccg ccgtctacta ctgcgctaga     300
gatagatcac ctagcgactc tagcgccttc gctatctggg gccagggcac cctggtcacc     360
gtgagttcag ctagcactaa gggcccaagt gtgtttcccc tggcccccag cagcaagtct     420
acttccggcg gaactgctgc cctgggttgc ctggtgaagg actacttccc cgagcccgtg     480
acagtgtcct ggaactctgg ggctctgact tccggcgtgc acaccttccc cgccgtgctg     540
cagagcagcg gcctgtacag cctgagcagc gtggtgacag tgccctccag ctctctggga     600
acccagacct atatctgcaa cgtgaaccac aagcccagca acaccaaggt ggacaagaga     660
gtggagccca gagctgcga caagacccac acctgccccc ctgcccagc tccagaactg       720 ctgggagggc cttccgtgtt cctgttcccc ccaagcccca aggacaccct gatgatcagc     780 aggaccccg aggtgacctg cgtggtggtg gacgtgtccc acgaggaccc agaggtgaag       840
ttcaactggt acgtggacgg cgtggaggtg cacaacgcca agaccaagcc agagaggag       900 cagtacaaca gcacctacag ggtggtgtcc gtgctgaccg tgctgcacca ggactggctg     960
aacggcaaag aatacaagtg caaagtctcc aacaaggccc tgccagcccc aatcgaaaag    1020
acaatcagca aggccaaggg ccagccacgg gagccccagg tgtacaccct gccccccagc    1080
cgggaggaga tgaccaagaa ccaggtgtcc ctgacctgtc tggtgaaggg cttctacccc    1140
agcgatatcg ccgtggagtg ggagagcaac ggccagcccg agaacaacta caagaccacc    1200
cccccagtgc tggacagcga cggcagcttc ttcctgtaca gcaagctgac cgtggacaag    1260
tccaggtggc agcagggcaa cgtgttcagc tgcagcgtga tgcacgaggc cctgcacaac    1320
cactacaccc agaagtccct gagcctgagc cccggcaag                          1359

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Gly Asp Asn Leu Gly Ser Gln Tyr Val Asp
1               5                   10
```

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asp Asp Asn Asp Arg Pro Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Ser Trp Asp Ser Leu Ser Val Val
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Asn Leu Gly Ser Gln Tyr
1               5

<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Asp Asn
1

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Trp Asp Ser Leu Ser Val
1               5

<210> SEQ ID NO 37
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Ser Gln Tyr Val
            20                  25                  30

Asp Trp Tyr Gln Gln Lys Pro Gly Gln Ala Pro Val Leu Val Ile Tyr
        35                  40                  45

Asp Asp Asn Asp Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Asp Ser Leu Ser Val Val
                85                  90                  95

Phe Gly Gly Gly Thr Lys Leu Thr Val Leu
            100                 105

<210> SEQ ID NO 38
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
gatatcgagc tgactcagcc ccctagcgtc agcgtcagcc ctggccagac cgcctctatc      60
acctgtagcg gcgataacct gggctctcag tacgtggact ggtatcagca gaagcccggc     120
caggcccccg tgctggtcat ctacgacgat aacgatagac tagcggaat ccccgagcgg      180 tttagcggct ctaatagcgg caacaccgct accctgacta ttagcggcac tcaggccgag    240
gacgaggccg actactactg tcagtcctgg gatagcctgt cagtggtgtt cggcggaggc    300
actaagctga ccgtgctc                                                  318

<210> SEQ ID NO 39
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Ser Gln Tyr Val
            20                  25                  30

Asp Trp Tyr Gln Gln Lys Pro Gly Gln Ala Pro Val Leu Val Ile Tyr
        35                  40                  45

Asp Asp Asn Asp Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Asp Ser Leu Ser Val Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn

```
            115                 120                 125
Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

<210> SEQ ID NO 40
<211> LENGTH: 636
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
gatatcgagc tgactcagcc ccctagcgtc agcgtcagcc ctggccagac cgcctctatc      60
acctgtagcg gcgataacct gggctctcag tacgtggact ggtatcagca gaagcccggc    120 caggccccg  tgctggtcat ctacgacgat aacgatagac tagcggaat  ccccgagcgg    180 tttagcggct ctaatagcgg caacaccgct accctgacta ttagcggcac tcaggccgag    240
gacgaggccg actactactg tcagtcctgg gatagcctgt cagtggtgtt cggcggaggc    300
actaagctga ccgtgctcgg ccagcctaag gctgccccca gcgtgaccct gttccccccc    360
agcagcgagg agctgcaggc caacaaggcc accctggtgt gcctgatcag cgacttctac    420
ccaggcgccg tgaccgtggc ctggaaggcc gacagcagcc ccgtgaaggc cggcgtggag    480
accaccaccc ccagcaagca gagcaacaac aagtacgccg ccagcagcta cctgagcctg    540 accccccgagc agtggaagag ccacaggtcc tacagctgcc aggtgaccca cgagggcagc    600
accgtggaaa agaccgtggc cccaaccgag tgcagc                               636

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asp Tyr Ala Met Ser
1               5

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Val Ile Glu Gly Asp Gly Ser Tyr Thr His Tyr Ala Asp Ser Val Lys
```

1 5 10 15

Gly

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

Glu Lys Thr Tyr Ser Ser Ala Phe Asp Tyr
1 5 10

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

Gly Phe Thr Phe Ser Asp Tyr
1 5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

Glu Gly Asp Gly Ser Tyr
1 5

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

Glu Lys Thr Tyr Ser Ser Ala Phe Asp Tyr
1 5 10

<210> SEQ ID NO 47
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

Gln Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Ala Met Ser Trp Val Arg Gln Ala Pro Gly Lys Gly Leu Glu Trp Val
35 40 45

```
Ser Val Ile Glu Gly Asp Gly Ser Tyr Thr His Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Lys Thr Tyr Ser Ser Ala Phe Asp Tyr Trp Gly Gln Gly
            100                 105                 110

Thr Leu Val Thr Val Ser Ser
            115
```

<210> SEQ ID NO 48
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48

```
caggtgcagc tgctggaatc aggcggcgga ctggtgcagc ctggcggtag cctgagactg      60
agctgtgccg cctccggctt cacctttagc gactacgcta tgagctgggt ccgacaggcc     120
cctggcaagg gactggaatg ggtgtcagtg atcgagggcg acggtagcta cactcactac     180
gccgatagcg tgaagggccg gttcactatc tctagggaca actctaagaa caccctgtac     240
ctgcagatga actcactgag agccgaggac accgccgtct actactgcgc tagagaaaag     300
acctactcta gcgccttcga ctactggggc cagggcaccc tggtcaccgt gtcatca        357
```

<210> SEQ ID NO 49
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

```
Gln Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
             20                  25                  30

Ala Met Ser Trp Val Arg Gln Ala Pro Gly Lys Gly Leu Glu Trp Val
         35                  40                  45

Ser Val Ile Glu Gly Asp Gly Ser Tyr Thr His Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Lys Thr Tyr Ser Ser Ala Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 50
<211> LENGTH: 1347
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 50
caggtgcagc tgctggaatc aggcggcgga ctggtgcagc ctggcggtag cctgagactg     60
agctgtgccg cctccggctt caccttagc gactacgcta tgagctgggt ccgacaggcc    120
cctggcaagg gactggaatg ggtgtcagtg atcgagggcg acggtagcta cactcactac    180
gccgatagcg tgaagggccg gttcactatc tctaggggaca actctaagaa caccctgtac    240
ctgcagatga actcactgag agccgaggac accgccgtct actactgcgc tagagaaaag    300
acctactcta gcgccttcga ctactggggc cagggcaccc tggtcaccgt gtcatcagct    360

```
agcactaagg gcccaagtgt gtttcccctg gcccccagca gcaagtctac ttccggcgga    420
actgctgccc tgggttgcct ggtgaaggac tacttccccg agcccgtgac agtgtcctgg    480
aactctgggg ctctgacttc cggcgtgcac accttccccg ccgtgctgca gagcagcggc    540
ctgtacagcc tgagcagcgt ggtgacagtg ccctccagct ctctgggaac ccagacctat    600
atctgcaacg tgaaccacaa gcccagcaac accaaggtgg acaagagagt ggagcccaag    660
agctgcgaca gacccacac ctgccccccc tgcccagctc cagaactgct gggagggcct    720
tccgtgttcc tgttcccccc caagcccaag gacaccctga tgatcagcag gacccccgag    780
gtgacctgcg tggtggtgga cgtgtcccac gaggacccag aggtgaagtt caactggtac    840
gtggacggcg tggaggtgca caacgccaag accaagccca gagaggagca gtacaacagc    900
acctacaggg tggtgtccgt gctgaccgtg ctgcaccagg actggctgaa cggcaaagaa    960
tacaagtgca agtctccaa caaggccctg ccagccccaa tcgaaaagac aatcagcaag    1020
gccaagggcc agccacggga gccccaggtg tacaccctgc cccccagccg ggaggagatg    1080
accaagaacc aggtgtccct gacctgtctg gtgaagggct tctaccccag cgatatcgcc    1140
gtggagtggg agagcaacgg ccagcccgag aacaactaca agaccacccc cccagtgctg    1200
gacagcgacg gcagcttctt cctgtacagc aagctgaccg tggacaagtc caggtggcag    1260
cagggcaacg tgttcagctg cagcgtgatg cacgaggccc tgcacaacca ctacacccag    1320
aagtccctga gcctgagccc cggcaag                                        1347
```

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Ala Ser Gln Asp Ile Ser Ser Asp Leu Asn
1               5                   10

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Ala Ser Asn Leu Gln Ser
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Gln His Tyr Ser Pro Ser His Thr
1               5

<210> SEQ ID NO 54

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Gln Asp Ile Ser Ser Asp
1               5

<210> SEQ ID NO 55
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Ala Ser
1

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

His Tyr Ser Pro Ser His
1               5

<210> SEQ ID NO 57
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Asp
            20                  25                  30

Leu Asn Trp Tyr Gln Gln Lys Pro Gly Lys Ala Pro Lys Leu Leu Ile
        35                  40                  45

Tyr Asp Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ser Pro Ser His
                85                  90                  95

Thr Phe Gly Gln Gly Thr Lys Val Glu Ile Lys
            100                 105

<210> SEQ ID NO 58
<211> LENGTH: 321
<212> TYPE: DNA
<213> ORGANISM: Artificial Sequence
<220> FEATURE:
<223> OTHER INFORMATION: Description of Artificial Sequence: Synthetic
```

-continued polynucleotide

<400> SEQUENCE: 58

```
gatattcaga tgactcagtc acctagtagc ctgagcgcct cagtgggcga tagagtgact      60
atcacctgta gagcctctca ggacatctct agcgacctga actggtatca gcagaagccc     120
ggcaaggccc ctaagctgct gatctacgac gcctctaacc tgcagagcgg cgtgccctct     180
aggtttagcg gtagcggctc aggcaccgac tttaccctga ctatctctag cctgcagccc     240
gaggacttcg ccgtctacta ctgtcagcag cactatagcc ctagtcacac cttcggccag     300
ggcactaagg tcgagattaa g                                               321
```

<210> SEQ ID NO 59
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 59

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Asp
            20                  25                  30

Leu Asn Trp Tyr Gln Gln Lys Pro Gly Lys Ala Pro Lys Leu Leu Ile
        35                  40                  45

Tyr Asp Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ser Pro Ser His
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 60
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 60

```
gatattcaga tgactcagtc acctagtagc ctgagcgcct cagtgggcga tagagtgact    60
atcacctgta gagcctctca ggacatctct agcgacctga actggtatca gcagaagccc   120
ggcaaggccc ctaagctgct gatctacgac gcctctaacc tgcagagcgg cgtgccctct   180
aggtttagcg gtagcggctc aggcaccgac tttacccctg atatctctag cctgcagccc   240
gaggacttcg ccgtctacta ctgtcagcag cactatagcc tagtcacac cttcggccag    300 ggcactaagg tcgagattaa gcgtacggtg gccgctccca gcgtgttcat cttcccccc    360 agcgacgagc agctgaagag cggcaccgcc agcgtggtgt gcctgctgaa caacttctac   420 ccccggggagg ccaaggtgca gtggaaggtg gacaacgccc tgcagagcgg caacagccag   480
gagagcgtca ccgagcagga cagcaaggac tccacctaca gcctgagcag cacctgacc   540 ctgagcaagg ccgactacga aagcataag gtgtacgcct gcgaggtgac ccaccagggc   600
ctgtccagcc ccgtgaccaa gagcttcaac aggggcgagt gc                      642
```

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser Tyr Ala Ile Ser
1               5

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Tyr Ile Ser Pro Tyr Met Gly Glu Thr His Tyr Ala Gln Arg Phe Gln
1               5                   10                  15
Gly

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Glu Ser Tyr Glu Tyr Phe Asp Ile
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Gly Thr Phe Ser Ser Tyr

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Pro Tyr Met Gly Glu
1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Glu Ser Tyr Glu Tyr Phe Asp Ile
1               5

<210> SEQ ID NO 67
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Tyr Ile Ser Pro Tyr Met Gly Glu Thr His Tyr Ala Gln Arg Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Tyr Glu Tyr Phe Asp Ile Trp Gly Gln Gly Thr Leu
            100                 105                 110

Val Thr Val Ser Ser
        115

<210> SEQ ID NO 68
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
caggtgcagc tggtgcagtc aggcgccgaa gtgaagaaac ccggctctag cgtgaaggtg      60
tcctgtaaag cctccggcgg caccttctct agctacgcta ttagctgggt ccgacaggcc     120

-continued

```
ccaggacagg gcctggaatg gatgggctat attagcccct atatgggcga gactcactac    180
gctcagcggt tcagggtag agtgactatc accgccgacg agtctactag caccgcctat    240
atggaactgt ctagcctgag atcagaggac accgccgtct actactgcgc tagagagtcc    300
tacgagtact tcgatatctg gggccagggc accctggtca ccgtgtcatc a            351
```

<210> SEQ ID NO 69
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Tyr Ile Ser Pro Tyr Met Gly Glu Thr His Tyr Ala Gln Arg Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Tyr Glu Tyr Phe Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

```
Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 70
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
caggtgcagc tggtgcagtc aggcgccgaa gtgaagaaac cggctctag cgtgaaggtg      60 tcctgtaaag cctccggcgg caccttctct agctacgcta ttagctgggt ccgacaggcc    120
ccaggacagg gctggaatg gatgggctat attagcccct atatgggcga gactcactac    180
gctcagcggt ttcagggtag agtgactatc accgccgacg agtctactag caccgcctat    240
atggaactgt ctagcctgag atcagaggac ccgccgtct actactgcgc tagagagtcc    300
tacgagtact cgatatctg gggccagggc accctggtca ccgtgtcatc agctagcact    360
aagggcccaa gtgtgttcc cctggcccc agcagcaagt ctacttccgg cggaactgct    420
gccctgggtt gcctggtgaa ggactactc cccgagcccg tgacagtgtc ctggaactct    480
ggggctctga cttccggcgt gcacaccttc ccgccgtgc tgcagagcag cggcctgtac    540
agcctgagca gcgtggtgac agtgccctcc agctctctgg aacccagac ctatatctgc    600 aacgtgaacc acaagcccag caacaccaag gtggacaaga gagtggagcc caagagctgc    660
gacaagaccc acacctgccc ccctgcccca gctccagaac tgctgggagg ccttccgtg    720 ttcctgttcc cccccaagcc caaggacacc ctgatgatca gcaggacccc cgaggtgacc    780
tgcgtggtgg tggacgtgtc ccacgaggac ccagaggtga agttcaactg gtacgtggac    840
ggcgtggagg tgcacaacgc caagaccaag cccagagagg agcagtacaa cagcacctac    900
agggtggtgt ccgtgctgac cgtgctgcac caggactggc tgaacggcaa agaatacaag    960
tgcaaagtct ccaacaaggc cctgccagcc ccaatcgaaa agacaatcag caaggccaag   1020
ggccagccac gggagcccca ggtgtacacc ctgccccca gccggagga gatgaccaag   1080 aaccaggtgt ccctgacctg tctggtgaag ggcttctacc ccagcgatat cgccgtggag   1140
tgggagagca acggccagcc cgagaacaac tacaagacca cccccccagt gctggacagc   1200
gacggcagct tcttcctgta cagcaagctg accgtggaca gtccaggtg cagcagggc   1260 aacgtgttca gctgcagcgt gatgcacgag gccctgcaca accactacac ccagaagtcc   1320
```
ctgagcctga gccccggcaa g                                              1341

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Arg Ala Ser Gln Ser Ile Ser Asn Asp Leu Ala
1               5                   10

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ala Thr Ser Ile Leu Gln Ser
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Leu Gln Tyr Tyr Asp Tyr Ser Tyr Thr
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Gln Ser Ile Ser Asn Asp
1               5

<210> SEQ ID NO 75
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Thr Ser
1

<210> SEQ ID NO 76
<211> LENGTH: 6
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 76

Tyr Tyr Asp Tyr Ser Tyr
1               5

<210> SEQ ID NO 77
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asp
            20                  25                  30

Leu Ala Trp Tyr Gln Gln Lys Pro Gly Lys Ala Pro Lys Leu Leu Ile
        35                  40                  45

Tyr Ala Thr Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Tyr Asp Tyr Ser Tyr
                85                  90                  95

Thr Phe Gly Gln Gly Thr Lys Val Glu Ile Lys
            100                 105

<210> SEQ ID NO 78
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
gatattcaga tgactcagtc acctagtagc ctgagcgcct cagtgggcga tagagtgact      60
atcacctgta gagcctccca gtctatctct aacgacctgg cctggtatca gcagaagccc    120
ggcaaggccc ctaagctgct gatctacgct acctctatcc tgcagagcgg cgtgccctct    180
aggtttagcg gtagcggctc aggcaccgac tttaccctga ctatctctag cctgcagccc    240
gaggacttcg ctacctacta ctgcctgcag tactacgact actcctacac cttcggccag    300
ggcactaagg tcgagattaa g                                              321

<210> SEQ ID NO 79
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asp
            20                  25                  30

```
Leu Ala Trp Tyr Gln Gln Lys Pro Gly Lys Ala Pro Lys Leu Leu Ile
             35                  40                  45

Tyr Ala Thr Ser Ile Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Tyr Asp Tyr Ser Tyr
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 80
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 80

```
gatattcaga tgactcagtc acctagtagc ctgagcgcct cagtgggcga tagagtgact    60
atcacctgta gagcctccca gtctatctct aacgacctgg cctggtatca gcagaagccc   120
ggcaaggccc ctaagctgct gatctacgct acctctatcc tgcagagcgg cgtgccctct   180
aggtttagcg gtagcggctc aggcaccgac tttaccctga ctatctctag cctgcagccc   240
gaggacttcg ctacctacta ctgcctgcag tactacgact actcctacac cttcggccag   300
ggcactaagg tcgagattaa gcgtacggtg gccgctccca gcgtgttcat cttcccccc   360
agcgacgagc agctgaagag cggcaccgcc agcgtggtgt gcctgctgaa caacttctac   420
ccccgggagg ccaaggtgca gtggaaggtg gacaacgccc tgcagagcgg caacagccag   480
gagagcgtca ccgagcagga cagcaaggac tccacctaca gcctgagcag cacccctgacc   540
ctgagcaagg ccgactacga gaagcataag gtgtacgcct gcgaggtgac ccaccagggc   600
ctgtccagcc ccgtgaccaa gagcttcaac agggggcgagt gc                    642
```

<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 81

Asp Tyr Ala Met Ser
1               5

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Val Ile Glu Gly Asp Ala Ser Tyr Thr His Tyr Ala Asp Ser Val Arg
1               5                   10                  15

Gly

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Glu Arg Thr Tyr Ser Ser Ala Phe Asp Tyr
1               5                   10

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Phe Thr Phe Ser Asp Tyr
1               5

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Glu Gly Asp Ala Ser Tyr
1               5

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Glu Arg Thr Tyr Ser Ser Ala Phe Asp Tyr
1               5                   10

<210> SEQ ID NO 87
```

<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Val Ile Glu Gly Asp Ala Ser Tyr Thr His Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Thr Tyr Ser Ser Ala Phe Asp Tyr Trp Gly Gln Gly
            100                 105                 110

Thr Leu Val Thr Val Ser Ser
        115

<210> SEQ ID NO 88
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
gaggtgcagc tgctggaatc aggcggcgga ctggtgcagc ctggcggtag cctgagactg      60
agctgcgctg ctagtggctt cacctttagc gactacgcta tgagctgggt cagacaggcc     120
cctggtaaag gcctggagtg ggtcagcgtg atcgagggcg acgctagtta cactcactac     180
gccgatagcg tcagaggccg gttcactatc tctagggata actctaagaa caccctgtac     240
ctgcagatga atagcctgag agccgaggac accgccgtct actactgcgc tagagagcgg     300
acctactcta gcgccttcga ctactggggt cagggcaccc tggtcaccgt gtctagc        357

<210> SEQ ID NO 89
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Val Ile Glu Gly Asp Ala Ser Tyr Thr His Tyr Ala Asp Ser Val
    50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Thr Tyr Ser Ser Ala Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 90
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90

```
gaggtgcagc tgctggaatc aggcggcgga ctggtgcagc ctggcggtag cctgagactg      60
agctgcgctg ctagtggctt cacctttagc gactacgcta tgagctgggt cagacaggcc     120
cctggtaaag gcctggagtg ggtcagcgtg atcgagggcg acgctagtta cactcactac     180
gccgatagcg tcagaggccg gttcactatc tctagggata actctaagaa caccctgtac     240
ctgcagatga atagcctgag agccgaggac accgccgtct actactgcgc tagagagcgg     300
acctactcta gcgccttcga ctactgggt caggcaccc tggtcaccgt gtctagcgct       360
agcactaagg gcccaagtgt gtttcccctg gcccccagca gcaagtctac ttccggcgga     420
actgctgccc tgggttgcct ggtgaaggac tacttccccg agcccgtgac agtgtcctgg     480
aactctgggg ctctgacttc cggcgtgcac accttccccg ccgtgctgca gagcagcggc     540
ctgtacagcc tgagcagcgt ggtgacagtg ccctccagct ctctgggaac ccagacctat     600
atctgcaacg tgaaccacaa gcccagcaac accaaggtgg acaagagagt ggagcccaag     660
agctgcgaca gagacccacac ctgcccccccc tgcccagctc cagaactgct gggagggcct    720
tccgtgttcc tgttccccccc caagcccaag gacaccctga tgatcagcag gacccccgag    780
gtgacctgcg tggtggtgga cgtgtcccac gaggacccag aggtgaagtt caactggtac     840
gtggacggcg tggaggtgca caacgccaag accaagccca gagaggagca gtacaacagc     900
acctacaggg tggtgtccgt gctgaccgtg ctgcaccagg actggctgaa cggcaaagaa     960
tacaagtgca aagtctccaa caaggccctg ccagccccaa tcgaaaagac aatcagcaag    1020
gccaagggcc agccacggga gccccaggtg tacaccctgc cccccagccg ggaggagatg    1080
accaagaacc aggtgtccct gacctgtctg gtgaagggct tctaccccag cgatatcgcc    1140
gtggagtggg agagcaacgg ccagcccgag aacaactaca agaccacccc cccagtgctg    1200
gacagcgacg gcagcttctt cctgtacagc aagctgaccg tggacaagtc caggtggcag    1260
cagggcaacg tgttcagctg cagcgtgatg cacgaggccc tgcacaacca ctacacccag    1320
aagtccctga gcctgagccc cggcaag                                        1347
```

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Ala Ser Gln Asp Ile Ser Ser Asp Leu Asn
1               5                   10

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Asp Ala Ser Asn Leu Gln Ser
1               5

```
<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Gln His Tyr Ser Pro Ser His Thr
1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ser Gln Asp Ile Ser Ser Asp
1               5

<210> SEQ ID NO 95
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Asp Ala Ser
1

<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

His Tyr Ser Pro Ser His
1               5

<210> SEQ ID NO 97
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Asp
            20                  25                  30

Leu Asn Trp Tyr Gln Gln Lys Pro Gly Lys Ala Pro Lys Leu Leu Ile
        35                  40                  45

Tyr Asp Ala Ser Asn Leu Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Pro Ser His
                85                  90                  95

Thr Phe Gly Gln Gly Thr Lys Val Glu Ile Lys
            100                 105

<210> SEQ ID NO 98
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
gatattcaga tgactcagtc acctagtagc ctgagcgcta gtgtgggcga tagagtgact      60
atcacctgta gagcctctca ggatatctct agcgacctga actggtatca gcagaagccc     120
ggtaaagccc ctaagctgct gatctacgac gcctctaacc tgcagtcagg cgtgccctct     180
aggtttagcg gtagcggtag tggcaccgac ttcaccctga ctatctctag cctgcagccc     240
gaggacttcg ctacctacta ctgtcagcag cactatagcc ctagtcacac cttcggtcag     300
ggcactaagg tcgagattaa g                                                321

<210> SEQ ID NO 99
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Asp
                20                  25                  30

Leu Asn Trp Tyr Gln Gln Lys Pro Gly Lys Ala Pro Lys Leu Leu Ile
            35                  40                  45

Tyr Asp Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Pro Ser His
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 100
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
gatattcaga tgactcagtc acctagtagc ctgagcgcta gtgtgggcga tagagtgact      60
atcacctgta gagcctctca ggatatctct agcgacctga actggtatca gcagaagccc     120
ggtaaagccc ctaagctgct gatctacgac gcctctaacc tgcagtcagg cgtgccctct     180
aggtttagcg gtagcggtag tggcaccgac ttcaccctga ctatctctag cctgcagccc     240
gaggacttcg ctacctacta ctgtcagcag cactatagcc tagtcacac cttcggtcag      300 ggcactaagg tcgagattaa gcgtacggtg gccgctccca gcgtgttcat cttcccccc      360 agcgacgagc agctgaagag cggcaccgcc agcgtggtgt gcctgctgaa caacttctac     420
ccccgggagg ccaaggtgca gtggaaggtg acaacgccc tgcagagcgg caacagccag      480
gagagcgtca ccgagcagga cagcaaggac tccacctaca gcctgagcag caccctgacc     540
ctgagcaagg ccgactacga gaagcataag gtgtacgcct gcgaggtgac ccaccagggc     600
ctgtccagcc ccgtgaccaa gagcttcaac aggggcgagt gc                        642

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ser Tyr Ala Leu Ser
1               5

<210> SEQ ID NO 102
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Arg Ile Arg Ser Arg Ile Glu Gly Gly Thr Thr Asp Tyr Ala Ala Pro
1               5                   10                  15

Val Arg Gly

<210> SEQ ID NO 103
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 103

Asp Arg Ser Pro Ser Asp Ser Ser Ala Phe Ala Ile
1               5                   10

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Phe Thr Phe Ser Ser Tyr
1               5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Arg Ser Arg Ile Glu Gly Gly Thr
1               5

<210> SEQ ID NO 106
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Asp Arg Ser Pro Ser Asp Ser Ser Ala Phe Ala Ile
1               5                   10

<210> SEQ ID NO 107
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Leu Ser Trp Val Arg Gln Ala Pro Gly Lys Gly Leu Glu Trp Val
        35                  40                  45

Gly Arg Ile Arg Ser Arg Ile Glu Gly Gly Thr Thr Asp Tyr Ala Ala
    50                  55                  60

Pro Val Arg Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Arg Ser Pro Ser Asp Ser Ser Ala Phe Ala Ile
            100                 105                 110
```

Trp Gly Gln Gly Thr Leu Val Thr Val Ser Ser
        115                 120

<210> SEQ ID NO 108
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
gaggtgcagc tggtggaatc aggcggcgga ctggtcaagc ctggcggtag cctgagactg     60
agctgcgctg ctagtggctt caccttctct agctacgccc tgagctgggt cagacaggcc    120
cctggtaaag gcctggagtg ggtcggacgg attagatcta ggatcgaggg cggcactacc    180
gactacgccg ctcccgtcag aggccggttc actatctcta gggacgactc taagaacacc    240
ctgtacctgc agatgaatag cctgaaaacc gaggacaccg ccgtctacta ctgcgctaga    300
gatagatcac ctagcgactc tagcgccttc gctatctggg gtcagggcac cctggtcacc    360
gtgtctagc                                                            369

<210> SEQ ID NO 109
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Leu Ser Trp Val Arg Gln Ala Pro Gly Lys Gly Leu Glu Trp Val
        35                  40                  45

Gly Arg Ile Arg Ser Arg Ile Glu Gly Gly Thr Thr Asp Tyr Ala Ala
    50                  55                  60

Pro Val Arg Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Arg Ser Pro Ser Asp Ser Ser Ala Phe Ala Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 110
<211> LENGTH: 1359
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
gaggtgcagc tggtggaatc aggcggcgga ctggtcaagc ctggcggtag cctgagactg      60
agctgcgctg ctagtggctt caccttctct agctacgccc tgagctgggt cagacaggcc     120
cctggtaaag gcctggagtg gtcggacgg attagatcta ggatcgaggg cggcactacc      180
gactacgccg ctcccgtcag aggccggttc actatctcta gggacgactc taagaacacc     240
ctgtacctgc agatgaatag cctgaaaacc gaggacaccg ccgtctacta ctgcgctaga     300
gatagatcac ctagcgactc tagcgccttc gctatctggg gtcagggcac cctggtcacc     360
gtgtctagcg ctagcactaa gggcccaagt gtgtttcccc tggcccccag cagcaagtct     420
acttccggcg gaactgctgc cctgggttgc ctggtgaagg actacttccc cgagcccgtg     480
acagtgtcct ggaactctgg ggctctgact tccggcgtgc acaccttccc cgccgtgctg     540
cagagcagcg gcctgtacag cctgagcagc gtggtgacag tgccctccag ctctctggga     600
acccagacct atatctgcaa cgtgaaccac aagcccagca caccaaggt ggacaagaga     660 gtggagccca agagctgcga caagacccac acctgccccc cctgcccagc tccagaactg 720
ctgggagggc cttccgtgtt cctgttcccc cccaagccca aggacaccct gatgatcagc 780
aggacccccg aggtgacctg cgtggtggtg gacgtgtccc acgaggaccc agaggtgaag 840

ttcaactggt acgtggacgg cgtggaggtg cacaacgcca agaccaagcc cagagaggag 900
cagtacaaca gcacctacag ggtggtgtcc gtgctgaccg tgctgcacca ggactggctg 960
aacggcaaag aatacaagtg caaagtctcc aacaaggccc tgccagcccc aatcgaaaag 1020
acaatcagca aggccaaggg ccagccacgg gagccccagg tgtacaccct gcccccccagc 1080
cgggaggaga tgaccaagaa ccaggtgtcc ctgacctgtc tggtgaaggg cttctacccc 1140
agcgatatcg ccgtggagtg ggagagcaac ggccagcccg agaacaacta caagaccacc 1200
cccccagtgc tggacagcga cggcagcttc ttcctgtaca gcaagctgac cgtggacaag 1260
tccaggtggc agcagggcaa cgtgttcagc tgcagcgtga tgcacgaggc cctgcacaac 1320
cactacaccc agaagtccct gagcctgagc cccggcaag 1359

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

Ser Gly Asp Asn Leu Gly Ser Gln Tyr Val Asp
1 5 10

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

Asp Asp Asn Asp Arg Pro Ser
1 5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Gln Ser Trp Asp Ser Leu Ser Val Val
1 5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 114

Asp Asn Leu Gly Ser Gln Tyr

<210> SEQ ID NO 115
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 115

Asp Asp Asn
1

<210> SEQ ID NO 116
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 116

Trp Asp Ser Leu Ser Val
1               5

<210> SEQ ID NO 117
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 117

Ser Tyr Glu Leu Thr Gln Pro Leu Ser Val Ser Val Ala Leu Gly Gln
1               5                   10                  15

Thr Ala Arg Ile Thr Cys Ser Gly Asp Asn Leu Gly Ser Gln Tyr Val
            20                  25                  30

Asp Trp Tyr Gln Gln Lys Pro Gly Gln Ala Pro Val Leu Val Ile Tyr
        35                  40                  45

Asp Asp Asn Asp Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ser Trp Asp Ser Leu Ser Val Val
                85                  90                  95

Phe Gly Gly Gly Thr Lys Leu Thr Val Leu
            100                 105

<210> SEQ ID NO 118
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 118
agctacgagc tgactcagcc cctgagcgtc agcgtggccc tgggtcagac cgctagaatc      60
acctgtagcg gcgataacct gggctctcag tacgtggact ggtatcagca gaagcccggt     120
caggcccccg tgctggtgat ctacgacgat aacgatagac tagcggaat ccccgagcgg      180

```
tttagcggct ctaatagcgg taacaccgct accctgacta tctctagggc tcaggccggc    240
gacgaggccg actactactg tcagtcctgg gatagcctga gcgtggtgtt cggcggaggc    300
actaagctga ccgtgctg                                                  318
```

<210> SEQ ID NO 119
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

```
Ser Tyr Glu Leu Thr Gln Pro Leu Ser Val Ser Val Ala Leu Gly Gln
1               5                   10                  15

Thr Ala Arg Ile Thr Cys Ser Gly Asp Asn Leu Gly Ser Gln Tyr Val
            20                  25                  30

Asp Trp Tyr Gln Gln Lys Pro Gly Gln Ala Pro Val Leu Val Ile Tyr
        35                  40                  45

Asp Asp Asn Asp Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ser Trp Asp Ser Leu Ser Val Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210
```

<210> SEQ ID NO 120
<211> LENGTH: 636
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120

```
agctacgagc tgactcagcc cctgagcgtc agcgtggccc tgggtcagac cgctagaatc    60
acctgtagcg gcgataacct gggctctcag tacgtggact ggtatcagca gaagcccggt   120
caggcccccg tgctggtgat ctacgacgat aacgatagac tagcggaat ccccgagcgg    180 tttagcggct ctaatagcgg taacaccgct accctgacta tctctagggc tcaggccggc   240
gacgaggccg actactactg tcagtcctgg gatagcctga gcgtggtgtt cggcggaggc   300
```

```
actaagctga ccgtgctggg tcagcctaag gctgccccca gcgtgaccct gttcccccc    360 agcagcgagg agctgcaggc caacaaggcc accctggtgt gcctgatcag cgacttctac    420
ccaggcgccg tgaccgtggc ctggaaggcc gacagcagcc ccgtgaaggc cggcgtggag    480
accaccaccc ccagcaagca gagcaacaac aagtacgccg ccagcagcta cctgagcctg    540
acccccgagc agtggaagag ccacaggtcc tacagctgcc aggtgaccca cgagggcagc    600
accgtggaaa agaccgtggc cccaaccgag tgcagc                              636
```

<210> SEQ ID NO 121
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Asp Tyr Ala Met Ser
1               5

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Thr Ile Glu Gly Asp Ser Asn Tyr Ile Glu Tyr Ala Asp Ser Val Lys
1               5                   10                  15

Gly

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Glu Arg Thr Tyr Ser Ser Ala Phe Asp Tyr
1               5                   10

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gly Phe Thr Phe Ser Asp Tyr
1               5

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Glu Gly Asp Ser Asn Tyr
1               5

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Glu Arg Thr Tyr Ser Ser Ala Phe Asp Tyr
1               5                   10

<210> SEQ ID NO 127
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Thr Ile Glu Gly Asp Ser Asn Tyr Ile Glu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Thr Tyr Ser Ser Ala Phe Asp Tyr Trp Gly Gln Gly
            100                 105                 110

Thr Leu Val Thr Val Ser Ser
        115

<210> SEQ ID NO 128
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128
caggtgcaat tgctggaaag cggcggtggc ctggtgcagc cgggtggcag cctgcgtctg     60
agctgcgcgg cgtccggatt cacctttct gactacgcta tgtcttgggt gcgccaggcc    120
ccgggcaaag gtctcgagtg gtttccact atcgaaggtg acagcaacta catcgaatat    180
gcggatagcg tgaaaggccg ctttaccatc agccgcgata ttcgaaaaa caccctgtat    240 ctgcaaatga acagcctgcg tgcggaagat acggccgtgt attattgcgc gcgtgaacgt    300
acttactctt ctgctttcga ttactggggc caaggcaccc tggtgactgt tagctca      357

```
<210> SEQ ID NO 129
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129
```

| | | | | | | | | | | | | | | |
|---|---|---|---|---|---|---|---|---|---|---|---|---|---|---|
|Gln|Val|Gln|Leu|Leu|Glu|Ser|Gly|Gly|Gly|Leu|Val|Gln|Pro|Gly|
|1| | | |5| | | | |10| | | | |15|

| | | | | | | | | | | | | |
|---|---|---|---|---|---|---|---|---|---|---|---|---|
|Gly|Ser|Leu|Arg|Leu|Ser|Cys|Ala|Ala|Ser|Gly|Phe|Thr|
| | | |20| | | | |25| | | | |

| | | | | | | | | | | | | |
|---|---|---|---|---|---|---|---|---|---|---|---|---|
|Phe|Ser|Asp|Tyr|Ala|Met|Ser|Trp|Val|Arg|Gln|Ala|Pro|
|30| | | | |35| | | | |40| | |

Gly Lys Gly Leu Glu Trp Val Ser Thr Ile Glu Gly Asp Ser Asn Tyr
         45                  50                  55

Ile Glu Tyr Ala Asp Ser Val Lys Gly Arg Phe Thr Ile Ser Arg Asp
60                  65                  70                  75

Asn Ser Lys Asn Thr Leu Tyr Leu Gln Met Asn Ser Leu Arg Ala Glu
        80                  85                  90

Asp Thr Ala Val Tyr Tyr Cys Ala Arg Glu Arg Thr Tyr Ser Ser Ala
95                 100                 105                 110

Phe Asp Tyr Trp Gly Gln Gly Thr Leu Val Thr Val Ser Ser Ala Ser
            115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
        145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
210                 215                 220

Glu Pro Lys Ser Cys Asp Lys Thr His Thr Cys Pro Pro Cys Pro Ala
        225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
        305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr

```
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
                435                 440                 445
Lys
```

<210> SEQ ID NO 130
<211> LENGTH: 1347
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 130

```
caggtgcaat tgctggaaag cggcggtggc ctggtgcagc cgggtggcag cctgcgtctg      60
agctgcgcgg cgtccggatt caccttttct gactacgcta tgtcttgggt cgccaggcc     120
ccgggcaaag gtctcgagtg gtttccact atcgaaggtg acagcaacta catcgaatat     180
gcggatagcg tgaaaggccg ctttaccatc agccgcgata ttcgaaaaa caccctgtat     240
ctgcaaatga acagcctgcg tgcggaagat acggccgtgt attattgcgc gcgtgaacgt     300
acttactctt ctgctttcga ttactggggc caaggcaccc tggtgactgt tagctcagcc     360
tccaccaagg gtccatcggt cttccccctg caccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagagagt tgagcccaaa     660
tcttgtgaca aaactcacac atgcccaccg tgcccagcac ctgaactcct ggggggaccg     720
tcagtcttcc tcttccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccggg tggtcagcgt cctcaccgtc ctgcaccagg actggctgaa tggcaaggag     960
tacaagtgca aggtctccaa caaagccctc ccagccccca tcgagaaaac catctccaaa    1020
gccaaagggc agccccgaga accacaggtg tacaccctgc ccccatcccg ggaggagatg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaa                                        1347
```

<210> SEQ ID NO 131
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 131

Arg Ala Ser Gln Asp Ile Ser Ser Asp Leu Asn
1               5                   10

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Asp Ala Ser Asn Leu Gln Ser
1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

His Gln Trp Tyr Ser Thr Leu Tyr Thr
1               5

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ser Gln Asp Ile Ser Ser Asp
1               5

<210> SEQ ID NO 135
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asp Ala Ser
1

<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Trp Tyr Ser Thr Leu Tyr
1               5
```

<210> SEQ ID NO 137
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Asp
            20                  25                  30

Leu Asn Trp Tyr Gln Gln Lys Pro Gly Lys Ala Pro Lys Leu Leu Ile
        35                  40                  45

Tyr Asp Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Trp Tyr Ser Thr Leu Tyr
                85                  90                  95

Thr Phe Gly Gln Gly Thr Lys Val Glu Ile Lys
            100                 105

<210> SEQ ID NO 138
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138
gatatccaga tgacccagag cccgagcagc ctgagcgcca gcgtgggcga tcgcgtgacc      60
attacctgca gagccagcca ggacatttct tctgacctga actggtacca gcagaaaccg     120
ggcaaagcgc cgaaactatt aatctacgac gcttctaacc tgcaaagcgg cgtgccgagc     180
cgctttagcg gcagcggatc cggcaccgat ttcaccctga ccattagctc tctgcaaccg     240
gaagactttg cgacctatta ttgccatcag tggtactcta ctctgtacac ctttggccag     300
ggcacgaaag ttgaaattaa a                                               321

<210> SEQ ID NO 139
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Asp
            20                  25                  30

Leu Asn Trp Tyr Gln Gln Lys Pro Gly Lys Ala Pro Lys Leu Leu Ile
        35                  40                  45

Tyr Asp Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro

```
            65                  70                  75                  80
Glu Asp Phe Ala Thr Tyr Tyr Cys His Gln Trp Tyr Ser Thr Leu Tyr
                    85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 140
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140

```
gatatccaga tgacccagag cccgagcagc ctgagcgcca gcgtgggcga tcgcgtgacc    60
attacctgca gagccagcca ggacatttct tctgacctga actggtacca gcagaaaccg   120
ggcaaagcgc cgaaactatt aatctacgac gcttctaacc tgcaaagcgg cgtgccgagc   180
cgctttagcg gcagcggatc cggcaccgat ttcaccctga ccattagctc tctgcaaccg   240
gaagactttg cgacctatta ttgccatcag tggtactcta ctctgtacac ctttggccag   300
ggcacgaaag ttgaaattaa acgtacggtg gccgctccca gcgtgttcat cttccccccc   360
agcgacgagc agctgaagag cggcaccgcc agcgtggtgt gcctgctgaa caacttctac   420
ccccgggagg ccaaggtgca gtggaaggtg gacaacgccc tgcagagcgg caacagccag   480
gaaagcgtca ccgagcagga cagcaaggac tccacctaca gcctgagcag caccctgacc   540
ctgagcaagg ccgactacga aagcacaag gtgtacgcct gcgaggtgac ccaccagggc   600
ctgtccagcc ccgtgaccaa gagcttcaac cggggcgagt gt                      642
```

<210> SEQ ID NO 141
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

```
Ser Tyr Ala Ile Ser
1               5
```

<210> SEQ ID NO 142
<211> LENGTH: 17

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Tyr Ile Ser Pro Tyr Met Gly Glu Thr His Tyr Ala Gln Lys Phe Gln
1               5                   10                  15

Gly

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Glu Ser Tyr Glu Tyr Phe Asp Ile
1               5

<210> SEQ ID NO 144
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Gly Thr Phe Ser Ser Tyr
1               5

<210> SEQ ID NO 145
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ser Pro Tyr Met Gly Glu
1               5

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Glu Ser Tyr Glu Tyr Phe Asp Ile
1               5

<210> SEQ ID NO 147
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Tyr Ile Ser Pro Tyr Met Gly Glu Thr His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Tyr Glu Tyr Phe Asp Ile Trp Gly Gln Gly Thr Leu
            100                 105                 110

Val Thr Val Ser Ser
            115

<210> SEQ ID NO 148
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 148
caggtgcaat tggtgcagag cggtgccgaa gtgaaaaaac cgggcagcag cgtgaaagtt      60
agctgcaaag catccggagg gacgtttagc agctatgcga ttagctgggt gcgccaggcc     120
ccgggccagg gcctcgagtg gatgggctac atctctccgt acatgggcga aactcattac     180
gcccagaaat tcagggccgg ggtgaccatt accgccgatg aaagcaccag caccgcctat     240
atggaactga gcagcctgcg cagcgaagat acggccgtgt attattgcgc gcgtgaatct     300
tacgaatact cgacatctg gggccaaggc accctggtga ctgttagctc a                351

<210> SEQ ID NO 149
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Tyr Ile Ser Pro Tyr Met Gly Glu Thr His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Tyr Glu Tyr Phe Asp Ile Trp Gly Gln Gly Thr Leu
            100                 105                 110

Val Thr Val Ser Ser Ala Ser Thr Lys Gly Pro Ser Val Phe Pro Leu
    115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 150
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 150
caggtgcaat tggtgcagag cggtgccgaa gtgaaaaaac cgggcagcag cgtgaaagtt    60
agctgcaaag catccggagg gacgtttagc agctatgcga ttagctgggt gcgccaggcc   120

```
ccgggccagg gcctcgagtg gatgggctac atctctccgt acatgggcga aactcattac    180
gcccagaaat ttcagggccg ggtgaccatt accgccgatg aaagcaccag caccgcctat    240
atggaactga gcagcctgcg cagcgaagat acggccgtgt attattgcgc gcgtgaatct    300
tacgaatact tcgacatctg gggccaaggc accctggtga ctgttagctc agcctccacc    360
aagggtccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga gagttgagcc caaatcttgt    660
gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgggtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggagga tgaccaag    1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctcccctgt ctccgggtaa a                                            1341
```

<210> SEQ ID NO 151  
<211> LENGTH: 11  
<212> TYPE: PRT  
<213> ORGANISM: Artificial Sequence  
<220> FEATURE:  
<223> OTHER INFORMATION: Description of Artificial Sequence: Synthetic peptide

<400> SEQUENCE: 151

Arg Ala Ser Gln Ser Ile Ser Asn Asp Leu Ala  
1               5                   10

<210> SEQ ID NO 152  
<211> LENGTH: 7  
<212> TYPE: PRT  
<213> ORGANISM: Artificial Sequence  
<220> FEATURE:  
<223> OTHER INFORMATION: Description of Artificial Sequence: Synthetic peptide

<400> SEQUENCE: 152

Ala Thr Ser Ile Leu Gln Ser  
1               5

<210> SEQ ID NO 153  
<211> LENGTH: 9  
<212> TYPE: PRT  
<213> ORGANISM: Artificial Sequence  
<220> FEATURE:  
<223> OTHER INFORMATION: Description of Artificial Sequence: Synthetic peptide

```
<400> SEQUENCE: 153

Leu Gln Tyr Tyr Asp Tyr Ser Tyr Thr
1               5

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ser Gln Ser Ile Ser Asn Asp
1               5

<210> SEQ ID NO 155
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ala Thr Ser
1

<210> SEQ ID NO 156
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Tyr Tyr Asp Tyr Ser Tyr
1               5

<210> SEQ ID NO 157
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asp
                20                  25                  30

Leu Ala Trp Tyr Gln Gln Lys Pro Gly Lys Ala Pro Lys Leu Leu Ile
            35                  40                  45

Tyr Ala Thr Ser Ile Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Tyr Asp Tyr Ser Tyr
                85                  90                  95

Thr Phe Gly Gln Gly Thr Lys Val Glu Ile Lys
            100                 105
```

<210> SEQ ID NO 158
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 158

```
gatatccaga tgacccagag cccgagcagc ctgagcgcca gcgtgggcga tcgcgtgacc      60
attacctgca gagccagcca gtctatttct aacgacctgg cttggtacca gcagaaaccg     120
ggcaaagcgc cgaaactatt aatctacgct acttctatcc tgcaaagcgg cgtgccgagc     180
cgctttagcg gcagcggatc cggcaccgat ttcaccctga ccattagctc tctgcaaccg     240
gaagactttg cgacctatta ttgcctgcag tactacgact actcttacac ctttggccag     300
ggcacgaaag ttgaaattaa a                                               321
```

<210> SEQ ID NO 159
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asp
            20                  25                  30

Leu Ala Trp Tyr Gln Gln Lys Pro Gly Lys Ala Pro Lys Leu Leu Ile
        35                  40                  45

Tyr Ala Thr Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Tyr Asp Tyr Ser Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 160
<211> LENGTH: 642

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 160

```
gatatccaga tgacccagag cccgagcagc ctgagcgcca gcgtgggcga tcgcgtgacc      60
attacctgca gagccagcca gtctatttct aacgacctgg cttggtacca gcagaaaccg     120
ggcaaagcgc cgaaactatt aatctacgct acttctatcc tgcaaagcgg cgtgccgagc     180
cgctttagcg gcagcggatc cggcaccgat ttcaccctga ccattagctc tctgcaaccg     240
gaagactttg cgacctatta ttgcctgcag tactacgact actcttacac ctttggccag     300
ggcacgaaag ttgaaattaa acgtacggtg gccgctccca gcgtgttcat cttcccccccc     360
agcgacgagc agctgaagag cggcaccgcc agcgtggtgt gcctgctgaa caacttctac     420
ccccgggagg ccaaggtgca gtggaaggtg gacaacgccc tgcagagcgg caacagccag     480
gaaagcgtca ccgagcagga cagcaaggac tccacctaca gcctgagcag caccctgacc     540
ctgagcaagg ccgactacga gaagcacaag gtgtacgcct gcgaggtgac ccaccagggc     600
ctgtccagcc ccgtgaccaa gagcttcaac cggggcgagt gt                        642
```

<210> SEQ ID NO 161
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ser Tyr Asp Ile Ser
1               5

<210> SEQ ID NO 162
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Trp Ile Asn Pro Tyr Asn Gly Gly Thr Asn Tyr Ala Gln Lys Phe Gln
1               5                   10                  15

Gly

<210> SEQ ID NO 163
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Glu Gly Ser Gly Met Ile Val Tyr Pro Gly Trp Ser Tyr Ala Phe Asp
1               5                   10                  15

Tyr

<210> SEQ ID NO 164
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gly Tyr Thr Phe Thr Ser Tyr
1               5

<210> SEQ ID NO 165
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Asn Pro Tyr Asn Gly Gly
1               5

<210> SEQ ID NO 166
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Glu Gly Ser Gly Met Ile Val Tyr Pro Gly Trp Ser Tyr Ala Phe Asp
1               5                   10                  15

Tyr

<210> SEQ ID NO 167
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Ser Trp Val Arg Gln Ala Pro Gly Gln Gly Leu Glu Trp Met
            35                  40                  45

Gly Trp Ile Asn Pro Tyr Asn Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Glu Gly Ser Gly Met Ile Val Tyr Pro Gly Trp Ser Tyr Ala
                100                 105                 110

Phe Asp Tyr Trp Gly Gln Gly Thr Leu Val Thr Val Ser Ser
            115                 120                 125

<210> SEQ ID NO 168
<211> LENGTH: 378
```

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 168

```
caggtgcaat tggtgcagag cggtgcggaa gtgaaaaaac cgggtgccag cgtgaaagtt    60
agctgcaaag cgtccggata taccttcact tcttacgaca tctcttgggt gcgccaggcc   120
ccgggccagg gcctcgagtg gatgggctgg atcaacccgt acaacggcgg tacgaactac   180
gcgcagaaat tcagggccg ggtgaccatg acccgtgata ccagcattag caccgcgtat   240
atggaactga gccgtctgcg tagcgaagat acggccgtgt attattgcgc gcgtgaaggt   300
tctggtatga tcgtttaccc gggttggtct tacgctttcg attactgggg ccaaggcacc   360
ctggtgactg ttagctca                                                378
```

<210> SEQ ID NO 169
<211> LENGTH: 456
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 169

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Ser Trp Val Arg Gln Ala Pro Gly Gln Gly Leu Glu Trp Met
        35                  40                  45

Gly Trp Ile Asn Pro Tyr Asn Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Glu Gly Ser Gly Met Ile Val Tyr Pro Gly Trp Ser Tyr Ala
            100                 105                 110

Phe Asp Tyr Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
```

```
                245                 250                 255
Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 170
<211> LENGTH: 1368
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 170
caggtgcaat tggtgcagag cggtgcggaa gtgaaaaaac cgggtgccag cgtgaaagtt       60
agctgcaaag cgtccggata taccttcact tcttacgaca tctcttgggt gcgccaggcc      120
ccgggccagg gcctcgagtg gatgggctgg atcaacccgt acaacggcgg tacgaactac      180
gcgcagaaat tcagggccg gtgaccatg acccgtgata ccagcattag caccgcgtat      240
atggaactga ccgtctgcg tagcgaagat acgccgtgt attattgcgc gcgtgaaggt      300
tctggtatga tcgtttaccc gggttggtct tacgctttcg attactgggg ccaaggcacc      360
ctggtgactg ttagctcagc ctccaccaag ggtccatcgg tcttcccct ggcaccctcc      420 tccaagagca cctctggggg cacagcggcc ctgggctgcc tggtcaagga ctacttcccc      480
gaaccggtga cggtgtcgtg aactcaggc gccctgacca gcggcgtgca ccttcccg      540 gctgtcctac agtcctcagg actctactcc ctcagcagcg tggtgaccgt gccctccagc      600
agcttgggca cccagaccta catctgcaac gtgaatcaca agcccagcaa caccaaggtg      660
gacaagagag ttgagcccaa atcttgtgac aaaactcaca catgcccacc gtgcccagca      720
cctgaactcc tggggggacc gtcagtcttc ctcttcccc caaaacccaa ggacaccctc      780
atgatctccc ggaccctga ggtcacatgc gtggtggtgg acgtgagcca cgaagaccct      840
```

```
gaggtcaagt tcaactggta cgtggacggc gtggaggtgc ataatgccaa gacaaagccg      900
cgggaggagc agtacaacag cacgtaccgg gtggtcagcg tcctcaccgt cctgcaccag      960
gactggctga atggcaagga gtacaagtgc aaggtctcca acaaagccct cccagccccc     1020
atcgagaaaa ccatctccaa agccaaaggg cagccccgag aaccacaggt gtacaccctg     1080
cccccatccc gggaggagat gaccaagaac caggtcagcc tgacctgcct ggtcaaaggc     1140
ttctatccca gcgacatcgc cgtggagtgg gagagcaatg ggcagccgga gaacaactac     1200
aagaccacgc ctcccgtgct ggactccgac ggctccttct tcctctacag caagctcacc     1260
gtggacaaga gcaggtggca gcaggggaac gtcttctcat gctccgtgat gcatgaggct     1320
ctgcacaacc actacacgca gaagagcctc tccctgtctc cgggtaaa                  1368
```

<210> SEQ ID NO 171
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Arg Ala Ser Gln Asp Ile Ser Asn Asp Leu Gly
1               5                   10

<210> SEQ ID NO 172
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ala Ala Ser Ser Leu Gln Ser
1               5

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gln Gln His Tyr His Thr Pro Asn Thr
1               5

<210> SEQ ID NO 174
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ser Gln Asp Ile Ser Asn Asp
1               5

<210> SEQ ID NO 175
<211> LENGTH: 3
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 175

Ala Ala Ser
1

<210> SEQ ID NO 176
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

His Tyr His Thr Pro Asn
1               5

<210> SEQ ID NO 177
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Asp
                20                  25                  30

Leu Gly Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr His Thr Pro Asn
                85                  90                  95

Thr Phe Gly Gln Gly Thr Lys Val Glu Ile Lys
            100                 105

<210> SEQ ID NO 178
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178
gatatccaga tgacccagag cccgagcagc ctgagcgcca gcgtgggcga tcgcgtgacc      60
attacctgca gagccagcca ggacatttct aacgacctgg gttggtacca gcagaaaccg     120
ggcaaagcgc cgaaactatt aatctacgct gcttcttctc tgcaaagcgg cgtgccgagc     180
cgctttagcg gcagcggatc cggcaccgat ttcaccctga ccattagctc tctgcaaccg     240
gaagactttg cgacctatta ttgccagcag cattaccata ctccgaacac ctttggccag     300
ggcacgaaag ttgaaattaa a                                               321

<210> SEQ ID NO 179
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr His Thr Pro Asn
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 180
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 180
gatatccaga tgacccagag cccgagcagc ctgagcgcca gcgtgggcga tcgcgtgacc      60
attacctgca gagccagcca ggacatttct aacgacctgg gttggtacca gcagaaaccg     120
ggcaaagcgc cgaaactatt aatctacgct gcttcttctc tgcaaagcgg cgtgccgagc     180
cgctttagcg gcagcggatc cggcaccgat ttcaccctga ccattagctc tctgcaaccg     240
gaagactttg cgacctatta ttgccagcag cattaccata ctccgaacac ctttggccag     300
ggcacgaaag ttgaaattaa acgtacggtg gccgctccca gcgtgttcat cttccccccc     360
agcgacgagc agctgaagag cggcaccgcc agcgtggtgt gcctgctgaa caacttctac     420
ccccgggagg ccaaggtgca gtggaaggtg gacaacgccc tgcagagcgg caacagccag     480

```
gaaagcgtca ccgagcagga cagcaaggac tccacctaca gcctgagcag caccctgacc    540
ctgagcaagg ccgactacga aagcacaag gtgtacgcct gcgaggtgac ccaccagggc     600
ctgtccagcc ccgtgaccaa gagcttcaac cggggcgagt gt                       642
```

<210> SEQ ID NO 181
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

```
Ser Tyr Ala Ile Ser
1               5
```

<210> SEQ ID NO 182
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

```
Ser Ile Gln Pro Thr Ala Gly Pro Ala Arg Tyr Ala Gln Lys Phe Gln
1               5                   10                  15

Gly
```

<210> SEQ ID NO 183
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

```
Ala Ser Leu Tyr Ser Val Ala Thr Gly Ser Tyr Trp Lys Val Tyr His
1               5                   10                  15

Pro Phe Asp Ser
            20
```

<210> SEQ ID NO 184
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

```
Gly Gly Thr Phe Ser Ser Tyr
1               5
```

<210> SEQ ID NO 185
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gln Pro Thr Ala Gly Pro
1               5

<210> SEQ ID NO 186
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ala Ser Leu Tyr Ser Val Ala Thr Gly Ser Tyr Trp Lys Val Tyr His
1               5                   10                  15

Pro Phe Asp Ser
        20

<210> SEQ ID NO 187
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Ser Ile Gln Pro Thr Ala Gly Pro Ala Arg Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Leu Tyr Ser Val Ala Thr Gly Ser Tyr Trp Lys Val
            100                 105                 110

Tyr His Pro Phe Asp Ser Trp Gly Gln Gly Thr Leu Val Thr Val Ser
        115                 120                 125

Ser

<210> SEQ ID NO 188
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 188
caggtgcaat tggtgcagag cggtgccgaa gtgaaaaaac cgggcagcag cgtgaaagtt      60
agctgcaaag catccggagg gacgtttagc agctatgcga ttagctgggt gcgccaggcc     120
ccgggccagg gcctcgagtg gatgggctct atccagccga ctgctggccc ggctcgttac     180
gcccagaaat ttcagggccg ggtgaccatt accgccgatg aaagcaccag caccgcctat     240
atggaactga gcagcctgcg cagcgaagat acggccgtgt attattgcgc gcgtgcttct     300
ctgtactctg ttgctactgg ttcttactgg aaagtttacc atcctttcga ttcttgggc      360 caaggcaccc tggtgactgt tagctca              387

<210> SEQ ID NO 189
<211> LENGTH: 459
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Ser Ile Gln Pro Thr Ala Gly Pro Ala Arg Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Leu Tyr Ser Val Ala Thr Gly Ser Tyr Trp Lys Val
            100                 105                 110

Tyr His Pro Phe Asp Ser Trp Gly Gln Gly Thr Leu Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Arg Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350
```

```
Gly Gln Pro Arg Glu Pro Gln Val Tyr Thr Leu Pro Pro Ser Arg Glu
            355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys
    450                 455

<210> SEQ ID NO 190
<211> LENGTH: 1377
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 190
caggtgcaat tggtgcagag cggtgccgaa gtgaaaaaac cgggcagcag cgtgaaagtt      60
agctgcaaag catccggagg gacgtttagc agctatgcga ttagctgggt gcgccaggcc     120
ccgggccagg gcctcgagtg gatgggctct atccagccga ctgctggccc ggctcgttac     180
gcccagaaat tcagggccg gtgaccatt accgccgatg aaagcaccag caccgcctat      240
atggaactga gcagcctgcg cagcgaagat acggccgtgt attattgcgc gcgtgcttct     300
ctgtactctg ttgctactgg ttcttactgg aaagtttacc atcctttcga ttcttggggc     360
caaggcaccc tggtgactgt tagctcagcc tccaccaagg gtccatcggt cttccccctg     420
gcaccctcct ccaagagcac ctctgggggc acagcggccc tgggctgcct ggtcaaggac     480
tacttccccg aaccggtgac ggtgtcgtgg aactcaggcg ccctgaccag cggcgtgcac     540
accttcccgg ctgtcctaca gtcctcagga ctctactccc tcagcagcgt ggtgaccgtg     600
ccctccagca gcttgggcac ccagacctac atctgcaacg tgaatcacaa gcccagcaac     660
accaaggtgg acaagagagt tgagcccaaa tcttgtgaca aaactcacac atgcccaccg     720
tgcccagcac ctgaactcct ggggggaccg tcagtcttcc tcttcccccc aaaacccaag     780
gacaccctca tgatctcccg gacccctgag gtcacatgcg tggtggtgga cgtgagccac     840
gaagaccctg aggtcaagtt caactggtac gtggacggcg tggaggtgca taatgccaag     900
acaaagccgc gggaggagca gtacaacagc acgtaccggg tggtcagcgt cctcaccgtc     960
ctgcaccagg actggctgaa tggcaaggag tacaagtgca aggtctccaa caaagccctc    1020
ccagccccca tcgagaaaac catctccaaa gccaagggc agccccgaga accacaggtg    1080
tacaccctgc cccatcccg ggaggagatg accaagaacc aggtcagcct gacctgcctg    1140
gtcaaaggct tctatcccag cgacatcgcc gtggagtggg agagcaatgg gcagccggag    1200
aacaactaca agaccacgcc tcccgtgctg gactccgacg gctccttctt cctctacagc    1260
aagctcaccg tggacaagag caggtggcag caggggaacg tcttctcatg ctccgtgatg    1320
catgaggctc tgcacaacca ctacacgcag aagagcctct ccctgtctcc gggtaaa      1377
```

<210> SEQ ID NO 191
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Arg Ala Ser Gln Asp Ile Tyr Ser Tyr Leu Ala
1               5                   10

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Asp Ala Ser Ser Leu Gln Ser
1               5

<210> SEQ ID NO 193
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gln Gln Ala Asp Gln Tyr Pro Val Thr
1               5

<210> SEQ ID NO 194
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ser Gln Asp Ile Tyr Ser Tyr
1               5

<210> SEQ ID NO 195
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Asp Ala Ser
1

<210> SEQ ID NO 196
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Ala Asp Gln Tyr Pro Val
1               5

<210> SEQ ID NO 197
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Tyr Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asp Gln Tyr Pro Val
                85                  90                  95

Thr Phe Gly Gln Gly Thr Lys Val Glu Ile Lys
            100                 105

<210> SEQ ID NO 198
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 198
gatatccaga tgacccagag cccgagcagc ctgagcgcca gcgtgggcga tcgcgtgacc      60
attacctgca gagccagcca ggacatttac tcttacctgg cttggtacca gcagaaaccg     120
ggcaaagcgc cgaaactatt aatctacgac gcttcttctc tgcaaagcgg cgtgccgagc     180
cgctttagcg gcagcggatc cggcaccgat ttcaccctga ccattagctc tctgcaaccg     240
gaagactttg cgacctatta ttgccagcag gctgaccagt accccggttac ctttggccag     300 ggcacgaaag ttgaaattaa a                                                321

<210> SEQ ID NO 199
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Tyr Ser Tyr
            20                  25                  30

Leu Ala Trp Tyr Gln Gln Lys Pro Gly Lys Ala Pro Lys Leu Leu Ile
        35                  40                  45

```
Tyr Asp Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asp Gln Tyr Pro Val
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 200
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 200
gatatccaga tgacccagag cccgagcagc ctgagcgcca gcgtgggcga tcgcgtgacc      60
attacctgca gagccagcca ggacatttac tcttacctgg cttggtacca gcagaaaccg     120
ggcaaagcgc cgaaactatt aatctacgac gcttcttctc tgcaaagcgg cgtgccgagc     180
cgctttagcg gcagcggatc cggcaccgat ttcaccctga ccattagctc tctgcaaccg     240
gaagactttg cgacctatta ttgccagcag gctgaccagt acccggttac ctttggccag     300
ggcacgaaag ttgaaattaa acgtacggtg gccgctccca gcgtgttcat cttccccccc     360
agcgacgagc agctgaagag cggcaccgcc agcgtggtgt gcctgctgaa caacttctac     420
ccccgggagg ccaaggtgca gtggaaggtg gacaacgccc tgcagagcgg caacagccag     480
gaaagcgtca ccgagcagga cagcaaggac tccacctaca gcctgagcag cacccctgacc    540 ctgagcaagg ccgactacga gaagcacaag gtgtacgcct gcgaggtgac ccaccagggc    600
ctgtccagcc ccgtgaccaa gagcttcaac cggggcgagt gt                        642

<210> SEQ ID NO 201
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ser Tyr Ala Leu Ser
```

<210> SEQ ID NO 202
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Arg Ile Arg Ser Lys Ile Asp Gly Gly Thr Thr Asp Tyr Ala Ala Pro
1               5                   10                  15

Val Lys Gly

<210> SEQ ID NO 203
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Asp Arg Ser Pro Ser Asp Ser Ser Ala Phe Ala Ile
1               5                   10

<210> SEQ ID NO 204
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Gly Phe Thr Phe Ser Ser Tyr
1               5

<210> SEQ ID NO 205
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Arg Ser Lys Ile Asp Gly Gly Thr
1               5

<210> SEQ ID NO 206
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Asp Arg Ser Pro Ser Asp Ser Ser Ala Phe Ala Ile
1               5                   10

<210> SEQ ID NO 207
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Leu Ser Trp Val Arg Gln Ala Pro Gly Lys Gly Leu Glu Trp Val
        35                  40                  45

Gly Arg Ile Arg Ser Lys Ile Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Arg Ser Pro Ser Asp Ser Ser Ala Phe Ala Ile
            100                 105                 110

Trp Gly Gln Gly Thr Leu Val Thr Val Ser Ser
        115                 120
```

<210> SEQ ID NO 208
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 208

```
caggtgcaat tggtggaaag cggcggtggc ctggtgaaac aggcggcag cctgcgcctg      60
agctgcgccg cctccggatt cacctttct tcttacgctc tgtcttgggt gcgccaggcc     120
ccgggcaaag gtctcgagtg ggtgggccgt atccgttcta aaatcgacgg tggtactact     180
gactatgccg ccccagtgaa aggccgcttt accattagcc gcgatgattc gaaaaacacc     240
ctgtatctgc aaatgaacag cctgaaaacc gaagatacgg ccgtgtatta ttgcgcgcgt     300
gaccgttctc cgtctgactc ttctgctttc gctatctggg gccaaggcac cctggtgact     360
gttagctca                                                             369
```

<210> SEQ ID NO 209
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Leu Ser Trp Val Arg Gln Ala Pro Gly Lys Gly Leu Glu Trp Val
        35                  40                  45

Gly Arg Ile Arg Ser Lys Ile Asp Gly Gly Thr Thr Asp Tyr Ala Ala
    50                  55                  60

Pro Val Lys Gly Arg Phe Thr Ile Ser Arg Asp Asp Ser Lys Asn Thr
```

65                  70                  75                  80
Leu Tyr Leu Gln Met Asn Ser Leu Lys Thr Glu Asp Thr Ala Val Tyr
                    85                  90                  95

Tyr Cys Ala Arg Asp Arg Ser Pro Asp Ser Ser Ala Phe Ala Ile
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 210
<211> LENGTH: 1359
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 210

```
caggtgcaat tggtggaaag cggcggtggc ctggtgaaac caggcggcag cctgcgcctg      60
agctgcgccg cctccggatt caccttttct tcttacgctc tgtcttgggt gcgccaggcc     120
ccgggcaaag gtctcgagtg gtgggccgt atccgttcta aaatcgacgg tggtactact      180
gactatgccg ccccagtgaa aggccgcttt accattagcc gcgatgattc gaaaaacacc     240
ctgtatctgc aaatgaacag cctgaaaacc gaagatacgg ccgtgtatta ttgcgcgcgt     300
gaccgttctc cgtctgactc ttctgctttc gctatctggg gccaaggcac cctggtgact     360
gttagctcag cctccaccaa gggtccatcg gtcttccccc tggcaccctc ctccaagagc     420
acctctgggg gcacagcggc cctgggctgc ctggtcaagg actacttccc cgaaccggtg     480
acggtgtcgt ggaactcagg cgccctgacc agcggcgtgc acaccttccc ggctgtccta     540
cagtcctcag gactctactc cctcagcagc gtggtgaccg tgccctccag cagcttgggc     600
acccagacct acatctgcaa cgtgaatcac aagcccagca acaccaaggt ggacaagaga     660
gttgagccca aatcttgtga caaaactcac acatgcccac cgtgcccagc acctgaactc     720
ctggggggac cgtcagtctt cctcttcccc ccaaaaccca aggacaccct catgatctcc     780
cggacccctg aggtcacatg cgtggtggtg gacgtgagcc acgaagaccc tgaggtcaag     840
ttcaactggt acgtggacgg cgtggaggtg cataatgcca agacaaagcc gcgggaggag     900
cagtacaaca gcacgtaccg ggtggtcagc gtcctcaccg tcctgcacca ggactggctg     960
aatggcaagg agtacaagtg caaggtctcc aacaaagccc tcccagcccc catcgagaaa    1020
accatctcca aagccaaagg gcagccccga gaaccacagg tgtacaccct gcccccatcc    1080
cgggaggaga tgaccaagaa ccaggtcagc ctgacctgcc tggtcaaagg cttctatccc    1140
agcgacatcg ccgtggagtg ggagagcaat gggcagccgg agaacaacta caagaccacg    1200
cctcccgtgc tggactccga cggctccttc ttcctctaca gcaagctcac cgtggacaag    1260
agcaggtggc agcaggggaa cgtcttctca tgctccgtga tgcatgaggc tctgcacaac    1320
cactacacgc agaagagcct ctccctgtct ccgggtaaa                           1359
```

<210> SEQ ID NO 211
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Ser Gly Asp Asn Leu Gly Ser Gln Tyr Val Asp
1               5                   10

<210> SEQ ID NO 212
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Asp Asp Asn Asp Arg Pro Ser
1               5

<210> SEQ ID NO 213
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ala Val Thr Ala Phe His Ser Met Thr Asp Val
1               5                   10

<210> SEQ ID NO 214
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Asp Asn Leu Gly Ser Gln Tyr
1               5

<210> SEQ ID NO 215
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Asp Asp Asn
1

<210> SEQ ID NO 216
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Thr Ala Phe His Ser Met Thr Asp
1               5

<210> SEQ ID NO 217
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Asp Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Ser Gln Tyr Val
            20                  25                  30

Asp Trp Tyr Gln Gln Lys Pro Gly Gln Ala Pro Val Leu Val Ile Tyr
        35                  40                  45

Asp Asp Asn Asp Arg Pro Ser Gly Ile Pro Glu Arg Phe Ser Gly Ser
    50                  55                  60

```
Asn Ser Gly Asn Thr Ala Thr Leu Thr Ile Ser Gly Thr Gln Ala Glu
 65                  70                  75                  80

Asp Glu Ala Asp Tyr Tyr Cys Ala Val Thr Ala Phe His Ser Met Thr
                 85                  90                  95

Asp Val Phe Gly Gly Gly Thr Lys Leu Thr Val Leu
            100                 105
```

<210> SEQ ID NO 218
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 218

```
gatatcgaac tgacccagcc gccgagcgtg agcgtgagcc cgggccagac cgcgagcatt      60
acctgtagcg gcgataacct gggttctcag tacgttgact ggtaccagca gaaaccgggc     120
caggcgccgg tgctggtgat ctacgacgac aacgaccgtc cgagcggcat cccggaacgt     180
tttagcggat ccaacagcgg caacaccgcg accctgacca ttagcggcac ccaggcggaa     240
gacgaagcgg attattactg cgctgttact gctttccatt ctatgactga cgtgtttggc     300
ggcggcacga agttaaccgt ccta                                             324
```

<210> SEQ ID NO 219
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

```
Asp Ile Glu Leu Thr Gln Pro Pro Ser Val Ser Val Ser Pro Gly Gln
 1               5                  10                  15

Thr Ala Ser Ile Thr Cys Ser Gly Asp Asn Leu Gly Ser Gln Tyr Val
             20                  25                  30

Asp Trp Tyr Gln Gln Lys Pro Gly Gln Ala Pro Val Leu Val Ile Tyr
         35                  40                  45

Asp Asp Asn Asp Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Ala Val Thr Ala Phe His Ser Met Thr
                 85                  90                  95

Asp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190
```

Tyr Ser Cys Gln Val Thr His Glu Gly Ser Thr Val Glu Lys Thr Val
        195                 200                 205

Ala Pro Thr Glu Cys Ser
    210

<210> SEQ ID NO 220
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 220
gatatcgaac tgacccagcc gccgagcgtg agcgtgagcc cgggccagac cgcgagcatt      60
acctgtagcg gcgataacct gggttctcag tacgttgact ggtaccagca gaaaccgggc     120
caggcgccgg tgctggtgat ctacgacgac aacgaccgtc gagcggcat cccggaacgt     180 tttagcggat ccaacagcgg caacaccgcg accctgacca ttagcggcac ccaggcggaa     240
gacgaagcgg attattactg cgctgttact gctttccatt ctatgactga cgtgtttggc     300
ggcggcacga agttaaccgt cctaggtcag cccaaggctg cccctcggt cactctgttc     360 ccgccctcct ctgaggagct tcaagccaac aaggccacac tggtgtgtct cataagtgac     420
ttctacccgg agccgtgac agtggcctgg aaggcagata gcagcccgt caaggcggga     480 gtggagacca ccacaccctc caaacaaagc aacaacaagt acgcggccag cagctatctg     540
agcctgacgc ctgagcagtg gaagtcccac agaagctaca gctgccaggt cacgcatgaa     600
gggagcaccg tggagaagac agtggcccct acagaatgtt ca                        642

<210> SEQ ID NO 221
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Thr Tyr Trp Leu His
1               5

<210> SEQ ID NO 222
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Val Ile Ser Ser Asp Ser Ser Ser Thr Tyr Tyr Ala Asp Ser Val Lys
1               5                   10                  15

Gly

<210> SEQ ID NO 223
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 223

Asp Ser Arg Leu Asp Tyr
1               5

<210> SEQ ID NO 224
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Gly Phe Thr Phe Asn Thr Tyr
1               5

<210> SEQ ID NO 225
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Ser Ser Asp Ser Ser Ser
1               5

<210> SEQ ID NO 226
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Asp Ser Arg Leu Asp Tyr
1               5

<210> SEQ ID NO 227
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Trp Leu His Trp Val Arg Gln Ala Pro Gly Lys Gly Leu Glu Trp Val
        35                  40                  45

Ser Val Ile Ser Ser Asp Ser Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Arg Leu Asp Tyr Trp Gly Gln Gly Thr Leu Val Thr
            100                 105                 110
```

Val Ser Ser
    115

<210> SEQ ID NO 228
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 228
caggtgcaat tgctggaaag cggcggtggc ctggtgcagc cgggtggcag cctgcgtctg      60
agctgcgcgg cgtccggatt caccttaac acttactggc tgcattgggt gcgccaggcc     120
ccgggcaaag gtctcgagtg gtttccgtt atctcttctg actcttcttc tacctactat     180
gcggatagcg tgaaaggccg ctttaccatc agccgcgata ttcgaaaaa caccctgtat     240 ctgcaaatga acagcctgcg tgcggaagat acggccgtgt attattgcgc gcgtgactct     300
cgtctggact actggggcca aggcaccctg gtgactgtta gctca                    345

<210> SEQ ID NO 229
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Trp Leu His Trp Val Arg Gln Ala Pro Gly Lys Gly Leu Glu Trp Val
        35                  40                  45

Ser Val Ile Ser Ser Asp Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Arg Leu Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 230
<211> LENGTH: 1335
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 230
caggtgcaat tgctggaaag cggcggtggc ctggtgcagc cgggtggcag cctgcgtctg      60
agctgcgcgg cgtccggatt caccttttaac acttactggc tgcattgggt gcgccaggcc    120
ccgggcaaag gtctcgagtg ggtttccgtt atctcttctg actcttcttc tacctactat    180
gcggatagcg tgaaaggccg cttttaccatc agccgcgata ttcgaaaaaa caccctgtat    240
ctgcaaatga acagcctgcg tgcggaagat acggccgtgt attattgcgc gcgtgactct    300
cgtctggact actggggcca aggcaccctg gtgactgtta gctcagcctc caccaagggt    360
ccatcggtct tccccctggc accctcctcc aagagcacct ctgggggcac agcggccctg    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcaccc agacctacat ctgcaacgtg    600
aatcacaagc ccagcaacac caaggtggac aagagagttg agcccaaatc ttgtgacaaa    660
actcacacat gcccaccgtg cccagcacct gaactcctgg ggggaccgtc agtcttcctc    720
ttccccccaa aacccaagga caccctcatg atctcccgga cccctgaggt cacatgcgtg    780

```
gtggtggacg tgagccacga agaccctgag gtcaagttca actggtacgt ggacggcgtg      840
gaggtgcata atgccaagac aaagccgcgg gaggagcagt acaacagcac gtaccgggtg      900
gtcagcgtcc tcaccgtcct gcaccaggac tggctgaatg gcaaggagta caagtgcaag      960
gtctccaaca aagccctccc agccccatc gagaaaacca tctccaaagc caaagggcag      1020
ccccgagaac cacaggtgta caccctgccc ccatcccggg aggagatgac caagaaccag      1080
gtcagcctga cctgcctggt caaaggcttc tatcccagcg acatcgccgt ggagtgggag      1140
agcaatgggc agccggagaa caactacaag accacgcctc ccgtgctgga ctccgacggc      1200
tccttcttcc tctacagcaa gctcaccgtg gacaagagca ggtggcagca ggggaacgtc      1260
ttctcatgct ccgtgatgca tgaggctctg cacaaccact acacgcagaa gagcctctcc      1320
ctgtctccgg gtaaa                                                      1335
```

<210> SEQ ID NO 231
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Ser Gly Asp Ser Ile Gly Asp Thr Tyr Val Asp
1               5                   10

<210> SEQ ID NO 232
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Asp Asp Ile Asp Arg Pro Ser
1               5

<210> SEQ ID NO 233
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Tyr Val Tyr Ala Trp Thr Gly Thr Ser Asn Val
1               5                   10

<210> SEQ ID NO 234
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Asp Ser Ile Gly Asp Thr Tyr
1               5

<210> SEQ ID NO 235
<211> LENGTH: 3

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Asp Asp Ile
1

<210> SEQ ID NO 236
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Tyr Ala Trp Thr Gly Thr Ser Asn
1               5

<210> SEQ ID NO 237
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Asp Ile Glu Leu Thr Gln Pro Pro Ser Val Ser Val Ser Pro Gly Gln
1               5                   10                  15

Thr Ala Ser Ile Thr Cys Ser Gly Asp Ser Ile Gly Asp Thr Tyr Val
            20                  25                  30

Asp Trp Tyr Gln Gln Lys Pro Gly Gln Ala Pro Val Leu Val Ile Tyr
        35                  40                  45

Asp Asp Ile Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Tyr Val Tyr Ala Trp Thr Gly Thr Ser
                85                  90                  95

Asn Val Phe Gly Gly Gly Thr Lys Leu Thr Val Leu
            100                 105

<210> SEQ ID NO 238
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 238
gatatcgaac tgacccagcc gccgagcgtg agcgtgagcc cgggccagac cgcgagcatt      60
acctgtagcg gcgattctat cggtgacact tacgttgact ggtaccagca gaaaccgggc     120
caggcgccgg tgctggtgat ctacgacgac atcgaccgtc cgagcggcat cccggaacgt     180
tttagcggat ccaacagcgg caacaccgcg accctgacca ttagcggcac ccaggcggaa     240
gacgaagcgg attattactg ctacgtttac gcttggactg gtacttctaa cgtgtttggc     300
ggcggcacga agttaaccgt ccta                                            324
```

<210> SEQ ID NO 239
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 239

```
Asp Ile Glu Leu Thr Gln Pro Pro Ser Val Ser Val Ser Pro Gly Gln
1               5                   10                  15

Thr Ala Ser Ile Thr Cys Ser Gly Asp Ser Ile Gly Asp Thr Tyr Val
            20                  25                  30

Asp Trp Tyr Gln Gln Lys Pro Gly Gln Ala Pro Val Leu Val Ile Tyr
        35                  40                  45

Asp Asp Ile Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Tyr Val Tyr Ala Trp Thr Gly Thr Ser
                85                  90                  95

Asn Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 240
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 240

```
gatatcgaac tgacccagcc gccgagcgtg agcgtgagcc cgggccagac cgcgagcatt      60
acctgtagcg gcgattctat cggtgacact tacgttgact ggtaccagca gaaaccgggc     120
caggcgccgg tgctggtgat ctacgacgac atcgaccgtc gagcggcat cccggaacgt      180 tttagcggat ccaacagcgg caacaccgcg accctgacca ttagcggcac ccaggcggaa     240
gacgaagcgg attattactg ctacgtttac gcttggactg gtacttctaa cgtgtttggc     300
ggcggcacga agttaaccgt cctaggtcag cccaaggctg ccccctcggt cactctgttc     360 ccgcccctcct ctgaggagct tcaagccaac aaggccacac tggtgtgtct cataagtgac     420
```

```
ttctacccgg gagccgtgac agtggcctgg aaggcagata gcagccccgt caaggcggga    480
gtggagacca ccacaccctc caaacaaagc aacaacaagt acgcggccag cagctatctg    540
agcctgacgc ctgagcagtg gaagtcccac agaagctaca gctgccaggt cacgcatgaa    600
gggagcaccg tggagaagac agtggcccct acagaatgtt ca                       642

<210> SEQ ID NO 241
<211> LENGTH: 16
<212> TYPE: PRT
<213> ORGANISM: Homo sapiens

<400> SEQUENCE: 241

Val Lys Phe Arg Cys Pro Ala Gly Gly Asn Pro Met Pro Thr Met Arg
1               5                   10                  15

<210> SEQ ID NO 242
<211> LENGTH: 19
<212> TYPE: PRT
<213> ORGANISM: Homo sapiens

<400> SEQUENCE: 242

Lys Met Glu Lys Arg Leu His Ala Val Pro Ala Ala Asn Thr Val Lys
1               5                   10                  15

Phe Arg Cys

<210> SEQ ID NO 243
<211> LENGTH: 5911
<212> TYPE: DNA
<213> ORGANISM: Homo sapiens

<400> SEQUENCE: 243
agatgcaggg gcgcaaacgc caaaggagac caggctgtag gaagagaagg gcagagcgcc     60
ggacagctcg gcccgctccc cgtcctttgg ggccgcggct ggggaactac aaggcccagc    120
aggcagctgc aggggcgga ggcggaggag ggaccagcgc gggtgggagt gagagagcga    180
gccctcgcgc cccgccggcg catagcgctc ggagcgctct tgcgccaca ggcgcggcgt     240 cctcggcggc gggcggcagc tagcgggagc cgggacgccg gtgcagccgc agcgcgcgga    300
ggaacccggg tgtgccggga gctgggcggc cacgtccgga cgggaccgag accccctcgta    360 gcgcattgcg cgacctcgc cttccccggc cgcgagcgcg ccgctgcttg aaaagccgcg    420
gaacccaagg acttttctcc ggtccgagct cggggcgccc cgcagggcgc acggtacccg    480
tgctgcagtc gggcacgccg cggcgccggg gcctccgcag ggcgatggag cccggtctgc    540
aaggaaagtg aggcgccgcc gctgcgttct ggaggagggg ggcacaaggt ctggagaccc    600
cgggtggcgg acgggagccc tcccccgcc ccgcctccgg ggaccagct ccggctccat    660 tgttcccgcc cgggctggag gcgccgagca ccgagcgccg ccgggagtcg agcgccggcc    720
gcggagctct tgcgaccccg ccaggacccg aacagagccc ggggggcggcg ggccggagcc    780 ggggacgcgc gcacacgccc gctcgcacaa gccacggcgg actctcccga ggcggaacct    840
ccacgccgag cgagggtcag tttgaaaagg aggatcgagc tcactgtgga gtatccatgg    900
agatgtggag ccttgtcacc aacctctaac tgcagaactg gatgtggag ctggaagtgc    960 ctcctcttct gggctgtgct ggtcacagcc acactctgca ccgctaggcc gtccccgacc    1020
ttgcctgaac aagcccagcc ctggggagcc cctgtggaag tggagtcctt cctggtccac    1080
cccggtgacc tgctgcagct tcgctgtcgg ctgcgggacg atgtgcagag catcaactgg    1140
ctgcgggacg gggtgcagct ggcggaaagc aaccgcaccc gcatcacagg ggaggaggtg    1200
```

```
gaggtgcagg actccgtgcc cgcagactcc ggcctctatg cttgcgtaac cagcagcccc    1260
tcgggcagtg acaccaccta cttctccgtc aatgtttcag atgctctccc ctcctcggag    1320
gatgatgatg atgatgatga ctcctcttca gaggagaaag aaacagataa caccaaacca    1380
aaccccgtag ctccatattg gacatcccca gaaaagatgg aaaagaaatt gcatgcagtg    1440
ccggctgcca agacagtgaa gttcaaatgc ccttccagtg gaccccaaa ccccacactg     1500 cgctggttga aaaatggcaa agaattcaaa cctgaccaca gaattggagg ctacaaggtc    1560
cgttatgcca cctggagcat cataatggac tctgtggtgc cctctgacaa gggcaactac    1620
acctgcattg tggagaatga gtacggcagc atcaaccaca cataccagct ggatgtcgtg    1680
gagcggtccc ctcaccggcc catcctgcaa gcagggttgc ccgccaacaa aacagtggcc    1740
ctgggtagca acgtggagtt catgtgtaag gtgtacagtg acccgcagcc gcacatccag    1800
tggctaaagc acatcgaggt gaatgggagc aagattggcc cagacaacct gccttatgtc    1860
cagatcttga agactgctgg agttaatacc accgacaaag atgggaggt gcttcactta    1920 agaaatgtct cctttgagga cgcaggggag tatacgtgct tggcgggtaa ctctatcgga    1980
ctctcccatc actctgcatg gttgaccgtt ctggaagccc tggaagagag gccggcagtg    2040
atgacctcgc ccctgtacct ggagatcatc atctattgca caggggcctt cctcatctcc    2100
tgcatggtgg ggtcggtcat cgtctacaag atgaagagtg gtaccaagaa gagtgacttc    2160
cacagccaga tggctgtgca aagctggcc aagagcatcc ctctgcgcag acaggtaaca     2220
gtgtctgctg actccagtgc atccatgaac tctgggttc ttctggttcg gccatcacgg     2280
ctctcctcca gtgggactcc catgctagca ggggtctctg agtatgagct tcccgaagac    2340
cctcgctggg agctgcctcg ggacagactg gtcttaggca aacccctggg agagggctgc    2400
tttgggcagg tggtgttggc agaggctatc gggctggaca aggacaaacc caaccgtgtg    2460
accaaagtgg ctgtgaagat gttgaagtcg gacgcaacag agaaagactt gtcagacctg    2520
atctcagaaa tggagatgat gaagatgatc gggaagcata gaatatcat caacctgctg    2580 ggggcctgca gcaggatgg tcccttgtat gtcatcgtgg agtatgcctc caagggcaac    2640
ctgcgggagt acctgcaggc ccggaggccc ccagggctgg aatactgcta caaccccagc    2700
cacaacccag aggagcagct ctcctccaag gacctggtgt cctgcgccta ccaggtggcc    2760
cgaggcatgg agtatctggc ctccaagaag tgcatacacc gagacctggc agccaggaat    2820
gtcctggtga cagaggacaa tgtgatgaag atagcagact ttggcctcgc acgggacatt    2880
caccacatcg actactataa aaagacaacc aacggccgac tgcctgtgaa gtggatggca    2940
cccgaggcat tatttgaccg gatctacacc caccagagtg atgtgtggtc tttcggggtg    3000
ctcctgtggg agatcttcac tctgggcggc tccccatacc ccgtgtgcc tgtggaggaa    3060 cttttcaagc tgctgaagga gggtcaccgc atggacaagc ccagtaactg caccaacgag    3120
ctgtacatga tgatgcggga ctgctggcat gcagtgccct cacagagacc caccttcaag    3180
cagctggtgg aagacctgga ccgcatcgtg gccttgacct ccaaccagga gtacctggac    3240
ctgtccatgc ccctggacca gtactccccc agctttcccg acaccgggag ctctacgtgc    3300
tcctcagggg aggattccgt cttctctcat gagccgctgc ccgaggagcc ctgcctgccc    3360
cgacacccag cccagcttgc caatggcgga ctcaaacgcc gctgactgcc acccacacgc    3420
cctccccaga ctccaccgtc agctgtaacc ctcacccaca gccctgctg ggcccaccac     3480 ctgtccgtcc ctgtccccttt cctgctggc aggagccggc tgcctaccag gggccttcct    3540
```

```
gtgtggcctg ccttcacccc actcagctca cctctccctc cacctcctct ccacctgctg    3600
gtgagaggtg caaagaggca gatctttgct gccagccact tcatcccctc ccagatgttg    3660
gaccaacacc cctccctgcc accaggcact gcctggaggg cagggagtgg gagccaatga    3720
acaggcatgc aagtgagagc ttcctgagct ttctcctgtc ggtttggtct gttttgcctt    3780
cacccataag cccctcgcac tctggtggca ggtgccttgt cctcagggct acagcagtag    3840
ggaggtcagt gcttcgtgcc tcgattgaag gtgacctctg ccccagatag gtggtgccag    3900
tggcttatta attccgatac tagtttgctt tgctgaccaa atgcctggta ccagaggatg    3960
gtgaggcgaa ggccaggttg ggggcagtgt tgtggccctg gggcccagcc ccaaactggg    4020
ggctctgtat atagctatga agaaaacaca aagtgtataa atctgagtat atatttacat    4080
gtcttttaa aagggtcgtt accagagatt tacccatcgg gtaagatgct cctggtggct    4140
gggaggcatc agttgctata tattaaaaac aaaaaagaaa aaaaggaaa atgttttaa    4200
aaaggtcata tatttttgc tacttttgct gttttatttt tttaaattat gttctaaacc    4260
tattttcagt ttaggtccct caataaaaat tgctgctgct tcatttatct atgggctgta    4320
tgaaagggt gggaatgtcc actgaaaga agggacaccc acgggccctg ggctaggtc    4380
tgtcccgagg gcaccgcatg ctcccggcgc aggttccttg taacctcttc ttcctaggtc    4440
ctgcacccag acctcacgac gcacctcctg cctctccgct gcttttggaa agtcagaaaa    4500
agaagatgtc tgcttcgagg gcaggaaccc catccatgca gtagaggcgc tgggcagaga    4560
gtcaaggccc agcagccatc gaccatggat ggtttcctcc aaggaaaccg gtggggttgg    4620
gctggggagg gggcacctac ctaggaatag ccacggggta gagctacagt gattaagagg    4680
aaagcaaggg cgcggttgct cacgcctgta atcccagcac tttgggacac cgaggtgggc    4740
agatcacttc aggtcaggag tttgagacca gcctggccaa cttagtgaaa ccccatctct    4800
actaaaaatg caaaaattat ccaggcatgg tggcacacgc ctgtaatccc agctccacag    4860
gaggctgagg cagaatccct tgaagctggg aggcggaggt tgcagtgagc cgagattgcg    4920
ccattgcact ccagcctggg caacagagaa acaaaaagg aaaacaaatg atgaaggtct    4980
gcagaaactg aaacccagac atgtgtctgc cccctctatg tgggcatggt tttgccagtg    5040
cttctaagtg caggagaaca tgtcacctga ggctagtttt gcattcaggt ccctggcttc    5100
gtttcttgtt ggtatgcctc cccagatcgt ccttcctgta tccatgtgac cagactgtat    5160
ttgttgggac tgtcgcagat cttggcttct tacagttctt cctgtccaaa ctccatcctg    5220
tccctcagga acgggggaa aattctccga atgttttgg ttttttggct gcttggaatt    5280
tacttctgcc acctgctggt catcactgtc ctcactaagt ggattctggc tccccgtac    5340
ctcatggctc aaactaccac tcctcagtcg ctatattaaa gcttatattt tgctggatta    5400
ctgctaaata caaagaaag ttcaatatgt tttcatttct gtagggaaaa tgggattgct    5460
gctttaaatt tctgagctag ggatttttg gcagctgcag tgttggcgac tattgtaaaa    5520
ttctctttgt ttctctctgt aaatagcacc tgctaacatt acaatttgta tttatgttta    5580
aagaaggcat catttggtga acagaactag gaaatgaatt tttagctctt aaaagcattt    5640
gctttgagac cgcacaggag tgtctttcct tgtaaaacag tgatgataat ttctgccttg    5700
gccctacctt gaagcaatgt tgtgtgaagg gatgaagaat ctaaagtct tcataagtcc    5760
ttgggagagg tgctagaaaa atataaggca ctatcataat tacagtgatg tccttgctgt    5820
tactactcaa atcaccccaca aatttcccca aagactgcgc tagctgtcaa ataaaagaca    5880
gtgaaattga cctgaaaaaa aaaaaaaaaa a                                   5911
```

<210> SEQ ID NO 244
<211> LENGTH: 4657
<212> TYPE: DNA
<213> ORGANISM: Homo sapiens

<400> SEQUENCE: 244

| | | | | | | |
|---|---|---|---|---|---|---|
| ggcggcggct | ggaggagagc | gcggtggaga | gccgagcggg | cgggcggcgg | gtgcggagcg | 60 |
| ggcgagggag | cgcgcgcggc | cgccacaaag | ctcgggcgcc | gcggggctgc | atgcggcgta | 120 |
| cctggcccgg | cgcggcgact | gctctccggg | ctggcggggg | ccggccgcga | gccccggggg | 180 |
| ccccgaggcc | gcagcttgcc | tgcgcgctct | gagccttcgc | aactcgcgag | caaagtttgg | 240 |
| tggaggcaac | gccaagcctg | agtcctttct | tcctctcgtt | ccccaaatcc | gagggcagcc | 300 |
| cgcgggcgtc | atgcccgcgc | tcctccgcag | cctggggtac | gcgtgaagcc | cgggaggctt | 360 |
| ggcgccggcg | aagacccaag | gaccactctt | ctgcgtttgg | agttgctccc | cgcaaccccg | 420 |
| ggctcgtcgc | tttctccatc | ccgacccacg | cggggcgcgg | ggacaacaca | ggtcgcggag | 480 |
| gagcgttgcc | attcaagtga | ctgcagcagc | agcggcagcg | cctcggttcc | tgagcccacc | 540 |
| gcaggctgaa | ggcattgcgc | gtagtccatg | cccgtagagg | aagtgtgcag | atgggattaa | 600 |
| cgtccacatg | gagatatgga | agaggaccgg | ggattggtac | cgtaaccatg | gtcagctggg | 660 |
| gtcgtttcat | ctgcctggtc | gtggtcacca | tggcaacctt | gtccctggcc | cggccctcct | 720 |
| tcagtttagt | tgaggatacc | acattagagc | cagaagagcc | accaaccaaa | taccaaatct | 780 |
| ctcaaccaga | agtgtacgtg | gctgcgccag | gggagtcgct | agaggtgcgc | tgcctgttga | 840 |
| aagatgccgc | cgtgatcagt | tggactaagg | atggggtgca | cttggggccc | aacaatagga | 900 |
| cagtgcttat | tggggagtac | ttgcagataa | agggcgccac | gcctagagac | tccggcctct | 960 |
| atgcttgtac | tgccagtagg | actgtagaca | gtgaaacttg | gtacttcatg | gtgaatgtca | 1020 |
| cagatgccat | ctcatccgga | gatgatgagg | atgacaccga | tggtgcggaa | gattttgtca | 1080 |
| gtgagaacag | taacaacaag | agagcaccat | actggaccaa | cacagaaaag | atggaaaagc | 1140 |
| ggctccatgc | tgtgcctgcg | gccaacactg | tcaagtttcg | ctgcccagcc | gggggggaacc | 1200 |
| caatgccaac | catgcggtgg | ctgaaaaacg | ggaaggagtt | taagcaggag | catcgcattg | 1260 |
| gaggctacaa | ggtacgaaac | cagcactgga | gcctcattat | ggaaagtgtg | gtcccatctg | 1320 |
| acaagggaaa | ttatacctgt | gtagtggaga | tgaatacgg | gtccatcaat | cacacgtacc | 1380 |
| acctggatgt | tgtggagcga | tcgcctcacc | ggcccatcct | ccaagccgga | ctgccggcaa | 1440 |
| atgcctccac | agtggtcgga | ggagacgtag | agtttgtctg | caaggtttac | agtgatgccc | 1500 |
| agccccacat | ccagtggatc | aagcacgtgg | aaaagaacgg | cagtaaatac | gggcccgacg | 1560 |
| ggctgcccta | cctcaaggtt | ctcaagcact | cggggataaa | tagttccaat | gcagaagtgc | 1620 |
| tggctctgtt | caatgtgacc | gaggcggatg | ctggggaata | tatatgtaag | gtctccaatt | 1680 |
| atatagggca | ggccaaccag | tctgcctggc | tcactgtcct | gccaaaacag | caagcgcctg | 1740 |
| gaagagaaaa | ggagattaca | gcttccccag | actacctgga | gatagccatt | tactgcatag | 1800 |
| gggtcttctt | aatcgcctgt | atggtggtaa | cagtcatcct | gtgccgaatg | aagaacacga | 1860 |
| ccaagaagcc | agacttcagc | agccagccgg | ctgtgcacaa | gctgaccaaa | cgtatccccc | 1920 |
| tgcggagaca | ggtaacagtt | tcggctgagt | ccagctcctc | catgaactcc | aacacccccg | 1980 |
| tggtgaggat | aacaacacgc | ctctcttcaa | cggcagacac | ccccatgctg | cagggggtct | 2040 |
| ccgagtatga | acttccagag | gacccaaaat | gggagtttcc | aagagataag | ctgacactgg | 2100 |

```
gcaagcccct gggagaaggt tgctttgggc aagtggtcat ggcggaagca gtgggaattg      2160
acaaagacaa gcccaaggag gcggtcaccg tggccgtgaa gatgttgaaa gatgatgcca      2220
cagagaaaga cctttctgat ctggtgtcag agatggagat gatgaagatg attgggaaac      2280
acaagaatat cataaatctt cttggagcct gcacacagga tgggcctctc tatgtcatag      2340
ttgagtatgc ctctaaaggc aacctccgag aatacctccg agcccggagg ccacccggga      2400
tggagtactc ctatgacatt aaccgtgttc ctgaggagca gatgaccttc aaggacttgg      2460
tgtcatgcac ctaccagctg gccagaggca tggagtactt ggcttcccaa aaatgtattc      2520
atcgagattt agcagccaga aatgttttgg taacagaaaa caatgtgatg aaaatagcag      2580
actttggact cgccagagat atcaacaata tagactatta caaaaagacc accaatgggc      2640
ggcttccagt caagtggatg gctccagaag ccctgtttga tagagtatac actcatcaga      2700
gtgatgtctg gtccttcggg gtgttaatgt gggagatctt cactttaggg ggctcgccct      2760
acccagggat tcccgtggag gaactttta agctgctgaa ggaaggacac agaatggata      2820
agccagccaa ctgcaccaac gaactgtaca tgatgatgag ggactgttgg catgcagtgc      2880
cctcccagag accaacgttc aagcagttgg tagaagactt ggatcgaatt ctcactctca      2940
caaccaatga ggaatacttg gacctcagcc aacctctcga acagtattca cctagttacc      3000
ctgacacaag aagttcttgt tcttcaggag atgattctgt tttttctcca gaccccatgc      3060
cttacgaacc atgccttcct cagtatccac acataaacgg cagtgttaaa acatgaatga      3120
ctgtgtctgc ctgtccccaa acaggacagc actgggaacc tagctacact gagcagggag      3180
accatgcctc ccagagcttg ttgtctccac ttgtatatat ggatcagagg agtaaataat      3240
tggaaaagta atcagcatat gtgtaaagat ttatacagtt gaaaacttgt aatcttcccc      3300
aggaggagaa gaaggtttct ggagcagtgg actgccacaa gccaccatgt aaccccctctc     3360 acctgccgtg cgtactggct gtggaccagt aggactcaag gtggacgtgc gttctgcctt      3420
ccttgttaat tttgtaataa ttggagaaga tttatgtcag cacacactta cagagcacaa      3480
atgcagtata taggtgctgg atgtatgtaa atatattcaa attatgtata aatatatatt      3540
atatatttac aaggagttat tttttgtatt gattttaaat ggatgtccca atgcacctag      3600
aaaattggtc tctctttttt taatagctat ttgctaaatg ctgttcttac acataatttc      3660
ttaattttca ccgagcagag gtggaaaaat acttttgctt tcagggaaaa tggtataacg      3720
ttaatttatt aataaattgg taatatacaa aacaattaat catttatagt ttttttttgta     3780 atttaagtgg catttctatg caggcagcac agcagactag ttaatctatt gcttggactt      3840
aactagttat cagatccttt gaaaagagaa tatttacaat atatgactaa tttggggaaa      3900
atgaagtttt gatttatttg tgtttaaatg ctgctgtcag acgattgttc ttagacctcc      3960
taaatgcccc atattaaaag aactcattca taggaaggtg tttcattttg gtgtgcaacc      4020
ctgtcattac gtcaacgcaa cgtctaactg gacttcccaa gataaatggt accagcgtcc      4080
tcttaaaaga tgccttaatc cattccttga ggacagacct tagttgaaat gatagcagaa      4140
tgtgcttctc tctggcagct ggccttctgc ttctgagttg cacattaatc agattagcct      4200
gtattctctt cagtgaattt tgataatggc ttccagactc tttggcgttg gagacgcctg      4260
ttaggatctt caagtcccat catagaaaat tgaaacacag agttgttctg ctgatagttt      4320
tggggatacg tccatctttt taagggattg ctttcatcta attctggcag gacctcacca      4380
aaagatccag cctcatacct acatcagaca aaatatcgcc gttgttcctt ctgtactaaa      4440
gtattgtgtt ttgctttgga aacacccact cactttgcaa tagccgtgca agatgaatgc      4500
```

```
agattacact gatcttatgt gttacaaaat tggagaaagt atttaataaa acctgttaat    4560
ttttatactg acaataaaaa tgtttctaca gatattaatg ttaacaagac aaaataaatg    4620
tcacgcaact tattttttta ataaaaaaaa aaaaaaa                              4657

<210> SEQ ID NO 245
<211> LENGTH: 4304
<212> TYPE: DNA
<213> ORGANISM: Homo sapiens

<400> SEQUENCE: 245
gtcgcgggca gctggcgccg cgcggtcctg ctctgccggt cgcacggacg caccggcggg      60
ccgccggccg gagggacggg gcgggagctg ggcccgcgga cagcgagccg gagcgggagc     120
cgcgcgtagc gagccgggct ccggcgctcg ccagtctccc gagcggcgcc cgcctcccgc     180
cggtgcccgc gccgggccgt ggggggcagc atgcccgcgc gcgctgcctg aggacgccgc     240
ggcccccgcc cccgccatgg gcgccccctgc ctgcgccctc gcgctctgcg tggccgtggc     300
catcgtggcc ggcgcctcct cggagtcctt ggggacggag cagcgcgtcg tggggcgagc     360
ggcagaagtc ccgggcccag agcccggcca gcaggagcag ttggtcttcg gcagcgggga     420
tgctgtggag ctgagctgtc ccccgcccgg gggtggtccc atggggccca ctgtctgggt     480
caaggatggc acagggctgg tgccctcgga gcgtgtcctg gtgggccccc agcggctgca     540
ggtgctgaat gcctcccacg aggactccgg ggcctacagc tgccggcagc ggctcacgca     600
gcgcgtactg tgccacttca gtgtgcgggt gacagacgct ccatcctcgg agatgacga      660 agacggggag gacgaggctg aggacacagg tgtggacaca ggggcccctt actggacacg     720
gcccgagcgg atggacaaga gctgctggc cgtgccggcc gccaacaccg tccgcttccg     780
ctgcccagcc gctggcaacc ccactccctc catctcctgg ctgaagaacg gcagggagtt     840
ccgcggcgag caccgcattg gaggcatcaa gctgcggcat cagcagtgga gcctggtcat     900
ggaaagcgtg gtgccctcgg accgcggcaa ctacacctgc gtcgtggaga caagtttgg      960 cagcatccgg cagacgtaca cgctggacgt gctggagcgc tccccgcacc ggcccatcct    1020
gcaggcgggg ctgccggcca accagacggc ggtgctgggc agcgacgtgg agttccactg    1080
caaggtgtac agtgacgcac agccccacat ccagtggctc aagcacgtgg aggtgaatgg    1140
cagcaaggtg ggcccggacg gcacacccta cgttaccgtg ctcaagacgg cgggcgctaa    1200
caccaccgac aaggagctag aggttctctc cttgcacaac gtcacctttg aggacgccgg    1260
ggagtacacc tgcctggcgg gcaattctat tgggttttct catcactctg cgtggctggt    1320
ggtgctgcca gccgaggagg agctggtgga ggctgacgag gcgggcagtg tgtatgcagg    1380
catcctcagc tacggggtgg gcttcttcct gttcatcctg gtggtggcgg ctgtgacgct    1440
ctgccgcctg cgcagccccc caagaaaagg cctgggctcc cccaccgtgc acaagatctc    1500
ccgcttcccg ctcaagcgac aggtgtccct ggagtccaac gcgtccatga gctccaacac    1560
accactggtg cgcatcgcaa ggctgtcctc aggggagggc cccacgctgg ccaatgtctc    1620
cgagctcgag ctgcctgccg accccaaatg ggagctgtct cgggcccggc tgaccctggg    1680
caagcccctt ggggagggct gcttcggcca ggtggtcatg gcgagggcca tcggcattga    1740
caaggaccgg gccgccaagc ctgtcaccgt agccgtgaag atgctgaaag acgatgccac    1800
tgacaaggac ctgtcggacc tggtgtctga gatggagatg atgaagatga tcggaaaca    1860 caaaaacatc atcaacctgc tgggcgcctg cacgcagggc gggcccctgt acgtgctggt    1920
```

```
ggagtacgcg gccaagggta acctgcggga gtttctgcgg gcgcggcggc ccccgggcct    1980
ggactactcc ttcgacacct gcaagccgcc cgaggagcag ctcaccttca aggacctggt    2040
gtcctgtgcc taccaggtgg cccggggcat ggagtacttg gcctcccaga agtgcatcca    2100
cagggacctg gctgcccgca atgtgctggt gaccgaggac aacgtgatga agatcgcaga    2160
cttcgggctg gcccgggacg tgcacaacct cgactactac aagaagacaa ccaacggccg    2220
gctgcccgtg aagtggatgg cgcctgaggc cttgttttgac cgagtctaca ctcaccagag    2280
tgacgtctgg tcctttgggg tcctgctctg ggagatcttc acgctggggg gctccccgta    2340
ccccggcatc cctgtggagg agctcttcaa gctgctgaag gagggccacc gcatggacaa    2400
gcccgccaac tgcacacacg acctgtacat gatcatgcgg gagtgctggc atgccgcgcc    2460
ctcccagagg cccaccttca agcagctggt ggaggacctg gaccgtgtcc ttaccgtgac    2520
gtccaccgac gagtacctgg acctgtcggc gcctttcgag cagtactccc cgggtggcca    2580
ggacaccccc agctccagct cctcagggga cgactccgtg tttgcccacg acctgctgcc    2640
cccggcccca cccagcagtg ggggctcgcg gacgtgaagg gccactggtc cccaacaatg    2700
tgaggggtcc ctagcagccc accctgctgc tggtgcacag ccactccccg gcatgagact    2760
cagtgcagat ggagagacag ctacacagag ctttggtctg tgtgtgtgtg tgtgcgtgtg    2820
tgtgtgtgtg tgtgcacatc cgcgtgtgcc tgtgtgcgtg cgcatcttgc ctccaggtgc    2880
agaggtaccc tgggtgtccc cgctgctgtg caacggtctc ctgactggtg ctgcagcacc    2940
gaggggcctt tgttctgggg ggacccagtg cagaatgtaa gtgggcccac ccggtgggac    3000
ccccgtgggg cagggagctg ggcccgacat ggctccggcc tctgcctttg caccacggga    3060
catcacaggg tgggcctcgg cccctcccac acccaaagct gagcctgcag ggaagcccca    3120
catgtccagc accttgtgcc tggggtgtta gtggcaccgc ctccccacct ccaggctttc    3180
ccacttccca ccctgcccct cagagactga aattacgggt acctgaagat gggagccttt    3240
accttttatg caaaaggttt attccggaaa ctagtgtaca tttctataaa tagatgctgt    3300
gtatatggta tatatacata tatatatata acatatatgg aagaggaaaa ggctggtaca    3360
acggaggcct gcgaccctgg gggcacagga ggcaggcatg gccctgggcg gggcgtgggg    3420
gggcgtggag ggaggcccca gggggtctca cccatgcaag cagaggacca gggccttttc    3480
tggcaccgca gttttgtttt aaaactggac ctgtatattt gtaaagctat ttatgggccc    3540
ctggcactct tgttcccaca ccccaacact tccagcattt agctggccac atggcggaga    3600
gttttaatttt ttaacttatt gacaaccgag aaggtttatc ccgccgatag agggacggcc    3660
aagaatgtac gtccagcctg ccccggagct ggaggatccc ctccaagcct aaaaggttgt    3720
taatagttgg aggtgattcc agtgaagata ttttatttcc tttgtccttt ttcaggagaa    3780
ttagatttct ataggatttt tctttaggag atttattttt tggacttcaa agcaagctgg    3840
tattttcata caaattcttc taattgctgt gtgtcccagg cagggagacg gtttccaggg    3900
aggggccggc cctgtgtgca ggttccgatg ttattagatg ttacaagttt atatatatct    3960
atatatataa tttattgagt ttttacaaga tgtatttgtt gtagacttaa cacttcttac    4020
gcaatgcttc tagagtttta tagcctggac tgctaccttt caaagcttgg agggaagccg    4080
tgaattcagt tggttcgttc tgtactgtta ctgggccctg agtctgggca gctgtccctt    4140
gcttgcctgc agggccatgg ctcagggtgg tctcttcttg gggcccagtg catggtggcc    4200
agaggtgtca cccaaaccgg caggtgcgat tttgttaacc cagcgacgaa ctttccgaaa    4260
aataaagaca cctggttgct aacctggaaa aaaaaaaaaa aaaa              4304
```

<210> SEQ ID NO 246
<211> LENGTH: 3040
<212> TYPE: DNA
<213> ORGANISM: Homo sapiens

<400> SEQUENCE: 246

| | | | | | |
|---|---|---|---|---|---|
| ctcgctcccg | gccgaggagc | gctcgggctg | tctgcggacc | ctgccgcgtg | cagggggtcgc | 60 |
| ggccggctgg | agctgggagt | gaggcggcgg | aggagccagg | tgaggaggag | ccaggaaggc | 120 |
| agttggtggg | aagtccagct | tgggtccctg | agagctgtga | aaggagatg | cggctgctgc | 180 |
| tggccctgtt | gggggtcctg | ctgagtgtgc | ctgggcctcc | agtcttgtcc | ctggaggcct | 240 |
| ctgaggaagt | ggagcttgag | ccctgcctgg | ctcccagcct | ggagcagcaa | gagcaggagc | 300 |
| tgacagtagc | ccttgggcag | cctgtgcgtc | tgtgctgtgg | gcgggctgag | cgtggtggcc | 360 |
| actggtacaa | ggagggcagt | cgcctggcac | ctgctggccg | tgtacggggc | tggagggggcc | 420 |
| gcctagagat | tgccagcttc | ctacctgagg | atgctggccg | ctacctctgc | ctggcacgag | 480 |
| gctccatgat | cgtcctgcag | aatctcacct | tgattacagg | tgactccttg | acctccagca | 540 |
| acgatgatga | ggaccccaag | tcccatagg | accctcgaa | taggcacagt | accccccagc | 600 |
| aagcaccta | ctggacacac | cccagcgca | tggagaagaa | actgcatgca | gtacctgcgg | 660 |
| ggaacaccgt | caagttccgc | tgtccagctg | caggcaaccc | cacgccacc | atccgctggc | 720 |
| ttaaggatgg | acaggccttt | catggggaga | accgcattgg | aggcattcgg | ctgcgccatc | 780 |
| agcactggag | tctcgtgatg | gagagcgtgg | tgccctcgga | ccgcggcaca | tacacctgcc | 840 |
| tggtagagaa | cgctgtgggc | agcatccgct | ataactacct | gctagatgtg | ctggagcggt | 900 |
| ccccgcaccg | gccatcctg | caggccgggc | tccggccaa | caccacagcc | gtggtgggca | 960 |
| gcgacgtgga | gctgctgtgc | aaggtgtaca | gcgatgccca | gccccacatc | cagtggctga | 1020 |
| agcacatcgt | catcaacggc | agcagcttcg | gagccgacgg | tttccccctat | gtgcaagtcc | 1080 |
| taaagactgc | agacatcaat | agctcagagg | tggaggtcct | gtacctgcgg | aacgtgtcag | 1140 |
| ccgaggacgc | aggcgagtac | acctgcctcg | caggcaattc | catcggcctc | tcctaccagt | 1200 |
| ctgcctggct | cacggtgctg | ccagaggagg | accccacatg | gaccgcagca | gcgcccgagg | 1260 |
| ccaggtatac | ggacatcatc | ctgtacgcgt | cgggctccct | ggccttggct | gtgctcctgc | 1320 |
| tgctggccgg | gctgtatcga | gggcaggcgc | tccacgcccg | gcaccccgc | ccgcccgcca | 1380 |
| ctgtgcagaa | gctctcccgc | ttccctctgg | cccgacagtt | ctccctggag | tcaggctctt | 1440 |
| ccggcaagtc | aagctcatcc | ctggtacgag | gcgtgcgtct | ctcctccagc | ggccccgcct | 1500 |
| tgctcgccgg | cctcgtgagt | ctagatctac | ctctcgaccc | actatgggag | ttccccggg | 1560 |
| acaggctggt | gcttgggaag | ccctaggcg | agggctgctt | tggccaggta | gtacgtgcag | 1620 |
| aggcctttgg | catggaccct | gcccggcctg | accaagccag | cactgtggcc | gtcaagatgc | 1680 |
| tcaaagacaa | cgcctctgac | aaggacctgg | ccgacctggt | ctcggagatg | gaggtgatga | 1740 |
| agctgatcgg | ccgacacaag | aacatcatca | acctgcttgg | tgtctgcacc | caggaagggc | 1800 |
| ccctgtacgt | gatcgtggag | tgcgccgcca | agggaaacct | gcgggagttc | ctgcgggccc | 1860 |
| ggcgccccc | aggccccgac | ctcagcccccg | acggtcctcg | gagcagtgag | gggccgctct | 1920 |
| ccttcccagt | cctggtctcc | tgcgcctacc | aggtggcccg | aggcatgcag | tatctggagt | 1980 |
| cccggaagtg | tatccaccgg | gacctggctg | cccgcaatgt | gctggtgact | gaggacaatg | 2040 |
| tgatgaagat | tgctgacttt | gggctggccc | gcggcgtcca | ccacattgac | tactataaga | 2100 |

| | |
|---|---|
| aaaccagcaa cggccgcctg cctgtgaagt ggatggcgcc cgaggccttg tttgaccggg | 2160 |
| tgtacacaca ccagagtgac gtgtggtctt ttgggatcct gctatgggag atcttcaccc | 2220 |
| tcgggggctc cccgtatcct ggcatccggg tggaggagct gttctcgctg ctgcgggagg | 2280 |
| gacatcggat ggaccgaccc ccacactgcc ccccagagct gtacgggctg atgcgtgagt | 2340 |
| gctggcacgc agcgccctcc cagaggccta ccttcaagca gctggtggag gcgctggaca | 2400 |
| aggtcctgct ggccgtctct gaggagtacc tcgacctccg cctgaccttc ggacccctatt | 2460 |
| ccccctctgg tggggacgcc agcagcacct gctcctccag cgattctgtc ttcagccacg | 2520 |
| accccctgcc attgggatcc agctccttcc ccttcgggtc tggggtgcag acatgagcaa | 2580 |
| ggctcaaggc tgtgcaggca cataggctgg tggccttggg ccttggggct cagccacagc | 2640 |
| ctgacacagt gctcgacctt gatagcatgg ggccctggc ccagagttgc tgtgccgtgt | 2700 |
| ccaagggccg tgcccttgcc cttggagctg ccgtgcctgt gtcctgatgg cccaaatgtc | 2760 |
| agggttctgc tcggcttctt ggaccttggc gcttagtccc catcccgggt ttggctgagc | 2820 |
| ctggctggag agctgctatg ctaaacctcc tgcctcccaa taccagcagg aggttctggg | 2880 |
| cctctgaacc ccctttcccc acacctcccc ctgctgctgc tgcccagcg tcttgacggg | 2940 |
| agcattggcc cctgagccca gagaagctgg aagcctgccg aaaacaggag caaatggcgt | 3000 |
| tttataaatt atttttttga aataaaaaaa aaaaaaaaa | 3040 |

<210> SEQ ID NO 247
<211> LENGTH: 4657
<212> TYPE: DNA
<213> ORGANISM: Homo sapiens

<400> SEQUENCE: 247

| | |
|---|---|
| ggcggcggct ggaggagagc gcggtggaga gccgagcggg cggcggcgg gtgcggagcg | 60 |
| ggcgagggag cgcgcgcggc cgccacaaag ctcgggcgcc gcgggctgc atgcggcgta | 120 |
| cctgccccgg cgcggcgact gctctccggg ctggcggggg ccggccgcga gccccggggg | 180 |
| ccccgaggcc gcagcttgcc tgcgcgctct gagccttcgc aactcgcgag caaagtttgg | 240 |
| tggaggcaac gccaagcctg agtccttcct cctctcgtt ccccaaatcc gagggcagcc | 300 |
| cgcgggcgtc atgcccgcgc tcctccgcag cctggggtac gcgtgaagcc cgggaggctt | 360 |
| ggcgccggcg aagacccaag gaccactctt ctgcgtttgg agttgctccc cgcaaccccg | 420 |
| ggctcgtcgc tttctccatc ccgacccacg cggggcgcgg gacaacaca ggtcgcggag | 480 |
| gagcgttgcc attcaagtga ctgcagcagc agcggcagcg cctcggttcc tgagcccacc | 540 |
| gcaggctgaa ggcattgcgc gtagtccatg cccgtagagg aagtgtgcag atgggattaa | 600 |
| cgtccacatg gagatatgga agaggaccgg ggattggtac cgtaaccatg gtcagctggg | 660 |
| gtcgtttcat ctgcctggtc gtggtcacca tggcaacctt gtccctggcc cggccctcct | 720 |
| tcagtttagt tgaggatacc acattagagc cagaagagcc accaaccaaa taccaaatct | 780 |
| ctcaaccaga agtgtacgtg gctgcgccag gggagtcgct agaggtgcgc tgcctgttga | 840 |
| aagatgccgc cgtgatcagt tggactaagg atgggtgca cttggggccc aacaatagga | 900 |
| cagtgctttat tggggagtac ttgcagataa agggcgccac gcctagagac tccggcctct | 960 |
| atgcttgtac tgccagtagg actgtagaca gtgaaacttg gtacttcatg gtgaatgtca | 1020 |
| cagatgccat ctcatccgga gatgatgagg atgacaccga tggtgcggaa gattttgtca | 1080 |
| gtgagaacag taacaacaag agagcaccat actggaccaa cacagaaaag atggaaaagc | 1140 |
| ggctccatgc tgtgcctgcg gccaacactg tcaagtttcg ctgcccagcc gggggggaacc | 1200 |

```
caatgccaac catgcggtgg ctgaaaaacg ggaaggagtt taagcaggag catcgcattg   1260
gaggctacaa ggtacgaaac cagcactgga gcctcattat ggaaagtgtg gtcccatctg   1320
acaagggaaa ttatacctgt gtagtggaga atgaatacgg gtccatcaat cacacgtacc   1380
acctggatgt tgtggagcga tcgcctcacc ggcccatcct ccaagccgga ctgccggcaa   1440
atgcctccac agtggtcgga ggagacgtag agtttgtctg caaggtttac agtgatgccc   1500
agccccacat ccagtggatc aagcacgtgg aaaagaacgg cagtaaatac gggcccgacg   1560
ggctgcccta cctcaaggtt ctcaagcact cggggataaa tagttccaat gcagaagtgc   1620
tggctctgtt caatgtgacc gaggcggatg ctggggaata tatatgtaag gtctccaatt   1680
atatagggca ggccaaccag tctgcctggc tcactgtcct gccaaaacag caagcgcctg   1740
gaagagaaaa ggagattaca gcttccccag actacctgga gatagccatt tactgcatag   1800
gggtcttctt aatcgcctgt atggtggtaa cagtcatcct gtgccgaatg aagaacacga   1860
ccaagaagcc agacttcagc agccagccgg ctgtgcacaa gctgaccaaa cgtatccccc   1920
tgcggagaca ggtaacagtt tcggctgagt ccagctcctc catgaactcc aacacccgc   1980 tggtgaggat aacaacacgc ctctcttcaa cggcagacac ccccatgctg cagggggtct   2040
ccgagtatga acttccagag gacccaaaat gggagtttcc aagagataag ctgacactgg   2100
gcaagcccct gggagaaggt tgctttgggc aagtggtcat ggcggaagca gtgggaattg   2160
acaaagacaa gcccaaggag gcggtcaccg tggccgtgaa gatgttgaaa gatgatgcca   2220
cagagaaaga cctttctgat ctggtgtcag agatggagat gatgaagatg attgggaaac   2280
acaagaatat cataaatctt cttggagcct gcacacagga tgggcctctc tatgtcatag   2340
ttgagtatgc ctctaaaggc aacctccgag aatacctccg agcccggagg ccacccggga   2400
tggagtactc ctatgacatt aaccgtgttc ctgaggagca gatgaccttc aaggacttgg   2460
tgtcatgcac ctaccagctg ccagaggca tggagtactt ggcttcccaa aaatgtattc   2520
atcgagattt agcagccaga atgttttggg taacagaaaa caatgtgatg aaaatagcag   2580
actttggact cgccagagat atcaacaata tagactatta caaaaagacc accaatgggc   2640
ggcttccagt caagtggatg gctccagaag ccctgtttga tagagtatac actcatcaga   2700
gtgatgtctg gtccttcggg gtgttaatgt gggagatctt cactttaggg ggctcgccct   2760
acccagggat tcccgtggag gaactttta agctgctgaa ggaaggacac agaatggata   2820
agccagccaa ctgcaccaac gaactgtaca tgatgatgag ggactgttgg catgcagtgc   2880
cctcccagag accaacgttc aagcagttgg tagaagactt ggatcgaatt ctcactctca   2940
caaccaatga ggaatacttg gacctcagcc aacctctcga acagtattca cctagttacc   3000
ctgacacaag aagttcttgt tcttcaggag atgattctgt tttttctcca gaccccatgc   3060
cttacgaacc atgccttcct cagtatccac acataaacgg cagtgttaaa acatgaatga   3120
ctgtgtctgc ctgtccccaa acaggacagc actgggaacc tagctacact gagcagggag   3180
accatgcctc ccagagcttg ttgtctccac ttgtatatat ggatcagagg agtaaataat   3240
tggaaaagta atcagcatat gtgtaaagat ttatacagtt gaaaacttgt aatcttcccc   3300
aggaggagaa gaaggtttct ggagcagtgg actgccacaa gccaccatgt aaccctctc   3360 acctgccgtg cgtactggct gtggaccagt aggactcaag gtggacgtgc gttctgcctt   3420
ccttgttaat tttgtaataa ttggagaaga tttatgtcag cacacactta cagagcacaa   3480
atgcagtata taggtgctgg atgtatgtaa atatattcaa attatgtata aatatatatt   3540
```

-continued

```
atatatttac aaggagttat tttttgtatt gattttaaat ggatgtccca atgcacctag    3600
aaaattggtc tctctttttt taatagctat ttgctaaatg ctgttcttac acataatttc    3660
ttaattttca ccgagcagag gtggaaaaat acttttgctt tcagggaaaa tggtataacg    3720
ttaatttatt aataaattgg taatatacaa acaattaat catttatagt tttttttgta     3780
atttaagtgg catttctatg caggcagcac agcagactag ttaatctatt gcttggactt    3840
aactagttat cagatccttt gaaaagagaa tatttacaat atatgactaa tttggggaaa    3900
atgaagtttt gatttatttg tgtttaaatg ctgctgtcag acgattgttc ttagacctcc    3960
taaatgcccc atattaaaag aactcattca taggaaggtg tttcattttg gtgtgcaacc    4020
ctgtcattac gtcaacgcaa cgtctaactg gacttcccaa gataaatggt accagcgtcc    4080
tcttaaaaga tgccttaatc cattccttga ggacagacct tagttgaaat gatagcagaa    4140
tgtgcttctc tctggcagct ggccttctgc ttctgagttg cacattaatc agattagcct    4200
gtattctctt cagtgaattt tgataatggc ttccagactc tttggcgttg gagacgcctg    4260
ttaggatctt caagtcccat catagaaaat tgaaacacag agttgttctg ctgatagttt    4320
tggggatacg tccatctttt taagggattg ctttcatcta attctggcag gacctcacca    4380
aaagatccag cctcatacct acatcagaca aaatatcgcc gttgttcctt ctgtactaaa    4440
gtattgtgtt ttgctttgga aacacccact cactttgcaa tagccgtgca agatgaatgc    4500
agattacact gatcttatgt gttacaaaat tggagaaagt atttaataaa acctgttaat    4560
ttttatactg acaataaaaa tgtttctaca gatattaatg ttaacaagac aaaataaatg    4620
tcacgcaact tattttttta ataaaaaaaa aaaaaaa                            4657
```

<210> SEQ ID NO 248
<211> LENGTH: 400
<212> TYPE: PRT
<213> ORGANISM: Macaca fascicularis

<400> SEQUENCE: 248

```
Met Glu Thr Asp Thr Leu Leu Leu Trp Val Leu Leu Leu Trp Val Pro
1               5                   10                  15

Gly Ser Thr Gly Arg Pro Ser Phe Ser Leu Val Glu Asp Thr Thr Leu
            20                  25                  30

Glu Pro Glu Glu Pro Pro Thr Lys Tyr Gln Ile Ser Gln Pro Glu Val
        35                  40                  45

Tyr Val Ala Ala Pro Gly Glu Ser Leu Glu Val Arg Cys Leu Leu Lys
    50                  55                  60

Asp Ala Ala Val Ile Ser Trp Thr Lys Asp Gly Val His Leu Gly Pro
65                  70                  75                  80

Asn Asn Arg Thr Val Leu Ile Gly Glu Tyr Leu Gln Ile Lys Gly Ala
                85                  90                  95

Thr Pro Arg Asp Ser Gly Leu Tyr Ala Cys Thr Ala Thr Arg Thr Val
            100                 105                 110

Asp Ser Glu Thr Trp Tyr Phe Met Val Asn Val Thr Asp Ala Ile Ser
        115                 120                 125

Ser Gly Asp Asp Glu Asp Asp Thr Asp Gly Ala Glu Asp Phe Val Ser
    130                 135                 140

Glu Asn Gly Asn Asn Lys Arg Ala Pro Tyr Trp Thr Asn Thr Glu Lys
145                 150                 155                 160

Met Glu Lys Arg Leu His Ala Val Pro Ala Ala Asn Thr Val Lys Phe
                165                 170                 175
```

```
Arg Cys Pro Ala Gly Gly Asn Pro Thr Pro Thr Met Arg Trp Leu Lys
            180                 185                 190
Asn Gly Lys Glu Phe Lys Gln Glu His Arg Ile Gly Gly Tyr Lys Val
        195                 200                 205
Arg Asn Gln His Trp Ser Leu Ile Met Glu Ser Val Val Pro Ser Asp
    210                 215                 220
Lys Gly Asn Tyr Thr Cys Val Val Glu Asn Glu Tyr Gly Ser Ile Asn
225                 230                 235                 240
His Thr Tyr His Leu Asp Val Val Glu Arg Ser Pro His Arg Pro Ile
            245                 250                 255
Leu Gln Ala Gly Leu Pro Ala Asn Ala Ser Thr Val Val Gly Gly Asp
            260                 265                 270
Val Glu Phe Val Cys Lys Val Tyr Ser Asp Ala Gln Pro His Ile Gln
            275                 280                 285
Trp Ile Lys His Val Glu Lys Asn Gly Ser Lys Tyr Gly Pro Asp Gly
            290                 295                 300
Leu Pro Tyr Leu Lys Val Leu Lys His Ser Gly Ile Asn Ser Ser Asn
305                 310                 315                 320
Ala Glu Val Leu Ala Leu Phe Asn Val Thr Glu Ala Asp Ala Gly Glu
                325                 330                 335
Tyr Ile Cys Lys Val Ser Asn Tyr Ile Gly Gln Ala Asn Gln Ser Ala
                340                 345                 350
Trp Leu Thr Val Leu Pro Lys Gln Gln Ala Pro Gly Arg Glu Lys Glu
            355                 360                 365
Ile Thr Ala Ser Pro Asp Tyr Leu Glu Lys Leu Glu Phe Arg His Asp
            370                 375                 380
Ser Gly Leu Asn Asp Ile Phe Glu Ala Gln Lys Ile Glu Trp His Glu
385                 390                 395                 400

<210> SEQ ID NO 249
<211> LENGTH: 5223
<212> TYPE: DNA
<213> ORGANISM: Mus musculus

<400> SEQUENCE: 249
gatgtgcgga taagtacaat tacctattca cgtgttccct tcctaaagga gggtttccca    60
aacactcgtc ccctgtctat tgttcagagg aacaagacaa cgcaacatct cccacgaaca   120
tccgctgctt ccaccctcaa agcttcatga catgaaatgt ctggcccag tatgctgcag   180 acctattcta aggtgtctga agttgcacag cattctgtca tttgtttcct aacttgacat   240
aaaacaacgt aacgcatcca ctgtgcacca agctggcta ggaactgggg cagtggcgta    300
cagaggccgt tcaccaacag ggttccgaga ggtcatctgt gcaccctgc gggcagcgcg    360 gcggggcccc tcgcctgcct ggcgggtgtc tctttgcggc tgctaggctt cgggggcagc    420
gcggggctcg ggactgcccc agcgcgaggc gctgattggc agagcgggcg ccgccgtcca    480
ggaaacggct cgggtttcag cggggggcgt gaccgcccg aggaggctgc ggcggcggcg    540
cgggcggcga ggggagagag ccgggagagg cgagcggcgg cggcggcagg cgcggaacgg    600
gcgcacggac gatcgaacgc gcggccgcca gagctccggc gcggggctg cctgtgtgtt    660 cctggcccgg cgtggcgact gctctccggg ctggcggggg ccgggcgtga ccccgggc    720 ctcagcgttc ctgagcgctg cgagtgttca ctactcgcca gcaaagtttg gagtaggcaa    780
cgccaagctc cagtccttc ttctgctgct gcccagatcc gagagcagct ccggtgtcat    840
gtcctagctg ttctgcgatc cccggcgcgc gtgaagcctc ggaaccttgg cgccggctgc    900
```

```
tacccaagga atcgttctct ttttggagtt ttcctccgag atcatcgcct gctccatccc     960
gatccactct gggctccggc gcagcaccga gcgcagagga gcgctgccat tcaagtggca    1020
gccacagcag cagcagcagc agcagtggga gcaggaacag cagtaacaac agcaacagca    1080
gcacagccgc ctcagagctt tggctcctga gcccccctgtg gctgaaggc attgcaggta    1140
gcccatggtc tcagaagaag tgtgcagatg ggattaccgt ccacgtggag atatggaaga    1200
ggaccaggga ttggcactgt gaccatggtc agctgggggc gcttcatctg cctggtcttg    1260
gtcaccatgg caaccttgtc cctggcccgg ccctccttca gtttagttga ggataccact    1320
ttagaaccag aagagccacc aaccaaatac caaatctccc aaccagaagc gtacgtggtt    1380
gcccccgggg aatcgctaga gttgcagtgc atgttgaaag atgccgccgt gatcagttgg    1440
actaaggatg gggtgcactt ggggcccaac aataggacag tgcttattgg ggagtatctc    1500
cagataaaag gtgccacacc tagagactcc ggcctctatg cttgtactgc agctaggacg    1560
gtagacagtg aaacttggta cttcatggtg aatgtcacag atgccatctc atctggagat    1620
gatgaggacg acacagatag ctccgaagac gttgtcagtg agaacaggag caaccagaga    1680
gcaccgtact ggaccaacac cgagaagatg gagaagcggc tccacgctgt ccctgccgcc    1740
aacactgtga agttccgctg tccggctggg gggaatccaa cgcccacaat gaggtggtta    1800
aaaaacggga aggagtttaa gcaggagcat cgcattggag gctataaggt acgaaaccag    1860
cactggagcc ttattatgga aagtgtggtc ccgtcagaca aaggcaacta cacctgcctg    1920
gtggagaatg aatacgggtc catcaaccac acctaccacc tcgatgtcgt tgaacggtca    1980
ccacaccggc ccatcctcca agctggactg cctgcaaatg cctccacggt ggtcggaggg    2040
gatgtggagt ttgtctgcaa ggtttacagc gatgcccagc cccacatcca gtggatcaag    2100
cacgtggaaa agaacggcag taaatacggg cctgatgggc tgccctacct caaggtcctg    2160
aaggccgccg tgttaacac cacggacaaa gagattgagg ttctctatat tcggaatgta    2220
acttttgagg atgctgggga atatacgtgc ttggcgggta attctatcgg gatatccttt    2280
cactctgcat ggttgacagt tctgccagcg cctgtgagag agaaggagat cacggcttcc    2340
ccagattatc tggagatagc tatttactgc ataggggtct tcttaatcgc ctgcatggtg    2400
gtgacagtca tcttttgccg aatgaagacc acgaccaaga gccagactt cagcagccag    2460
ccagctgtgc acaagctgac caagcgcatc ccccctgcgga acaggtaac agtttcggcc    2520
gagtccagct cctccatgaa ctccaacacc ccgctggtga ggataacaac gcgtctgtcc    2580
tcaacagcgg acaccccgat gctagcaggg gtctccgagt atgagttgcc agaggatcca    2640
aagtgggaat tccccagaga taagctgacg ctgggcaaac ccctggggga aggttgcttc    2700
gggcaagtag tcatggctga agcagtggga atcgataaag acaaacccaa ggaggcggtc    2760
accgtggcag tgaagatgtt gaaagatgat gccacagaga aggacctgtc tgatctggta    2820
tcagagatgg agatgatgaa gatgattggg aaacataaga acattatcaa cctcctgggg    2880
gcctgcacgc aggatggacc tctctacgtc atagttgaat atgcatcgaa aggcaacctc    2940
cgggaatacc tccgagcccg gaggccacct ggcatggagt actcctatga cattaaccgt    3000
gtccccgagg agcagatgac cttcaaggac ttggtgtcct gcacctacca gctggctaga    3060
ggcatggagt acacttggctt ccaaaaaatgt atccatcgag atttggctgc cagaaacgtg    3120
ttggtaacag aaaacaatgt gatgaagata gcagactttg gcctggccag ggatatcaac    3180
aacatagact actataaaaa gaccacaaat gggcgacttc cagtcaagtg gatggctcct    3240
```

```
gaagcccttt tgatagagt ttacactcat cagagcgatg tctggtcctt cggggtgtta   3300
atgtgggaga tctttacttt aggggggctca ccctacccag ggattcccgt ggaggaactt   3360
tttaagctgc tcaaagaggg acacaggatg acaagccca ccaactgcac caatgaactg    3420
tacatgatga tgagggattg ctggcatgct gtaccctcac agagacccac attcaagcag   3480
ttggtcgaag acttggatcg aattctgact ctcacaacca atgaggaata cttggatctc   3540
acccagcctc tcgaacagta ttctcctagt taccccgaca caaggagctc ttgttcttca   3600
ggggacgatt ctgtgttttc tccagacccc atgccttatg aaccctgtct gcctcagtat   3660
ccacacataa acggcagtgt taaaacatga gtgaatgtgt cttcctgtcc caaacagga    3720
cagcaccagg aacctactta cactgagcag agaggctgtg cctccagagc ctgtgacacg   3780
cctccacttg tatatatgga tcagaggagt aaatagtggg aagcatattt gtcacgtgtg   3840
taaagattta tacagttgga aacatgttac ctaaccagga aggaagact gtttcctgat    3900
aagtggacag ccgcaagcca ccatgccacc ctctctgacc caccatgtat gctggctgtg   3960
ccccagttgg actcaaggca gacaggtgtt ctgccttcct tgttaatttt gtaataattg   4020
gagaagatat atgtcagcac acacttacag agcacaaacg cagtatatag gtgctggatg   4080
tatgtaaata tattcaaatt atgtataaat atatattata tatttacaag gaattatttt   4140
ttgtattgat tttaaatgga tgtcctgatg cacctagaaa attggtctct cttttttta   4200
aatagatatt tgctaaatgc tgttcttaga gtttcttaat tttcaccgag cagaggtggg   4260
aaaatacttt tgctttcagg gaaaatggtg tcacattaat ttattaacga attggtaata   4320
tacgaaacga ttaatcatct atagtttttt ttttttgta atttaagtgg catttctatg    4380
caggcagcac ggaggactag ttaatctatt gcttggactt aactggttat tggatccttt   4440
gagaagagaa atatttacga tatatgacta atttgggggg aaatggtgtt ttgatttatt   4500
tgtgtttcaa ctctgctgtc cgatgagcat gtctagacac cctaatgccc atgtttcaag   4560
aaacctgtta aactctgtca ccccagggta acaattaacc agacttccca agacaaatgg   4620
taccagcatc ctcatcccaa gatgccttaa tccacttctc tggagaacag acttccatgg   4680
gaatgatagc agggtcctct cgtccggcag ctggccttct gcccgggtta cacattcatc   4740
acgtttgcct tgcttctcag tgagttttaa taacagcttc agattcttca gcaccaagag   4800
cccttttgggg aatctccatc ctctcgaagg atggcaaaag cccagcatca ttcggttgag   4860
agtctgggac ctccttccat cttcttaagg gtttgcttct ggcttctacc cacttctgac   4920
aagacctcac ctcacaaaaa gatctggcct aatagctaca tccgacaaga taacgcttat   4980
tgttgatttc cgtattcaag tattgttttg ctttggatac gcccactcac tttgctacag   5040
tcatgcgaca tgtatgcaga ttacactgat tttatgtgtt ttggaattgg agaaagtatt   5100
taataaaacc tgttaatttt tatactgaca ataaaaatgt ttctacagat attaatgtta   5160
acaagacaaa ataaatgtca cgcagcttat tttttaaaa aaaaaaaaa aaaaaaaaa     5220
aaa                                                                5223

<210> SEQ ID NO 250
<211> LENGTH: 4277
<212> TYPE: DNA
<213> ORGANISM: Rattus norvegicus

<400> SEQUENCE: 250
gcggccgcag cagcagcagc agcgacagca gcagcaacaa cagcctgagc aagccacagc      60
agcgccctgg ctcctgagcc ccccgtgggc tgaaggcatt gcaggtagcc catggtccct    120
```

```
gaagaagtgt gcagatggga ttaccgtcca catggagata tggaacagga ccagggattg    180
gcaccgtgac catggtcagc tgggggcgct tcatctgcct ggtcttggtc accatggcaa    240
ccttgtccct ggcccggccc tccttcagtt tagttgaaga taccacttta gaaccagaag    300
agccaccaac caaataccaa atctcccaac cagaagcgtg cgtggttgcc cccggggagt    360
cgctagagtt gcgctgcatg ttgaaagatg ccgccgtgat cagttggact aaggatgggg    420
tgcacttggg gcccaacaat aggacagtgc ttattgggga gtacctccag ataaaaggtg    480
ccacacctag agactccggc ctctatgctt gtgctgcagc taggacggta gacagtgaaa    540
ctttgtactt catggtgaat gtcacagatg ccatctcatc tggagatgac gaggacgaca    600
cagatagctc cgaagacttt gtcagtgaga acaggagcaa ccagagagca ccgtactgga    660
ccaacaccga aaagatggag aagcggctcc atgctgtccc tgccgccaac actgtgaagt    720
tccgctgtcc agccgggggg aatccaacac ccacaatgag gtggctaaaa acgggaagg    780 agtttaagca ggagcatcgc atcggaggct ataaggtacg aaaccagcac tggagccttt    840
ttatggaaag tgtggtccca tcagacaaag gcaattacac ctgcctggtg agaatgaat    900 acgggtccat caaccacacc taccaccttg atgttgttga cgatcacca caccggccca    960 tcctccaagc tggactgcct gcaaatgcct ccacggtggt cggaggggac gtagaatttg   1020
tctgcaaggt ttatagtgat gcccagcccc atatccagtg gatcaaacat gtggaaaaga   1080
acggcagtaa atatggacct gatgggctgc cctacctcaa ggtcctgaag gtgagaaagg   1140
ccgccggtgt taacaccacg gacaaagaaa ttgaggttct ctatattcgg aatgtaactt   1200
ttgaggatgc tggggaatat acgtgcttgg cgggtaattc tatcgggata tcctttcact   1260
ctgcatggtt gacagttctg ccagcacctg tgagagagaa ggagatcaca gcttccccag   1320
attacctgga gatagctatt tactgcatag gggtcttctt aatcgcctgc atggtggtga   1380
cagtcatctt ttgccgaatg aagaccacga ccaagaagcc agacttcagc agccagccag   1440
ctgtgcacaa gctgaccaag cgcatccccc tgcggagaca ggtttcggcc gagtccagct   1500
cgtccatgaa ctccaacacc ccactggtga ggataacgac acgtctgtcc tcaacggcgg   1560
acaccccgat gctagcaggg gtctctgagt acgagttgcc agaggatcca aagtgggaat   1620
tccccagaga taagctgacg ctgggcaaac ccctggggga aggctgcttc gggcaagtag   1680
tcatggctga agcggtggga atcgataagg acagacccaa ggaggcagtc accgtggcgg   1740
tgaagatgtt gaaagatgac gccacagaga aggacctgtc tgacctggtg tcagagatgg   1800
agatgatgaa gatgattggt aaacataaga acatcatcaa cctcctgggg gcctgcaccc   1860
aggatggacc cctctatgtc atagtcgaat acgcatcgaa aggcaacctc cgggaatacc   1920
tccgggcccg gaggccacct ggcatggagt actcctatga cattaaccga gttcccgagg   1980
agcagatgac cttcaaggac ttggtgtcct gcacctacca gctggcgaga ggcatggagt   2040
acttggcttc ccaaaaatgt atccatcgag acttggcagc cagaaatgtg ctggtaacag   2100
aaaacaacgt gatgaagata gcagactttg gcctggccag ggatatcaac aacatagact   2160
attacaaaaa gaccacgaat gggcgacttc cagtcaagtg gatggctcct gaagcccttt   2220
ttgatagagt ttacactcat cagagtgatg tctggtcctt cggggtgtta atgtgggaga   2280
tcttcacttt agggggttca ccctacccag ggattcccgt ggaggaactt tttaagctgc   2340
tcaaagaggg ccacaggatg gacaagccca ccaactgcac caatgaactg tacatgatga   2400
tgagggactg ctggcatgct gtaccctcac agaggcccac gtttaagcag ttggtggaag   2460
```

```
acttggatcg aattctgact ctcacaacca atgaggaata cttggacctc agtcagcctc    2520
tcgaaccgta ttcaccttgt tatcctgacc caaggtgaaa taaaacgtct ctcttccctt    2580
cttgcaggaa tacttggacc tcacccagcc tctcgaacag tattctccta gttaccccga    2640
cacaaggagc tcttgttctt caggggacga ttctgtgttt tctccagacc ccatgcctta    2700
tgaccectgc ctgcctcagt atccacacat aaacggcagt gttaaaacat gagcgggtgt    2760
gtcttcctgt ccccaaacag gacagcacca ggaacctact tacactgagc agagaggctg    2820
tgcccccaaa gcgtgtggca tgcctccaca tgtatatatg gatcagagga gtaaatagtg    2880
ggaagagtat ttgtcacgtg tgtgaagatt tatacagttg gaaacatgtt actttcccag    2940
gaaaggaaga ctgtttcctg ataagtggac agccgcaagc caccgccacc ctctctgacc    3000
taccatgtat gctggctgtg ccccagttgg actcaaggca gaccgctgtt ctgccttcct    3060
tgttaatttt gtaataattg gagaagatat atgtcagcac atacttacag agcacaaatg    3120
cagtatatag gtgctggatg tatgtaaata tattcaaatt atgtataaat atatattata    3180
tatttacaag gaattatttt ttgtattgat cttaaatgga tgtcctgatg cacctagaaa    3240
attggtctct ccattttttt taaatagata tttgctaaat gctgttctta gaatttctta    3300
attttcaccg agcagaggtg ggaaaatact tttgctttca gggaaaatgg tgtcacatta    3360
atttattaat gaattggtaa tatacgaaac aattaatcat ctatagtttg tttttttttt    3420
tttgtaattt aagtggcatt tctatgcaga cagcacagag gactagttaa tctattgctt    3480
ggacttaact ggttattgga tcctttgaga agagaaatat ttacgatata tgactaattt    3540
gggggggaaat gatgtcttga tttatttgtg tttcaactct gctgtccgat gattatgtct    3600
aaacacctca atgcccacct ttcaagaaac cttttaaact ctgtcacccc agtgtaacaa    3660
ttaaccagac ttcccatgac aaatggtacc agagtcctca tcccaagatg ccttaatcct    3720
cttctctgga gaacagactc ccatcggaga cggcagggtg ggtcttgtct ggcagctggc    3780
cttctgcctg agttacacac ccgtcacatt cgccttgctc cctctccgtg agttttgata    3840
acagcttcag attcttcagc atcaaaaact cctttgggac tctccatcct ctcggagaat    3900
agtgaaagcc cagggttatt ctgtcgagag tttgggacct ccttccatct tctgcagggt    3960
ttgcttctgg cttccaccca cttctgacaa gacctctcct cactaaaaga tctggcccga    4020
gagctacacc cgacaagaga acgcttacca ttgatttccg tgttcaagtc ttgtgctttg    4080
ctttggacac gcccactcac cttgctaccg tcatgtgaca ggagtgcaga ctacactgat    4140
tttatgtgtt ttgaaattgg agaaagtatt taataaaacc tgttaatttt tatactgaca    4200
ataaaaatgt ttctacagat attaatgtta acgagacaaa aataaatgtc gcgcagctta    4260
tttttttaat actcgtg                                                   4277
```

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256
<211> LENGTH: 237
<212> TYPE: PRT
<213> ORGANISM: Homo sapiens

<400> SEQUENCE: 256

Met Ala Glu Asp Phe Val Ser Glu Asn Ser Asn Asn Lys Arg Ala Pro
1               5                   10                  15

Tyr Trp Thr Asn Thr Glu Lys Met Glu Lys Arg Leu His Ala Val Pro
            20                  25                  30

Ala Ala Asn Thr Val Lys Phe Arg Cys Pro Ala Gly Gly Asn Pro Met
        35                  40                  45

Pro Thr Met Arg Trp Leu Lys Asn Gly Lys Glu Phe Lys Gln Glu His
    50                  55                  60

Arg Ile Gly Gly Tyr Lys Val Arg Asn Gln His Trp Ser Leu Ile Met
65                  70                  75                  80

Glu Ser Val Val Pro Ser Asp Lys Gly Asn Tyr Thr Cys Val Val Glu
                85                  90                  95

Asn Glu Tyr Gly Ser Ile Asn His Thr Tyr His Leu Asp Val Val Glu
            100                 105                 110

Arg Ser Pro His Arg Pro Ile Leu Gln Ala Gly Leu Pro Ala Asn Ala
        115                 120                 125

Ser Thr Val Val Gly Gly Asp Val Glu Phe Val Cys Lys Val Tyr Ser
    130                 135                 140

Asp Ala Gln Pro His Ile Gln Trp Ile Lys His Val Glu Lys Asn Gly
145                 150                 155                 160

Ser Lys Tyr Gly Pro Asp Gly Leu Pro Tyr Leu Lys Val Leu Lys His
                165                 170                 175

Ser Gly Ile Asn Ser Ser Asn Ala Glu Val Leu Ala Leu Phe Asn Val
            180                 185                 190

Thr Glu Ala Asp Ala Gly Glu Tyr Ile Cys Lys Val Ser Asn Tyr Ile
        195                 200                 205

Gly Gln Ala Asn Gln Ser Ala Trp Leu Thr Val Leu Pro Lys Gln Gln
    210                 215                 220

Ala Pro Gly Arg Glu Lys Glu His His His His His His
225                 230                 235

<210> SEQ ID NO 257
<211> LENGTH: 822
<212> TYPE: PRT
<213> ORGANISM: Homo sapiens

<400> SEQUENCE: 257

```
Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
        290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
            340                 345                 350

Ala Trp Leu Thr Val Leu Pro Lys Gln Gln Ala Pro Gly Arg Glu Lys
        355                 360                 365

Glu Ile Thr Ala Ser Pro Asp Tyr Leu Glu Ile Ala Ile Tyr Cys Ile
        370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415
```

```
His Lys Leu Thr Lys Arg Ile Pro Leu Arg Arg Gln Val Thr Val Ser
            420                 425                 430

Ala Glu Ser Ser Ser Met Asn Ser Asn Thr Pro Leu Val Arg Ile
        435                 440                 445

Thr Thr Arg Leu Ser Ser Thr Ala Asp Thr Pro Met Leu Ala Gly Val
    450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Asp Lys Pro Lys Glu Ala
            500                 505                 510

Val Thr Val Ala Val Lys Met Leu Lys Asp Asp Ala Thr Glu Lys Asp
        515                 520                 525

Leu Ser Asp Leu Val Ser Glu Met Glu Met Met Lys Met Ile Gly Lys
    530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
            580                 585                 590

Arg Val Pro Glu Glu Gln Met Thr Phe Lys Asp Leu Val Ser Cys Thr
        595                 600                 605

Tyr Gln Leu Ala Arg Gly Met Glu Tyr Leu Ala Ser Gln Lys Cys Ile
    610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
        675                 680                 685

Ser Phe Gly Val Leu Met Trp Glu Ile Phe Thr Leu Gly Gly Ser Pro
    690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
        755                 760                 765

Glu Tyr Leu Asp Leu Ser Gln Pro Leu Glu Gln Tyr Ser Pro Ser Tyr
    770                 775                 780

Pro Asp Thr Arg Ser Ser Cys Ser Ser Gly Asp Asp Ser Val Phe Ser
785                 790                 795                 800

Pro Asp Pro Met Pro Tyr Glu Pro Cys Leu Pro Gln Tyr Pro His Ile
                805                 810                 815

Asn Gly Ser Val Lys Thr
            820
```

```
<210> SEQ ID NO 258
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Met Asn Ser Asn Asn Lys Arg Ala Pro Tyr Trp Thr Asn Thr Glu Lys
1               5                   10                  15

Met Glu Lys Arg Leu His Ala Val Pro Ala Asn Thr Val Lys Phe
            20                  25                  30

Arg Cys Pro Ala Gly Gly Asn Pro Met Pro Thr Met Arg Trp Leu Lys
        35                  40                  45

Asn Gly Lys Glu Phe Lys Gln Glu His Arg Ile Gly Gly Tyr Lys Val
    50                  55                  60

Arg Asn Gln His Trp Ser Leu Ile Met Glu Ser Val Val Pro Ser Asp
65                  70                  75                  80

Lys Gly Asn Tyr Thr Cys Val Val Glu Asn Tyr Gly Ser Ile Asn
                85                  90                  95

His Thr Tyr His Leu Asp Val Val Leu Val Pro Arg Gly Ser Leu Glu
            100                 105                 110

His His His His His His
        115

<210> SEQ ID NO 259
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Val Ile Glu Gly Asp Gly Ser Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Lys Thr Tyr Ser Ser Ala Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His
225

<210> SEQ ID NO 260
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Asp
            20                  25                  30

Leu Asn Trp Tyr Gln Gln Lys Pro Gly Lys Ala Pro Lys Leu Leu Ile
        35                  40                  45

Tyr Asp Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ser Pro Ser His
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 261
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

```
<400> SEQUENCE: 261

His His His His His His
1               5

<210> SEQ ID NO 262
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Tyr Gly Arg Lys Lys Arg Arg Gln Arg Arg Leu Tyr Arg Ser Pro
1               5                   10                  15

Ala Met Pro Glu Asn Leu
            20
```

ANTIBODY DRUG CONJUGATES

SEQUENCE LISTING

The instant application contains a Sequence Listing which has been submitted electronically in ASCII format and is hereby incorporated by reference in its entirety. Said ASCII copy, created on Jun. 30, 2014, is named PAT055644-US-NP_SL.txt and is 243,611 bytes in size.

FIELD OF THE INVENTION

The present invention generally relates to anti-FGFR2 antibodies, antibody fragments, antibody drug conjugates, and their uses for the treatment of cancer.

BACKGROUND OF THE INVENTION

Fibroblast Growth Factor Receptors

Fibroblast growth factors (FGFs) that signal through FGF receptors (FGFRs) regulate fundamental developmental pathways and are expressed in a wide variety of tissues. FGFs stimulate proliferation, cell migration, differentiation, and play a major role in skeletal and limb development, wound healing, tissue repair, hematopoiesis, angiogenesis, and tumorigenesis (see, e.g., Turner and Crose, Nature Reviews Cancer 10: 116-129 (2010)).

The mammalian FGF family comprises many ligands, which exert their actions through four highly conserved transmembrane tyrosine kinase receptors, FGFR1, FGFR2, FGFR3, and FGFR4. A typical FGFR has a signal peptide that is cleaved off, three immunoglobulin (Ig)-like domains (Ig domain I, II and III), an acidic box, a transmembrane domain, and a split tyrosine kinase domain (see, e.g., Ullrich and Schlessinger, Cell 61: 203 (1990); Johnson and Williams, Adv. Cancer Res. 60:1-41 (1992)).

Additionally, alternative splicing of the transcribed receptor genes results in a variety of receptor isoforms, including soluble, secreted FGFRs, FGFRs with truncated COOH—terminal domain, FGFRs with either two or three Ig-like domains, as well as FGFR isoforms arising via alternative splicing of the third Ig-like domain occurs only for FGFR1, FGFR2, and FGFR3 and specifies the second half of the third Ig-like domain, resulting in either the IIIb or the IIIc isoform of the receptor. The $2^{nd}$ and the $3^{rd}$ Ig-like domains of the receptors are necessary and sufficient for ligand binding, whereas the first Ig-like domain is thought to play a role in receptor autoinhibition. Thus, the different receptors and their isoforms display different ligand-binding specificities (see, e.g., Haugsten et al., Mol. Cancer. Res. 8:1439-1452 (2010)).

The FGFs can also bind to heparin sulfate proteoglycans (HSPG), besides binding to distinct FGFRs and their splice variants. Thereby a dimeric FGF-FGFR-HSPG ternary complex forms on the cell surface. The ternary complex is stabilized by multiple interactions between the different components in the complex. Two FGF-binding sites, a heparin-binding site, and a receptor-receptor interaction site have been identified within the Ig-like domains II and III of the receptor. (Haugsten et al., 2010).

Binding of FGFs to FGFRs induces receptor dimerization, which enables transphosphorylation of a tyrosine in the activation loop of the kinase domain. The active FGFRs have been shown to phosphorylate multiple intracellular proteins such as FRS2, and PLCγ (Eswarakumar et al., Cytokine Growth Factor Rev 16:139-149 (2005)). FGFR signaling produces distinct biological responses in different cell types, ranging from stimulation of cell proliferation and survival to growth arrest, migration, and differentiation.

FGFRs and Cancer

FGF signaling mediates a powerful combination of effects: self-sufficiency in growth/survival, neoangiogenesis and tumor cell migration. Consequently, FGF signaling has the potential of being strongly oncogenic once the tight regulation exerted on its physiological functions is lost (see, e.g., Heinzle et al., Expert Opin. Ther. Targets 15(7):829-846 (2011)).

Gene amplification and/or overexpression of FGFR1, FGFR2 and FGFR4 has been implicated in breast cancer (Penault-Llorca et al., Int J Cancer 1995; Theillet et al., Genes Chrom. Cancer 1993; Adnane et al., Oncogene 1991; Jaakola et al., Int J Cancer 1993; Yamada et al., Neuro Res 2002). Overexpression of FGFR1 and FGFR4 is also associated with pancreatic adenocarcinomas and astrocytomas (Kobrin et al., Cancer Research 1993; Yamanaka et al., Cancer Research 1993; Shah et al., Oncogene 2002; Yamaguchi et al., PNAS 1994; Yamada et al., Neuro Res 2002). Prostate cancer has also been related to FGFR1 overexpression (Giri et al., Clin Cancer Res 1999).

In general FGFR2 and FGFR1 are more commonly deregulated by gene amplification. In gastric cancer an amplified FGFR2 gene is associated with poor prognosis (Kunii et al., Cancer Res. 68:2340-2348 (2008)). A FGFR2-IIIb to IIIc switch can also be a sign of tumor progression, epithelial-mesenchymal transition and high invasiveness in bladder and prostate cancers. Switching in this case substitutes a IIIb receptor variant that exerts anti-tumorigenic activity with a protumorigenic IIIc receptor (see, e.g., Heinzle et al., 2011). So far FGFR2 mutations have been implicated in skin, endometrial, ovary, and lung cancer (see, e.g., Heinzle et al., 2011).

Antibody Drug Conjugates

Antibody drug conjugates ("ADCs") have been used for the local delivery of cytotoxic agents in the treatment of cancer (see e.g., Lambert, Curr. Opinion In Pharmacology 5:543-549, 2005). ADCs allow targeted delivery of the drug moiety where maximum efficacy with minimal toxicity may be achieved. As more ADCs show promising clinical results, there is an increased need to develop new therapeutics for cancer therapy.

SUMMARY OF THE INVENTION

The present invention provides antibody drug conjugates of the formula

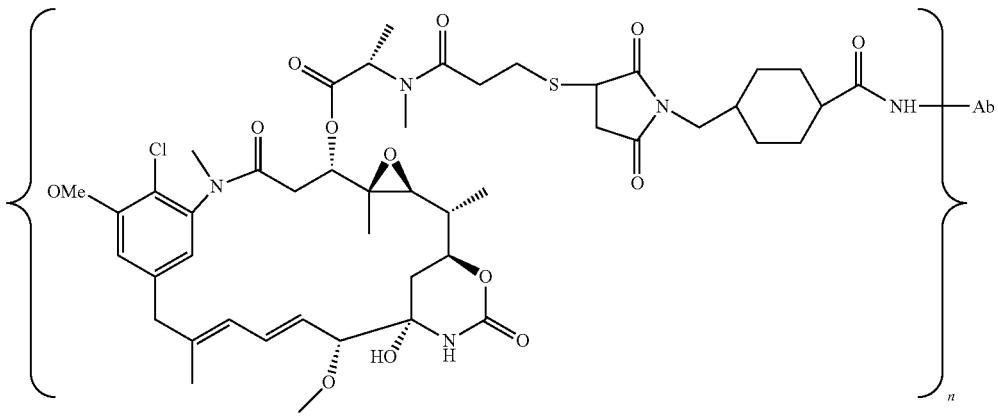

or a pharmaceutically acceptable salt thereof; wherein Ab is an antibody or antigen binding fragment thereof that specifically binds to human FGFR2; and n is an integer from 1 to 10. In a specific embodiment, n is an integer of 3 or 4.

In some embodiments, the antibodies or antigen binding fragments described herein specifically bind to all isoforms of human FGFR2. In some embodiments, the antibodies or antigen binding fragments described herein specifically bind to an epitope of human FGFR2 comprising amino acids 174-189 and 198-216 of SEQ ID NO:256. In some embodiments, the antibodies or antigen binding fragments described herein specifically bind to the human FGFR2 IIIb isoform. In some embodiments, the antibody or antigen binding fragments described herein specifically bind to an epitope of human FGFR2 comprising amino acids 346-354 of SEQ ID NO:256. The present invention also provides antibody drug conjugates comprising the antibodies or antigen binding fragments described herein.

In some embodiments, the present inventions provides antibodies or antigen binding fragments as described in Table 1, as well as antibody drug conjugates comprising such antibodies or antigen binding fragments. In some embodiments, the antibodies or antigen binding fragments described herein comprise a heavy chain variable region that comprises: (a) a VH CDR1 of SEQ ID NO: 21, (b) a VH CDR2 of SEQ ID NO: 22, (c) a VH CDR3 of SEQ ID NO: 23; and a light chain variable region that comprises: (d) a VL CDR1 of SEQ ID NO: 31, (e) a VL CDR2 of SEQ ID NO: 32, (f) a VL CDR3 of SEQ ID NO: 33, wherein the CDR is defined in accordance with the Kabat definition.

In some embodiments, the antibodies or antigen binding fragments described herein comprise a heavy chain variable region that comprises: (a) a VH CDR1 of SEQ ID NO: 101, (b) a VH CDR2 of SEQ ID NO: 102, (c) a VH CDR3 of SEQ ID NO: 103; and a light chain variable region that comprises: (d) a VL CDR1 of SEQ ID NO: 111, (e) a VL CDR2 of SEQ ID NO: 112, (f) a VL CDR3 of SEQ ID NO: 113, wherein the CDR is defined in accordance with the Kabat definition.

In some embodiments, the antibodies or antigen binding fragments described herein comprise a heavy chain variable region that comprises: (a) a VH CDR1 of SEQ ID NO: 201, (b) a VH CDR2 of SEQ ID NO: 202, (c) a VH CDR3 of SEQ ID NO: 203; and a light chain variable region that comprises: (d) a VL CDR1 of SEQ ID NO: 211, (e) a VL CDR2 of SEQ ID NO: 212, (f) a VL CDR3 of SEQ ID NO: 213, wherein the CDR is defined in accordance with the Kabat definition.

In some embodiments, the antibodies or antigen binding fragments described herein comprise a heavy chain variable region that comprises: (a) a VH CDR1 of SEQ ID NO: 221, (b) a VH CDR2 of SEQ ID NO: 222, (c) a VH CDR3 of SEQ ID NO: 223; and a light chain variable region that comprises: (d) a VL CDR1 of SEQ ID NO: 231, (e) a VL CDR2 of SEQ ID NO: 232, (f) a VL CDR3 of SEQ ID NO: 233, wherein the CDR is defined in accordance with the Kabat definition.

In some embodiments, the antibodies or antigen binding fragments described herein comprise a heavy chain variable region that comprises: (a) a VH CDR1 of SEQ ID NO: 1, (b) a VH CDR2 of SEQ ID NO: 2, (c) a VH CDR3 of SEQ ID NO: 3; and a light chain variable region that comprises: (d) a VL CDR1 of SEQ ID NO: 11, (e) a VL CDR2 of SEQ ID NO: 12, (f) a VL CDR3 of SEQ ID NO: 13, wherein the CDR is defined in accordance with the Kabat definition.

In some embodiments, the antibodies or antigen binding fragments described herein comprise a heavy chain variable region that comprises: (a) a VH CDR1 of SEQ ID NO: 181, (b) a VH CDR2 of SEQ ID NO: 182, (c) a VH CDR3 of SEQ ID NO: 183; and a light chain variable region that comprises: (d) a VL CDR1 of SEQ ID NO: 191, (e) a VL CDR2 of SEQ ID NO: 192, (f) a VL CDR3 of SEQ ID NO: 193, wherein the CDR is defined in accordance with the Kabat definition.

The present invention also provides antibody drug conjugates comprising the antibodies and antigen binding fragments described herein. In some embodiments, the antibody drug conjugates of the invention have the formula: Ab-(L-(D)$_m$)$_n$, wherein Ab is an antibody or antigen binding fragment thereof that specifically binds to an epitope of human FGFR2 comprising amino acids 174-189, 198-216, or 346-354 of SEQ ID NO:256; Lisa linker; D is a drug moiety; m is an integer from 1 to 8; and n is an integer from 1 to 10, or a pharmaceutically acceptable salt thereof. In some embodiments, m is 1. In some embodiments, n is 3 or 4. In some embodiments, m is 1 and n is 3 or 4. In some embodiments, Ab is an antibody or antigen binding fragment thereof that specifically bind to human FGFR2 and comprises a heavy chain variable region that comprises: (a) a VH CDR1 of SEQ ID NO: 101, (b) a VH CDR2 of SEQ ID NO: 102, (c) a VH CDR3 of SEQ ID NO: 103; and a light chain variable region that comprises: (d) a VL CDR1 of SEQ ID NO: 111, (e) a VL CDR2 of SEQ ID NO: 112, (f) a VL CDR3 of SEQ ID NO: 113, wherein the CDR is defined in accordance with the Kabat definition. In some other embodiments, Ab is an antibody or antigen binding fragment thereof that specifically bind to human FGFR2 and comprises a heavy chain variable region that comprises: (a) a VH CDR1 of SEQ ID NO: 1, (b) a VH CDR2 of SEQ ID NO: 2, (c) a VH CDR3 of SEQ ID NO: 3; and a light chain variable region that comprises: (d) a VL CDR1 of SEQ ID NO: 11, (e) a VL CDR2 of SEQ ID NO: 12, (f) a VL CDR3 of SEQ ID NO: 13, wherein the CDR is defined in accordance with the Kabat definition.

In some embodiments, the antibodies or antigen binding fragments described herein have enhanced ADCC activity as compared to an antibody consisting of a heavy chain of SEQ ID NO: 9 and a light chain of SEQ ID NO: 19. In some embodiments, the antibodies or antigen binding fragments described herein do not have enhanced ADCC activity as compared to an antibody consisting of a heavy chain of SEQ ID NO: 109 and a light chain of SEQ ID NO: 119. In some embodiments, the antibodies described herein are human or humanized antibodies. In some embodiments, the antibodies described herein are monoclonal antibodies. In some embodiments, the antibodies described herein are monoclonal human or humanized antibodies. The present invention also provides antibody drug conjugates comprising such antibodies or antigen binding fragments.

In some embodiments, the present invention provides antibody drug conjugates comprising an antibody or antigen binding fragment described herein, and a drug moiety, wherein the drug moiety is linked to the antibody or antigen binding fragment via a linke, and wherein said linker is selected from the group consisting of a cleavable linker, a non-cleavable linker, a hydrophilic linker, a procharged linker and a dicarboxylic acid based linker. In some embodiments, the linker is derived from a cross-linking reagent selected from the group consisting of: N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)-2-sulfo-butanoate (sulfo-SPDB), N-succinimidyl iodoacetate (SIA), N-succinimidyl(4-iodoacetyl)aminobenzoate (SIAB), maleimide PEG NHS, N-succinimidyl 4-(maleimidomethyl)cyclohexanecarboxylate (SMCC), N-sulfosuccinimidyl 4-(maleimidomethyl)cyclohexanecarboxylate (sulfo-SMCC) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1). In a specific embodiment, the linker is derived from the cross-linking reagent N-succinimidyl 4-(maleimidomethyl)cyclohexanecarboxylate (SMCC).

In some embodiments, the present invention provides antibody drug conjugates comprising an antibody or antigen binding fragment described herein, and a drug moiety, wherein said drug moiety is selected from a group consisting of: a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, proteasome inhibitors, inhibitors of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder and a DHFR inhibitor. In a specific embodiment, the drug moiety of an antibody drug conjugate of the invention is maytansinoid. In another specific embodiment, the drug moiety of an antibody drug conjugate of the invention is N(2')-deacetyl-N(2')-(3-mercapto-1-oxopropyl)-maytansine (DM1) or N(2')-deacetyl-N2-(4-mercapto-4-methyl-1-oxopentyl)-maytansine (DM4).

The present invention also provides pharmaceutical compositions comprising the antibody drug conjugate described herein and a pharmaceutically acceptable carrier. In some embodiments, the pharmaceutical compositions of the invention is prepared as a lyophilisate. In some embodiments, the lyophilisate comprises an antibody drug conjugate described herein, sodium succinate, and polysorbate 20.

The present invention provides methods of treating an FGFR2 positive cancer in a patient in need thereof comprising administering to said patient an antibody drug conjugate or a pharmaceutical composition described herein. In some embodiments, the cancer is selected from the group consisting of gastric cancer, breast cancer, alveolar rhabdomyosarcoma, liver cancer, adrenal cancer, lung cancer, colon cancer and endometrial cancer. In some embodiments, the treatment methods described herein further comprise administering to said patient a tyrosine kinase inhibitor, an IAP inhibitor, a Bcl2 inhibitor, an MCL1 inhibitor, or another FGFR2 inhibitor. In a specific embodiment, the treatment method comprises administering to a patient in need thereof an antibody drug conjugate described herein in combination with 3-(2,6-Dichloro-3,5-dimethoxy-phenyl)-1-{6-[4-(4-ethyl-piperazin-1-yl)-phenylamino]-pyrimidin-4-yl}-1-methyl-urea.

The present invention further provides antibody drug conjugates described herein for use as a medicament. The present invention provides antibody drug conjugates or pharmaceutical compositions for use in the treatment of an FGFR2 positive cancer.

In some embodiments, the antibodies or antigen binding fragments described herein are a single chain antibody (scFv).

The present invention also provides nucleic acids that encodes the antibodies or antigen binding fragments described herein. In some embodiments, the present invention provides nucleic acids that encodes the antibodies or antigen binding fragments as those described in Table 1. The present invention further provides vectors comprising the nucleic acid described herein, and host cells comprising such vectors.

The present invention provides processes for producing an antibody or antigen binding fragment comprising cultivating the host cells described herein and recovering the antibody from the culture.

In one embodiment, the present invention provides a process for producing an anti-FGFR2 antibody drug conjugate comprising: (a) chemically linking SMCC to a drug moiety DM-1; (b) conjugating said linker-drug to the antibody recovered from the cell culture; and (c) purifying the antibody drug conjugate. In some embodiments, the antibody drug conjugates made according the process have an average DAR, measured with a UV spectrophotometer, about 3.5.

The present invention also provides diagnostic reagents comprising an antibody or antigen binding fragment described herein, or the antibody drug conjugate described herein which is labeled. In some embodiments, the label is selected from the group consisting of a radiolabel, a fluorophore, a chromophore, an imaging agent, and a metal ion.

DEFINITIONS

Unless stated otherwise, the following terms and phrases as used herein are intended to have the following meanings:

The term "alkyl" refers to a monovalent saturated hydrocarbon chain having the specified number of carbon atoms. For example, $C_{1-6}$ alkyl refers to an alkyl group having from 1 to 6 carbon atoms. Alkyl groups may be straight or branched. Representative branched alkyl groups have one, two, or three branches. Examples of alkyl groups include, but are not limited to, methyl, ethyl, propyl (n-propyl and isopropyl), butyl (n-butyl, isobutyl, sec-butyl, and t-butyl), pentyl (n-pentyl, isopentyl, and neopentyl), and hexyl.

The term "antibody" as used herein refers to a polypeptide of the immunoglobulin family that is capable of binding a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antibody" includes, but is not limited to, monoclonal antibodies, human antibodies, humanized antibodies, chimeric antibodies, and anti-idiotypic (anti-Id) antibodies (including, e.g., anti-Id antibodies to antibodies of the invention). The antibodies can be of any isotype/class (e.g., IgG, IgE, IgM, IgD, IgA and IgY), or subclass (e.g., IgG1, IgG2, IgG3, IgG4, IgA1 and IgA2).

"Complementarity-determining domains" or "complementary-determining regions" ("CDRs") interchangeably refer to the hypervariable regions of VL and VH. The CDRs are the target protein-binding site of the antibody chains that harbors specificity for such target protein. There are three CDRs (CDR1-3, numbered sequentially from the N-terminus) in each human VL or VH, constituting about 15-20% of the variable domains. The CDRs are structurally complementary to the epitope of the target protein and are thus directly responsible for the binding specificity. The remaining stretches of the VL or VH, the so-called framework regions, exhibit less variation in amino acid sequence (Kuby, Immunology, 4th ed., Chapter 4. W.H. Freeman & Co., New York, 2000).

The positions of the CDRs and framework regions can be determined using various well known definitions in the art, e.g., Kabat, Chothia, international ImMunoGeneTics database (IMGT) (on the worldwide web at imgt.cines.fr/), and AbM (see, e.g., Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J. Mol. Biol., 273:927-748 (1997)). Definitions of antigen combining sites are also described in the following: Ruiz et al., Nucleic Acids Res., 28:219-221 (2000); and Lefranc, M. P., Nucleic Acids Res., 29:207-209 (2001); MacCallum et al., J. Mol. Biol., 262:732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996).

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and CL domains actually comprise the carboxy-terminal domains of the heavy and light chain, respectively.

The term "antigen binding fragment", as used herein, refers to one or more portions of an antibody that retain the ability to specifically interact with (e.g., by binding, steric hindrance, stabilizing/destabilizing, spatial distribution) an epitope of an antigen. Examples of binding fragments include, but are not limited to, single-chain Fvs (scFv), camelid antibodies, disulfide-linked Fvs (sdFv), Fab fragments, F(ab') fragments, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., Nature 341:544-546, 1989), which consists of a VH domain; and an isolated complementarity determining region (CDR), or other epitope-binding fragments of an antibody.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFv"); see, e.g., Bird et al., Science 242:423-426, 1988; and Huston et al., Proc. Natl. Acad. Sci. 85:5879-5883, 1988). Such single chain antibodies are also intended to be encompassed within the term "antigen binding fragment." These antigen binding fragments are obtained using conventional techniques known to those of skill in the art, and the fragments are screened for utility in the same manner as are intact antibodies.

Antigen binding fragments can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can be grafted into scaffolds based on polypeptides such as fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., Protein Eng. 8:1057-1062, 1995; and U.S. Pat. No. 5,641,870).

The term "monoclonal antibody" or "monoclonal antibody composition" as used herein refers to polypeptides, including antibodies and antigen binding fragments that have substantially identical amino acid sequence or are derived from the same genetic source. This term also includes preparations of antibody molecules of single molecular composition. A monoclonal antibody composition displays a single binding specificity and affinity for a particular epitope.

The term "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000).

The human antibodies of the invention may include amino acid residues not encoded by human sequences (e.g., mutations introduced by random or site-specific mutagenesis in vitro or by somatic mutation in vivo, or a conservative substitution to promote stability or manufacturing).

The term "recognize" as used herein refers to an antibody or antigen binding fragment thereof that finds and interacts (e.g., binds) with its epitope, whether that epitope is linear or conformational. The term "epitope" refers to a site on an antigen to which an antibody or antigen binding fragment of the invention specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art, for example, x-ray crystallography and 2-dimensional nuclear magnetic resonance (see, e.g., Epitope Mapping Protocols in Methods in Molecular Biology, Vol. 66, G. E. Morris, Ed. (1996)).

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "isolated antibody" refers to an antibody that is substantially free of other antibodies having different antigenic specificities. An isolated antibody that specifically binds to one antigen may, however, have cross-reactivity to other antigens. Moreover, an isolated antibody may be substantially free of other cellular material and/or chemicals.

The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other all other known variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementarity determining regions only, framework and complementarity determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 92%, 93%, 94%, 95%, 96%, 97%, 98%, 99%, or 100% sequence identity with the reference variable region nucleic acid or amino acid sequence. Corresponding human germline sequences can be determined, for example, through the publicly available international ImMunoGeneTics database (IMGT) (on the worldwide web at imgt.cines.fr/) and V-base (on the worldwide web at vbase.mrc-cpe.cam.ac.uk).

The phrase "specifically binds" or "selectively binds," when used in the context of describing the interaction between an antigen (e.g., a protein) and an antibody, antibody fragment, or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the antibodies or binding agents with a particular binding specificity bind to a particular antigen at least two times the background and do not substantially bind in a significant amount to other antigens present in the sample. In one embodiment, under designated immunoassay conditions, the antibody or binding agent with a particular binding specificity binds to a particular antigen at least ten (10) times the background and does not substantially bind in a significant amount to other antigens present in the sample. Specific binding to an antibody or binding agent under such conditions may require the antibody or agent to have been selected for its specificity for a particular protein. As desired or appropriate, this selection may be achieved by subtracting out antibodies that cross-react with molecules from other species (e.g., mouse or rat) or other subtypes. Alternatively, in some embodiments, antibodies or antibody fragments are selected that cross-react with certain desired molecules.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least 10 to 100 times over the background.

The term "equilibrium dissociation constant (KD, M)" refers to the dissociation rate constant (kd, time−1) divided by the association rate constant (ka, time−1, M−1). Equilibrium dissociation constants can be measured using any known method in the art. The antibodies of the present invention generally will have an equilibrium dissociation constant of less than about $10^{-7}$ or $10^{-8}$ M, for example, less than about $10^{-9}$ M or $10^{-10}$ M, in some embodiments, less than about $10^{-11}$ M, $10^{-12}$ M or $10^{-13}$ M.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

As used herein, the phrase "consisting essentially of" refers to the genera or species of active pharmaceutical agents included in a method or composition, as well as any excipients inactive for the intended purpose of the methods or compositions. In some embodiments, the phrase "consisting essentially of" expressly excludes the inclusion of one or more additional active agents other than an antibody drug conjugate of the invention. In some embodiments, the phrase "consisting essentially of" expressly excludes the inclusion of one or more additional active agents other than an antibody drug conjugate of the invention and a second co-administered agent.

The term "amino acid" refers to naturally occurring, synthetic, and unnatural amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The term "optimized" as used herein refers to a nucleotide sequence that has been altered to encode an amino acid sequence using codons that are preferred in the production cell or organism, generally a eukaryotic cell, for example, a yeast cell, a *Pichia* cell, a fungal cell, a *Trichoderma* cell, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence.

The terms "percent identical" or "percent identity," in the context of two or more nucleic acids or polypeptide sequences, refers to the extent to which two or more sequences or subsequences that are the same. Two sequences are "identical" if they have the same sequence of amino acids or nucleotides over the region being compared. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 30 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, Adv. Appl. Math. 2:482c (1970), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, 2003).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=-4 and a comparison of both strands. For amino acid sequences, the BLASTP program uses as defaults a word length of 3, and expectation (E) of 10, and the BLOSUM62 scoring matrix (see Henikoff and Henikoff, (1989) Proc. Natl. Acad. Sci. USA 89:10915) alignments (B) of 50, expectation (E) of 10, M=5, N=-4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller, Comput. Appl. Biosci. 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch, J. Mol. Biol. 48:444-453, 1970) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., (1991) Nucleic Acid Res. 19:5081; Ohtsuka et al., (1985) J. Biol. Chem. 260:2605-2608; and Rossolini et al., (1994) Mol. Cell. Probes 8:91-98).

The term "operably linked" in the context of nucleic acids refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "immunoconjugate" or "antibody drug conjugate" as used herein refers to the linkage of an antibody or an antigen binding fragment thereof with another agent, such as a chemotherapeutic agent, a toxin, an immunotherapeutic agent, an imaging probe, and the like. The linkage can be covalent bonds, or non-covalent interactions such as through electrostatic forces. Various linkers, known in the art, can be employed in order to form the immunoconjugate. Additionally, the immunoconjugate can be provided in the form of a fusion protein that may be expressed from a polynucleotide encoding the immunoconjugate. As used herein, "fusion protein" refers to proteins created through the joining of two or more genes or gene fragments which originally coded for separate proteins (including peptides and polypeptides). Translation of the fusion gene results in a single protein with functional properties derived from each of the original proteins.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The term "cytotoxin", or "cytotoxic agent" as used herein, refers to any agent that is detrimental to the growth and proliferation of cells and may act to reduce, inhibit, or destroy a cell or malignancy.

The term "anti-cancer agent" as used herein refers to any agent that can be used to treat a cell proliferative disorder such as cancer, including but not limited to, cytotoxic agents, chemotherapeutic agents, radiotherapy and radiotherapeutic agents, targeted anti-cancer agents, and immunotherapeutic agents.

The term "drug moiety" or "payload" as used herein refers to a chemical moiety that is conjugated to an antibody or antigen binding fragment of the invention, and can include any therapeutic or diagnostic agent, for example, an anti-cancer, anti-inflammatory, anti-infective (e.g., anti-fungal, antibacterial, anti-parasitic, anti-viral), or an anesthetic agent. In certain embodiments, a drug moiety is selected from a V-ATPase inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, an inhibitor of phosphoryl transfer reactions in mitochondria, a protein synthesis inhibitor, a kinase inhibitor, a CDK2 inhibitor, a CDK9 inhibitor, a proteasome inhibitor, a kinesin inhibitor, an HDAC inhibitor, a DNA damaging agent, a DNA alkylating agent, a DNA intercalator, a DNA minor groove binder and a DHFR inhibitor. Methods for attaching each of these to a linker compatible with the antibodies and method of the invention are known in the art. See, e.g., Singh et al., (2009) Therapeutic Antibodies: Methods and Protocols, vol. 525, 445-457. In addition, a payload can be a biophysical probe, a fluorophore, a spin label, an infrared probe, an affinity probe, a chelator, a spectroscopic probe, a radioactive probe, a lipid molecule, a polyethylene glycol, a polymer, a spin label, DNA, RNA, a protein, a peptide, a surface, an antibody, an antibody fragment, a nanoparticle, a quantum dot, a liposome, a PLGA particle, a saccharide or a polysaccharide.

The term "maytansinoid drug moiety" means the substructure of an antibody-drug conjugate that has the structure of a maytansinoid compound. Maytansine was first isolated from the east African shrub *Maytenus serrata* (U.S. Pat. No. 3,896, 111). Subsequently, it was discovered that certain microbes also produce maytansinoids, such as maytansinol and C-3 maytansinol esters (U.S. Pat. No. 4,151,042). Synthetic maytansinol and maytansinol analogues have been reported. See U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, and Kawai et al (1984) Chem. Pharm. Bull. 3441-3451), each of which are expressly incorporated by reference. Examples of specific maytansinoids useful for conjugation include DM1, DM3, and DM4.

"Tumor" refers to neoplastic cell growth and proliferation, whether malignant or benign, and all pre-cancerous and cancerous cells and tissues.

The term "anti-tumor activity" means a reduction in the rate of tumor cell proliferation, viability, or metastatic activity. For example, anti-tumor activity can be shown by a decline in growth rate of abnormal cells that arises during therapy or tumor size stability or reduction, or longer survival due to therapy as compared to control without therapy. Such activity can be assessed using accepted in vitro or in vivo tumor models, including but not limited to xenograft models, allograft models, MMTV models, and other known models known in the art to investigate anti-tumor activity.

The term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas.

The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

The term "FGFR2" refers to fibroblast growth factor receptor 2 that is a member of the receptor tyrosine kinase superfamily. The nucleic acid and amino acid sequences of FGFR2 are known, and have been published in GenBank Accession Nos. NM_000141.4, NM_001144913.1, NM_001144914.1, NM_001144915.1, NM_001144916.1, NM_001144917.1, NM_001144918.1, NM_001144919.1, NM_022970.3, NM_023029.2. Structurally, a FGFR2 amino acid sequence is a receptor tyrosine kinase protein having a signal peptide that is cleaved off, at least one or more immunoglobulin (Ig)-like domains, an acidic box, a transmembrane domain, and a split tyrosine kinase domain and has over its full length at least about 90%, 91%, 92%, 93%, 94%, 95%, 96%, 97%, 98%, 99%, or 100% sequence identity with the amino acid sequence of GenBank accession numbers NM_000141.4, NM_001144913.1, NM_001144914.1, NM_001144915.1, NM_001144916.1, NM_001144917.1, NM_001144918.1, NM_001144919.1, NM_022970.3, NM_023029.2. Structurally, a FGFR2 nucleic acid sequence has over its full length at least about 90%, 91%, 92%, 93%, 94%, 95%, 96%, 97%, 98%, 99%, or 100% sequence identity with the nucleic acid sequence of GenBank accession numbers NM_000141.4, NM_001144913.1, NM_001144914.1, NM_001144915.1, NM_001144916.1, NM_001144917.1, NM_001144918.1, NM_001144919.1, NM_022970.3, NM_023029.2.

The terms "FGFR2 expressing cancer" or "FGFR2 positive cancer" refers to a cancer that express FGFR2 or a mutation form of FGFR2 on the surface of cancer cells.

As used herein, the terms "treat," "treating," or "treatment" of any disease or disorder refer in one embodiment, to ameliorating the disease or disorder (i.e., slowing or arresting or reducing the development of the disease or at least one of the clinical symptoms thereof). In another embodiment, "treat," "treating," or "treatment" refers to alleviating or ameliorating at least one physical parameter including those which may not be discernible by the patient. In yet another embodiment, "treat," "treating," or "treatment" refers to modulating the disease or disorder, either physically, (e.g., stabilization of a discernible symptom), physiologically, (e.g., stabilization of a physical parameter), or both. In yet another embodiment, "treat," "treating," or "treatment" refers to preventing or delaying the onset or development or progression of the disease or disorder.

The term "therapeutically acceptable amount" or "therapeutically effective dose" interchangeably refers to an amount sufficient to effect the desired result (i.e., a reduction in tumor size, inhibition of tumor growth, prevention of metastasis, inhibition or prevention of viral, bacterial, fungal or parasitic infection). In some embodiments, a therapeutically acceptable amount does not induce or cause undesirable side effects. In some embodiments, a therapeutically acceptable amount induces or causes side effects but only those that are acceptable by the healthcare providers in view of a patient's condition. A therapeutically acceptable amount can be determined by first administering a low dose, and then incrementally increasing that dose until the desired effect is achieved. A "prophylactically effective dosage," and a "therapeutically effective dosage," of the molecules of the invention can prevent the onset of, or result in a decrease in severity of, respectively, disease symptoms, including symptoms associated with cancer.

The term "co-administer" refers to the presence of two active agents in the blood of an individual. Active agents that are co-administered can be concurrently or sequentially delivered.

DETAILED DESCRIPTION OF THE INVENTION

Figure 1:
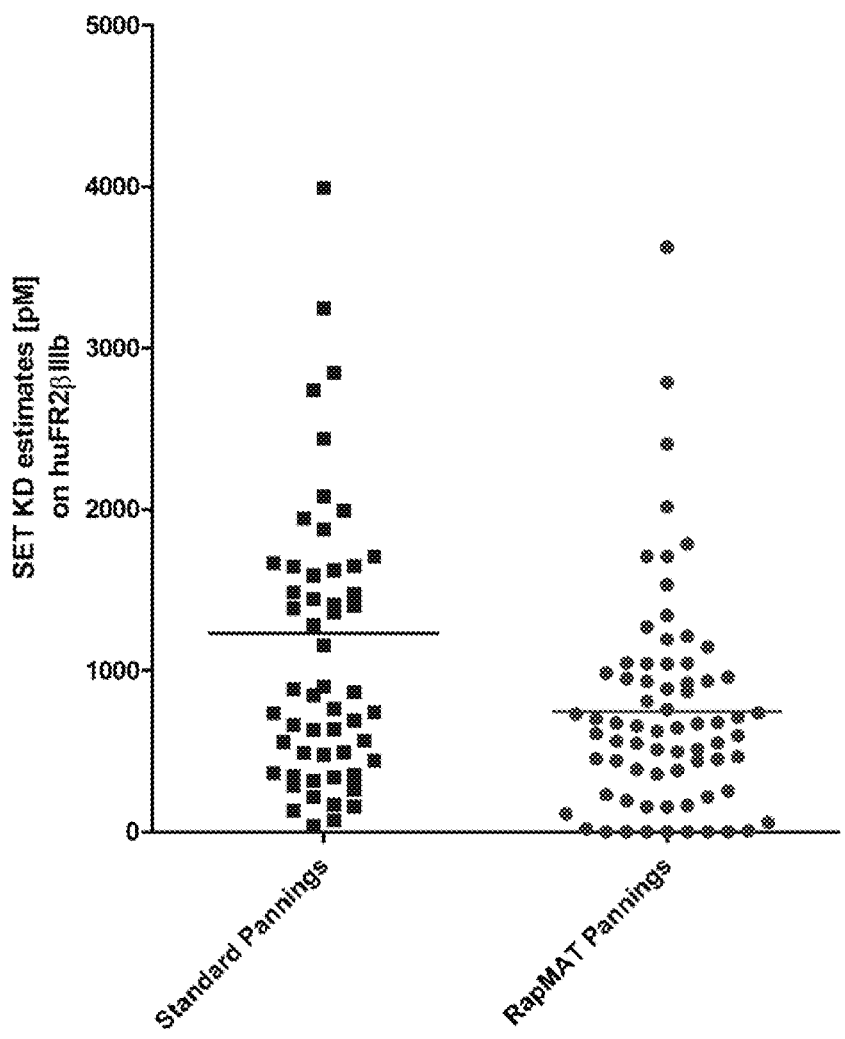
FIG. 1 shows affinity estimates for a panel of antibodies to recombinant human FGFR2 IIIb.

The present invention provides antibodies, antibody fragments (e.g., antigen binding fragments), and antibody drug conjugates that bind to FGFR2. In particular, the present invention provides antibodies and antibody fragments (e.g., antigen binding fragments) that bind to FGFR2, and internalize upon such binding. The antibodies and antibody fragments (e.g., antigen binding fragments) of the present invention can be used for producing antibody drug conjugates. Furthermore, the present invention provides antibody drug conjugates that have desirable pharmacokinetic characteristics and other desirable attributes, and thus can be used for treating cancer expressing FGFR2, such as gastric cancer, breast cancer, lung cancer, colon cancer and endometrial cancer. The present invention further provides pharmaceutical compositions comprising the antibody drug conjugates of the invention, and methods of making and using such pharmaceutical compositions for the treatment of cancer.

Antibody Drug Conjugates

The present invention provides antibody drug conjugates, where an antibody, antigen binding fragment or its functional equivalent that specifically binds to FGFR2 is linked to a drug moiety. In one aspect, the antibodies, antigen binding fragments or their functional equivalents of the invention are linked, via covalent attachment by a linker, to a drug moiety that is an anti-cancer agent. The antibody drug conjugates of the invention can selectively deliver an effective dose of an anti-cancer agent (e.g., a cytotoxic agent) to tumor tissues expressing FGFR2, whereby greater selectivity (and lower efficacious dose) may be achieved.

In one aspect, the invention provides an immunoconjugate of Formula (I):

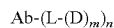

Wherein Ab represents an FGFR2 binding antibody or antibody fragment (e.g., antigen binding fragment) described herein;
L is a linker;
D is a drug moiety;
m is an integer from 1-8; and
n is an integer from 1-20. In one embodiment, n is an integer from 1 to 10, 2 to 8, or 2 to 5. In a specific embodiment, n is 3 to 4. In some embodiments, m is 1. In some embodiments, m is 2, 3 or 4.

While the drug to antibody ratio has an exact value for a specific conjugate molecule (e.g., n multiplied by m in Formula (I)), it is understood that the value will often be an average value when used to describe a sample containing many molecules, due to some degree of inhomogeneity, typically associated with the conjugation step. The average loading for a sample of an immunoconjugate is referred to herein as the drug to antibody ratio, or "DAR." In some embodiments, when the drug is maytansinoid, it is referred to as "MAR." In some embodiments, the DAR is between about 1 and about 5, and typically is about 3, 3.5, 4, 4.5, or 5. In some embodiments, at least 50% of a sample by weight is compound having the average DAR plus or minus 2, and preferably at least 50% of the sample is a conjugate that contains the average DAR plus or minus 1. Preferred embodiments include immunoconjugates wherein the DAR is about 3.5. In some embodiments, a DAR of 'about n' means the measured value for DAR is within 20% of n.

The present invention is also directed to immunoconjugates comprising the antibodies, antibody fragments (e.g., antigen binding fragments) and their functional equivalents as disclosed herein, linked or conjugated to a drug moiety. In one embodiment, the drug moiety D is a maytansinoid drug moiety, including those having the structure:

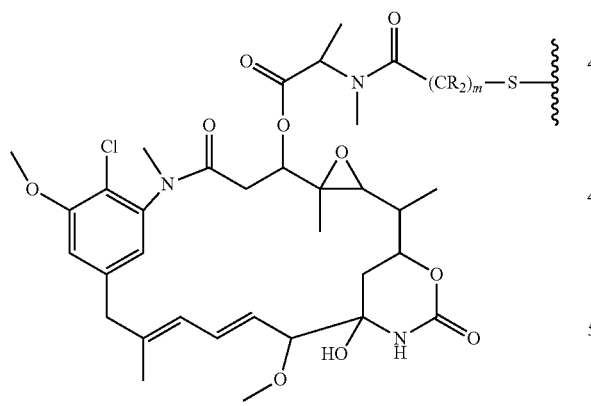

where the wavy line indicates the covalent attachment of the sulfur atom of the maytansinoid to a linker of an antibody drug conjugate. R at each occurrence is independently H or a $C_1$-$C_6$ alkyl. The alkylene chain attaching the amide group to the sulfur atom may be methanyl, ethanyl, or proyl, i.e. m is 1, 2, or 3. (U.S. Pat. No. 633,410, U.S. Pat. No. 5,208,020, Chari et al. (1992) Cancer Res. 52; 127-131, Lui et al. (1996) Proc. Natl. Acad. Sci. 93:8618-8623).

All stereoisomers of the maytansinoid drug moiety are contemplated for the immunoconjugates of the invention, i.e. any combination of R and S configurations at the chiral carbons of the maytansinoid. In one embodiment the maytansinoid drug moiety has the following stereochemistry.

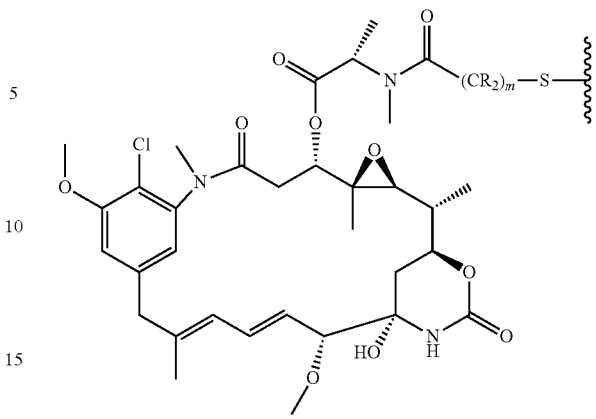

In one embodiment, the maytansinoid drug moiety is $N^{2'}$-deacetyl-$N^{2'}$-(3-mercapto-1-oxopropyl)-maytansine (also known as DM1). DM1 is represented by the following structural formula.

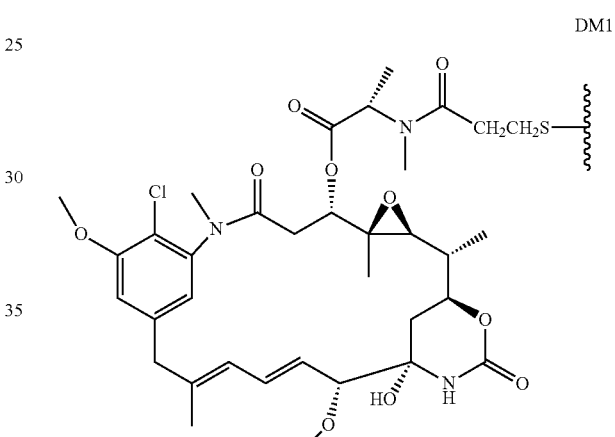

In another embodiment the maytansinoid drug moiety is $N^{2'}$-deacetyl-$N^{2'}$-(4-mercapto-1-oxopentyl)-maytansine (also known as DM3). DM3 is represented by the following structural formula.

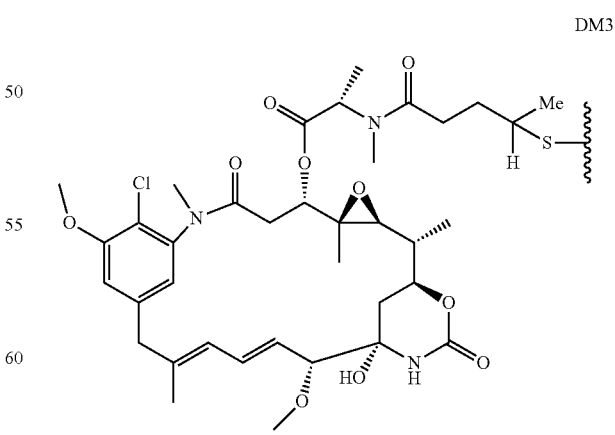

In another embodiment the maytansinoid drug moiety is $N^{2'}$-deacetyl-$N^{2'}$-(4-methyl-4-mercapto-1-oxopentyl)-maytansine (also known as DM4). DM4 is represented by the following structural formula.

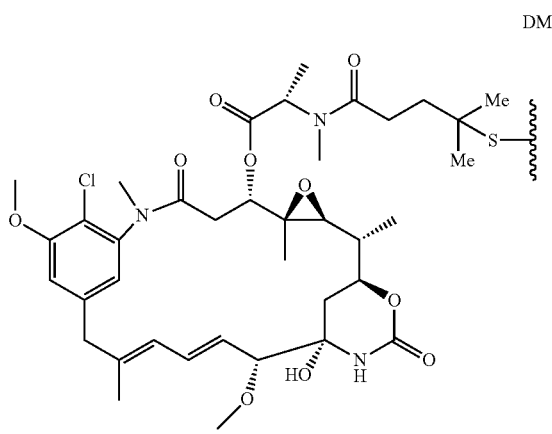

DM4

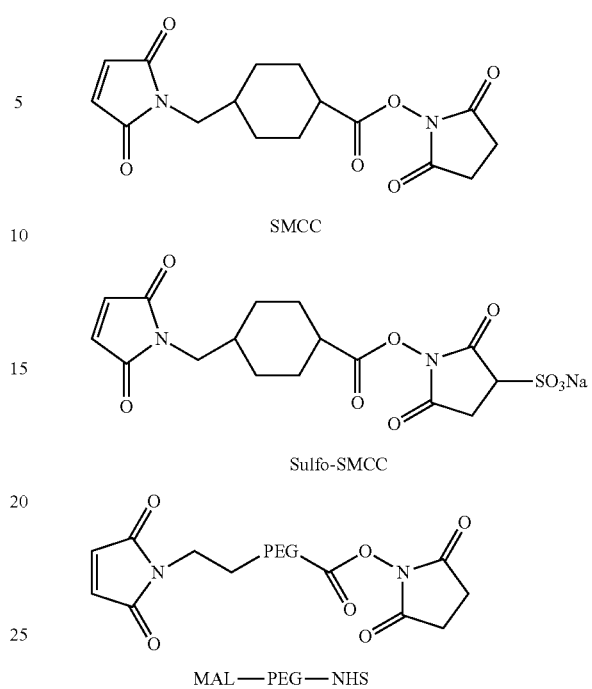

SMCC

Sulfo-SMCC

MAL—PEG—NHS

The drug moiety D can be linked to the antibody Ab through linker L. L is any chemical moiety capable of linking the drug moiety to the antibody through covalent bonds. A cross-linking reagent is a bifunctional or multifunctional reagent that can be used to link a drug moiety and an antibody to form antibody drug conjugates. Antibody drug conjugates can be prepared using a cross-linking reagent having a reactive functionality capable of binding to both the drug moiety and the antibody. For example, a cysteine, thiol or an amine, e.g. N-terminus or an amino acid side chain, such as lysine of the antibody, can form a bond with a functional group of a cross-linking reagent.

In one embodiment, L is a cleavable linker. In another embodiment, L is a non-cleavable linker. In some embodiments, L is an acid-labile linker, photo-labile linker, peptidase cleavable linker, esterase cleavable linker, a disulfide bond cleavable linker, a hydrophilic linker, a procharged linker, or a dicarboxylic acid based linker.

Suitable cross-linking reagents that form a non-cleavable linker between the drug moiety, for example maytansinoid, and the antibody are well known in the art, and can form non-cleavable linkers that comprise a sulfur atom (such as SMCC) or those that are without a sulfur atom. Preferred cross-linking reagents that form non-cleavable linkers between the drug moiety, for example maytansinoid, and the antibody comprise a maleimido- or haloacetyl-based moiety. According to the present invention, such non-cleavable linkers are said to be derived from maleimido- or haloacetyl-based moieties.

Cross-linking reagents comprising a maleimido-based moiety include but not limited to, N-succinimidyl-4-(maleimidomethyl)cyclohexanecarboxylate (SMCC), sulfosuccinimidyl 4-(N-maleimidomethyl)cyclohexane-1-carboxylate (sulfo-SMCC), N-succinimidyl-4-(maleimidomethyl)cyclohexane-1-carboxy-(6-amidocaproate), which is a "long chain" analog of SMCC (LC-SMCC), κ-maleimidoundeconoic acid N-succinimidyl ester (KMUA), γ-maleimidobutyric acid N-succinimidyl ester (GMBS), ε-maleimidocaproic acid N-succinimidyl ester (EMCS), m-maleimidobenzoyl-N-hydroxysuccinimide ester (MBS), N-(α-maleimidoacetoxy)-succinimide ester (AMSA), succinimidyl-6-(β-maleimidopropionamido)hexanoate (SMPH), N-succinimidyl-4-(p-maleimidophenyl)-butyrate (SMPB), N-(-p-maleomidophenyl)isocyanate (PMIP) and maleimido-based cross-linking reagents containing a polyethythene glycol spacer, such as MAL-PEG-NHS. These cross-linking reagents form non-cleavable linkers derived from maleimido-based moieties. Representative structures of maleimido-based cross-linking reagents are shown below.

In another embodiment, the linker L is derived from N-succinimidyl-4-(maleimidomethyl)cyclohexanecarboxylate (SMCC), sulfosuccinimidyl 4-(N-maleimidomethyl)cyclohexane-1-carboxylate (sulfo-SMCC) or MAL-PEG-NHS.

Cross-linking reagents comprising a haloacetyle-based moiety include N-succinimidyl iodoacetate (SIA), N-succinimidyl(4-iodoacetyl)aminobenzoate (SIAB), N-succinimidyl bromoacetate (SBA) and N-succinimidyl 3-(bromoacetamido)propionate (SBAP). These cross-linking reagents form a non-cleavable linker derived from haloacetyl-based moieties. Representative structures of haloacetyl-based cross-linking reagents are shown below.

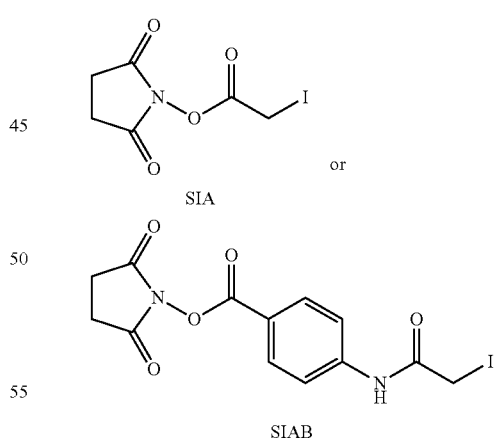

SIA or

SIAB

In one embodiment, the linker L is derived from N-succinimidyl iodoacetate (SIA) or N-succinimidyl(4-iodoacetyl) aminobenzoate (SIAB).

Suitable cross-linking reagents that form a cleavable linker between the drug moiety, for example maytansinoid, and the antibody are well known in the art. Disulfide containing linkers are linkers cleavable through disulfide exchange, which can occur under physiological conditions. According to the present invention, such cleavable linkers are said to be derived from disulfide-based moieties. Suitable disulfide cross-linking reagents include N-succinimidyl-3-(2-pyridyldithio)propionate (SPDP), N-succinimidyl-4-(2-pyridyldithio)pentanoate (SPP), N-succinimidyl-4-(2-pyridyldithio)butanoate (SPDB) and N-succinimidyl-4-(2-pyridyldithio)-2-sulfo-butanoate (sulfo-SPDB), the structures of which are shown below. These disulfide cross-linking reagents form a cleavable linker derived from disulfide-based moieties.

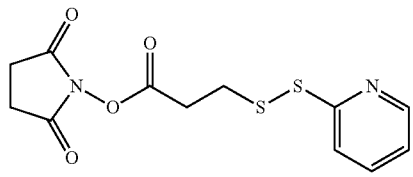

N-succinimidyl-3-(2-pyridyldithio)propionate (SPDP)

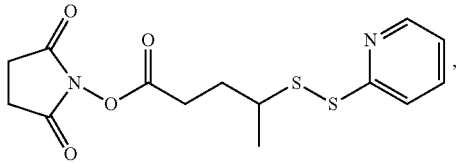

N-succinimidyl-4-(2-pyridyldithio)pentanoate (SPP)

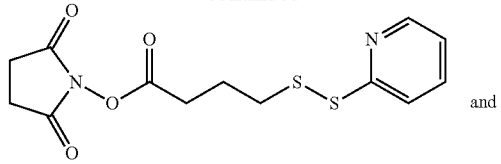

and

N-succinimidyl-4-(2-pyridyldithio)butanoate (SPDB)

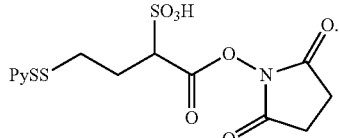

N-succinimidyl-4-(2-pyridyldithio)-2-sulfo-butanoate (sulfo-SPDB)

In one embodiment, the linker L is derived from N-succinimidyl-4-(2-pyridyldithio)butanoate (SPDB).

Suitable cross-linking reagents that form a charged linker between the drug moiety, for example maytansinoid, and the antibody are known as procharged cross-linking reagents. In one embodiment, the linker L is derived from the procharged cross-linking reagent CX1-1. The structure of CX1-1 is below.

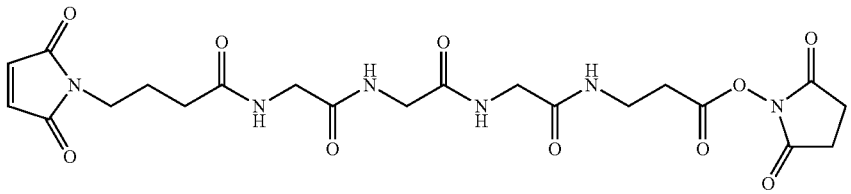 [SMILES: O=C(CCCN1C(=O)C=CC1=O)NCC(=O)NCC(=O)NCC(=O)NCCC(=O)ON1C(=O)CCC1=O]

2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1)

Each of the cross-linking reagents depicted above contains, at one end of the cross-linking reagent, a NHS-ester which reacts with a primary amine of the antibody to form an amide bond and, at the other end, a maleimide group or pyridinyldisulfide group which reacts with the sulfhydryl of the maytansionoid drug moiety to form a thioether or disulfide bond.

In one embodiment, the conjugate of the present invention is represented by any one of the following structural formulae

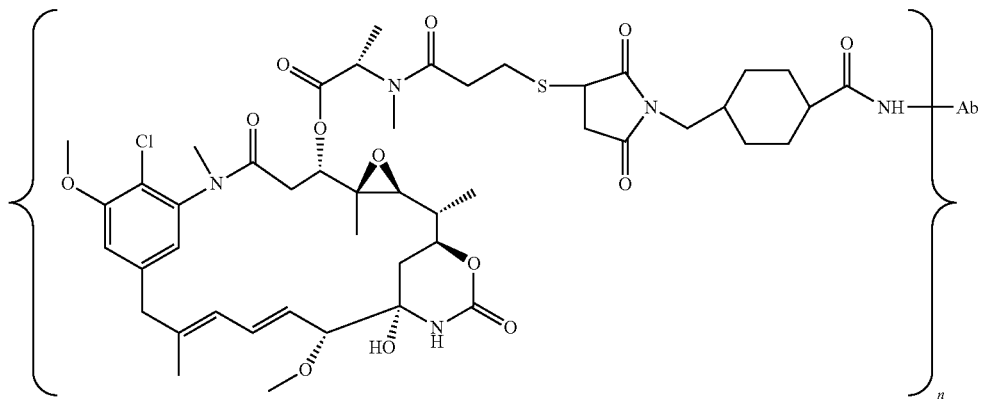

Ab-MCC-DM1

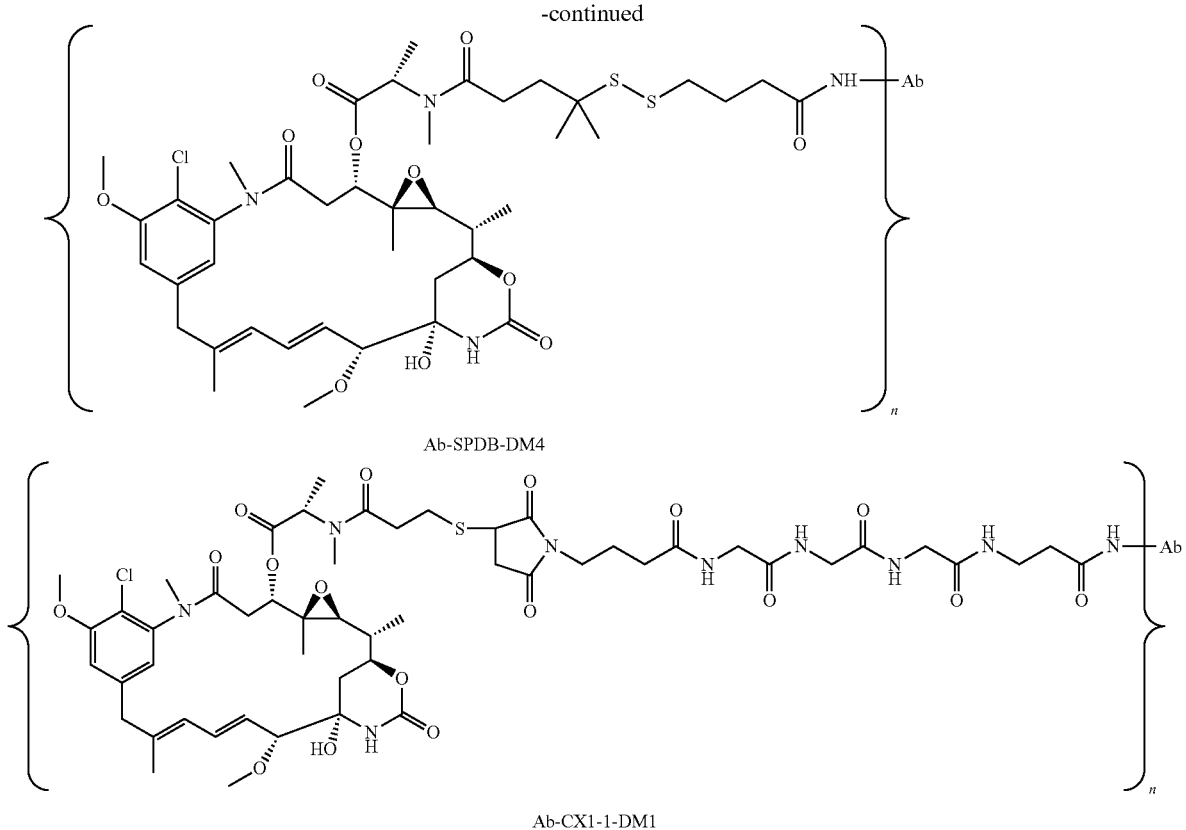

Ab-SPDB-DM4

Ab-CX1-1-DM1 wherein:

Ab is an antibody or antigen binding fragment thereof that specifically binds to human FGFR2;

n, which indicates the number of D-L groups attached the Ab through the formation of an amide bond with a primary amine of the Ab, is an integer from 1 to 20. In one embodiment, n is an integer from 1 to 10, 2 to 8 or 2 to 5. In a specific embodiment, n is 3 or 4.

In one embodiment, the average molar ratio of drug (e.g., DM1 or DM4) to the antibody in the conjugate (i.e., average n value, also known as Maytanisnoid Antibody Ratio (MAR)) is about 1 to about 10, about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, or 8.1), about 2.5 to about 7, about 3 to about 5, about 2.5 to about 4.5 (e.g., about 2.5, about 2.6, about 2.7, about 2.8, about 2.9, about 3.0, about 3.1, about 3.3, about 3.4, about 3.5, about 3.6, about 3.7, about 3.8, about 3.9, about 4.0, about 4.1, about 4.2, about 4.3, about 4.4, about 4.5), about 3.0 to about 4.0, about 3.2 to about 4.2, or about 4.5 to 5.5 (e.g., about 4.5, about 4.6, about 4.7, about 4.8, about 4.9, about 5.0, about 5.1, about 5.2, about 5.3, about 5.4, or about 5.5).

In one aspect of the invention, the conjugate of the present invention has substantially high purity and has one or more of the following features: (a) greater than about 90% (e.g., greater than or equal to about 91%, 92%, 93%, 94%, 95%, 96%, 97%, 98%, 99%, or 100%), preferably greater than about 95%, of conjugate species are monomeric, (b) unconjugated linker level in the conjugate preparation is less than about 10% (e.g., less than or equal to about 9%, 8%, 7%, 6%, 5%, 4%, 3%, 2%, 1%, or 0%) (relative to total linker), (c) less than 10% of conjugate species are crosslinked (e.g., less than or equal to about 9%, 8%, 7%, 6%, 5%, 4%, 3%, 2%, 1%, or 0%), (d) free drug (e.g., DM1 or DM4) level in the conjugate preparation is less than about 2% (e.g., less than or equal to about 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, or 0%) (mol/mol relative to total cytotoxic agent) and/or (e) no substantial increase in the level of free drug (e.g., DM1 or DM4) occurs upon storage (e.g., after about 1 week, about 2 weeks, about 3 weeks, about 1 month, about 2 months, about 3 months, about 4 months, about 5 months, about 6 months, about 1 year, about 2 years, about 3 years, about 4 years, or about 5 years). "Substantial increase" in the level of free drug (e.g., DM1 or DM4) means that after certain storage time (e.g., about 1 week, about 2 weeks, about 3 weeks, about 1 month, about 2 months, about 3 months, about 4 months, about 5 months, about 6 months, about 1 year, about 2 years, about 3 years, about 4 years, or about 5 years), the increase in the level of free drug (e.g., DM1 or DM4) is less than about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.2%, about 2.5%, about 2.7%, about 3.0%, about 3.2%, about 3.5%, about 3.7%, or about 4.0%.

As used herein, the term "unconjugated linker" refers to the antibody that is covalently linked with a linker derived from a cross-linking reagent (e.g., SMCC, Sulfo-SMCC, SPDB, Sulfo-SPDB or CX1-1), wherein the antibody is not covalently coupled to the drug (e.g., DM1 or DM4) through a linker (i.e., the "unconjugated linker" can be represented by Ab-MCC, Ab-SPDB, or Ab-CX1-1).

1. Drug Moiety

The present invention provides immunoconjugates that specifically bind to FGFR2. The immunoconjugates of the invention comprise anti-FGFR2 antibodies, antibody fragments (e.g., antigen binding fragments) or functional equivalents that are conjugated to a drug moiety, e.g., an anti-cancer agent, an autoimmune treatment agent, an anti-inflammatory agent, an antifungal agent, an antibacterial agent, an antiparasitic agent, an anti-viral agent, or an anesthetic agent. The antibodies, antibody fragments (e.g., antigen binding fragments) or functional equivalents of the invention can be conjugated to several identical or different drug moieties using any methods known in the art.

In certain embodiments, the drug moiety of the immunoconjugates of the present invention is selected from a group consisting of a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizers, an auristatin, a dolastatin, a maytansinoid, a MetAP (methionine aminopeptidase), an inhibitor of nuclear export of proteins CRM1, a DPPIV inhibitor, proteasome inhibitors, an inhibitors of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder and a DHFR inhibitor.

In one embodiment, the drug moiety of the immunoconjugates of the present invention is a maytansinoid drug moiety, such as but not limited to, DM1, DM3, or DM4.

Further, the antibodies, antibody fragments (e.g., antigen binding fragments) or functional equivalents of the present invention may be conjugated to a drug moiety that modifies a given biological response. Drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, pseudomonas exotoxin, cholera toxin, or diphtheria toxin, a protein such as tumor necrosis factor, α-interferon, β-interferon, nerve growth factor, platelet derived growth factor, tissue plasminogen activator, a cytokine, an apoptotic agent, an anti-angiogenic agent, or, a biological response modifier such as, for example, a lymphokine.

In one embodiment, the antibodies, antibody fragments (e.g., antigen binding fragments) or functional equivalents of the present invention are conjugated to a drug moiety, such as a cytotoxin, a drug (e.g., an immunosuppressant) or a radiotoxin. Examples of cytotoxin include but are not limited to, taxanes (see, e.g., International (PCT) Patent Application Nos. WO 01/38318 and PCT/US03/02675), DNA-alkylating agents (e.g., CC-1065 analogs), anthracyclines, tubulysin analogs, duocarmycin analogs, auristatin E, auristatin F, maytansinoids, and cytotoxic agents comprising a reactive polyethylene glycol moiety (see, e.g., Sasse et al., J. Antibiot. (Tokyo), 53, 879-85 (2000), Suzawa et al., Bioorg. Med. Chem., 8, 2175-84 (2000), Ichimura et al., J. Antibiot. (Tokyo), 44, 1045-53 (1991), Francisco et al., Blood (2003) (electronic publication prior to print publication), U.S. Pat. Nos. 5,475,092, 6,340,701, 6,372,738, and 6,436,931, U.S. Patent Application Publication No. 2001/0036923 A1, Pending U.S. patent application Ser. Nos. 10/024,290 and 10/116,053, and International (PCT) Patent Application No. WO 01/49698), taxon, cytochalasin B, gramicidin D, ethidium bromide, emetine, mitomycin, etoposide, tenoposide, vincristine, vinblastine, t. colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, anti-metabolites (e.g., methotrexate, 6-mercaptopurine, 6-thioguanine, cytarabine, 5-fluorouracil decarbazine), ablating agents (e.g., mechlorethamine, thiotepa chlorambucil, meiphalan, carmustine (BSNU) and lomustine (CCNU), cyclophosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). (See e.g., Seattle Genetics US20090304721).

Other examples of cytotoxins that can be conjugated to the antibodies, antibody fragments (antigen binding fragments) or functional equivalents of the invention include duocarmycins, calicheamicins, maytansines and auristatins, and derivatives thereof.

Various types of cytotoxins, linkers and methods for conjugating therapeutic agents to antibodies are known in the art, see, e.g., Saito et al., (2003) Adv. Drug Deliv. Rev. 55:199-215; Trail et al., (2003) Cancer Immunol. Immunother. 52:328-337; Payne, (2003) Cancer Cell 3:207-212; Allen, (2002) Nat. Rev. Cancer 2:750-763; Pastan and Kreitman, (2002) Cuff. Opin. Investig. Drugs 3:1089-1091; Senter and Springer, (2001) Adv. Drug Deliv. Rev. 53:247-264.

The antibodies, antibody fragments (e.g., antigen binding fragments) or functional equivalents of the present invention can also be conjugated to a radioactive isotope to generate cytotoxic radiopharmaceuticals, referred to as radioimmunoconjugates. Examples of radioactive isotopes that can be conjugated to antibodies for use diagnostically or therapeutically include, but are not limited to, iodine-131, indium-111, yttrium-90, and lutetium-177. Methods for preparing radioimmunoconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the invention. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., (1998) Clin Cancer Res. 4(10):2483-90; Peterson et al., (1999) Bioconjug. Chem. 10(4):553-7; and Zimmerman et al., (1999) Nucl. Med. Biol. 26(8):943-50, each incorporated by reference in their entireties.

The antibodies, antibody fragments (e.g., antigen binding fragments) or functional equivalents of the present invention can also conjugated to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antibody fragment (e.g., antigen binding fragment) described herein (e.g., a Fab fragment, Fd fragment, Fv fragment, F(ab)2 fragment, a VH domain, a VH CDR, a VL domain or a VL CDR) and a heterologous protein, polypeptide, or peptide.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., (1997) Curr. Opinion Biotechnol. 8:724-33; Harayama, (1998) Trends Biotechnol. 16(2):76-82; Hansson et al., (1999) J. Mol. Biol. 287:265-76; and Lorenzo and Blasco, (1998) Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to an antigen may be recombined with one or more components, motifs, sections, parts, domains, fragments, etc. of one or more heterologous molecules.

Moreover, the antibodies, antibody fragments (e.g., antigen binding fragments) or functional equivalents of the present invention can be conjugated to marker sequences, such as a peptide, to facilitate purification. In preferred embodiments, the marker amino acid sequence is a hexa-histidine peptide (SEQ ID NO: 261), such as the tag provided in a pQE vector (QIAGEN, Inc., 9259 Eton Avenue, Chatsworth, Calif., 91311), among others, many of which are commercially available. As described in Gentz et al., (1989) Proc. Natl. Acad. Sci. USA 86:821-824, for instance, hexa-histidine (SEQ ID NO: 261) provides for convenient purification of the fusion protein. Other peptide tags useful for purification include, but are not limited to, the hemagglutinin ("HA") tag, which corresponds to an epitope derived from the influenza hemagglutinin protein (Wilson et al., (1984) Cell 37:767), and the "FLAG" tag (A. Einhauer et al, J. Biochem. Biophys. Methods 49: 455-465, 2001). According to the present invention, antibodies or antigen binding fragments can also be conjugated to tumor-penetrating peptides in order to enhance their efficacy.

In other embodiments, the antibodies, antibody fragments (e.g., antigen binding fragments) or functional equivalents of the present invention are conjugated to a diagnostic or detectable agent. Such immunoconjugates can be useful for monitoring or prognosing the onset, development, progression and/or severity of a disease or disorder as part of a clinical testing procedure, such as determining the efficacy of a particular therapy. Such diagnosis and detection can be accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, umbelliferone, fluorescein, fluorescein isothiocyanate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}$I, $^{125}$I, $^{123}$I, and $^{121}$I), carbon ($^{14}$C), sulfur ($^{35}$S), tritium ($^{3}$H), indium ($^{115}$In, $^{113}$In, $^{112}$In, and $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{64}$Cu, $^{113}$Sn, and $^{117}$Sn; and positron emitting metals using various positron emission tomographies, and non-radioactive paramagnetic metal ions.

The antibodies, antibody fragments (e.g., antigen binding fragments) or functional equivalents of the invention may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

2. Linker

As used herein, a "linker" is any chemical moiety that is capable of linking an antibody, antibody fragment (e.g., antigen binding fragments) or functional equivalent to another moiety, such as a drug moiety. Linkers can be susceptible to cleavage (cleavable linker), such as, acid-induced cleavage, photo-induced cleavage, peptidase-induced cleavage, esterase-induced cleavage, and disulfide bond cleavage, at conditions under which the compound or the antibody remains active. Alternatively, linkers can be substantially resistant to cleavage (e.g., stable linker or noncleavable linker). In some aspects, the linker is a procharged linker, a hydrophilic linker, or a dicarboxylic acid based linker.

In one aspect, the linker used in the present invention is derived from a crosslinking reagent such as N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)-2-sulfo-butanoate (sulfo-SPDB), N-succinimidyl iodoacetate (SIA), N-succinimidyl(4-iodoacetyl)aminobenzoate (SIAB), maleimide PEG NHS, N-succinimidyl 4-(maleimidomethyl)cyclohexanecarboxylate (SMCC), N-sulfosuccinimidyl 4-(maleimidomethyl)cyclohexanecarboxylate (sulfo-SMCC) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1). In another aspect, the linker used in the present invention is derived from a cross-linking agent such as N-succinimidyl-3-(2-pyridyldithio)propionate (SPDP), N-succinimidyl 4-(maleimidomethyl)cyclohexanecarboxylate (SMCC), N-sulfosuccinimidyl 4-(maleimidomethyl)cyclohexanecarboxylate (sulfo-SMCC), N-succinimidyl-4-(2-pyridyldithio)-2-sulfo-butanoate (sulfo-SPDB) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1).

Non-cleavable linkers are any chemical moiety capable of linking a drug, such as a maytansinoid, to an antibody in a stable, covalent manner and does not fall off under the categories listed above for cleaveable linkers. Thus, non-cleavable linkers are substantially resistant to acid-induced cleavage, photo-induced cleavage, peptidase-induced cleavage, esterase-induced cleavage and disulfide bond cleavage. Furthermore, non-cleavable refers to the ability of the chemical bond in the linker or adjoining to the linker to withstand cleavage induced by an acid, photolabile-cleaving agent, a peptidase, an esterase, or a chemical or physiological compound that cleaves a disulfide bond, at conditions under which the drug, such as maytansionoid or the antibody does not lose its activity.

Acid-labile linkers are linkers cleavable at acidic pH. For example, certain intracellular compartments, such as endosomes and lysosomes, have an acidic pH (pH 4-5), and provide conditions suitable to cleave acid-labile linkers.

Photo-labile linkers are linkers that are useful at the body surface and in many body cavities that are accessible to light. Furthermore, infrared light can penetrate tissue.

Some linkers can be cleaved by peptidases, i.e. peptidase cleavable linkers. Only certain peptides are readily cleaved inside or outside cells, see e.g. Trout et al., 79 Proc. Natl. Acad. Sci. USA, 626-629 (1982) and Umemoto et al. 43 Int. J. Cancer, 677-684 (1989). Furthermore, peptides are composed of α-amino acids and peptidic bonds, which chemically are amide bonds between the carboxylate of one amino acid and the amino group of a second amino acid. Other amide bonds, such as the bond between a carboxylate and the s-amino group of lysine, are understood not to be peptidic bonds and are considered non-cleavable.

Some linkers can be cleaved by esterases, i.e. esterase cleavable linkers. Again, only certain esters can be cleaved by esterases present inside or outside of cells. Esters are formed by the condensation of a carboxylic acid and an alcohol. Simple esters are esters produced with simple alcohols, such as aliphatic alcohols, and small cyclic and small aromatic alcohols.

Procharged linkers are derived from charged cross-linking reagents that retain their charge after incorporation into an antibody drug conjugate. Examples of procharged linkers can be found in US 2009/0274713.

3. Conjugation and Preparation of ADCs

The conjugates of the present invention can be prepared by any methods known in the art, such as those described in U.S. Pat. Nos. 7,811,572, 6,411,163, 7,368,565, and 8,163,888, and US application publications 2011/0003969, 2011/0166319, 2012/0253021 and 2012/0259100. The entire teachings of these patents and patent application publications are herein incorporated by reference.

One-Step Process

In one embodiment, the conjugates of the present invention can be prepared by a one-step process. The process comprises combining the antibody, drug and cross-linking agent in a substantially aqueous medium, optionally containing one or more co-solvents, at a suitable pH. In one embodiment, the process comprises the step of contacting the antibody of the present invention with a drug (e.g., DM1 or DM4) to form a first mixture comprising the antibody and the drug, and then contacting the first mixture comprising the antibody and the drug with a cross-linking agent (e.g., SMCC, Sulfo-SMCC, SPDB, Sulfo-SPDB or CX1-1) in a solution having a pH of about 4 to about 9 to provide a mixture comprising (i) the conjugate (e.g., Ab-MCC-DM1, Ab-SPDB-DM4, or Ab-CX1-1-DM1), (ii) free drug (e.g., DM1 or DM4), and (iii) reaction by-products.

In one embodiment, the one-step process comprises contacting the antibody with the drug (e.g., DM1 or DM4) and then the cross-linking agent (e.g., SMCC, Sulfo-SMCC, SPDB, Sulfo-SPDB or CX1-1) in a solution having a pH of about 6 or greater (e.g., about 6 to about 9, about 6 to about 7, about 7 to about 9, about 7 to about 8.5, about 7.5 to about 8.5, about 7.5 to about 8.0, about 8.0 to about 9.0, or about 8.5 to about 9.0). For example, the inventive process comprises contacting a cell-binding agent with the drug (DM1 or DM4) and then the cross-linking agent (e.g., SMCC, Sulfo-SMCC, SPDB, Sulfo-SPDB or CX1-1) in a solution having a pH of about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, or about 9.0. In a specific embodiment, the inventive process comprises contacting a cell-binding agent with the drug (e.g., DM1 or DM4) and then the cross-linking agent (e.g., SMCC, Sulfo-SMCC, SPDB, Sulfo-SPDB or CX1-1) in a solution having a pH of about 7.8 (e.g., a pH of 7.6 to 8.0 or a pH of 7.7 to 7.9).

The one-step process (i.e., contacting the antibody with the drug (e.g., DM1 or DM4) and then the cross-linking agent (e.g., SMCC, Sulfo-SMCC, SPDB, Sulfo-SPDB or CX1-1) can be carried out at any suitable temperature known in the art. For example, the one-step process can occur at about 20° C. or less (e.g., about −10° C. (provided that the solution is prevented from freezing, e.g., by the presence of organic solvent used to dissolve the cytotoxic agent and the bifunctional crosslinking reagent) to about 20° C., about 0° C. to about 18° C., about 4° C. to about 16° C.), at room temperature (e.g., about 20° C. to about 30° C. or about 20° C. to about 25° C.), or at an elevated temperature (e.g., about 30° C. to about 37° C.). In one embodiment, the one-step process occurs at a temperature of about 16° C. to about 24° C. (e.g., about 16° C., about 17° C., about 18° C., about 19° C., about 20° C., about 21° C., about 22° C., about 23° C., about 24° C., or about 25° C.). In another embodiment, the one-step process is carried out at a temperature of about 15° C. or less (e.g., about −10° C. to about 15° C., or about 0° C. to about 15° C.). For example, the process comprises contacting the antibody with the drug (e.g., DM1 or DM4) and then the cross-linking agent (e.g., SMCC, Sulfo-SMCC, SPDB, Sulfo-SPDB or CX1-1) at a temperature of about 15° C., about 14° C., about 13° C., about 12° C., about 11° C., about 10° C., about 9° C., about 8° C., about 7° C., about 6° C., about 5° C., about 4° C., about 3° C., about 2° C., about 1° C., about 0° C., about −1° C., about −2° C., about −3° C., about −4° C., about −5° C., about −6° C., about −7° C., about −8° C., about −9° C., or about −10° C., provided that the solution is prevented from freezing, e.g., by the presence of organic solvent(s) used to dissolve the cross-linking agent (e.g., SMCC, Sulfo-SMCC, Sulfo-SPDB SPDB, or CX1-1). In one embodiment, the process comprises contacting the antibody with the drug (e.g., DM1 or DM4) and then the cross-linking agent (e.g., SMCC, Sulfo-SMCC, SPDB, Sulfo-SPDB or CX1-1) at a temperature of about −10° C. to about 15° C., about 0° C. to about 15° C., about 0° C. to about 10° C., about 0° C. to about 5° C., about 5° C. to about 15° C., about 10° C. to about 15° C., or about 5° C. to about 10° C. In another embodiment, the process comprises contacting the antibody with the drug (e.g., DM1 or DM4) and then the cross-linking agent (e.g., SMCC, Sulfo-SMCC, SPDB, Sulfo-SPDB or CX1-1) at a temperature of about 10° C. (e.g., a temperature of 8° C. to 12° C. or a temperature of 9° C. to 11° C.).

In one embodiment, the contacting described above is effected by providing the antibody, then contacting the antibody with the drug (e.g., DM1 or DM4) to form a first mixture comprising the antibody and the drug (e.g., DM1 or DM4), and then contacting the first mixture comprising the antibody and the drug (e.g., DM1 or DM4) with the cross-linking agent (e.g., SMCC, Sulfo-SMCC, SPDB, Sulfo-SPDB or CX1-1). For example, in one embodiment, the antibody is provided in a reaction vessel, the drug (e.g., DM1 or DM4) is added to the reaction vessel (thereby contacting the antibody), and then the cross-linking agent (e.g., SMCC, Sulfo-SMCC, SPDB, Sulfo-SPDB or CX1-1) is added to the mixture comprising the antibody and the drug (e.g., DM1 or DM4) (thereby contacting the mixture comprising the antibody and the drug). In one embodiment, the antibody is provided in a reaction vessel, and the drug (e.g., DM1 or DM4) is added to the reaction vessel immediately following providing the antibody to the vessel. In another embodiment, the antibody is provided in a reaction vessel, and the drug (e.g., DM1 or DM4) is added to the reaction vessel after a time interval following providing the antibody to the vessel (e.g., about 5 minutes, about 10 minutes, about 20 minutes, about 30 minutes, about 40 minutes, about 50 minutes, about 1 hour, about 1 day or longer after providing the cell-binding agent to the space). The drug (e.g., DM1 or DM4) can be added quickly (i.e., within a short time interval, such as about 5 minutes, about 10 minutes) or slowly (such as by using a pump).

The mixture comprising the antibody and the drug (e.g., DM1 or DM4) can then be contacted with the cross-linking agent (e.g., SMCC, Sulfo-SMCC, SPDB, Sulfo-SPDB or CX1-1) either immediately after contacting the antibody with the drug (e.g., DM1 or DM4) or at some later point (e.g., about 5 minutes to about 8 hours or longer) after contacting the antibody with the drug (e.g., DM1 or DM4). For example, in one embodiment, the cross-linking agent (e.g., SMCC, Sulfo-SMCC, SPDB, Sulfo-SPDB or CX1-1) is added to the mixture comprising the antibody and the drug (e.g., DM1 or DM4) immediately after the addition of the drug (e.g., DM1 or DM4) to the reaction vessel comprising the antibody. Alternatively, the mixture comprising the antibody and the drug (e.g., DM1 or DM4) can be contacted with the cross-linking agent (e.g., SMCC, Sulfo-SMCC, SPDB, Sulfo-SPDB or CX1-1) at about 5 minutes, about 10 minutes, about 20 minutes, about 30 minutes, about 1 hour, about 2 hours, about 3 hours, about 4 hours, about 5 hours, about 6 hours, about 7 hours, about 8 hours, or longer after contacting the antibody with the drug (e.g., DM1 or DM4).

After the mixture comprising the antibody and the drug (e.g., DM1 or DM4) is contacted with the cross-linking agent (e.g., SMCC, Sulfo-SMCC, SPDB, Sulfo-SPDB or CX1-1) the reaction is allowed to proceed for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or longer (e.g., about 30 hours, about 35 hours, about 40 hours, about 45 hours, or about 48 hrs).

In one embodiment, the one-step process further comprises a quenching step to quench any unreacted drug (e.g., DM1 or DM4) and/or unreacted cross-linking agent (e.g., SMCC, Sulfo-SMCC, SPDB, Sulfo-SPDB or CX1-1). The quenching step is typically performed prior to purification of the conjugate. In one embodiment, the mixture is quenched by contacting the mixture with a quenching reagent. As used herein, the "quenching reagent" refers to a reagent that reacts with the free drug (e.g., DM1 or DM4) and/or cross-linking agent (e.g., SMCC, Sulfo-SMCC, SPDB, Sulfo-SPDB or CX1-1). In one embodiment, maleimide or haloacetamide quenching reagents, such as 4-maleimidobutyric acid, 3-maleimidopropionic acid, N-ethylmaleimide, iodoacetamide, or iodoacetamidopropionic acid, can be used to ensure that any unreacted group (such as thiol) in the drug (e.g., DM1 or DM4) is quenched. The quenching step can help prevent the dimerization of the drug (e.g., DM1). The dimerized DM1 can be difficult to remove. Upon quenching with polar, charged thiol-quenching reagents (such as 4-maleimidobutyric acid or 3-maleimidopropionic acid), the excess, unreacted DM1 is converted into a polar, charged, water-soluble adduct that can be easily separated from the covalently-linked conjugate during the purification step. Quenching with non-polar and neutral thiol-quenching reagents can also be used. In one embodiment, the mixture is quenched by contacting the mixture with a quenching reagent that reacts with the unreacted cross-linking agent (e.g., SMCC, Sulfo-SMCC, SPDB, Sulfo-SPDB or CX1-1). For example, nucleophiles can be added to the mixture in order to quench any unreacted SMCC. The nucleophile preferably is an amino group containing nucleophile, such as lysine, taurine and hydroxylamine.

In a preferred embodiment, the reaction (i.e., contacting the antibody with the drug (e.g., DM1 or DM4) and then cross-linking agent (e.g., SMCC, Sulfo-SMCC, SPDB, Sulfo-SPDB or CX1-1)) is allowed to proceed to completion prior to contacting the mixture with a quenching reagent. In this regard, the quenching reagent is added to the mixture about 1 hour to about 48 hours (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or about 25 hours to about 48 hours) after the mixture comprising the antibody and the drug (e.g., DM1 or DM4) is contacted with the cross-linking agent (e.g., SMCC, Sulfo-SMCC, SPDB, Sulfo-SPDB or CX1-1).

Alternatively, the mixture is quenched by lowering the pH of the mixture to about 5.0 (e.g., 4.8, 4.9, 5.0, 5.1 or 5.2). In another embodiment, the mixture is quenched by lowering the pH to less than 6.0, less than 5.5, less than 5.0, less than 4.8, less than 4.6, less than 4.4, less than 4.2, less than 4.0. Alternatively, the pH is lowered to about 4.0 (e.g., 3.8, 3.9, 4.0, 4.1 or 4.2) to about 6.0 (e.g., 5.8, 5.9, 6.0, 6.1 or 6.2), about 4.0 to about 5.0, about 4.5 (e.g., 4.3, 4.4, 4.5, 4.6 or 4.7) to about 5.0. In one embodiment, the mixture is quenched by lowering the pH of the mixture to 4.8. In another embodiment, the mixture is quenched by lowering the pH of the mixture to 5.5.

In one embodiment, the one-step process further comprises a holding step to release the unstably bound linkers from the antibody. The holding step comprises holding the mixture prior to purification of the conjugate (e.g., after the reaction step, between the reaction step and the quenching step, or after the quenching step). For example, the process comprises (a) contacting the antibody with the drug (e.g., DM1 or DM4) to form a mixture comprising the antibody and the drug (e.g., DM1 or DM4); and then contacting the mixture comprising the antibody and drug (e.g., DM1 or DM4) with the cross-linking agent (e.g., SMCC, Sulfo-SMCC, SPDB, Sulfo-SPDB or CX1-1), in a solution having a pH of about 4 to about 9 to provide a mixture comprising (i) the conjugate (e.g., Ab-MCC-DM1, Ab-SPDB-DM4 or Ab-CX1-1-DM1), (ii) free drug (e.g., DM1 or DM4), and (iii) reaction by-products, (b) holding the mixture prepared in step (a) to release the unstably bound linkers from the cell-binding agent, and (c) purifying the mixture to provide a purified conjugate.

In another embodiment, the process comprises (a) contacting the antibody with the drug (e.g., DM1 or DM4) to form a mixture comprising the antibody and the drug (e.g., DM1 or DM4); and then contacting the mixture comprising the antibody and the drug (e.g., DM1 or DM4) with the cross-linking agent (e.g., SMCC, Sulfo-SMCC, SPDB, Sulfo-SPDB or CX1-1), in a solution having a pH of about 4 to about 9 to provide a mixture comprising (i) the conjugate, (ii) free drug (e.g., DM1 or DM4), and (iii) reaction by-products, (b) quenching the mixture prepared in step (a) to quench any unreacted drug (e.g., DM1 or DM4) and/or unreacted cross-linking agent (e.g., SMCC, Sulfo-SMCC, SPDB, Sulfo-SPDB or CX1-1), (c) holding the mixture prepared in step (b) to release the unstably bound linkers from the cell-binding agent, and (d) purifying the mixture to provide a purified conjugate (e.g., Ab-MCC-DM1, Ab-SPDB-DM4 or Ab-CX1-1-DM1).

Alternatively, the holding step can be performed after purification of the conjugate, followed by an additional purification step.

In a preferred embodiment, the reaction is allowed to proceed to completion prior to the holding step. In this regard, the holding step can be performed about 1 hour to about 48 hours (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or about 24 hours to about 48 hours) after the mixture comprising the antibody and the drug (e.g., DM1 or DM4) is contacted with the cross-linking agent (e.g., SMCC, Sulfo-SMCC, SPDB, Sulfo-SPDB or CX1-1).

The holding step comprises maintaining the solution at a suitable temperature (e.g., about 0° C. to about 37° C.) for a suitable period of time (e.g., about 1 hour to about 1 week, about 1 hour to about 24 hours, about 1 hour to about 8 hours, or about 1 hour to about 4 hours) to release the unstably bound linkers from the antibody while not substantially releasing the stably bound linkers from the antibody. In one embodiment, the holding step comprises maintaining the solution at about 20° C. or less (e.g., about 0° C. to about 18° C., about 4° C. to about 16° C.), at room temperature (e.g., about 20° C. to about 30° C. or about 20° C. to about 25° C.), or at an elevated temperature (e.g., about 30° C. to about 37° C.). In one embodiment, the holding step comprises maintaining the solution at a temperature of about 16° C. to about 24° C. (e.g., about 15° C., about 16° C., about 17° C., about 18° C., about 19° C., about 20° C., about 21° C., about 22° C., about 23° C., about 24° C., or about 25° C.). In another embodiment, the holding step comprises maintaining the solution at a temperature of about 2° C. to about 8° C. (e.g., about 0° C., about 1° C., about 2° C., about 3° C., about 4° C., about 5° C., about 6° C., about 7° C., about 8° C., about 9° C., or about 10° C.). In another embodiment, the holding step comprises maintaining the solution at a temperature of about 37° C. (e.g., about 34° C., about 35° C., about 36° C., about 37° C., about 38° C., about 39° C., or about 40° C.).

The duration of the holding step depends on the temperature and the pH at which the holding step is performed. For example, the duration of the holding step can be substantially reduced by performing the holding step at elevated temperature, with the maximum temperature limited by the stability of the cell-binding agent-cytotoxic agent conjugate. The holding step can comprise maintaining the solution for about 1 hour to about 1 day (e.g., about 1 hour, about 2 hours, about 3 hours, about 4 hours, about 5 hours, about 6 hours, about 7 hours, about 8 hours, about 9 hours, about 10 hours, about 12 hours, about 14 hours, about 16 hours, about 18 hours, about 20 hours, about 22 hours, or about 24 hours), about 10 hours to about 24 hours, about 12 hours to about 24 hours, about 14 hours to about 24 hours, about 16 hours to about 24 hours, about 18 hours to about 24 hours, about 20 hours to about 24 hours, about 5 hours to about 1 week, about 20 hours to about 1 week, about 12 hours to about 1 week (e.g., about 12 hours, about 16 hours, about 20 hours, about 24 hours, about 2 days, about 3 days, about 4 days, about 5 days, about 6 days, or about 7 days), or about 1 day to about 1 week.

In one embodiment, the holding step comprises maintaining the solution at a temperature of about 2° C. to about 8° C. for a period of at least about 12 hours for up to a week. In another embodiment, the holding step comprises maintaining the solution at a temperature of about 2° C. to about 8° C. overnight (e.g., about 12 to about 24 hours, preferably about 20 hours).

The pH value for the holding step preferably is about 4 to about 10. In one embodiment, the pH value for the holding step is about 4 or more, but less than about 6 (e.g., 4 to 5.9) or about 5 or more, but less than about 6 (e.g., 5 to 5.9). In another embodiment, the pH values for the holding step range from about 6 to about 10 (e.g., about 6.5 to about 9, about 6 to about 8). For example, pH values for the holding step can be about 6, about 6.5, about 7, about 7.5, about 8, about 8.5, about 9, about 9.5, or about 10.

In specific embodiments, the holding step can comprise incubating the mixture at 25° C. at a pH of about 6-7.5 for about 12 hours to about 1 week, incubating the mixture at 4° C. at a pH of about 4.5-5.9 for about 5 hours to about 5 days, or incubating the mixture at 25° C. at a pH of about 4.5-5.9 for about 5 hours to about 1 day.

The one-step process may optionally include the addition of sucrose to the reaction step to increase solubility and recovery of the conjugates. Desirably, sucrose is added at a concentration of about 0.1% (w/v) to about 20% (w/v) (e.g., about 0.1% (w/v), 1% (w/v), 5% (w/v), 10% (w/v), 15% (w/v), or 20% (w/v)). Preferably, sucrose is added at a concentration of about 1% (w/v) to about 10% (w/v) (e.g., about 0.5% (w/v), about 1% (w/v), about 1.5% (w/v), about 2% (w/v), about 3% (w/v), about 4% (w/v), about 5% (w/v), about 6% (w/v), about 7% (w/v), about 8% (w/v), about 9% (w/v), about 10% (w/v), or about 11% (w/v)). In addition, the reaction step also can comprise the addition of a buffering agent. Any suitable buffering agent known in the art can be used. Suitable buffering agents include, for example, a citrate buffer, an acetate buffer, a succinate buffer, and a phosphate buffer. In one embodiment, the buffering agent is selected from the group consisting of HEPPSO (N-(2-hydroxyethyl) piperazine-N'-(2-hydroxypropanesulfonic acid)), POPSO (piperazine-1,4-bis-(2-hydroxy-propane-sulfonic acid) dehydrate), HEPES (4-(2-hydroxyethyl)piperazine-1-ethanesulfonic acid), HEPPS (EPPS) (4-(2-hydroxyethyl) piperazine-1-propanesulfonic acid), TES (N-[tris(hydroxymethyl)methyl]-2-aminoethanesulfonic acid), and a combination thereof.

In one embodiment, the one-step process can further comprise the step of purifying the mixture to provide purified conjugate (e.g., Ab-MCC-DM1, Ab-SPDB-DM4 or Ab-CX1-1-DM1). Any purification methods known in the art can be used to purify the conjugates of the present invention. In one embodiment, the conjugates of the present invention using tangential flow filtration (TFF), non-adsorptive chromatography, adsorptive chromatography, adsorptive filtration, selective precipitation, or any other suitable purification process, as well as combinations thereof. In another embodiment, prior to subjecting the conjugates to purification process described above, the conjugates are first filtered through one or more PVDF membranes. Alternatively, the conjugates are filtered through one or more PVDF membranes after subjecting the conjugates to the purification process described above. For example, in one embodiment, the conjugates are filtered through one or more PVDF membranes and then purified using tangential flow filtration. Alternatively, the conjugates are purified using tangential flow filtration and then filtered through one or more PVDF membranes.

Any suitable TFF systems may be utilized for purification, including a Pellicon type system (Millipore, Billerica, Mass.), a Sartocon Cassette system (Sartorius AG, Edgewood, N.Y.), and a Centrasette type system (Pall Corp., East Hills, N.Y.).

Any suitable adsorptive chromatography resin may be utilized for purification. Preferred adsorptive chromatography resins include hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof. Examples of suitable hydroxyapatite resins include ceramic hydroxyapatite (CHT Type I and Type II, Bio-Rad Laboratories, Hercules, Calif.), HA Ultrogel hydroxyapatite (Pall Corp., East Hills, N.Y.), and ceramic fluoroapatite (CFT Type I and Type II, Bio-Rad Laboratories, Hercules, Calif.). An example of a suitable HCIC resin is MEP Hypercel resin (Pall Corp., East Hills, N.Y.). Examples of suitable HIC resins include Butyl-Sepharose, Hexyl-Sepaharose, Phenyl-Sepharose, and Octyl Sepharose resins (all from GE Healthcare, Piscataway, N.J.), as well as Macro-prep Methyl and Macro-Prep t-Butyl resins (Biorad Laboratories, Hercules, Calif.). Examples of suitable ion exchange resins include SP-Sepharose, CM-Sepharose, and Q-Sepharose resins (all from GE Healthcare, Piscataway, N.J.), and Unosphere S resin (Bio-Rad Laboratories, Hercules, Calif.). Examples of suitable mixed mode ion exchangers include Bakerbond ABx resin (JT Baker, Phillipsburg N.J.). Examples of suitable IMAC resins include Chelating Sepharose resin (GE Healthcare, Piscataway, N.J.) and Profinity IMAC resin (Bio-Rad Laboratories, Hercules, Calif.). Examples of suitable dye ligand resins include Blue Sepharose resin (GE Healthcare, Piscataway, N.J.) and Affigel Blue resin (Bio-Rad Laboratories, Hercules, Calif.). Examples of suitable affinity resins include Protein A Sepharose resin (e.g., MabSelect, GE Healthcare, Piscataway, N.J.) and lectin affinity resins, e.g. Lentil Lectin Sepharose resin (GE Healthcare, Piscataway, N.J.), where the antibody bears appropriate lectin binding sites. Examples of suitable reversed phase resins include C4, C8, and C18 resins (Grace Vydac, Hesperia, Calif.).

Any suitable non-adsorptive chromatography resin may be utilized for purification. Examples of suitable non-adsorptive chromatography resins include, but are not limited to, SEPHADEX™ G-25, G-50, G-100, SEPHACRYL™ resins (e.g., S-200 and S-300), SUPERDEX™ resins (e.g., SUPERDEX™ 75 and SUPERDEX™ 200), BIO-GEL® resins (e.g., P-6, P-10, P-30, P-60, and P-100), and others known to those of ordinary skill in the art.

Two-Step Process and One-Pot Process

In one embodiment, the conjugates of the present invention can be prepared as described in the U.S. Pat. No. 7,811,572 and U.S. Patent Application Publication No. 2006/0182750. The process comprises the steps of (a) contacting the antibody of the present invention with the cross-linking agent (e.g., SMCC, Sulfo-SMCC, SPDB, Sulfo-SPDB or CX1-1) to covalently attach the linker (i.e., Ab-SMCC, Ab-SPDB or Ab-CX1-1) to the antibody and thereby prepare a first mixture comprising the antibody having the linker bound thereto; (b) optionally subjecting the first mixture to a purification process to prepare a purified first mixture of the antibody having the linker bound thereto; (c) conjugating the drug (e.g., DM1 or DM4) to the antibody having the linker bound thereto in the first mixture by reacting the antibody having the linker bound thereto with the drug (e.g., DM1 or DM4) in a solution having a pH of about 4 to about 9 to prepare a second mixture comprising (i) conjugate (e.g., Ab-MCC-DM1, Ab-SPDB-DM4 or Ab-CX1-1-DM1), (ii) free drug (e.g., DM1 or DM4); and (iii) reaction by-products; and (d) subjecting the second mixture to a purification process to purify the conjugate from the other components of the second mixture. Alternatively, the purification step (b) can be omitted. Any purification methods described herein can be used for steps (b) and (d). In one embodiment, TFF is used for both steps (b) and (d). In another embodiment, TFF is used for step (b) and absorptive chromatography (e.g., CHT) is used for step (d).

One-Step Reagent and In-Situ Process

In one embodiment, the conjugates of the present invention can be prepared by conjugating pre-formed drug-linker compound (e.g., SMCC-DM1, Sulfo-SMCC-DM1, SPDB-DM4 or CX1-1-DM1) to the antibody of the present invention, as described in U.S. Pat. No. 6,441,163 and U.S. Patent Application Publication Nos. 2011/0003969 and 2008/0145374, followed by a purification step. Any purification methods described herein can be used. The drug-linker compound is prepared by reacting the drug (e.g., DM1 or DM4) with the cross-linking agent (e.g., SMCC, Sulfo-SMCC, SPDB, Sulfo-SPDB or CX1-1). The drug-linker compound (e.g., SMCC-DM1, Sulfo-SMCC-DM1, SPDB-DM4 or CX1-1-DM1) is optionally subjected to purification before being conjugated to the antibody.

4. Characterization and Selection of Desirable Antibodies and Antibody Drug Conjugates The antibodies, antibody fragments (e.g., antigen binding fragments) or antibody drug conjugates of the present invention can be characterized and selected for their physical/chemical properties and/or biological activities by various assays known in the art.

For example, an antibody of the invention can be tested for its antigen binding activity by known methods such as ELISA, FACS, Biacore or Western blot.

Transgenic animals and cell lines are particularly useful in screening antibody drug conjugates (ADCs) that have potential as prophylactic or therapeutic treatments of cancer overexpression of tumor-associated antigens and cell surface receptors. Screening for a useful ADC may involve administering a candidate ADC over a range of doses to the transgenic animal, and assaying at various time points for the effect(s) of the ADC on the disease or disorder being evaluated. Alternatively, or additionally, the drug can be administered prior to or simultaneously with exposure to an inducer of the disease, if applicable. The candidate ADC may be screened serially and individually, or in parallel under medium or high-throughput screening format.

One embodiment is a screening method comprising (a) transplanting cells from a stable cancer cell line or human patient tumor expressing FGFR2 (e.g., a breast cancer cell line or tumor fragment, a gastric cancer cell line or tumor fragment) into a non-human animal, (b) administering an ADC drug candidate to the non-human animal and (c) determining the ability of the candidate to inhibit the growth of tumors from the transplanted cell line. The invention also encompasses a method of screening ADC candidates for the treatment of a disease or disorder characterized by the overexpression of FGFR2 comprising (a) contacting cells from a stable cancer cell line expressing FGFR2 with a drug candidate, and (b) evaluating the ability of the ADC candidate to inhibit the growth of the stable cell line.

One embodiment is a screening method comprising (a) contacting cells from a stable cancer cell line expressing FGFR2 with an ADC drug candidate and (b) evaluating the ability of the ADC candidate to block ligand activation of FGFR2. In another embodiment the ability of the ADC candidate to block ligand-stimulated tyrosine phosphorylation is evaluated.

Another embodiment is a screening method comprising (a) contacting cells from a stable cancer cell line expressing FGFR2 with an ADC drug candidate and (b) evaluating the ability of the ADC candidate to induce cell death. In one embodiment the ability of the ADC candidate to induce apoptosis is evaluated.

In one embodiment, candidate ADC are screened by being administered to the transgenic animal over a range of doses, and evaluating the animal's physiological response to the compounds over time. In some cases, it may be appropriate to administer the compound in conjunction with co-factors that would enhance the efficacy of the compound. If cell lines derived from the subject transgenic animals are used to screen for ADCs useful in treating various disorders associated with overexpression of FGFR2, the test ADCs are added to the cell culture medium at an appropriate time, and the cellular response to the ADCs is evaluated over time using the appropriate biochemical and/or histological assays.

Thus, the present invention provides assays for identifying ADC which specifically target and bind to FGFR2, the overexpression and amplification of which on the tumor cells is correlated with abnormal cellular function. According to the present invention, anti-FGFR2 antibodies or antibody fragments (e.g., antigen binding fragments) with the following properties are better candidates for making ADCs: affinity to human FGFR2 of <10 nM, following conjugation to SMCC-DM1 or SPDB-DM4, ability to inhibit growth of FGFR2 amplified and/or overexpressing cells with an IC50 of <2 nM, a slow clearance rate, for example, <45 ml/d/kg in a mouse following a single 3 mg/kg IV dose FGFR2 Antibodies The present invention provides antibodies or antibody fragments (e.g., antigen binding fragments) that specifically bind to human FGFR2. Antibodies or antibody fragments (e.g., antigen binding fragments) of the invention include, but are not limited to, the human monoclonal antibodies or fragments thereof, isolated as described, in the Examples (see Section 6 below).

The present invention in certain embodiments provides antibodies or antibody fragments (e.g., antigen binding fragments) that specifically bind FGFR2, said antibodies or antibody fragments (e.g., antigen binding fragments) comprise a VH domain having an amino acid sequence of SEQ ID NO: 7, 27, 47, 67, 87, 107, 127, 147, 167, 187, 207, or 227. The present invention in certain embodiments also provides antibodies or antibody fragments (e.g., antigen binding fragments) that specifically bind to FGFR2, said antibodies or antibody fragments (e.g., antigen binding fragments) comprise a VH CDR having an amino acid sequence of any one of the VH CDRs listed in Table 1, infra. In particular embodiments, the invention provides antibodies or antibody fragments (e.g., antigen binding fragments) that specifically bind to FGFR2, said antibodies comprising (or alternatively, consist of) one, two, three, four, five or more VH CDRs having an amino acid sequence of any of the VH CDRs listed in Table 1, infra.

The present invention provides antibodies or antibody fragments (e.g., antigen binding fragments) that specifically bind to FGFR2, said antibodies or antibody fragments (e.g., antigen binding fragments) comprise a VL domain having an amino acid sequence of SEQ ID NO: 17, 37, 57, 77, 97, 117, 137, 157, 177, 197, 217 or 237. The present invention also provides antibodies or antibody fragments (e.g., antigen binding fragments) that specifically bind to FGFR2, said antibodies or antibody fragments (e.g., antigen binding fragments) comprise a VL CDR having an amino acid sequence of any one of the VL CDRs listed in Table 1, infra. In particular, the invention provides antibodies or antibody fragments (e.g., antigen binding fragments) that specifically bind to FGFR2, said antibodies or antibody fragments (e.g., antigen binding fragments) comprise (or alternatively, consist of) one, two, three or more VL CDRs having an amino acid sequence of any of the VL CDRs listed in Table 1, infra.

Other antibodies or antibody fragments (e.g., antigen binding fragments) of the invention include amino acids that have been mutated, yet have at least 60, 70, 80, 90 or 95 percent identity in the CDR regions with the CDR regions depicted in the sequences described in Table 1. In some embodiments, it includes mutant amino acid sequences wherein no more than 1, 2, 3, 4 or 5 amino acids have been mutated in the CDR regions when compared with the CDR regions depicted in the sequence described in Table 1.

The present invention also provides nucleic acid sequences that encode VH, VL, the full length heavy chain, and the full length light chain of the antibodies that specifically bind to FGFR2. Such nucleic acid sequences can be optimized for expression in mammalian cells.

TABLE 1

Examples of anti-FGFR2 Antibodies of the Present Invention mAb12433

| | | | |
|---|---|---|---|
| SEQ ID NO 1: | (Kabat) | HCDR1 | NYYIH |
| SEQ ID NO 2: | (Kabat) | HCDR2 | AIYPDNSDTTYSPSFQG |
| SEQ ID NO 3: | (Kabat) | HCDR3 | GADI |
| SEQ ID NO 4: | (Chothia) | HCDR1 | GYSFTNY |
| SEQ ID NO 5: | (Chothia) | HCDR2 | YPDNSD |
| SEQ ID NO 6: | (Chothia) | HCDR3 | GADI |
| SEQ ID NO 7: | | VH | QVQLVQSGAEVKKPGESLKISCKGSGYSFTNYYIHWVRQMPGKGLEWMGAIYP DNSDTTYSPSFQGQVTISADKSISTAYLQWSSLKASDTAMYYCARGADIWGQGTL VTVSS |
| SEQ ID NO 8: | | DNA VH | CAGGTGCAGCTGGTGCAGTCAGGCGCCGAAGTGAAGAAGCCCGGCGAGTCA CTGAAGATTAGCTGTAAAGGCTCCGGCTATAGCTTCACTAACTACTATATTCAC TGGGTCCGACAGATGCCCGGCAAGGGCCTGGAATGGATGGGCGCTATCTACC CCGATAATAGCGACACTACCTACTCACCTAGCTTTCAGGGCCAGGTCACAATT AGCGCCGATAAGTCTATTAGCACCGCCTACCTGCAGTGGTCTAGCCTGAAGGC CTCAGACACCGCTATGTACTACTGCGCTAGAGGCGCCGACATCTGGGGCCAG GGCACCCTGGTCACCGTGTCTTCA |

TABLE 1-continued

Examples of anti-FGFR2 Antibodies of the Present Invention

| SEQ ID NO 9: | Heavy Chain | QVQLVQSGAEVKKPGESLKISCKGSGYSFTNYYIHWVRQMPGKGLEWMGAIYP DNSDTTYSPSFQGQVTISADKSISTAYLQWSSLKASDTAMYYCARGADIWGQGTL VTVSSASTKGPSVFPLAPSSKSTSGGTAALGCLVKDYFPEPVTVSWNSGALTSGVH TFPAVLQSSGLYSLSSVVTVPSSSLGTQTYICNVNHKPSNTKVDKRVEPKSCDKTHT CPPCPAPELLGGPSVFLFPPKPKDTLMISRTPEVTCVVVDVSHEDPEVKFNWYVD GVEVHNAKTKPREEQYNSTYRVVSVLTVLHQDWLNGKEYKCKVSNKALPAPIEKT ISKAKGQPREPQVYTLPPSREEMTKNQVSLTCLVKGFYPSDIAVEWESNGQPENN YKTTPPVLDSDGSFFLYSKLTVDKSRWQQGNVFSCSVMHEALHNHYTQKSLSLSP GK |
| --- | --- | --- |
| SEQ ID NO 10: | DNA Heavy Chain | CAGGTGCAGCTGGTGCAGTCAGGCGCCGAAGTGAAGAAGCCCGGCGAGTCA CTGAAGATTAGCTGTAAAGGCTCCGGCTATAGCTTCACTAACTACTATATTCAC TGGGTCCGACAGATGCCCGGCAAGGGCCTGGAATGGATGGGCGCTATCTACC CCGATAATAGCGACACTACCTACTCACCTAGCTTTCAGGGCCAGGTCACAATT AGCGCCGATAAGTCTATTAGCACCGCCTACCTGCAGTGGTCTAGCCTGAAGGC CTCAGACACCGCTATGTACTACTGCGCTAGAGGCGCCGACATCTGGGGCCAG GGCACCCTGGTCACCGTGTCTTCAGCTAGCACTAAGGGCCCAAGTGTGTTTCC CCTGGCCCCCAGCAGCAAGTCTACTTCCGGCGGAACTGCTGCCCTGGGTTGCC TGGTGAAGGACTACTTCCCCGAGCCGTGACAGTGTCCTGGAACTCTGGGGC TCTGACTTCCGGCGTGCACACCTTCCCGCCGTGCTGCAGAGCAGCGGCCTGT ACAGCCTGAGCAGCGTGGTGACAGTGCCCTCCAGCTCTCTGGGAACCCAGAC CTATATCTGCAACGTGAACCACAAGCCCAGCAACACCAAGGTGGACAAGAGA GTGGAGCCCAAGAGCTGCGACAAGACCCACACCTGCCCCCCCTGCCCAGCTCC AGAACTGCTGGGAGGGCCTTCCGTGTTCCTGTTCCCCCCCAAGCCCAAGGACA CCCTGATGATCAGCAGGACCCCCGAGGTGACCTGCGTGGTGGTGGACGTGTC CCACGAGGACCCAGAGGTGAAGTTCAACTGGTACGTGGACGGCGTGGAGGT GCACAACGCCAAGACCAAGCCCAGAGAGGAGCAGTACAACAGCACCTACAG GGTGGTGTCCGTGCTGACCGTGCTGCACCAGGACTGGCTGAACGGCAAAGAA TACAAGTGCAAAGTCTCCAACAAGGCCCTGCCAGCCCCAATCGAAAAGACAAT CAGCAAGGCCAAGGGCCAGCCACGGGAGCCCCAGGTGTACACCCTGCCCCCC AGCCGGGAGGAGATGACCAAGAACCAGGTGTCCCTGACCTGTCTGGTGAAG GGCTTCTACCCCAGCGATATCGCCGTGGAGTGGGAGAGCAACGGCCAGCCCG AGAACAACTACAAGACCACCCCCCCAGTGCTGGACAGCGACGGCAGCTTCTTC CTGTACAGCAAGCTGACCGTGGACAAGTCCAGGTGGCAGCAGGGCAACGTGT TCAGCTGCAGCGTGATGCACGAGGCCCTGCACAACCACTACACCCAGAAGTCC CTGAGCCTGAGCCCCGGCAAG |
| SEQ ID NO 11: (Kabat) | LCDR1 | RASQDIDPYLSN |
| SEQ ID NO 12: (Kabat) | LCDR2 | DASNLQS |
| SEQ ID NO 13: (Kabat) | LCDR3 | QQTTSHPYT |
| SEQ ID NO 14: (Chothia) | LCDR1 | SQDIDPYL |
| SEQ ID NO 15: (Chothia) | LCDR2 | DAS |
| SEQ ID NO 16: (Chothia) | LCDR3 | TTSHPY |
| SEQ ID NO 17: | VL | DIQMTQSPSSLSASVGDRVTITCRASQDIDPYLSNWYQQKPGKAPKLLIYDASNL QSGVPSRFSGSGSGTDFTLTISSLQPEDFATYYCQQTTSHPYTFGQGTKVEIK |
| SEQ ID NO 18: | DNA VL | GACATTCAGATGACTCAGTCACCTAGTAGCCTGAGCGCCTCAGTGGGCGATA GAGTGACTATCACCTGTAGAGCCTCTCAGGACATCGACCCCTACCTGTCTAAC TGGTATCAGCAGAAGCCCGGCAAGGCCCCTAAGCTGCTGATCTACGACGCCTC TAACCTGCAGTCAGGCGTGCCCTCTAGGTTTAGCGGTAGCGGCTCAGGCACC GACTTCACCCTGACTATCTCTAGCCTGCAGCCCGAGGACTTCGCTACCTACTAC TGTCAGCAGACTACTAGTCACCCCTACACCTTCGGCCAGGGCACTAAGGTCGA GATTAAG |
| SEQ ID NO 19: | Light Chain | DIQMTQSPSSLSASVGDRVTITCRASQDIDPYLSNWYQQKPGKAPKLLIYDASNL QSGVPSRFSGSGSGTDFTLTISSLQPEDFATYYCQQTTSHPYTFGQGTKVEIKRTVA APSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC |
| SEQ ID NO 20: | DNA Light Chain | GACATTCAGATGACTCAGTCACCTAGTAGCCTGAGCGCCTCAGTGGGCGATA GAGTGACTATCACCTGTAGAGCCTCTCAGGACATCGACCCCTACCTGTCTAAC TGGTATCAGCAGAAGCCCGGCAAGGCCCCTAAGCTGCTGATCTACGACGCCTC TAACCTGCAGTCAGGCGTGCCCTCTAGGTTTAGCGGTAGCGGCTCAGGCACC GACTTCACCCTGACTATCTCTAGCCTGCAGCCCGAGGACTTCGCTACCTACTAC TGTCAGCAGACTACTAGTCACCCCTACACCTTCGGCCAGGGCACTAAGGTCGA GATTAAGCGTACGGTGGCCGCTCCCAGCGTGTTCATCTTCCCCCCAGCGACG AGCAGCTGAAGAGCGGCACCGCCAGCGTTGTGCCTGCTGAACAACTTCTA CCCCCGGGAGGCCAAGGTGCAGTGGAAGGTGGACAACGCCCTGCAGAGCGG CAACAGCCAGGAGAGCGTCACCGAGCAGGACAGCAAGGACTCCACCTACAGC CTGAGCAGCACCCTGACCCTGAGCAAGGCCGACTACGAGAAGCATAAGGTGT ACGCCTGCGAGGTGACCCACCAGGGCCTGTCCAGCCCCGTGACCAAGAGCTT CAACAGGGGCGAGTGC |

TABLE 1-continued

Examples of anti-FGFR2 Antibodies of the Present Invention mAb10164

| | | | |
|---|---|---|---|
| SEQ ID NO 21: | (Kabat) | HCDR1 | SYALS |
| SEQ ID NO 22: | (Kabat) | HCDR2 | RIRSKIDGGTTDYAAPVKG |
| SEQ ID NO 23: | (Kabat) | HCDR3 | DRSPSDSSAFAI |
| SEQ ID NO 24: | (Chothia) | HCDR1 | GFTFSSY |
| SEQ ID NO 25: | (Chothia) | HCDR2 | RSKIDGGT |
| SEQ ID NO 26: | (Chothia) | HCDR3 | DRSPSDSSAFAI |
| SEQ ID NO 27: | | VH | QVQLVESGGGLVKPGGSLRLSCAASGFTFSSYALSWVRQAPGKGLEWVGRIRSKI DGGTTDYAAPVKGRFTISRDDSKNTLYLQMNSLKTEDTAVYYCARDRSPSDSSAF AIWGQGTLVTVSS |
| SEQ ID NO 28: | | DNA VH | CAGGTGCAGCTGGTGGAATCAGGCGGCGGACTGGTCAAGCCTGGCGGTAGC CTGAGACTGAGCTGCGCCGCCTCCGGCTTCACCTTCTCTAGCTACGCCCTGAG CTGGGTCCGACAGGCTCCTGGCAAGGGCCTGGAATGGGTCGGACGGATTAG ATCTAAGATCGACGGCGGCACTACCGACTACGCCGCTCCTGTGAAGGGACGG TTCACTATCTCTAGGGACGACTCTAAGAACACCCTGTACCTGCAGATGAATAG CCTGAAAACCGAGGACACCGCCGTCTACTACTGCGCTAGAGATAGATCACCTA GCGACTCTAGCGCCTTCGCTATCTGGGGCCAGGGCACCCTGGTCACCGTGAGT TCA |
| SEQ ID NO 29: | | Heavy Chain | QVQLVESGGGLVKPGGSLRLSCAASGFTFSSYALSWVRQAPGKGLEWVGRIRSKI DGGTTDYAAPVKGRFTISRDDSKNTLYLQMNSLKTEDTAVYYCARDRSPSDSSAF AIWGQGTLVTVSSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKVDKRV EPKSCDKTHTCPPCPAPELLGGPSVFLFPPKPKDTLMISRTPEVTCVVVDVSHEDP EVKFNWYVDGVEVHNAKTKPREEQYNSTYRVVSVLTVLHQDWLNGKEYKCKVS NKALPAPIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHEALH NHYTQKSLSLSPGK |
| SEQ ID NO 30: | | DNA Heavy Chain | CAGGTGCAGCTGGTGGAATCAGGCGGCGGACTGGTCAAGCCTGGCGGTAGC CTGAGACTGAGCTGCGCCGCCTCCGGCTTCACCTTCTCTAGCTACGCCCTGAG CTGGGTCCGACAGGCTCCTGGCAAGGGCCTGGAATGGGTCGGACGGATTAG ATCTAAGATCGACGGCGGCACTACCGACTACGCCGCTCCTGTGAAGGGACGG TTCACTATCTCTAGGGACGACTCTAAGAACACCCTGTACCTGCAGATGAATAG CCTGAAAACCGAGGACACCGCCGTCTACTACTGCGCTAGAGATAGATCACCTA GCGACTCTAGCGCCTTCGCTATCTGGGGCCAGGGCACCCTGGTCACCGTGAGT TCAGCTAGCACTAAGGGCCCAAGTGTGTTTCCCCTGGCCCCCAGCAGCAAGTC TACTTCCGGCGGAACTGCTGCCCTGGGTTGCCTGGTGAAGGACTACTTCCCCG AGCCCGTGACAGTGTCCTGGAACTCTGGGGCTCTGACTTCCGGCGTGCACACC TTCCCCGCCGTGCTGCAGAGCAGCGGCCTGTACAGCCTGAGCAGCGTGGTGA CAGTGCCCTCCAGCTCTCTGGGAACCCAGACCTATATCTGCAACGTGAACCAC AAGCCCAGCAACACCAAGGTGGACAAGAGAGTGGAGCCCAAGAGCTGCGAC AAGACCCACACCTGCCCCCCTGCCCAGCTCCAGAACTGCTGGGAGGGCCTTC CGTGTTCCTGTTCCCCCCCAAGCCCAAGGACACCCTGATGATCAGCAGGACCC CCGAGGTGACCTGCGTGGTGGTGGACGTGTCCCACGAGGACCCAGAGGTGA AGTTCAACTGGTACGTGGACGGCGTGGAGGTGCACAACGCCAAGACCAAGCC CAGAGAGGAGCAGTACAACAGCACCTACAGGGTGGTGTCCGTGCTGACCGTG CTGCACCAGGACTGGCTGAACGGCAAAGAATACAAGTGCAAAGTCTCCAACA AGGCCCTGCCAGCCCCAATCGAAAAGACAATCAGCAAGGCCAAGGGCCAGCC ACGGGAGCCCCAGGTGTACACCCTGCCCCCCAGCCGGGAGGAGATGACCAAG AACCAGGTGTCCCTGACCTGTCTGGTGAAGGGCTTCTACCCCAGCGATATCGC CGTGGAGTGGGAGAGCAACGGCCAGCCCGAGAACAACTACAAGACCACCCC CCCAGTGCTGGACAGCGACGGCAGCTTCTTCCTGTACAGCAAGCTGACCGTG GACAAGTCCAGGTGGCAGCAGGGCAACGTGTTCAGCTGCAGCGTGATGCACG AGGCCCTGCACAACCACTACACCCAGAAGTCCCTGAGCCTGAGCCCCGGCAAG |
| SEQ ID NO 31: | (Kabat) | LCDR1 | SGDNLGSQYVD |
| SEQ ID NO 32: | (Kabat) | LCDR2 | DDNDRPS |
| SEQ ID NO 33: | (Kabat) | LCDR3 | QSWDSLSVV |
| SEQ ID NO 34: | (Chothia) | LCDR1 | DNLGSQY |
| SEQ ID NO 35: | (Chothia) | LCDR2 | DDN |
| SEQ ID NO 36: | (Chothia) | LCDR3 | WDSLSV |
| SEQ ID NO 37: | | VL | DIELTQPPSVSVSPGQTASITCSGDNLGSQYVDWYQQKPGQAPVLVIYDDNDRP SGIPERFSGSNSGNTATLTISGTQAEDEADYYCQSWDSLSVVFGGGTKLTVL |

TABLE 1-continued

Examples of anti-FGFR2 Antibodies of the Present Invention

| SEQ ID NO 38: | DNA VL | GATATCGAGCTGACTCAGCCCCCTAGCGTCAGCGTCAGCCCTGGCCAGACCGC<br>CTCTATCACCTGTAGCGGCGATAACCTGGGCTCTCAGTACGTGGACTGGTATC<br>AGCAGAAGCCCGGCCAGGCCCCCGTGCTGGTCATCTACGACGATAACGATAG<br>ACCTAGCGGAATCCCCGAGCGGTTTAGCGGCTCTAATAGCGGCAACACCGCT<br>ACCCTGACTATTAGCGGCACTCAGGCCGAGGACGAGGCCGACTACTACTGTC<br>AGTCCTGGGATAGCCTGTCAGTGGTGTTCGGCGGAGGCACTAAGCTGACCGT<br>GCTC |
|---|---|---|
| SEQ ID NO 39: | Light<br>Chain | DIELTQPPSVSVSPGQTASITCSGDNLGSQYVDWYQQKPGQAPVLVIYDDNDRP<br>SGIPERFSGSNSGNTATLTISGTQAEDEADYYCQSWDSLSVVFGGGTKLTVLGQP<br>KAAPSVTLFPPSSEELQANKATLVCLISDFYPGAVTVAWKADSSPVKAGVETTTPS<br>KQSNNKYAASSYLSLTPEQWKSHRSYSCQVTHEGSTVEKTVAPTECS |
| SEQ ID NO 40: | DNA<br>Light<br>Chain | GATATCGAGCTGACTCAGCCCCCTAGCGTCAGCGTCAGCCCTGGCCAGACCGC<br>CTCTATCACCTGTAGCGGCGATAACCTGGGCTCTCAGTACGTGGACTGGTATC<br>AGCAGAAGCCCGGCCAGGCCCCCGTGCTGGTCATCTACGACGATAACGATAG<br>ACCTAGCGGAATCCCCGAGCGGTTTAGCGGCTCTAATAGCGGCAACACCGCT<br>ACCCTGACTATTAGCGGCACTCAGGCCGAGGACGAGGCCGACTACTACTGTC<br>AGTCCTGGGATAGCCTGTCAGTGGTGTTCGGCGGAGGCACTAAGCTGACCGT<br>GCTCGGCCAGCCTAAGGCTGCCCCAGCGTGACCCTGTTCCCCCCCAGCAGCG<br>AGGAGCTGCAGGCCAACAAGGCCACCCTGGTGTGCCTGATCAGCGACTTCTA<br>CCCAGGCGCCGTGACCGTGGCCTGGAAGGCCGACAGCAGCCCCGTGAAGGC<br>CGGCGTGGAGACCACCACCCCCAGCAAGCAGAGCAACAACAAGTACGCCGCC<br>AGCAGCTACCTGAGCCTGACCCCCGAGCAGTGGAAGAGCCACAGGTCCTACA<br>GCTGCCAGGTGACCCACGAGGGCAGCACCGTGGAAAAGACCGTGGCCCCCAA<br>CCGAGTGCAGC | mAb12425

| SEQ ID NO 41: | (Kabat) | HCDR1 | DYAMS |
|---|---|---|---|
| SEQ ID NO 42: | (Kabat) | HCDR2 | VIEGDGSYTHYADSVKG |
| SEQ ID NO 43: | (Kabat) | HCDR3 | EKTYSSAFDY |
| SEQ ID NO 44: | (Chothia) | HCDR1 | GFTFSDY |
| SEQ ID NO 45: | (Chothia) | HCDR2 | EGDGSY |
| SEQ ID NO 46: | (Chothia) | HCDR3 | EKTYSSAFDY |
| SEQ ID NO 47: | | VH | QVQLLESGGGLVQPGGSLRLSCAASGFTFSDYAMSWVRQAPGKGLEWVSVIEG<br>DGSYTHYADSVKGRFTISRDNSKNTLYLQMNSLRAEDTAVYYCAREKTYSSAFDY<br>WGQGTLVTVSS |
| SEQ ID NO 48: | | DNA VH | CAGGTGCAGCTGCTGGAATCAGGCGGCGGACTGGTGCAGCCTGGCGGTAGC<br>CTGAGACTGAGCTGTGCCGCCTCCGGCTTCACCTTTAGCGACTACGCTATGAG<br>CTGGGTCCGACAGGCCCCTGGCAAGGGACTGGAATGGGTGTCAGTGATCGA<br>GGGCGACGGTAGCTACACTCACTACGCCGATAGCGTGAAGGGCCGGTTCACT<br>ATCTCTAGGGACAACTCTAAGAACACCCTGTACCTGCAGATGAACTCACTGAG<br>AGCCGAGGACACCGCCGTCTACTACTGCGCTAGAGAAAAGACCTACTCTAGC<br>GCCTTCGACTACTGGGGCCAGGGCACCCTGGTCACCGTGTCATCA |
| SEQ ID NO 49: | | Heavy<br>Chain | QVQLLESGGGLVQPGGSLRLSCAASGFTFSDYAMSWVRQAPGKGLEWVSVIEG<br>DGSYTHYADSVKGRFTISRDNSKNTLYLQMNSLRAEDTAVYYCAREKTYSSAFDY<br>WGQGTLVTVSSASTKGPSVFPLAPSSKSTSGGTAALGCLVKDYFPEPVTVSWNSG<br>ALTSGVHTFPAVLQSSGLYSLSSVVTVPSSSLGTQTYICNVNHKPSNTKVDKRVEPK<br>SCDKTHTCPPCPAPELLGGPSVFLFPPKPKDTLMISRTPEVTCVVVDVSHEDPEVK<br>FNWYVDGVEVHNAKTKPREEQYNSTYRVVSVLTVLHQDWLNGKEYKCKVSNKA<br>LPAPIEKTISKAKGQPREPQVYTLPPSREEMTKNQVSLTCLVKGFYPSDIAVEWES<br>NGQPENNYKTTPPVLDSDGSFFLYSKLTVDKSRWQQGNVFSCSVMHEALHNHY<br>TQKSLSLSPGK |
| SEQ ID NO 50: | | DNA<br>Heavy<br>Chain | CAGGTGCAGCTGCTGGAATCAGGCGGCGGACTGGTGCAGCCTGGCGGTAGC<br>CTGAGACTGAGCTGTGCCGCCTCCGGCTTCACCTTTAGCGACTACGCTATGAG<br>CTGGGTCCGACAGGCCCCTGGCAAGGGACTGGAATGGGTGTCAGTGATCGA<br>GGGCGACGGTAGCTACACTCACTACGCCGATAGCGTGAAGGGCCGGTTCACT<br>ATCTCTAGGGACAACTCTAAGAACACCCTGTACCTGCAGATGAACTCACTGAG<br>AGCCGAGGACACCGCCGTCTACTACTGCGCTAGAGAAAAGACCTACTCTAGC<br>GCCTTCGACTACTGGGGCCAGGGCACCCTGGTCACCGTGTCATCAGCTAGCAC<br>TAAGGGCCCAAGTGTGTTTCCCCTGGCCCCCAGCAGCAAGTCTACTTCCGGCG<br>GAACTGCTGCCCTGGGTTGCCTGGTGAAGGACTACTTCCCCGAGCCCGTGACA<br>GTGTCCTGGAACTCTGGGGCTGACTTCTGGAGCCACACCTTCCCCGCCGT<br>GCTGCAGAGCAGCGGCCTGTACAGCCTGAGCAGCGTGGTGACAGTGCCCTCC<br>AGCTCTCTGGGAACCCAGACCTATATCTGCAACGTGAACCACAAGCCCAGCAA<br>CACCAAGGTGGACAAGAGAGTGGAGCCCAAGAGCTGCGACAAGACCCACAC<br>CTGCCCCCCCTGCCCAGCTCCAGAACTGCTGGGAGGGCCTTCCGTGTTCCTGT<br>TCCCCCCCAAGCCCAAGGACACCCTGATGATCAGCAGGACCCCCGAGGTGAC |

TABLE 1-continued

Examples of anti-FGFR2 Antibodies of the Present Invention

```
                    CTGCGTGGTGGTGGACGTGTCCCACGAGGACCCAGAGGTGAAGTTCAACTGG
                    TACGTGGACGGCGTGGAGGTGCACAACGCCAAGACCAAGCCCAGAGAGGAG
                    CAGTACAACAGCACCTACAGGGTGGTGTCCGTGCTGACCGTGCTGCACCAGG
                    ACTGGCTGAACGGCAAAGAATACAAGTGCAAAGTCTCCAACAAGGCCCTGCC
                    AGCCCCAATCGAAAAGACAATCAGCAAGGCCAAGGGCCAGCCACGGGAGCC
                    CCAGGTGTACACCCTGCCCCCCAGCCGGGAGGAGATGACCAAGAACCAGGTG
                    TCCCTGACCTGTCTGGTGAAGGGCTTCTACCCCAGCGATATCGCCGTGGAGTG
                    GGAGAGCAACGGCCAGCCCGAGAACAACTACAAGACCACCCCCCCAGTGCTG
                    GACAGCGACGGCAGCTTCTTCCTGTACAGCAAGCTGACCGTGGACAAGTCCA
                    GGTGGCAGCAGGGCAACGTGTTCAGCTGCAGCGTGATGCACGAGGCCCTGC
                    ACAACCACTACACCCAGAAGTCCCTGAGCCTGAGCCCCGGCAAG
```

| SEQ ID NO 51: | (Kabat) | LCDR1 | RASQDISSDLN |
| --- | --- | --- | --- |
| SEQ ID NO 52: | (Kabat) | LCDR2 | DASNLQS |
| SEQ ID NO 53: | (Kabat) | LCDR3 | QQHYSPSHT |
| SEQ ID NO 54: | (Chothia) | LCDR1 | SQDISSD |
| SEQ ID NO 55: | (Chothia) | LCDR2 | DAS |
| SEQ ID NO 56: | (Chothia) | LCDR3 | HYSPSH |
| SEQ ID NO 57: | | VL | DIQMTQSPSSLSASVGDRVTITCRASQDISSDLNWYQQKPGKAPKLLIYDASNLQS GVPSRFSGSGSGTDFTLTISSLQPEDFAVYYCQQHYSPSHTFGQGTKVEIK |
| SEQ ID NO 58: | | DNA VL | GATATTCAGATGACTCAGTCACCTAGTAGCCTGAGCGCCTCAGTGGGCGATA GAGTGACTATCACCTGTAGAGCCTCTCAGGACATCTCTAGCGACCTGAACTGG TATCAGCAGAAGCCCGGCAAGGCCCCTAAGCTGCTGATCTACGACGCCTCTAA CCTGCAGAGCGGCGTGCCCTCTAGGTTTAGCGGTAGCGGCTCAGGCACCGAC TTTACCCTGACTATCTCTAGCCTGCAGCCCGAGGACTTCGCCGTCTACTACTGT CAGCAGCACTATAGCCCTAGTCACACCTTCGGCCAGGGCACTAAGGTCGAGAT TAAG |
| SEQ ID NO 59: | | Light Chain | DIQMTQSPSSLSASVGDRVTITCRASQDISSDLNWYQQKPGKAPKLLIYDASNLQS GVPSRFSGSGSGTDFTLTISSLQPEDFAVYYCQQHYSPSHTFGQGTKVEIKRTVAA PSVFIFPPSDEQLKSGTASVVCLLNNFYPREAKVQWKVDNALQSGNSQESVTEQD SKDSTYSLSSTLTLSKADYEKHKVYACEVTHQGLSSPVTKSFNRGEC |
| SEQ ID NO 60: | | DNA Light Chain | GATATTCAGATGACTCAGTCACCTAGTAGCCTGAGCGCCTCAGTGGGCGATA GAGTGACTATCACCTGTAGAGCCTCTCAGGACATCTCTAGCGACCTGAACTGG TATCAGCAGAAGCCCGGCAAGGCCCCTAAGCTGCTGATCTACGACGCCTCTAA CCTGCAGAGCGGCGTGCCCTCTAGGTTTAGCGGTAGCGGCTCAGGCACCGAC TTTACCCTGACTATCTCTAGCCTGCAGCCCGAGGACTTCGCCGTCTACTACTGT CAGCAGCACTATAGCCCTAGTCACACCTTCGGCCAGGGCACTAAGGTCGAGAT TAAGCGTACGGTGGCCGCTCCCAGCGTGTTCATCTTCCCCCCCAGCGACGAGC AGCTGAAGAGCGGCACCGCCAGCGTGGTGTGCCTGCTGAACAACTTCTACCC CCGGGAGGCCAAGGTGCAGTGGAAGGTGGACAACGCCCTGCAGAGCGGCAA CAGCCAGGAGAGCGTCACCGAGCAGGACAGCAAGGACTCCACCTACAGCCTG AGCAGCACCCTGACCCTGAGCAAGGCCGACTACGAGAAGCATAAGGTGTACG CCTGCGAGGTGACCCACCAGGGCCTGTCCAGCCCCGTGACCAAGAGCTTCAA CAGGGGCGAGTGC | mAb14629

| SEQ ID NO 61: | (Kabat) | HCDR1 | SYAIS |
| --- | --- | --- | --- |
| SEQ ID NO 62: | (Kabat) | HCDR2 | YISPYMGETHYAQRFQG |
| SEQ ID NO 63: | (Kabat) | HCDR3 | ESYEYFDI |
| SEQ ID NO 64: | (Chothia) | HCDR1 | GGTFSSY |
| SEQ ID NO 65: | (Chothia) | HCDR2 | SPYMGE |
| SEQ ID NO 66: | (Chothia) | HCDR3 | ESYEYFDI |
| SEQ ID NO 67: | | VH | QVQLVQSGAEVKKPGSSVKVSCKASGGTFSSYAISWVRQAPGQGLEWMGYISPY MGETHYAQRFQGRVTITADESTSTAYMELSSLRSEDTAVYYCARESYEYFDIWGQ GTLVTVSS |
| SEQ ID NO 68: | | DNA VH | CAGGTGCAGCTGGTGCAGTCAGGCGCCGAAGTGAAGAAACCCGGCTCTAGC GTGAAGGTGTCCTGTAAAGCCTCCGGCGGCACCTTCTCTAGCTACGCTATTAG CTGGGTCCGACAGGCCCCAGGACAGGGCCTGGAATGGATGGGCTATATTAGC CCCTATATGGGCGAGACTCACTACGCTCAGCGGTTTCAGGGTAGAGTGACTAT |

TABLE 1-continued

Examples of anti-FGFR2 Antibodies of the Present Invention

| | | |
|---|---|---|
| | | CACCGCCGACGAGTCTACTAGCACCGCCTATATGGAACTGTCTAGCCTGAGAT<br>CAGAGGACACCGCCGTCTACTACTGCGCTAGAGAGTCCTACGAGTACTTCGAT<br>ATCTGGGGCCAGGGCACCCTGGTCACCGTGTCATCA |
| SEQ ID NO 69: | Heavy<br>Chain | QVQLVQSGAEVKKPGSSVKVSCKASGGTFSSYAISWVRQAPGQGLEWMGYISPY<br>MGETHYAQRFQGRVTITADESTSTAYMELSSLRSEDTAVYYCARESYEYFDIWGQ<br>GTLVTVSSASTKGPSVFPLAPSSKSTSGGTAALGCLVKDYFPEPVTVSWNSGALTS<br>GVHTFPAVLQSSGLYSLSSVVTVPSSSLGTQTYICNVNHKPSNTKVDKRVEPKSCD<br>KTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPAP<br>IEKTISKAKGQPREPQVYTLPPSREEMTKNQVSLTCLVKGFYPSDIAVEWESNGQP<br>ENNYKTTPPVLDSDGSFFLYSKLTVDKSRWQQGNVFSCSVMHEALHNHYTQKSL<br>SLSPGK |
| SEQ ID NO 70: | DNA<br>Heavy<br>Chain | CAGGTGCAGCTGGTGCAGTCAGGCGCCGAAGTGAAGAAACCCGGCTCTAGC<br>GTGAAGGTGTCCTGTAAAGCCTCCGGCGGCACCTTCTCTAGCTACGCTATTAG<br>CTGGGTCCGACAGGCCCCAGGACAGGGCCTGGAATGGATGGGCTATATTAGC<br>CCCTATATGGGCGAGACTCACTACGCTCAGCGGTTTCAGGGTAGAGTGACTAT<br>CACCGCCGACGAGTCTACTAGCACCGCCTATATGGAACTGTCTAGCCTGAGAT<br>CAGAGGACACCGCCGTCTACTACTGCGCTAGAGAGTCCTACGAGTACTTCGAT<br>ATCTGGGGCCAGGGCACCCTGGTCACCGTGTCATCAGCTAGCACTAAGGGCC<br>CAAGTGTGTTTCCCCTGGCCCCAGCAGCAAGTCTACTTCCGGCGGAACTGCT<br>GCCCTGGGTTGCCTGGTGAAGGACTACTTCCCCGAGCCCGTGACAGTGTCCTG<br>GAACTCTGGGGCTCTGACTTCCGGCGTGCACACCTTCCCCGCCGTGCTGCAGA<br>GCAGCGGCCTGTACAGCCTGAGCAGCGTGGTGACAGTGCCCTCCAGCTCTCT<br>GGGAACCCAGACCTATATCTGCAACGTGAACCACAAGCCCAGCAACACCAAG<br>GTGGACAAGAGAGTGGAGCCCAAGAGCTGCGACAAGACCCACACCTGCCCCC<br>CCTGCCCAGCTCCAGAACTGCTGGGAGGGCCTTCCGTGTTCCTGTTCCCCCCC<br>AAGCCCAAGGACACCCTGATGATCAGCAGGACCCCCGAGGTGACCTGCGTGG<br>TGGTGGACGTGTCCCACGAGGACCCAGAGGTGAAGTTCAACTGGTACGTGGA<br>CGGCGTGGAGGTGCACAACGCCAAGACCAAGCCCAGAGAGGAGCAGTACAA<br>CAGCACCTACAGGGTGGTGTCCGTGCTGACCGTGCTGCACCAGGACTGGCTG<br>AACGGCAAAGAATACAAGTGCAAAGTCTCCAACAAGGCCCTGCCAGCCCCAA<br>TCGAAAAGACAATCAGCAAGGCCAAGGGCCAGCCACGGGAGCCCCAGGTGT<br>ACACCCTGCCCCCCAGCCGGGAGGAGATGACCAAGAACCAGGTGTCCCTGAC<br>CTGTCTGGTGAAGGGCTTCTACCCCAGCGATATCGCCGTGGAGTGGGAGAGC<br>AACGGCCAGCCCGAGAACAACTACAAGACCACCCCCCCAGTGCTGGACAGCG<br>ACGGCAGCTTCTTCCTGTACAGCAAGCTGACCGTGGACAAGTCCAGGTGGCA<br>GCAGGGCAACGTGTTCAGCTGCAGCGTGATGCACGAGGCCCTGCACAACCAC<br>TACACCCAGAAGTCCCTGAGCCTGAGCCCCGGCAAG |
| SEQ ID NO 71: (Kabat) | LCDR1 | RASQSISNDLA |
| SEQ ID NO 72: (Kabat) | LCDR2 | ATSILQS |
| SEQ ID NO 73: (Kabat) | LCDR3 | LQYYDYSYT |
| SEQ ID NO 74: (Chothia) | LCDR1 | SQSISND |
| SEQ ID NO 75: (Chothia) | LCDR2 | ATS |
| SEQ ID NO 76: (Chothia) | LCDR3 | YYDYSY |
| SEQ ID NO 77: | VL | DIQMTQSPSSLSASVGDRVTITCRASQSISNDLAWYQQKPGKAPKLLIYATSILQS<br>GVPSRFSGSGSGTDFTLTISSLQPEDFATYYCLQYYDYSYTFGQGTKVEIK |
| SEQ ID NO 78: | DNA VL | GATATTCAGATGACTCAGTCACCTAGTAGCCTGAGCGCCTCAGTGGGCGATA<br>GAGTGACTATCACCTGTAGAGCCTCCCAGTCTATCTCTAACGACCTGGCCTGG<br>TATCAGCAGAAGCCCGGCAAGGCCCCTAAGCTGCTGATCTACGCTACCTCTAT<br>CCTGCAGAGCGGCGTGCCCTCTAGGTTTAGCGGTAGCGGCTCAGGCACCGAC<br>TTTACCCTGACTATCTCTAGCCTGCAGCCCGAGGACTTCGCTACCTACTACTGC<br>CTGCAGTACTACGACTACTCCTACACCTTCGGCCAGGGCACTAAGGTCGAGAT<br>TAAG |
| SEQ ID NO 79: | Light<br>Chain | DIQMTQSPSSLSASVGDRVTITCRASQSISNDLAWYQQKPGKAPKLLIYATSILQS<br>GVPSRFSGSGSGTDFTLTISSLQPEDFATYYCLQYYDYSYTFGQGTKVEIKRTVAAP<br>SVFIFPPSDEQLKSGTASVVCLLNNFYPREAKVQWKVDNALQSGNSQESVTEQDS<br>KDSTYSLSSTLTLSKADYEKHKVYACEVTHQGLSSPVTKSFNRGEC |
| SEQ ID NO 80: | DNA<br>Light<br>Chain | GATATTCAGATGACTCAGTCACCTAGTAGCCTGAGCGCCTCAGTGGGCGATA<br>GAGTGACTATCACCTGTAGAGCCTCCCAGTCTATCTCTAACGACCTGGCCTGG<br>TATCAGCAGAAGCCCGGCAAGGCCCCTAAGCTGCTGATCTACGCTACCTCTAT<br>CCTGCAGAGCGGCGTGCCCTCTAGGTTTAGCGGTAGCGGCTCAGGCACCGAC<br>TTTACCCTGACTATCTCTAGCCTGCAGCCCGAGGACTTCGCTACCTACTACTGC<br>CTGCAGTACTACGACTACTCCTACACCTTCGGCCAGGGCACTAAGGTCGAGAT<br>TAAGCGTACGGTGGCCGCTCCCAGCGTGTTCATCTTCCCCCCCAGCGACGAGC<br>AGCTGAAGAGCGGCACCGCCAGCGTGGTGTGCCTGCTGAACAACTTCTACCC<br>CCGGGAGGCCAAGGTGCAGTGGAAGGTGGACAACGCCCTGCAGAGCGGCAA |

TABLE 1-continued

Examples of anti-FGFR2 Antibodies of the Present Invention

```
CAGCCAGGAGAGCGTCACCGAGCAGGACAGCAAGGACTCCACCTACAGCCTG
AGCAGCACCCTGACCCTGAGCAAGGCCGACTACGAGAAGCATAAGGTGTACG
CCTGCGAGGTGACCCACCAGGGCCTGTCCAGCCCCGTGACCAAGAGCTTCAA
CAGGGGCGAGTGC
``` mAb20562

| | | | |
|---|---|---|---|
| SEQ ID NO 81: | (Kabat) | HCDR1 | DYAMS |
| SEQ ID NO 82: | (Kabat) | HCDR2 | VIEGDASYTHYADSVRG |
| SEQ ID NO 83: | (Kabat) | HCDR3 | ERTYSSAFDY |
| SEQ ID NO 84: | (Chothia) | HCDR1 | GFTFSDY |
| SEQ ID NO 85: | (Chothia) | HCDR2 | EGDASY |
| SEQ ID NO 86: | (Chothia) | HCDR3 | ERTYSSAFDY |
| SEQ ID NO 87: | | VH | EVQLLESGGGLVQPGGSLRLSCAASGFTFSDYAMSWVRQAPGKGLEWVSVIEGD ASYTHYADSVRGRFTISRDNSKNTLYLQMNSLRAEDTAVYYCARERTYSSAFDYW GQGTLVTVSS |
| SEQ ID NO 88: | | DNA VH | GAGGTGCAGCTGCTGGAATCAGGCGGCGGACTGGTGCAGCCTGGCGGTAGC CTGAGACTGAGCTGCGCTGCTAGTGGCTTCACCTTTAGCGACTACGCTATGAG CTGGGTCAGACAGGCCCCTGGTAAAGGCCTGGAGTGGGTCAGCGTGATCGA GGGCGACGCTAGTTACACTCACTACGCCGATAGCGTCAGAGGCCGGTTCACT ATCTCTAGGGATAACTCTAAGAACACCCTGTACCTGCAGATGAATAGCCTGAG AGCCGAGGACACCGCCGTCTACTACTGCGCTAGAGAGCGGACCTACTCTAGC GCCTTCGACTACTGGGGTCAGGGCACCCTGGTCACCGTGTCTAGC |
| SEQ ID NO 89: | | Heavy Chain | EVQLLESGGGLVQPGGSLRLSCAASGFTFSDYAMSWVRQAPGKGLEWVSVIEGD ASYTHYADSVRGRFTISRDNSKNTLYLQMNSLRAEDTAVYYCARERTYSSAFDYW GQGTLVTVSSASTKGPSVFPLAPSSKSTSGGTAALGCLVKDYFPEPVTVSWNSGAL TSGVHTFPAVLQSSGLYSLSSVVTVPSSSLGTQTYICNVNHKPSNTKVDKRVEPKSC DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALP APIEKTISKAKGQPREPQVYTLPPSREEMTKNQVSLTCLVKGFYPSDIAVEWESNG QPENNYKTTPPVLDSDGSFFLYSKLTVDKSRWQQGNVFSCSVMHEALHNHYTQK SLSLSPGK |
| SEQ ID NO 90: | | DNA Heavy Chain | GAGGTGCAGCTGCTGGAATCAGGCGGCGGACTGGTGCAGCCTGGCGGTAGC CTGAGACTGAGCTGCGCTGCTAGTGGCTTCACCTTTAGCGACTACGCTATGAG CTGGGTCAGACAGGCCCCTGGTAAAGGCCTGGAGTGGGTCAGCGTGATCGA GGGCGACGCTAGTTACACTCACTACGCCGATAGCGTCAGAGGCCGGTTCACT ATCTCTAGGGATAACTCTAAGAACACCCTGTACCTGCAGATGAATAGCCTGAG AGCCGAGGACACCGCCGTCTACTACTGCGCTAGAGAGCGGACCTACTCTAGC GCCTTCGACTACTGGGGTCAGGGCACCCTGGTCACCGTGTCTAGCGCTAGCAC TAAGGGCCCAAGTGTGTTTCCCCTGGCCCCCAGCAGCAAGTCTACTTCCGGCG GAACTGCTGCCCTGGGTTGCCTGGTGAAGGACTACTTCCCCGAGCCCGTGACA GTGTCCTGGAACTCTGGGGCTCTGACTTCCGGCGTGCACACCTTCCCCGCCGT GCTGCAGAGCAGCGGCCTGTACAGCCTGAGCAGCGTGGTGACAGTGCCCTCC AGCTCTCTGGGAACCCAGACCTATATCTGCAACGTGAACCACAAGCCCAGCAA CACCAAGGTGGACAAGAGAGTGGAGCCCAAGAGCTGCGACAAGACCCACAC CTGCCCCCCCTGCCCAGCTCCAGAACTGCTGGGAGGGCTTCCGTGTTCCTGT TCCCCCCCAAGCCCAAGGACACCCTGATGATCAGCAGGACCCCCGAGGTGAC CTGCGTGGTGGTGGACGTGTCCCACGAGGACCCAGAGGTGAAGTTCAACTGG TACGTGGACGGCGTGGAGGTGCACAACGCCAAGACCAAGCCCAGAGAGGAG CAGTACAACAGCACCTACAGGGTGGTGTCCGTGCTGACCGTGCTGCACCAGG ACTGGCTGAACGGCAAAGAATACAAGTGCAAGTCTCCAACAAGGCCCTGCC AGCCCCAATCGAAAAGACAATCAGCAAGGCCAAGGGCCAGCCACGGGAGCC CCAGGTGTACACCCTGCCCCCCAGCCGGGAGGAGATGACCAAGAACCAGGTG TCCCTGACCTGTCTGGTGAAGGCTTCTACCCCAGCGATATCGCCGTGGAGTG GGAGAGCAACGGCCAGCCCGAGAACAACTACAAGACCACCCCCCCAGTGCTG GACAGCGACGGCAGCTTCTTCCTGTACAGCAAGCTGACCGTGGACAAGTCCA GGTGGCAGCAGGGCAACGTGTTCAGCTGCAGCGTGATGCACGAGGCCCTGC ACAACCACTACACCCAGAAGTCCCTGAGCCTGAGCCCCGGCAAG |
| SEQ ID NO 91: | (Kabat) | LCDR1 | RASQDISSDLN |
| SEQ ID NO 92: | (Kabat) | LCDR2 | DASNLQS |
| SEQ ID NO 93: | (Kabat) | LCDR3 | QQHYSPSHT |
| SEQ ID NO 94: | (Chothia) | LCDR1 | SQDISSD |
| SEQ ID NO 95: | (Chothia) | LCDR2 | DAS |

TABLE 1-continued

Examples of anti-FGFR2 Antibodies of the Present Invention

| SEQ ID NO 96: (Chothia) | LCDR3 | HYSPSH |
|---|---|---|
| SEQ ID NO 97: | VL | DIQMTQSPSSLSASVGDRVTITCRASQDISSDLNWYQQKPGKAPKLLIYDASNLQS<br>GVPSRFSGSGSGTDFTLTISSLQPEDFATYYCQQHYSPSHTFGQGTKVEIK |
| SEQ ID NO 98: | DNA VL | GATATTCAGATGACTCAGTCACCTAGTAGCCTGAGCGCTAGTGTGGGCGATA<br>GAGTGACTATCACCTGTAGAGCCTCTCAGGATATCTCTAGCGACCTGAACTGG<br>TATCAGCAGAAGCCCGGTAAAGCCCCTAAGCTGCTGATCTACGACGCCTCTAA<br>CCTGCAGTCAGGCGTGCCCTCTAGGTTTAGCGGTAGCGGTAGTGGCACCGAC<br>TTCACCCTGACTATCTCTAGCCTGCAGCCCGAGGACTTCGCTACCTACTACTGT<br>CAGCAGCACTATAGCCCTAGTCACACCTTCGGTCAGGGCACTAAGGTCGAGAT<br>TAAG |
| SEQ ID NO 99: | Light<br>Chain | DIQMTQSPSSLSASVGDRVTITCRASQDISSDLNWYQQKPGKAPKLLIYDASNLQS<br>GVPSRFSGSGSGTDFTLTISSLQPEDFATYYCQQHYSPSHTFGQGTKVEIKRTVAA<br>PSVFIFPPSDEQLKSGTASVVCLLNNFYPREAKVQWKVDNALQSGNSQESVTEQD<br>SKDSTYSLSSTLTLSKADYEKHKVYACEVTHQGLSSPVTKSFNRGEC |
| SEQ ID NO 100: | DNA<br>Light<br>Chain | GATATTCAGATGACTCAGTCACCTAGTAGCCTGAGCGCTAGTGTGGGCGATA<br>GAGTGACTATCACCTGTAGAGCCTCTCAGGATATCTCTAGCGACCTGAACTGG<br>TATCAGCAGAAGCCCGGTAAAGCCCCTAAGCTGCTGATCTACGACGCCTCTAA<br>CCTGCAGTCAGGCGTGCCCTCTAGGTTTAGCGGTAGCGGTAGTGGCACCGAC<br>TTCACCCTGACTATCTCTAGCCTGCAGCCCGAGGACTTCGCTACCTACTACTGT<br>CAGCAGCACTATAGCCCTAGTCACACCTTCGGTCAGGGCACTAAGGTCGAGAT<br>TAAGCGTACGGTGGCCGCTCCCAGCGTGTTCATCTTCCCCCCCAGCGACGAGC<br>AGCTGAAGAGCGGCACCGCCAGCGTGGTGTGCCTGCTGAACAACTTCTACCC<br>CCGGGAGGCCAAGGTGCAGTGGAAGGTGGACAACGCCCTGCAGAGCGGCAA<br>CAGCCAGGAGAGCGTCACCGAGCAGGACAGCAAGGACTCCACCTACAGCCTG<br>AGCAGCACCCTGACCCTGAGCAAGGCCGACTACGAGAAGCATAAGGTGTACG<br>CCTGCGAGGTGACCCACCAGGGCCTGTCCAGCCCCGTGACCAAGAGCTTCAA<br>CAGGGGCGAGTGC | mAb20437

| SEQ ID NO 101: (Kabat) | HCDR1 | SYALS |
|---|---|---|
| SEQ ID NO 102: (Kabat) | HCDR2 | RIRSRIEGGTTDYAAPVRG |
| SEQ ID NO 103: (Kabat) | HCDR3 | DRSPSDSSAFAI |
| SEQ ID NO 104: (Chothia) | HCDR1 | GFTFSSY |
| SEQ ID NO 105: (Chothia) | HCDR2 | RSRIEGGT |
| SEQ ID NO 106: (Chothia) | HCDR3 | DRSPSDSSAFAI |
| SEQ ID NO 107: | VH | EVQLVESGGGLVKPGGSLRLSCAASGFTFSSYALSWVRQAPGKGLEWVGRIRSRI<br>EGGTTDYAAPVRGRFTISRDDSKNTLYLQMNSLKTEDTAVYYCARDRSPSDSSAF<br>AIWGQGTLVTVSS |
| SEQ ID NO 108: | DNA VH | GAGGTGCAGCTGGTGGAATCAGGCGGCGGACTGGTCAAGCCTGGCGGTAGC<br>CTGAGACTGAGCTGCGCTGCTAGTGGCTTCACCTTCTCTAGCTACGCCCTGAG<br>CTGGGTCAGACAGGCCCCTGGTAAAGGCCTGGAGTGGGTCGGACGGATTAG<br>ATCTAGGATCGAGGGCGGCACTACCGACTACGCCGCTCCCGTCAGAGGCCGG<br>TTCACTATCTCTAGGGACGACTCTAAGAACACCCTGTACCTGCAGATGAATAG<br>CCTGAAAACCGAGGACACCGCCGTCTACTACTGCGCTAGAGATAGATCACCTA<br>GCGACTCTAGCGCCTTCGCTATCTGGGGTCAGGGCACCCTGGTCACCGTGTCT<br>AGC |
| SEQ ID NO 109: | Heavy<br>Chain | EVQLVESGGGLVKPGGSLRLSCAASGFTFSSYALSWVRQAPGKGLEWVGRIRSRI<br>EGGTTDYAAPVRGRFTISRDDSKNTLYLQMNSLKTEDTAVYYCARDRSPSDSSAF<br>AIWGQGTLVTVSSASTKGPSVFPLAPSSKSTSGGTAALGCLVKDYFPEPVTVSWN<br>SGALTSGVHTFPAVLQSSGLYSLSSVVTVPSSSLGTQTYICNVNHKPSNTKVDKRV<br>EPKSCDKTHTCPPCPAPELLGGPSVFLFPPKPKDTLMISRTPEVTCVVVDVSHEDP<br>EVKFNWYVDGVEVHNAKTKPREEQYNSTYRVVSVLTVLHQDWLNGKEYKCKVS<br>NKALPAPIEKTISKAKGQPREPQVYTLPPSREEMTKNQVSLTCLVKGFYPSDIAVE<br>WESNGQPENNYKTTPPVLDSDGSFFLYSKLTVDKSRWQQGNVFSCSVMHEALH<br>NHYTQKSLSLSPGK |
| SEQ ID NO 110: | DNA<br>Heavy<br>Chain | GAGGTGCAGCTGGTGGAATCAGGCGGCGGACTGGTCAAGCCTGGCGGTAGC<br>CTGAGACTGAGCTGCGCTGCTAGTGGCTTCACCTTCTCTAGCTACGCCCTGAG<br>CTGGGTCAGACAGGCCCCTGGTAAAGGCCTGGAGTGGGTCGGACGGATTAG<br>ATCTAGGATCGAGGGCGGCACTACCGACTACGCCGCTCCCGTCAGAGGCCGG<br>TTCACTATCTCTAGGGACGACTCTAAGAACACCCTGTACCTGCAGATGAATAG<br>CCTGAAAACCGAGGACACCGCCGTCTACTACTGCGCTAGAGATAGATCACCTA<br>GCGACTCTAGCGCCTTCGCTATCTGGGGTCAGGGCACCCTGGTCACCGTGTCT<br>AGCGCTAGCACTAAGGGCCCAAGTGTGTTTCCCCTGGCCCCCAGCAGCAAGTC<br>TACTTCCGGCGGAACTGCTGCCCTGGGTTGCCTGGTGAAGGACTACTTCCCCG<br>AGCCCGTGACAGTGTCCTGGAACTCTGGGGCTCTGACTTCCGGCGTGCACACC |

TABLE 1-continued

Examples of anti-FGFR2 Antibodies of the Present Invention

|  |  |  |  |
|---|---|---|---|
|  |  |  | TTCCCCGCCGTGCTGCAGAGCAGCGGCCTGTACAGCCTGAGCAGCGTGGTGA<br>CAGTGCCCTCCAGCTCTCTGGGAACCCAGACCTATATCTGCAACGTGAACCAC<br>AAGCCCAGCAACACCAAGGTGGACAAGAGAGTGGAGCCCAAGAGCTGCGAC<br>AAGACCCACACCTGCCCCCCCTGCCCAGCTCCAGAACTGCTGGGAGGGCCTTC<br>CGTGTTCCTGTTCCCCCCAAGCCCAAGGACACCCTGATGATCAGCAGGACCC<br>CCGAGGTGACCTGCGTGGTGGTGGACGTGTCCCACGAGGACCCAGAGGTGA<br>AGTTCAACTGGTACGTGGACGGCGTGGAGGTGCACAACGCCAAGACCAAGCC<br>CAGAGAGGAGCAGTACAACAGCACCTACAGGGTGGTGTCCGTGCTGACCGTG<br>CTGCACCAGGACTGGCTGAACGGCAAAGAATACAAGTGCAAAGTCTCCAACA<br>AGGCCCTGCCAGCCCCAATCGAAAAGACAATCAGCAAGGCCAAGGGCCAGCC<br>ACGGGAGCCCCAGGTGTACACCCTGCCCCCCAGCCGGGAGGAGATGACCAAG<br>AACCAGGTGTCCCTGACCTGTCTGGTGAAGGGCTTCTACCCCAGCGATATCGC<br>CGTGGAGTGGGAGAGCAACGGCCAGCCCGAGAACAACTACAAGACCACCCC<br>CCCAGTGCTGGACAGCGACGGCAGCTTCTTCCTGTACAGCAAGCTGACCGTG<br>GACAAGTCCAGGTGGCAGCAGGGCAACGTGTTCAGCTGCAGCGTGATGCACG<br>AGGCCCTGCACAACCACTACACCCAGAAGTCCCTGAGCCTGAGCCCCGGCAAG |
| SEQ ID NO 111: | (Kabat) | LCDR1 | SGDNLGSQYVD |
| SEQ ID NO 112: | (Kabat) | LCDR2 | DDNDRPS |
| SEQ ID NO 113: | (Kabat) | LCDR3 | QSWDSLSVV |
| SEQ ID NO 114: | (Chothia) | LCDR1 | DNLGSQY |
| SEQ ID NO 115: | (Chothia) | LCDR2 | DDN |
| SEQ ID NO 116: | (Chothia) | LCDR3 | WDSLSV |
| SEQ ID NO 117: |  | VL | SYELTQPLSVSVALGQTARITCSGDNLGSQYVDWYQQKPGQAPVLVIYDDNDRP<br>SGIPERFSGSNSGNTATLTISRAQAGDEADYYCQSWDSLSVVFGGGTKLTVL |
| SEQ ID NO 118: |  | DNA VL | AGCTACGAGCTGACTCAGCCCCTGAGCGTCAGCGTGGCCCTGGGTCAGACCG<br>CTAGAATCACCTGTAGCGGCGATAACCTGGGCTCTCAGTACGTGGACTGGTAT<br>CAGCAGAAGCCCGGTCAGGCCCCCGTGCTGGTGATCTACGACGATAACGATA<br>GACCTAGCGGAATCCCCGAGCGGTTTAGCGGCTCTAATAGCGGTAACACCGC<br>TACCCTGACTATCTCTAGGGCTCAGGCCGGCGACGAGGCCGACTACTACTGTC<br>AGTCCTGGGATAGCCTGAGCGTGGTGTTCGGCGGAGGCACTAAGCTGACCGT<br>GCTG |
| SEQ ID NO 119: |  | Light<br>Chain | SYELTQPLSVSVALGQTARITCSGDNLGSQYVDWYQQKPGQAPVLVIYDDNDRP<br>SGIPERFSGSNSGNTATLTISRAQAGDEADYYCQSWDSLSVVFGGGTKLTVLGQP<br>KAAPSVTLFPPSSEELQANKATLVCLISDFYPGAVTVAWKADSSPVKAGVETTTPS<br>KQSNNKYAASSYLSLTPEQWKSHRSYSCQVTHEGSTVEKTVAPTECS |
| SEQ ID NO 120: |  | DNA<br>Light<br>Chain | AGCTACGAGCTGACTCAGCCCCTGAGCGTCAGCGTGGCCCTGGGTCAGACCG<br>CTAGAATCACCTGTAGCGGCGATAACCTGGGCTCTCAGTACGTGGACTGGTAT<br>CAGCAGAAGCCCGGTCAGGCCCCCGTGCTGGTGATCTACGACGATAACGATA<br>GACCTAGCGGAATCCCCGAGCGGTTTAGCGGCTCTAATAGCGGTAACACCGC<br>TACCCTGACTATCTCTAGGGCTCAGGCCGGCGACGAGGCCGACTACTACTGTC<br>AGTCCTGGGATAGCCTGAGCGTGGTGTTCGGCGGAGGCACTAAGCTGACCGT<br>GCTGGGTCAGCCTAAGGCTGCCCCCAGCGTGACCCTGTTCCCCCCCAGCAGCG<br>AGGAGCTGCAGGCCAACAAGGCCACCCTGGTGTGCCTGATCAGCGACTTCTA<br>CCCAGGCGCCGTGACCGTGGCCTGGAAGGCCGACAGCAGCCCCGTGAAGGC<br>CGGCGTGGAGACCACCACCCCCAGCAAGCAGAGCAACAACAAGTACGCCGCC<br>AGCAGCTACCTGAGCCTGACCCCCGAGCAGTGGAAGAGCCACAGGTCCTACA<br>GCTGCCAGGTGACCCACGAGGGCAGCACCGTGGAAAAGACCGTGGCCCCAA<br>CCGAGTGCAGC |
| mAb20811 |  |  |  |
| SEQ ID NO 121: | (Kabat) | HCDR1 | DYAMS |
| SEQ ID NO 122: | (Kabat) | HCDR2 | TIEGDSNYIEYADSVKG |
| SEQ ID NO 123: | (Kabat) | HCDR3 | ERTYSSAFDY |
| SEQ ID NO 124: | (Chothia) | HCDR1 | GFTFSDY |
| SEQ ID NO 125: | (Chothia) | HCDR2 | EGDSNY |
| SEQ ID NO 126: | (Chothia) | HCDR3 | ERTYSSAFDY |
| SEQ ID NO 127: |  | VH | QVQLLESGGGLVQPGGSLRLSCAASGFTFSDYAMSWVRQAPGKGLEWVSTIEG<br>DSNYIEYADSVKGRFTISRDNSKNTLYLQMNSLRAEDTAVYYCARERTYSSAFDYW<br>GQGTLVTVSS |
| SEQ ID NO 128: |  | DNA VH | CAGGTGCAATTGCTGGAAAGCGGCGGTGGCCTGGTGCAGCCGGGTGGCAGC<br>CTGCGTCTGAGCTGCGCGGCGTCCGGATTCACCTTTTCTGACTACGCTATGTCT |

TABLE 1-continued

Examples of anti-FGFR2 Antibodies of the Present Invention

|  |  |  |  |
|---|---|---|---|
|  |  |  | TGGGTGCGCCAGGCCCCGGGCAAAGGTCTCGAGTGGGTTTCCACTATCGAAG<br>GTGACAGCAACTACATCGAATATGCGGATAGCGTGAAAGGCCGCTTTACCATC<br>AGCCCGCGATAATTCGAAAAACACCCTGTATCTGCAAATGAACAGCCTGCGTGC<br>GGAAGATACGGCCGTGTATTATTGCGCGCGTGAACGTACTTACTCTTCTGCTT<br>TCGATTACTGGGGCCAAGGCACCCTGGTGACTGTTAGCTCA |
| SEQ ID NO 129: |  | Heavy<br>Chain | QVQLLESGGGLVQPGGSLRLSCAASGFTFSDYAMSWVRQAPGKGLEWVSTIEG<br>DSNYIEYADSVKGRFTISRDNSKNTLYLQMNSLRAEDTAVYYCARERTYSSAFDYW<br>GQGTLVTVSSASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNTKVDKRVEPKSC<br>DKTHTCPPCPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKALP<br>APIEKTISKAKGQPREPQVYTLPPSREEMTKNQVSLTCLVKGFYPSDIAVEWESNG<br>QPENNYKTTPPVLDSDGSFFLYSKLTVDKSRWQQGNVFSCSVMHEALHNHYTQK<br>SLSLSPGK |
| SEQ ID NO 130: |  | DNA<br>Heavy<br>Chain | CAGGTGCAATTGCTGGAAAGCGGCGGTGGCCTGGTGCAGCCGGGTGGCAGC<br>CTGCGTCTGAGCTGCGCGGCGTCCGGATTCACCTTTTCTGACTACGCTATGTCT<br>TGGGTGCGCCAGGCCCCGGGCAAAGGTCTCGAGTGGGTTTCCACTATCGAAG<br>GTGACAGCAACTACATCGAATATGCGGATAGCGTGAAAGGCCGCTTTACCATC<br>AGCCCGCGATAATTCGAAAAACACCCTGTATCTGCAAATGAACAGCCTGCGTGC<br>GGAAGATACGGCCGTGTATTATTGCGCGCGTGAACGTACTTACTCTTCTGCTT<br>TCGATTACTGGGGCCAAGGCACCCTGGTGACTGTTAGCTCAGCCTCCACCAAG<br>GGTCCATCGGTCTTCCCCCTGGCACCCTCCTCCAAGAGCACCTCTGGGGGCAC<br>AGCGGCCCTGGGCTGCCTGGTCAAGGACTACTTCCCCGAACCGGTGACGGTG<br>TCGTGGAACTCAGGCGCCCTGACCAGCGGCGTGCACACCTTCCCGGCTGTCCT<br>ACAGTCCTCAGGACTCTACTCCCTCAGCAGCGTGGTGACCGTGCCCTCCAGCA<br>GCTTGGGCACCCAGACCTACATCTGCAACGTGAATCACAAGCCCAGCAACACC<br>AAGGTGGACAAGAGAGTTGAGCCCAAATCTTGTGACAAAACTCACACATGCC<br>CACCGTGCCCAGCACCTGAACTCCTGGGGGGACCGTCAGTCTTCCTCTTCCCC<br>CCAAAACCCAAGGACACCCTCATGATCTCCCGGACCCCTGAGGTCACATGCGT<br>GGTGGTGGACGTGAGCCACGAAGACCCTGAGGTCAAGTTCAACTGGTACGTG<br>GACGGCGTGGAGGTGCATAATGCCAAGACAAAGCCGCGGGAGGAGCAGTAC<br>AACAGCACGTACCGGGTGGTCAGCGTCCTCACCGTCCTGCACCAGGACTGGC<br>TGAATGGCAAGGAGTACAAGTGCAAGGTCTCCAACAAAGCCCTCCCAGCCCC<br>CATCGAGAAAACCATCTCCAAAGCCAAAGGGCAGCCCCGAGAACCACAGGTG<br>TACACCCTGCCCCCATCCCGGGAGGAGATGACCAAGAACCAGGTCAGCCTGA<br>CCTGCCTGGTCAAAGGCTTCTATCCCAGCGACATCGCCGTGGAGTGGGAGAG<br>CAATGGGCAGCCGGAGAACAACTACAAGACCACGCCTCCCGTGCTGGACTCC<br>GACGGCTCCTTCTTCCTCTACAGCAAGCTCACCGTGGACAAGAGCAGGTGGCA<br>GCAGGGGAACGTCTTCTCATGCTCCGTGATGCATGAGGCTCTGCACAACCACT<br>ACACGCAGAAGAGCCTCTCCCTGTCTCCGGGTAAA |
| SEQ ID NO 131: | (Kabat) | LCDR1 | RASQDISSDLN |
| SEQ ID NO 132: | (Kabat) | LCDR2 | DASNLQS |
| SEQ ID NO 133: | (Kabat) | LCDR3 | HQWYSTLYT |
| SEQ ID NO 134: | (Chothia) | LCDR1 | SQDISSD |
| SEQ ID NO 135: | (Chothia) | LCDR2 | DAS |
| SEQ ID NO 136: | (Chothia) | LCDR3 | WYSTLY |
| SEQ ID NO 137: |  | VL | DIQMTQSPSSLSASVGDRVTITCRASQDISSDLNWYQQKPGKAPKLLIYDASNLQS<br>GVPSRFSGSGSGTDFTLTISSLQPEDFATYYCHQWYSTLYTFGQGTKVEIK |
| SEQ ID NO 138: |  | DNA VL | GATATCCAGATGACCCAGAGCCCGAGCAGCCTGAGCGCCAGCGTGGGCGATC<br>GCGTGACCATTACCTGCAGAGCCAGCCAGGACATTTCTTCTGACCTGAACTGG<br>TACCAGCAGAAACCGGGCAAAGCGCCGAAACTATTAATCTACGACGCTTCTAA<br>CCTGCAAAGCGGCGTGCCGAGCCGCTTTAGCGGCAGCGGATCCGGCACCGAT<br>TTCACCCTGACCATTAGCTCTCTGCAACCGGAAGACTTTGCGACCTATTATTGC<br>CATCAGTGGTACTCTACTCTGTACACCTTTGGCCAGGGCACGAAAGTTGAAAT<br>TAAA |
| SEQ ID NO 139: |  | Light<br>Chain | DIQMTQSPSSLSASVGDRVTITCRASQDISSDLNWYQQKPGKAPKLLIYDASNLQS<br>GVPSRFSGSGSGTDFTLTISSLQPEDFATYYCHQWYSTLYTFGQGTKVEIKRTVAA<br>PSVFIFPPSDEQLKSGTASVVCLLNNFYPREAKVQWKVDNALQSGNSQESVTEQD<br>SKDSTYSLSSTLTLSKADYEKHKVYACEVTHQGLSSPVTKSFNRGEC |
| SEQ ID NO 140: |  | DNA<br>Light<br>Chain | GATATCCAGATGACCCAGAGCCCGAGCAGCCTGAGCGCCAGCGTGGGCGATC<br>GCGTGACCATTACCTGCAGAGCCAGCCAGGACATTTCTTCTGACCTGAACTGG<br>TACCAGCAGAAACCGGGCAAAGCGCCGAAACTATTAATCTACGACGCTTCTAA<br>CCTGCAAAGCGGCGTGCCGAGCCGCTTTAGCGGCAGCGGATCCGGCACCGAT<br>TTCACCCTGACCATTAGCTCTCTGCAACCGGAAGACTTTGCGACCTATTATTGC<br>CATCAGTGGTACTCTACTCTGTACACCTTTGGCCAGGGCACGAAAGTTGAAAT<br>TAAACGTACGGTGGCCGCTCCCAGCGTGTTCATCTTCCCCCCCAGCGACGAGC |

TABLE 1-continued

Examples of anti-FGFR2 Antibodies of the Present Invention

```
AGCTGAAGAGCGGCACCGCCAGCGTGGTGTGCCTGCTGAACAACTTCTACCC
CCGGGAGGCCAAGGTGCAGTGGAAGGTGGACAACGCCCTGCAGAGCGGCAA
CAGCCAGGAAAGCGTCACCGAGCAGGACAGCAAGGACTCCACCTACAGCCTG
AGCAGCACCCTGACCCTGAGCAAGGCCGACTACGAGAAGCACAAGGTGTACG
CCTGCGAGGTGACCCACCAGGGCCTGTCCAGCCCCGTGACCAAGAGCTTCAA
CCGGGGCGAGTGT
``` mAb12422

| SEQ ID NO 141: | (Kabat) | HCDR1 | SYAIS |
|---|---|---|---|
| SEQ ID NO 142: | (Kabat) | HCDR2 | YISPYMGETHYAQKFQG |
| SEQ ID NO 143: | (Kabat) | HCDR3 | ESYEYFDI |
| SEQ ID NO 144: | (Chothia) | HCDR1 | GGTFSSY |
| SEQ ID NO 145: | (Chothia) | HCDR2 | SPYMGE |
| SEQ ID NO 146: | (Chothia) | HCDR3 | ESYEYFDI |
| SEQ ID NO 147: | | VH | QVQLVQSGAEVKKPGSSVKVSCKASGGTFSSYAISWVRQAPGQGLEWMGYISPY MGETHYAQKFQGRVTITADESTSTAYMELSSLRSEDTAVYYCARESYEYFDIWGQ GTLVTVSS |
| SEQ ID NO 148: | | DNA VH | CAGGTGCAATTGGTGCAGAGCGGTGCCGAAGTGAAAAAACCGGGCAGCAGC GTGAAAGTTAGCTGCAAAGCATCCGGAGGGACGTTTAGCAGCTATGCGATTA GCTGGGTGCGCCAGGCCCCGGGCCAGGGCCTCGAGTGGATGGGCTACATCTC TCCGTACATGGGCGAAACTCATTACGCCCAGAAATTTCAGGGCCGGGTGACC ATTACCGCCGATGAAAGCACCAGCACCGCCTATATGGAACTGAGCAGCCTGC GCAGCGAAGATACGGCCGTGTATTATTGCGCGCGTGAATCTTACGAATACTTC GACATCTGGGGCCAAGGCACCCTGGTGACTGTTAGCTCA |
| SEQ ID NO 149: | | Heavy Chain | QVQLVQSGAEVKKPGSSVKVSCKASGGTFSSYAISWVRQAPGQGLEWMGYISPY MGETHYAQKFQGRVTITADESTSTAYMELSSLRSEDTAVYYCARESYEYFDIWGQ GTLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKRVEPKSCD KTHTCPPCPAPELLGGPSVFLFPPKPKDTLMISRTPEVTCVVVDVSHEDPEVKFNW YVDGVEVHNAKTKPREEQYNSTYRVVSVLTVLHQDWLNGKEYKCKVSNKALPAP IEKTISKAKGQPREPQVYTLPPSREEMTKNQVSLTCLVKGFYPSDIAVEWESNGQP ENNYKTTPPVLDSDGSFFLYSKLTVDKSRWQQGNVFSCSVMHEALHNHYTQKSL SLSPGK |
| SEQ ID NO 150: | | DNA Heavy Chain | CAGGTGCAATTGGTGCAGAGCGGTGCCGAAGTGAAAAAACCGGGCAGCAGC GTGAAAGTTAGCTGCAAAGCATCCGGAGGGACGTTTAGCAGCTATGCGATTA GCTGGGTGCGCCAGGCCCCGGGCCAGGGCCTCGAGTGGATGGGCTACATCTC TCCGTACATGGGCGAAACTCATTACGCCCAGAAATTTCAGGGCCGGGTGACC ATTACCGCCGATGAAAGCACCAGCACCGCCTATATGGAACTGAGCAGCCTGC GCAGCGAAGATACGGCCGTGTATTATTGCGCGCGTGAATCTTACGAATACTTC GACATCTGGGGCCAAGGCACCCTGGTGACTGTTAGCTCAGCCTCCACCAAGG GTCCATCGGTCTTCCCCCTGGCACCCTCCTCCAAGAGCACCTCTGGGGGCACA GCGGCCCTGGGCTGCCTGGTCAAGGACTACTTCCCCGAACCGGTGACGGTGT CGTGGAACTCAGGCGCCCTGACCAGCGGCGTGCACACCTTCCCGGCTGTCCTA CAGTCCTCAGGACTCTACTCCCTCAGCAGCGTGGTGACCGTGCCCTCCAGCAG CTTGGGCACCCAGACCTACATCTGCAACGTGAATCACAAGCCCAGCAACACCA AGGTGGACAAGAGAGTTGAGCCCAAATCTTGTGACAAAACTCACACATGCCC ACCGTGCCCAGCACCTGAACTCCTGGGGGGACCGTCAGTCTTCCTCTTCCCCC CAAAACCCAAGGACACCCTCATGATCTCCCGGACCCCTGAGGTCACATGCGTG GTGGTGGACGTGAGCCACGAAGACCCTGAGGTCAAGTTCAACTGGTACGTGG ACGGCGTGGAGGTGCATAATGCCAAGACAAAGCCGCGGGAGGAGCAGTACA ACAGCACGTACCGGGTGGTCAGCGTCCTCACCGTCCTGCACCAGGACTGGCT GAATGGCAAGGAGTACAAGTGCAAGGTCTCCAACAAAGCCCTCCCAGCCCCC ATCGAGAAAACCATCTCCAAAGCCAAAGGGCAGCCCCGAGAACCACAGGTGT ACACCCTGCCCCCATCCCGGGAGGAGATGACCAAGAACCAGGTCAGCCTGAC CTGCCTGGTCAAAGGCTTCTATCCCAGCGACATCGCCGTGGAGTGGGAGAGC AATGGGCAGCCGGAGAACAACTACAAGACCACGCCTCCCGTGCTGGACTCCG ACGGCTCCTTCTTCCTCTACAGCAAGCTCACCGTGGACAAGAGCAGGTGGCAG CAGGGGAACGTCTTCTCATGCTCCGTGATGCATGAGGCTCTGCACAACCACTA CACGCAGAAGAGCCTCTCCCTGTCTCCGGGTAAA |
| SEQ ID NO 151: | (Kabat) | LCDR1 | RASQSISNDLA |
| SEQ ID NO 152: | (Kabat) | LCDR2 | ATSILQS |
| SEQ ID NO 153: | (Kabat) | LCDR3 | LQYYDYSYT |
| SEQ ID NO 154: | (Chothia) | LCDR1 | SQSISND |

TABLE 1-continued

Examples of anti-FGFR2 Antibodies of the Present Invention

| SEQ ID NO 155: | (Chothia) LCDR2 | ATS |
|---|---|---|
| SEQ ID NO 156: | (Chothia) LCDR3 | YYDYSY |
| SEQ ID NO 157: | VL | DIQMTQSPSSLSASVGDRVTITCRASQSISNDLAWYQQKPGKAPKLLIYATSILQS GVPSRFSGSGSGTDFTLTISSLQPEDFATYYCLQYYDYSYTFGQGTKVEIK |
| SEQ ID NO 158: | DNA VL | GATATCCAGATGACCCAGAGCCCGAGCAGCCTGAGCGCCAGCGTGGGCGATC GCGTGACCATTACCTGCAGAGCCAGCCAGTCTATTTCTAACGACCTGGCTTGG TACCAGCAGAAACCGGGCAAAGCGCCGAAACTATTAATCTACGCTACTTCTAT CCTGCAAAGCGGCGTGCCGAGCCGCTTTAGCGGCAGCGGATCCGGCACCGAT TTCACCCTGACCATTAGCTCTCTGCAACCGGAAGACTTTGCGACCTATTATTGC CTGCAGTACTACGACTACTCTTACACCTTTGGCCAGGGCACGAAAGTTGAAAT TAAA |
| SEQ ID NO 159: | Light Chain | DIQMTQSPSSLSASVGDRVTITCRASQSISNDLAWYQQKPGKAPKLLIYATSILQS GVPSRFSGSGSGTDFTLTISSLQPEDFATYYCLQYYDYSYTFGQGTKVEIKRTVAAP SVFIFPPSDEQLKSGTASVVCLLNNFYPREAKVQWKVDNALQSGNSQESVTEQDS KDSTYSLSSTLTLSKADYEKHKVYACEVTHQGLSSPVTKSFNRGEC |
| SEQ ID NO 160: | DNA Light Chain | GATATCCAGATGACCCAGAGCCCGAGCAGCCTGAGCGCCAGCGTGGGCGATC GCGTGACCATTACCTGCAGAGCCAGCCAGTCTATTTCTAACGACCTGGCTTGG TACCAGCAGAAACCGGGCAAAGCGCCGAAACTATTAATCTACGCTACTTCTAT CCTGCAAAGCGGCGTGCCGAGCCGCTTTAGCGGCAGCGGATCCGGCACCGAT TTCACCCTGACCATTAGCTCTCTGCAACCGGAAGACTTTGCGACCTATTATTGC CTGCAGTACTACGACTACTCTTACACCTTTGGCCAGGGCACGAAAGTTGAAAT TAAACGTACGGTGGCCGCTCCCAGCGTGTTCATCTTCCCCCCAGCGACGAGC AGCTGAAGAGCGGCACCGCCAGCGTGGTGTGCCTGCTGAACAACTTCTACCC CCGGGAGGCCAAGGTGCAGTGGAAGGTGGACAACGCCCTGCAGAGCGGCAA CAGCCAGGAAAGCGTCACCGAGCAGGACAGCAAGGACTCCACCTACAGCCTG AGCAGCACCCTGACCCTGAGCAAGGCCGACTACGAGAAGCACAAGGTGTACG CCTGCGAGGTGACCCACCAGGGCCTGTCCAGCCCCGTGACCAAGAGCTTCAA CCGGGGCGAGTGT | mAb12439

| SEQ ID NO 161: | (Kabat) HCDR1 | SYDIS |
|---|---|---|
| SEQ ID NO 162: | (Kabat) HCDR2 | WINPYNGGTNYAQKFQG |
| SEQ ID NO 163: | (Kabat) HCDR3 | EGSGMIVYPGWSYAFDY |
| SEQ ID NO 164: | (Chothia) HCDR1 | GYTFTSY |
| SEQ ID NO 165: | (Chothia) HCDR2 | NPYNGG |
| SEQ ID NO 166: | (Chothia) HCDR3 | EGSGMIVYPGWSYAFDY |
| SEQ ID NO 167: | VH | QVQLVQSGAEVKKPGASVKVSCKASGYTFTSYDISWVRQAPGQGLEWMGWIN PYNGGTNYAQKFQG RVTMTRDTSISTAYMELSRLRSEDTAVYYCAREGSGMIVY PGWSYAFDYWGQGTLVTVSS |
| SEQ ID NO 168: | DNA VH | CAGGTGCAATTGGTGCAGAGCGGTGCGGAAGTGAAAAAACCGGGTGCCAGC GTGAAAGTTAGCTGCAAAGCGTCCGGATATACCTTCACTTCTTACGACATCTCT TGGGTGCGCCAGGCCCCGGGCCAGGGCCTCGAGTGGATGGGCTGGATCAAC CCGTACAACGGCGGTACGAACTACGCGCAGAAATTTCAGGGCCGGGTGACCA TGACCCGTGATACCAGCATTAGCACCGCGTATATGGAACTGAGCCGTCTGCGT AGCGAAGATACGGCCGTGTATTATTGCGCGCGTGAAGGTTCTGGTATGATCG TTTACCCGGGTTGGTCTTACGCTTTCGATTACTGGGGCCAAGGCACCCTGGTG ACTGTTAGCTCA |
| SEQ ID NO 169: | Heavy Chain | QVQLVQSGAEVKKPGASVKVSCKASGYTFTSYDISWVRQAPGQGLEWMGWIN PYNGGTNYAQKFQGRVTMTRDTSISTAYMELSRLRSEDTAVYYCAREGSGMIVY PGWSYAFDYWGQGTLVTVSSASTKGPSVFPLAPSSKSTSGGTAALGCLVKDYFPE PVTVSWNSGALTSGVHTFPAVLQSSGLYSLSSVVTVPSSSLGTQTYICNVNHKPSN TKVDKRVEPKSCDKTHTCPPCPAPELLGGPSVFLFPPKPKDTLMISRTPEVTCVVV DVSHEDPEVKFNWYVDGVEVHNAKTKPREEQYNSTYRVVSVLTVLHQDWLNGK EYKCKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVM HEALHNHYTQKSLSLSPGK |
| SEQ ID NO 170: | DNA Heavy Chain | CAGGTGCAATTGGTGCAGAGCGGTGCGGAAGTGAAAAAACCGGGTGCCAGC GTGAAAGTTAGCTGCAAAGCGTCCGGATATACCTTCACTTCTTACGACATCTCT TGGGTGCGCCAGGCCCCGGGCCAGGGCCTCGAGTGGATGGGCTGGATCAAC CCGTACAACGGCGGTACGAACTACGCGCAGAAATTTCAGGGCCGGGTGACCA TGACCCGTGATACCAGCATTAGCACCGCGTATATGGAACTGAGCCGTCTGCGT AGCGAAGATACGGCCGTGTATTATTGCGCGCGTGAAGGTTCTGGTATGATCG TTTACCCGGGTTGGTCTTACGCTTTCGATTACTGGGGCCAAGGCACCCTGGTG |

TABLE 1-continued

Examples of anti-FGFR2 Antibodies of the Present Invention

|  |  |  |
|---|---|---|
|  |  | ACTGTTAGCTCAGCCTCCACCAAGGGTCCATCGGTCTTCCCCCTGGCACCCTCC<br>TCCAAGAGCACCTCTGGGGGCACAGCGGCCCTGGGCTGCCTGGTCAAGGACT<br>ACTTCCCCGAACCGGTGACGGTGTCGTGGAACTCAGGCGCCCTGACCAGCGG<br>CGTGCACACCTTCCCGGCTGTCCTACAGTCCTCAGGACTCTACTCCCTCAGCAG<br>CGTGGTGACCGTGCCCTCCAGCAGCTTGGGCACCCAGACCTACATCTGCAACG<br>TGAATCACAAGCCCAGCAACACCAAGGTGGACAAGAGAGTTGAGCCCAAATC<br>TTGTGACAAAACTCACACATGCCCACCGTGCCCAGCACCTGAACTCCTGGGGG<br>GACCGTCAGTCTTCCTCTTCCCCCCAAAACCCAAGGACACCCTCATGATCTCCC<br>GGACCCCTGAGGTCACATGCGTGGTGGTGGACGTGAGCCACGAAGACCCTGA<br>GGTCAAGTTCAACTGGTACGTGGACGGCGTGGAGGTGCATAATGCCAAGACA<br>AAGCCGCGGGAGGAGCAGTACAACAGCACGTACCGGGTGGTCAGCGTCCTC<br>ACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGG<br>CAGCCCCGAGAACCACAGGTGTACACCCTGCCCCCATCCCGGGAGGAGATGA<br>CCAAGAACCAGGTCAGCCTGACCTGCCTGGTCAAAGGCTTCTATCCCAGCGAC<br>ATCGCCGTGGAGTGGGAGAGCAATGGGCAGCCGGAGAACAACTACAAGACC<br>ACGCCTCCCGTGCTGGACTCCGACGGCTCCTTCTTCCTCTACAGCAAGCTCACC<br>GTGGACAAGAGCAGGTGGCAGCAGGGGAACGTCTTCTCATGCTCCGTGATGC<br>ATGAGGCTCTGCACAACCACTACACGCAGAAGAGCCTCTCCCTGTCTCCGGGT<br>AAA |
| SEQ ID NO 171: (Kabat) | LCDR1 | RASQDISNDLG |
| SEQ ID NO 172: (Kabat) | LCDR2 | AASSLQS |
| SEQ ID NO 173: (Kabat) | LCDR3 | QQHYHTPNT |
| SEQ ID NO 174: (Chothia) | LCDR1 | SQDISND |
| SEQ ID NO 175: (Chothia) | LCDR2 | AAS |
| SEQ ID NO 176: (Chothia) | LCDR3 | HYHTPN |
| SEQ ID NO 177: | VL | DIQMTQSPSSLSASVGDRVTITCRASQDISNDLGWYQQKPGKAPKLLIYAASSLQS<br>GVPSRFSGSGSGTDFTLTISSLQPEDFATYYCQQHYHTPNTFGQGTKVEIK |
| SEQ ID NO 178: | DNA VL | GATATCCAGATGACCCAGAGCCCGAGCAGCCTGAGCGCCAGCGTGGGCGATC<br>GCGTGACCATTACCTGCAGAGCCAGCCAGGACATTTCTAACGACCTGGGTTG<br>GTACCAGCAGAAACCGGGCAAAGCGCCGAAACTATTAATCTACGCTGCTTCTT<br>CTCTGCAAAGCGGCGTGCCGAGCCGCTTTAGCGGCAGCGGATCCGGCACCGA<br>TTTCACCCTGACCATTAGCTCTCTGCAACCGGAAGACTTTGCGACCTATTATTG<br>CCAGCAGCATTACCATACTCCGAACACCTTTGGCCAGGGCACGAAAGTTGAAA<br>TTAAA |
| SEQ ID NO 179: | Light<br>Chain | DIQMTQSPSSLSASVGDRVTITCRASQDISNDLGWYQQKPGKAPKLLIYAASSLQS<br>GVPSRFSGSGSGTDFTLTISSLQPEDFATYYCQQHYHTPNTFGQGTKVEIKRTVAA<br>PSVFIFPPSDEQLKSGTASVVCLLNNFYPREAKVQWKVDNALQSGNSQESVTEQD<br>SKDSTYSLSSTLTLSKADYEKHKVYACEVTHQGLSSPVTKSFNRGEC |
| SEQ ID NO 180: | DNA<br>Light<br>Chain | GATATCCAGATGACCCAGAGCCCGAGCAGCCTGAGCGCCAGCGTGGGCGATC<br>GCGTGACCATTACCTGCAGAGCCAGCCAGGACATTTCTAACGACCTGGGTTG<br>GTACCAGCAGAAACCGGGCAAAGCGCCGAAACTATTAATCTACGCTGCTTCTT<br>CTCTGCAAAGCGGCGTGCCGAGCCGCTTTAGCGGCAGCGGATCCGGCACCGA<br>TTTCACCCTGACCATTAGCTCTCTGCAACCGGAAGACTTTGCGACCTATTATTG<br>CCAGCAGCATTACCATACTCCGAACACCTTTGGCCAGGGCACGAAAGTTGAAA<br>TTAAACGTACGGTGGCCGCTCCCAGCGTGTTCATCTTCCCCCCCAGCGACGAG<br>CAGCTGAAGAGCGGCACCGCCAGCGTGGTGTGCCTGCTGAACAACTTCTACC<br>CCCGGGAGGCCAAGGTGCAGTGGAAGGTGGACAACGCCCTGCAGAGCGGCA<br>ACAGCCAGGAAAGCGTCACCGAGCAGGACAGCAAGGACTCCACCTACAGCCT<br>GAGCAGCACCCTGACCCTGAGCAAGGCCGACTACGAGAAGCACAAGGTGTAC<br>GCCTGCGAGGTGACCCACCAGGGCCTGTCCAGCCCCGTGACCAAGAGCTTCA<br>ACCGGGGCGAGTGT | mAb12947

| SEQ ID NO 181: (Kabat) | HCDR1 | SYAIS |
|---|---|---|
| SEQ ID NO 182: (Kabat) | HCDR2 | SIQPTAGPARYAQKFQG |
| SEQ ID NO 183: (Kabat) | HCDR3 | ASLYSVATGSYWKVYHPFDS |
| SEQ ID NO 184: (Chothia) | HCDR1 | GGTFSSY |
| SEQ ID NO 185: (Chothia) | HCDR2 | QPTAGP |
| SEQ ID NO 186: (Chothia) | HCDR3 | ASLYSVATGSYWKVYHPFDS |

TABLE 1-continued

Examples of anti-FGFR2 Antibodies of the Present Invention

| | | |
|---|---|---|
| SEQ ID NO 187: | VH | QVQLVQSGAEVKKPGSSVKVSCKASGGTFSSYAISWVRQAPGQGLEWMGSIQP TAGPARYAQKFQGRVTITADESTSTAYMELSSLRSEDTAVYYCARASLYSVATGSY WKVYHPFDSWGQGTLVTVSS |
| SEQ ID NO 188: | DNA VH | CAGGTGCAATTGGTGCAGAGCGGTGCCGAAGTGAAAAAACCGGGCAGCAGC GTGAAAGTTAGCTGCAAAGCATCCGGAGGGACGTTTAGCAGCTATGCGATTA GCTGGGTGCGCCAGGCCCCGGGCCAGGGCCTCGAGTGGATGGGCTCTATCCA GCCGACTGCTGGCCCGGCTCGTTACGCCCAGAAATTTCAGGGCCGGGTGACC ATTACCGCCGATGAAAGCACCAGCACCGCCTATATGGAACTGAGCAGCCTGC GCAGCGAAGATACGGCCGTGTATTATTGCGCGCGTGCTTCTCTGTACTCTGTT GCTACTGGTTCTTACTGGAAAGTTTACCATCCTTTCGATTCTTGGGGCCAAGGC ACCCTGGTGACTGTTAGCTCA |
| SEQ ID NO 189: | Heavy Chain | QVQLVQSGAEVKKPGSSVKVSCKASGGTFSSYAISWVRQAPGQGLEWMGSIQP TAGPARYAQKFQGRVTITADESTSTAYMELSSLRSEDTAVYYCARASLYSVATGSY WKVYHPFDSWGQGTLVTVSSASTKGPSVFPLAPSSKSTSGGTAALGCLVKDYFPE PVTVSWNSGALTSGVHTFPAVLQSSGLYSLSSVVTVPSSSLGTQTYICNVNHKPSN TKVDKRVEPKSCDKTHTCPPCPAPELLGGPSVFLFPPKPKDTLMISRTPEVTCVVV DVSHEDPEVKFNWYVDGVEVHNAKTKPREEQYNSTYRVVSVLTVLHQDWLNGK EYKCKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVM HEALHNHYTQKSLSLSPGK |
| SEQ ID NO 190: | DNA Heavy Chain | CAGGTGCAATTGGTGCAGAGCGGTGCCGAAGTGAAAAAACCGGGCAGCAGC GTGAAAGTTAGCTGCAAAGCATCCGGAGGGACGTTTAGCAGCTATGCGATTA GCTGGGTGCGCCAGGCCCCGGGCCAGGGCCTCGAGTGGATGGGCTCTATCCA GCCGACTGCTGGCCCGGCTCGTTACGCCCAGAAATTTCAGGGCCGGGTGACC ATTACCGCCGATGAAAGCACCAGCACCGCCTATATGGAACTGAGCAGCCTGC GCAGCGAAGATACGGCCGTGTATTATTGCGCGCGTGCTTCTCTGTACTCTGTT GCTACTGGTTCTTACTGGAAAGTTTACCATCCTTTCGATTCTTGGGGCCAAGGC ACCCTGGTGACTGTTAGCTCAGCCTCCACCAAGGGTCCATCGGTCTTCCCCCTG GCACCCTCCTCCAAGAGCACCTCTGGGGGCACAGCGGCCCTGGGCTGCCTGG TCAAGGACTACTTCCCCGAACCGGTGACGGTGTCGTGGAACTCAGGCGCCCT GACCAGCGGCGTGCACACCTTCCCGGCTGTCCTACAGTCCTCAGGACTCTACT CCCTCAGCAGCGTGGTGACCGTGCCCTCCAGCAGCTTGGGCACCCAGACCTAC ATCTGCAACGTGAATCACAAGCCCAGCAACACCAAGGTGGACAAGAGAGTTG AGCCCAAATCTTGTGACAAAACTCACACATGCCCACCGTGCCCAGCACCTGAA CTCCTGGGGGGACCGTCAGTCTTCCTCTTCCCCCCAAAACCCAAGGACACCCT CATGATCTCCCGGACCCCTGAGGTCACATGCGTGGTGGTGGACGTGAGCCAC GAAGACCCTGAGGTCAAGTTCAACTGGTACGTGGACGGCGTGGAGGTGCATA ATGCCAAGACAAAGCCGCGGGAGGAGCAGTACAACAGCACGTACCGGGTGG TCAGCGTCCTCACCGTCCTGCACCAGGACTGGCTGAATGGCAAGGAGTACAA GTGCAAGGTCTCCAACAAAGCCCTCCCAGCCCCCATCGAGAAAACCATCTCCA AAGCCAAAGGGCAGCCCCGAGAACCACAGGTGTACACCCTGCCCCCATCCCG GGAGGAGATGACCAAGAACCAGGTCAGCCTGACCTGCCTGGTCAAAGGCTTC TATCCCAGCGACATCGCCGTGGAGTGGGAGAGCAATGGGCAGCCGGAGAAC AACTACAAGACCACGCCTCCCGTGCTGGACTCCGACGGCTCCTTCTTCCTCTAC AGCAAGCTCACCGTGGACAAGAGCAGGTGGCAGCAGGGGAACGTCTTCTCAT GCTCCGTGATGCATGAGGCTCTGCACAACCACTACACGCAGAAGAGCCTCTCC CTGTCTCCGGGTAAA |
| SEQ ID NO 191: (Kabat) | LCDR1 | RASQDIYSYLA |
| SEQ ID NO 192: (Kabat) | LCDR2 | DASSLQS |
| SEQ ID NO 193: (Kabat) | LCDR3 | QQADQYPVT |
| SEQ ID NO 194: (Chothia) | LCDR1 | SQDIYSY |
| SEQ ID NO 195: (Chothia) | LCDR2 | DAS |
| SEQ ID NO 196: (Chothia) | LCDR3 | ADQYPV |
| SEQ ID NO 197: | VL | DIQMTQSPSSLSASVGDRVTITCRASQDIYSYLAWYQQKPGKAPKLLIYDASSLQS GVPSRFSGSGSGTDFTLTISSLQPEDFATYYCQQADQYPVTFGQGTKVEIK |
| SEQ ID NO 198: | DNA VL | GATATCCAGATGACCCAGAGCCCGAGCAGCCTGAGCGCCAGCGTGGGCGATC GCGTGACCATTACCTGCAGAGCCAGCCAGGACATTTACTCTTACCTGGCTTGG TACCAGCAGAAACCGGGCAAAGCGCCGAAACTATTAATCTACGACGCTTCTTC TCTGCAAAGCGGCGTGCCGAGCCGCTTTAGCGGCAGCGGATCCGGCACCGAT TTCACCCTGACCATTAGCTCTCTGCAACCGGAAGACTTTGCGACCTATTATTGC CAGCAGGCTGACCAGTACCCGGTTACCTTTGGCCAGGGCACGAAAGTTGAAA TTAAA |
| SEQ ID NO 199: | Light Chain | DIQMTQSPSSLSASVGDRVTITCRASQDIYSYLAWYQQKPGKAPKLLIYDASSLQS GVPSRFSGSGSGTDFTLTISSLQPEDFATYYCQQADQYPVTFGQGTKVEIKRTVAA PSVFIFPPSDEQLKSGTASVVCLLNNFYPREAKVQWKVDNALQSGNSQESVTEQD SKDSTYSLSSTLTLSKADYEKHKVYACEVTHQGLSSPVTKSFNRGEC |

TABLE 1-continued

Examples of anti-FGFR2 Antibodies of the Present Invention

| SEQ ID NO 200: | DNA Light Chain | GATATCCAGATGACCCAGAGCCCGAGCAGCCTGAGCGCCAGCGTGGGCGATC GCGTGACCATTACCTGCAGAGCCAGCCAGGACATTTACTCTTACCTGGCTTGG TACCAGCAGAAACCGGGCAAAGCGCCGAAACTATTAATCTACGACGCTTCTTC TCTGCAAAGCGGCGTGCCGAGCCGCTTTAGCGGCAGCGGATCCGGCACCGAT TTCACCCTGACCATTAGCTCTCTGCAACCGGAAGACTTTGCGACCTATTATTGC CAGCAGGCTGACCAGTACCCGGTTACCTTTGGCCAGGGCACGAAAGTTGAAA TTAAACGTACGGTGGCCGCTCCCAGCGTGTTCATCTTCCCCCCCAGCGACGAG CAGCTGAAGAGCGGCACCGCCAGCGTGGTGTGCCTGCTGAACAACTTCTACC CCCGGGAGGCCAAGGTGCAGTGGAAGGTGGACAACGCCCTGCAGAGCGGCA ACAGCCAGGAAAGCGTCACCGAGCAGGACAGCAAGGACTCCACCTACAGCCT GAGCAGCACCCTGACCCTGAGCAAGGCCGACTACGAGAAGCACAAGGTGTAC GCCTGCGAGGTGACCCACCAGGGCCTGTCCAGCCCCGTGACCAAGAGCTTCA ACCGGGGCGAGTGT | mAb20809

| SEQ ID NO 201: (Kabat) | HCDR1 | SYALS |
| SEQ ID NO 202: (Kabat) | HCDR2 | RIRSKIDGGTTDYAAPVKG |
| SEQ ID NO 203: (Kabat) | HCDR3 | DRSPSDSSAFAI |
| SEQ ID NO 204: (Chothia) | HCDR1 | GFTFSSY |
| SEQ ID NO 205: (Chothia) | HCDR2 | RSKIDGGT |
| SEQ ID NO 206: (Chothia) | HCDR3 | DRSPSDSSAFAI |
| SEQ ID NO 207: | VH | QVQLVESGGGLVKPGGSLRLSCAASGFTFSSYALSWVRQAPGKGLEWVGRIRSKI DGGTTDYAAPVKGRFTISRDDSKNTLYLQMNSLKTEDTAVYYCARDRSPSDSSAF AIWGQGTLVTVSS |
| SEQ ID NO 208: | DNA VH | CAGGTGCAATTGGTGGAAAGCGGCGGTGGCCTGGTGAAACCAGGCGGCAGC CTGCGCCTGAGCTGCGCCGCCTCCGGATTCACCTTTTCTTCTTACGCTCTGTCTT GGGTGCGCCAGGCCCCGGGCAAAGGTCTCGAGTGGGTGGGCCGTATCCGTTC TAAAATCGACGGTGGTACTACTGACTATGCCGCCCCAGTGAAAGGCCGCTTTA CCATTAGCCGCGATGATTCGAAAAACACCCTGTATCTGCAAATGAACAGCCTG AAAACCGAAGATACGGCCGTGTATTATTGCGCGCGTGACCGTTCTCCGTCTGA CTCTTCTGCTTTCGCTATCTGGGGCAAGGCACCCTGGTGACTGTTAGCTCA |
| SEQ ID NO 209: | Heavy Chain | QVQLVESGGGLVKPGGSLRLSCAASGFTFSSYALSWVRQAPGKGLEWVGRIRSKI DGGTTDYAAPVKGRFTISRDDSKNTLYLQMNSLKTEDTAVYYCARDRSPSDSSAF AIWGQGTLVTVSSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKVDKRV EPKSCDKTHTCPPCPAPELLGGPSVFLFPPKPKDTLMISRTPEVTCVVVDVSHEDP EVKFNWYVDGVEVHNAKTKPREEQYNSTYRVVSVLTVLHQDWLNGKEYKCKVS NKALPAPIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHEALH NHYTQKSLSLSPGK |
| SEQ ID NO 210: | DNA Heavy Chain | CAGGTGCAATTGGTGGAAAGCGGCGGTGGCCTGGTGAAACCAGGCGGCAGC CTGCGCCTGAGCTGCGCCGCCTCCGGATTCACCTTTTCTTCTTACGCTCTGTCTT GGGTGCGCCAGGCCCCGGGCAAAGGTCTCGAGTGGGTGGGCCGTATCCGTTC TAAAATCGACGGTGGTACTACTGACTATGCCGCCCCAGTGAAAGGCCGCTTTA CCATTAGCCGCGATGATTCGAAAAACACCCTGTATCTGCAAATGAACAGCCTG AAAACCGAAGATACGGCCGTGTATTATTGCGCGCGTGACCGTTCTCCGTCTGA CTCTTCTGCTTTCGCTATCTGGGGCAAGGCACCCTGGTGACTGTTAGCTCAGC CTCCACCAAGGGTCCATCGGTCTTCCCCCTGGCACCCTCCTCCAAGAGCACCTC TGGGGGCACAGCGGCCCTGGGCTGCCTGGTCAAGGACTACTTCCCCGAACCG GTGACGGTGTCGTGGAACTCAGGCGCCCTGACCAGCGGCGTGCACACCTTCC CGGCTGTCCTACAGTCCTCAGGACTCTACTCCCTCAGCAGCGTGGTGACCGTG CCCTCCAGCAGCTTGGGCACCCAGACCTACATCTGCAACGTGAATCACAAGCC CAGCAACACCAAGGTGGACAAGAGAGTTGAGCCCAAATCTTGTGACAAAACT CACACATGCCCACCGTGCCCAGCACCTGAACTCCTGGGGGGACCGTCAGTCTT CCTCTTCCCCCCAAAACCCAAGGACACCCTCATGATCTCCCGGACCCCTGAGGT CACATGCGTGGTGGTGGACGTGAGCCACGAAGACCCTGAGGTCAAGTTCAAC TGGTACGTGGACGGCGTGGAGGTGCATAATGCCAAGACAAAGCCGCGGGAG GAGCAGTACAACAGCACGTACCGGGTGGTCAGCGTCCTCACCGTCCTGCACC AGGACTGGCTGAATGGCAAGGAGTACAAGTGCAAGGTCTCCAACAAAGCCCT CCCAGCCCCCATCGAGAAAACCATCTCCAAAGCCAAAGGGCAGCCCCGAGAA CCACAGGTGTACACCCTGCCCCCATCCCGGGAGGAGATGACCAAGAACCAGG TCAGCCTGACCTGCCTGGTCAAAGGCTTCTATCCCAGCGACATCGCCGTGGAG TGGGAGAGCAATGGGCAGCCGGAGAACAACTACAAGACCACGCCTCCCGTGC TGGACTCCGACGGCTCCTTCTTCCTCTACAGCAAGCTCACCGTGGACAAGAGC AGGTGGCAGCAGGGGAACGTCTTCTCATGCTCCGTGATGCATGAGGCTCTGC ACAACCACTACACGCAGAAGAGCCTCTCCCTGTCTCCGGGTAAA |

TABLE 1-continued

Examples of anti-FGFR2 Antibodies of the Present Invention

| SEQ ID NO 211: | (Kabat) | LCDR1 | SGDNLGSQYVD |
|---|---|---|---|
| SEQ ID NO 212: | (Kabat) | LCDR2 | DDNDRPS |
| SEQ ID NO 213: | (Kabat) | LCDR3 | AVTAFHSMTDV |
| SEQ ID NO 214: | (Chothia) | LCDR1 | DNLGSQY |
| SEQ ID NO 215: | (Chothia) | LCDR2 | DDN |
| SEQ ID NO 216: | (Chothia) | LCDR3 | TAFHSMTD |
| SEQ ID NO 217: | | VL | DIELTQPPSVSVSPGQTASITCSGDNLGSQYVDWYQQKPGQAPVLVIYDDNDRP SGIPERFSGSNSGNTATLTISGTQAEDEADYYCAVTAFHSMTDVFGGGTKLTVL |
| SEQ ID NO 218: | | DNA VL | GATATCGAACTGACCCAGCCGCCGAGCGTGAGCGTGAGCCCGGGCCAGACCG CGAGCATTACCTGTAGCGGCGATAACCTGGGTTCTCAGTACGTTGACTGGTAC CAGCAGAAACCGGGCCAGGCGCCGGTGCTGGTGATCTACGACGACAACGACC GTCCGAGCGGCATCCCGGAACGTTTTAGCGGATCCAACAGCGGCAACACCGC GACCCTGACCATTAGCGGCACCCAGGCGGAAGACGAAGCGGATTATTACTGC GCTGTTACTGCTTTCCATTCTATGACTGACGTGTTTGGCGGCGGCACGAAGTT AACCGTCCTA |
| SEQ ID NO 219: | | Light Chain | DIELTQPPSVSVSPGQTASITCSGDNLGSQYVDWYQQKPGQAPVLVIYDDNDRP SGIPERFSGSNSGNTATLTISGTQAEDEADYYCAVTAFHSMTDVFGGGTKLTVLG QPKAAPSVTLFPPSSEELQANKATLVCLISDFYPGAVTVAWKADSSPVKAGVETTT PSKQSNNKYAASSYLSLTPEQWKSHRSYSCQVTHEGSTVEKTVAPTECS |
| SEQ ID NO 220: | | DNA Light Chain | GATATCGAACTGACCCAGCCGCCGAGCGTGAGCGTGAGCCCGGGCCAGACCG CGAGCATTACCTGTAGCGGCGATAACCTGGGTTCTCAGTACGTTGACTGGTAC CAGCAGAAACCGGGCCAGGCGCCGGTGCTGGTGATCTACGACGACAACGACC GTCCGAGCGGCATCCCGGAACGTTTTAGCGGATCCAACAGCGGCAACACCGC GACCCTGACCATTAGCGGCACCCAGGCGGAAGACGAAGCGGATTATTACTGC GCTGTTACTGCTTTCCATTCTATGACTGACGTGTTTGGCGGCGGCACGAAGTT AACCGTCCTAGGTCAGCCCAAGGCTGCCCCCTCGGTCACTCTGTTCCCGCCCTC CTCTGAGGAGCTTCAAGCCAACAAGGCCACACTGGTGTGTCTCATAAGTGACT TCTACCCGGGAGCCGTGACAGTGGCCTGGAAGGCAGATAGCAGCCCCGTCAA GGCGGGAGTGGAGACCACCACACCCTCCAAACAAAGCAACAACAAGTACGCG GCCAGCAGCTATCTGAGCCTGACGCCTGAGCAGTGGAAGTCCCACAGAAGCT ACAGCTGCCAGGTCACGCATGAAGGGAGCACCGTGGAGAAGACAGTGGCCC CTACAGAATGTTCA | mAb11725

| SEQ ID NO 221: | (Kabat) | HCDR1 | TYWLH |
|---|---|---|---|
| SEQ ID NO 222: | (Kabat) | HCDR2 | VISSDSSSTYYADSVKG |
| SEQ ID NO 223: | (Kabat) | HCDR3 | DSRLDY |
| SEQ ID NO 224: | (Chothia) | HCDR1 | GFTFNTY |
| SEQ ID NO 225: | (Chothia) | HCDR2 | SSDSSS |
| SEQ ID NO 226: | (Chothia) | HCDR3 | DSRLDY |
| SEQ ID NO 227: | | VH | QVQLLESGGGLVQPGGSLRLSCAASGFTFNTYWLHWVRQAPGKGLEWVSVISS DSSSTYYADSVKGRFTISRDNSKNTLYLQMNSLRAEDTAVYYCARDSRLDYWGQ GTLVTVSS |
| SEQ ID NO 228: | | DNA VH | CAGGTGCAATTGCTGGAAAGCGGCGGTGGCCTGGTGCAGCCGGGTGGCAGC CTGCGTCTGAGCTGCGCGGCGTCCGGATTCACCTTTAACACTTACTGGCTGCA TTGGGTGCGCCAGGCCCCGGGCAAAGGTCTCGAGTGGGTTTCCGTTATCTCTT CTGACTCTTCTTCTACCTACTATGCGGATAGCGTGAAAGGCCGCTTTACCATCA GCCGCGATAATTCGAAAAACACCCTGTATCTGCAAATGAACAGCCTGCGTGCG GAAGATACGGCCGTGTATTATTGCGCGCGTGACTCTCGTCTGGACTACTGGG GCCAAGGCACCCTGGTGACTGTTAGCTCA |
| SEQ ID NO 229: | | Heavy Chain | QVQLLESGGGLVQPGGSLRLSCAASGFTFNTYWLHWVRQAPGKGLEWVSVISS DSSSTYYADSVKGRFTISRDNSKNTLYLQMNSLRAEDTAVYYCARDSRLDYWGQ GTLVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKRVEPKSCD KTHTCPPCPAPELLGGPSVFLFPPKPKDTLMISRTPEVTCVVVDVSHEDPEVKFNW YVDGVEVHNAKTKPREEQYNSTYRVVSVLTVLHQDWLNGKEYKCKVSNKALPAP IEKTISKAKGQPREPQVYTLPPSREEMTKNQVSLTCLVKGFYPSDIAVEWESNGQP ENNYKTTPPVLDSDGSFFLYSKLTVDKSRWQQGNVFSCSVMHEALHNHYTQKSL SLSPGK |

TABLE 1-continued

Examples of anti-FGFR2 Antibodies of the Present Invention

| SEQ ID NO 230: | DNA Heavy Chain | CAGGTGCAATTGCTGGAAAGCGGCGGTGGCCTGGTGCAGCCGGGTGGCAGC<br>CTGCGTCTGAGCTGCGCGGCGTCCGGATTCACCTTTAACACTTACTGGCTGCA<br>TTGGGTGCGCCAGGCCCCGGGCAAAGGTCTCGAGTGGGTTTCCGTTATCTCTT<br>CTGACTCTTCTTCTACCTACTATGCGGATAGCGTGAAAGGCCGCTTTACCATCA<br>GCCGCGATAATTCGAAAAACACCCTGTATCTGCAAATGAACAGCCTGCGTGCG<br>GAAGATACGGCCGTGTATTATTGCGCGCGTGACTCTCGTCTGGACTACTGGG<br>GCCAAGGCACCCTGGTGACTGTTAGCTCAGCCTCCACCAAGGGTCCATCGGTC<br>TTCCCCCTGGCACCCTCCTCCAAGAGCACCTCTGGGGGCACAGCGGCCCTGGG<br>CTGCCTGGTCAAGGACTACTTCCCCGAACCGGTGACGGTGTCGTGGAACTCA<br>GGCGCCCTGACCAGCGGCGTGCACACCTTCCCGGCTGTCCTACAGTCCTCAGG<br>ACTCTACTCCCTCAGCAGCGTGGTGACCGTGCCCTCCAGCAGCTTGGGCACCC<br>AGACCTACATCTGCAACGTGAATCACAAGCCCAGCAACACCAAGGTGGACAA<br>GAGAGTTGAGCCCAAATCTTGTGACAAAACTCACACATGCCCACCGTGCCCAG<br>CACCTGAACTCCTGGGGGACCGTCAGTCTTCCTCTTCCCCCCAAAACCCAAG<br>GACACCCTCATGATCTCCCGGACCCCTGAGGTCACATGCGTGGTGGTGGACGT<br>GAGCCACGAAGACCCTGAGGTCAAGTTCAACTGGTACGTGGACGGCGTGGA<br>GGTGCATAATGCCAAGACAAAGCCGCGGGAGGAGCAGTACAACAGCACGTA<br>CCGGGTGGTCAGCGTCCTCACCGTCCTGCACCAGGACTGGCTGAATGGCAAG<br>GAGTACAAGTGCAAGGTCTCCAACAAAGCCCTCCCAGCCCCCATCGAGAAAA<br>CCATCTCCAAAGCCAAAGGGCAGCCCCGAGAACCACAGGTGTACACCCTGCC<br>CCCATCCCGGGAGGAGATGACCAAGAACCAGGTCAGCCTGACCTGCCTGGTC<br>AAAGGCTTCTATCCCAGCGACATCGCCGTGGAGTGGGAGAGCAATGGGCAGC<br>CGGAGAACAACTACAAGACCACGCCTCCCGTGCTGGACTCCGACGGCTCCTTC<br>TTCCTCTACAGCAAGCTCACCGTGGACAAGAGCAGGTGGCAGCAGGGGAACG<br>TCTTCTCATGCTCCGTGATGCATGAGGCTCTGCACAACCACTACACGCAGAAG<br>AGCCTCTCCCTGTCTCCGGGTAAA |
| --- | --- | --- |
| SEQ ID NO 231: (Kabat) | LCDR1 | SGDSIGDTYVD |
| SEQ ID NO 232: (Kabat) | LCDR2 | DDIDRPS |
| SEQ ID NO 233: (Kabat) | LCDR3 | YVYAWTGTSNV |
| SEQ ID NO 234: (Chothia) | LCDR1 | DSIGDTY |
| SEQ ID NO 235: (Chothia) | LCDR2 | DDI |
| SEQ ID NO 236: (Chothia) | LCDR3 | YAWTGTSN |
| SEQ ID NO 237: | VL | DIELTQPPSVSVSPGQTASITCSGDSIGDTYVDWYQQKPGQAPVLVIYDDIDRPSG<br>IPERFSGSNSGNTATLTISGTQAEDEADYYCYVYAWTGTSNVFGGGTKLTVL |
| SEQ ID NO 238: | DNA VL | GATATCGAACTGACCCAGCCGCCGAGCGTGAGCGTGAGCCCGGGCCAGACCG<br>CGAGCATTACCTGTAGCGGCGATTCTATCGGTGACACTTACGTTGACTGGTAC<br>CAGCAGAAACCGGGCCAGGCGCCGGTGCTGGTGATCTACGACGACATCGACC<br>GTCCGAGCGGCATCCCGGAACGTTTTAGCGGATCCAACAGCGGCAACACCGC<br>GACCCTGACCATTAGCGGCACCCAGGCGGAAGACGAAGCGGATTATTACTGC<br>TACGTTTACGCTTGGACTGGTACTTCTAACGTGTTTGGCGGCGGCACGAAGTT<br>AACCGTCCTA |
| SEQ ID NO 239: | Light Chain | DIELTQPPSVSVSPGQTASITCSGDSIGDTYVDWYQQKPGQAPVLVIYDDIDRPSG<br>IPERFSGSNSGNTATLTISGTQAEDEADYYCYVYAWTGTSNVFGGGTKLTVLGQP<br>KAAPSVTLFPPSSEELQANKATLVCLISDFYPGAVTVAWKADSSPVKAGVETTTPS<br>KQSNNKYAASSYLSLTPEQWKSHRSYSCQVTHEGSTVEKTVAPTECS |
| SEQ ID NO 240: | DNA Light Chain | GATATCGAACTGACCCAGCCGCCGAGCGTGAGCGTGAGCCCGGGCCAGACCG<br>CGAGCATTACCTGTAGCGGCGATTCTATCGGTGACACTTACGTTGACTGGTAC<br>CAGCAGAAACCGGGCCAGGCGCCGGTGCTGGTGATCTACGACGACATCGACC<br>GTCCGAGCGGCATCCCGGAACGTTTTAGCGGATCCAACAGCGGCAACACCGC<br>GACCCTGACCATTAGCGGCACCCAGGCGGAAGACGAAGCGGATTATTACTGC<br>TACGTTTACGCTTGGACTGGTACTTCTAACGTGTTTGGCGGCGGCACGAAGTT<br>AACCGTCCTAGGTCAGCCCAAGGCTGCCCCTCGGTCACTCTGTTCCCGCCCTC<br>CTCTGAGGAGCTTCAAGCCAACAAGGCCACACTGGTGTGTCTCATAAGTGACT<br>TCTACCCGGGAGCCGTGACAGTGGCCTGGAAGGCAGATAGCAGCCCCGTCAA<br>GGCGGGAGTGGAGACCACCACACCCTCCAAACAAAGCAACAACAAGTACGCG<br>GCCAGCAGCTATCTGAGCCTGACGCCTGAGCAGTGGAAGTCCCACAGAAGCT<br>ACAGCTGCCAGGTCACGCATGAAGGGAGCACCGTGGAGAAGACAGTGGCCC<br>CTACAGAATGTTCA |

Other antibodies of the invention include those where the amino acids or nucleic acids encoding the amino acids have been mutated, yet have at least 60, 70, 80, 90 or 95 percent identity to the sequences described in Table 1. In some embodiments, it include mutant amino acid sequences wherein no more than 1, 2, 3, 4 or 5 amino acids have been mutated in the variable regions when compared with the variable regions depicted in the sequence described in Table 1, while retaining substantially the same therapeutic activity.

Since each of these antibodies can bind to FGFR2, the VH, VL, full length light chain, and full length heavy chain sequences (amino acid sequences and the nucleotide sequences encoding the amino acid sequences) can be "mixed and matched" to create other FGFR2-binding antibodies of the invention. Such "mixed and matched" FGFR2-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence. Accordingly, in one aspect, the invention provides an isolated monoclonal antibody or antigen binding region thereof having: a heavy chain variable region comprising an amino acid sequence selected from the group consisting of SEQ ID NOs: 7, 27, 47, 67, 87, 107, 127, 147, 167, 187, 207, and 227; and a light chain variable region comprising an amino acid sequence selected from the group consisting of SEQ ID NOs: 17, 37, 57, 77, 97, 117, 137, 157, 177, 197, 217 and 237; wherein the antibody specifically binds to FGFR2.

In another aspect, the invention provides (i) an isolated monoclonal antibody having: a full length heavy chain comprising an amino acid sequence that has been optimized for expression in the cell of a mammalian selected from the group consisting of SEQ ID NOs: 9, 29, 49, 69, 89, 109, 129, 149, 169, 189, 209, and 229; and a full length light chain comprising an amino acid sequence that has been optimized for expression in the cell of a mammalian selected from the group consisting of SEQ ID NOs: 19, 39, 59, 79, 99, 119, 139, 159, 179, 199, 219, and 239; or (ii) a functional protein comprising an antigen binding portion thereof.

In another aspect, the present invention provides FGFR2-binding antibodies that comprise the heavy chain and light chain CDR1s, CDR2s and CDR3s as described in Table 1, or combinations thereof. The amino acid sequences of the VH CDR1s of the antibodies are shown in SEQ ID NOs: 1, 21, 41, 61, 81, 101, 121, 141, 161, 181, 201, and 221. The amino acid sequences of the VH CDR2s of the antibodies and are shown in SEQ ID NOs: 2, 22, 42, 62, 82, 102, 122, 142, 162, 182, 202, and 222. The amino acid sequences of the VH CDR3s of the antibodies are shown in SEQ ID NOs: 3, 23, 43, 63, 83, 103, 123, 143, 163, 183, 203, and 223. The amino acid sequences of the VL CDR1s of the antibodies are shown in SEQ ID NOs: 11, 31, 51, 71, 91, 111, 131, 151, 171, 191, 211, and 231. The amino acid sequences of the VL CDR2s of the antibodies are shown in SEQ ID NOs 12, 32, 52, 72, 92, 112, 132, 152, 172, 192, 212, and 232. The amino acid sequences of the VL CDR3s of the antibodies are shown in SEQ ID NOs: 13, 33, 53, 73, 93, 113, 133, 153, 173, 193, 213, and 233.

Given that each of these antibodies can bind to FGFR2 and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and match, although each antibody must contain a VH CDR1, 2 and 3 and a VL CDR1, 2 and 3 to create other C5-binding binding molecules of the invention. Such "mixed and matched" FGFR2-binding antibodies can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present invention.

Accordingly, the present invention provides an isolated monoclonal antibody or antigen binding region thereof comprising a heavy chain CDR1 comprising an amino acid sequence selected from the group consisting of SEQ ID NOs: 1, 21, 41, 61, 81, 101, 121, 141, 161, 181, 201, and 221; a heavy chain CDR2 comprising an amino acid sequence selected from the group consisting of SEQ ID NOs: 2, 22, 42, 62, 82, 102, 122, 142, 162, 182, 202, and 222; a heavy chain CDR3 comprising an amino acid sequence selected from the group consisting of SEQ ID NOs: 3, 23, 43, 63, 83, 103, 123, 143, 163, 183, 203, and 223; a light chain CDR1 comprising an amino acid sequence selected from the group consisting of SEQ ID NOs: 11, 31, 51, 71, 91, 111, 131, 151, 171, 191, 211, and 231; a light chain CDR2 comprising an amino acid sequence selected from the group consisting of SEQ ID NOs: 12, 32, 52, 72, 92, 112, 132, 152, 172, 192, 212, and 232; and a light chain CDR3 comprising an amino acid sequence selected from the group consisting of SEQ ID NOs: 13, 33, 53, 73, 93, 113, 133, 153, 173, 193, 213, and 233; wherein the antibody specifically binds FGFR2.

In a specific embodiment, an antibody or antibody fragment (e.g., antigen binding fragments) that specifically binds to FGFR2 comprising a heavy chain CDR1 of SEQ ID NO:1, a heavy chain CDR2 of SEQ ID NO: 2; a heavy chain CDR3 of SEQ ID NO:3; a light chain CDR1 of SEQ ID NO:11; a light chain CDR2 of SEQ ID NO: 12; and a light chain CDR3 of SEQ ID NO: 13.

In a specific embodiment, an antibody or antibody fragment (e.g., antigen binding fragments) that specifically binds to FGFR2 comprising a heavy chain CDR1 of SEQ ID NO:21, a heavy chain CDR2 of SEQ ID NO: 22; a heavy chain CDR3 of SEQ ID NO:23; a light chain CDR1 of SEQ ID NO:31; a light chain CDR2 of SEQ ID NO: 32; and a light chain CDR3 of SEQ ID NO: 33.

In a specific embodiment, an antibody or antibody fragment (e.g., antigen binding fragments) that specifically binds to FGFR2 comprising a heavy chain CDR1 of SEQ ID NO:41, a heavy chain CDR2 of SEQ ID NO: 42; a heavy chain CDR3 of SEQ ID NO:43; a light chain CDR1 of SEQ ID NO:51; a light chain CDR2 of SEQ ID NO: 52; and a light chain CDR3 of SEQ ID NO: 53.

In a specific embodiment, an antibody or antibody fragment (e.g., antigen binding fragments) that specifically binds to FGFR2 comprising a heavy chain CDR1 of SEQ ID NO:61, a heavy chain CDR2 of SEQ ID NO: 62; a heavy chain CDR3 of SEQ ID NO:63; a light chain CDR1 of SEQ ID NO:71; a light chain CDR2 of SEQ ID NO: 72; and a light chain CDR3 of SEQ ID NO: 73.

In a specific embodiment, an antibody or antibody fragment (e.g., antigen binding fragments) that specifically binds to FGFR2 comprising a heavy chain CDR1 of SEQ ID NO:81, a heavy chain CDR2 of SEQ ID NO: 82; a heavy chain CDR3 of SEQ ID NO:83; a light chain CDR1 of SEQ ID NO:91; a light chain CDR2 of SEQ ID NO: 92; and a light chain CDR3 of SEQ ID NO: 93.

In a specific embodiment, an antibody or antibody fragment (e.g., antigen binding fragments) that specifically binds to FGFR2 comprising a heavy chain CDR1 of SEQ ID NO:101, a heavy chain CDR2 of SEQ ID NO: 102; a heavy chain CDR3 of SEQ ID NO:103; a light chain CDR1 of SEQ ID NO:111; a light chain CDR2 of SEQ ID NO: 112; and a light chain CDR3 of SEQ ID NO: 113.

In a specific embodiment, an antibody or antibody fragment (e.g., antigen binding fragments) that specifically binds to FGFR2 comprising a heavy chain CDR1 of SEQ ID NO:121, a heavy chain CDR2 of SEQ ID NO: 122; a heavy chain CDR3 of SEQ ID NO:123; a light chain CDR1 of SEQ ID NO:131; a light chain CDR2 of SEQ ID NO: 132; and a light chain CDR3 of SEQ ID NO: 133.

In a specific embodiment, an antibody or antibody fragment (e.g., antigen binding fragments) that specifically binds to FGFR2 comprising a heavy chain CDR1 of SEQ ID NO:141, a heavy chain CDR2 of SEQ ID NO: 142; a heavy chain CDR3 of SEQ ID NO:143; a light chain CDR1 of SEQ ID NO:151; a light chain CDR2 of SEQ ID NO: 152; and a light chain CDR3 of SEQ ID NO: 153.

In a specific embodiment, an antibody or antibody fragment (e.g., antigen binding fragments) that specifically binds to FGFR2 comprising a heavy chain CDR1 of SEQ ID NO:161, a heavy chain CDR2 of SEQ ID NO: 162; a heavy chain CDR3 of SEQ ID NO:163; a light chain CDR1 of SEQ ID NO:171; a light chain CDR2 of SEQ ID NO: 172; and a light chain CDR3 of SEQ ID NO: 173.

In a specific embodiment, an antibody or antibody fragment (e.g., antigen binding fragments) that specifically binds to FGFR2 comprising a heavy chain CDR1 of SEQ ID NO:181, a heavy chain CDR2 of SEQ ID NO: 182; a heavy chain CDR3 of SEQ ID NO:183; a light chain CDR1 of SEQ ID NO:191; a light chain CDR2 of SEQ ID NO: 192; and a light chain CDR3 of SEQ ID NO: 193.

In a specific embodiment, an antibody or antibody fragment (e.g., antigen binding fragments) that specifically binds to FGFR2 comprising a heavy chain CDR1 of SEQ ID NO:201, a heavy chain CDR2 of SEQ ID NO: 202; a heavy chain CDR3 of SEQ ID NO:203; a light chain CDR1 of SEQ ID NO:211; a light chain CDR2 of SEQ ID NO: 212; and a light chain CDR3 of SEQ ID NO: 213.

In a specific embodiment, an antibody or antibody fragment (e.g., antigen binding fragments) that specifically binds to FGFR2 comprising a heavy chain CDR1 of SEQ ID NO:221, a heavy chain CDR2 of SEQ ID NO: 222; a heavy chain CDR3 of SEQ ID NO:223; a light chain CDR1 of SEQ ID NO:231; a light chain CDR2 of SEQ ID NO: 232; and a light chain CDR3 of SEQ ID NO: 233.

In certain embodiments, an antibody that specifically binds to FGFR2 is an antibody or antibody fragment (e.g., antigen binding fragment) that is described in Table 1.

1. Identification of Epitopes and Antibodies that Bind to the Same Epitope

The present invention provides antibodies and antibody fragments (e.g., antigen binding fragments) that bind to an epitope of 174-189 (VKFRCPAGGNPMPTMR; SEQ ID NO:241) and 198-216 (KMEKRLHAVPAANTVKFRC; SEQ ID NO:242) amino acids (numbered according to P21802-3) of human FGFR2.

In some aspects, the present invention provides antibodies or antibody fragments (e.g., antigen binding fragments) that recognize amino acids at positions 173 (Asn), 174 (Thr), 175 (Val), 176 (Lys), 178 (Arg), 208 (Lys), 209 (Val), 210 (Arg), 212 (Gln), 213 (His), 217 (Ile), 219 (Glue) of human FGFR2 as shown in SEQ ID NO:257. In another embodiment, the present invention provides antibodies or antibody fragments (e.g., antigen binding fragments) that recognize amino acids at least in positions 176 (Lys) and 210 (Arg) of human FGFR2 as shown in SEQ ID NO:257.

The present invention also provides antibodies and antibody fragments (e.g., antigen binding fragments) that bind to the same epitope as do the anti-FGFR2 antibodies described in Table 1. Additional antibodies and antibody fragments (e.g., antigen binding fragments) can therefore be identified based on their ability to cross-compete (e.g., to competitively inhibit the binding of, in a statistically significant manner) with other antibodies of the invention in FGFR2 binding assays. The ability of a test antibody to inhibit the binding of antibodies and antibody fragments (e.g., antigen binding fragments) of the present invention to a FGFR2 protein (e.g., human FGFR2) demonstrates that the test antibody can compete with that antibody or antibody fragment (e.g., antigen binding fragments) for binding to FGFR2; such an antibody may, according to non-limiting theory, bind to the same or a related (e.g., a structurally similar or spatially proximal) epitope on the FGFR2 protein as the antibody or antibody fragment (e.g., antigen binding fragments) with which it competes. In a certain embodiment, the antibody that binds to the same epitope on FGFR2 as the antibodies or antibody fragments (e.g., antigen binding fragments) of the present invention is a human or humanized monoclonal antibody. Such human or humanized monoclonal antibodies can be prepared and isolated as described herein.

2. Further Alteration of the Framework of Fc Region

The present invention provides site-specific labeled immunoconjugates. The immunoconjugates of the invention may comprise modified antibodies or antigen binding fragments thereof that further comprise modifications to framework residues within VH and/or VL, e.g. to improve the properties of the antibody. Typically such framework modifications are made to decrease the immunogenicity of the antibody. For example, one approach is to "back-mutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back-mutated" to the germline sequence by, for example, site-directed mutagenesis. Such "back-mutated" antibodies are also intended to be encompassed by the invention.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in, e.g., U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in, e.g., U.S. Pat. No. 6,194,551 by Idusogie et al.

Figure 4:
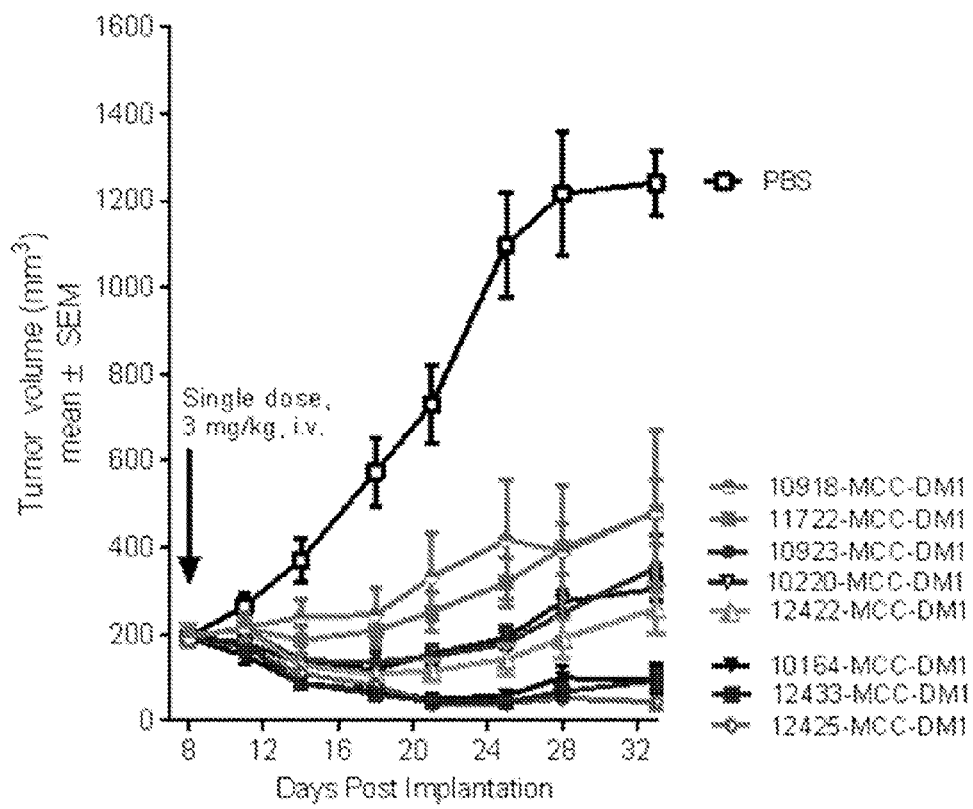
FIG. 4 (A)-(B) show the anti-tumor activity of anti-FGFR2-MCC-DM1ADCs in a SNU16 tumor xenograft mouse model; (C) shows the anti-tumor activity of the 12433 antibody as an ADC conjugated to SMCC-DM1 and SPDB-DM4 linker-payloads; (D)-(E) show the pharmacokinetic properties of anti-FGFR2-MCC-DM1 ADCs ADCs; (F) shows the anti-tumor activity against ADC clearance for a panel of anti-FGFR2-MCC-DM1ADCs.
Figure 4:
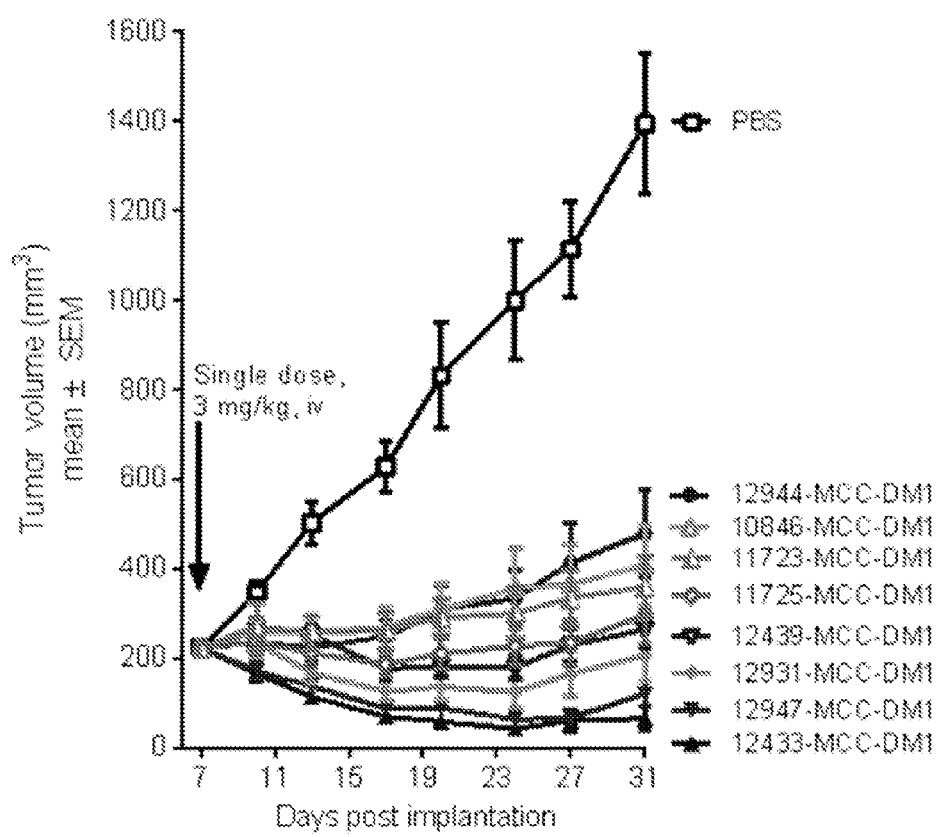
Figure 4:
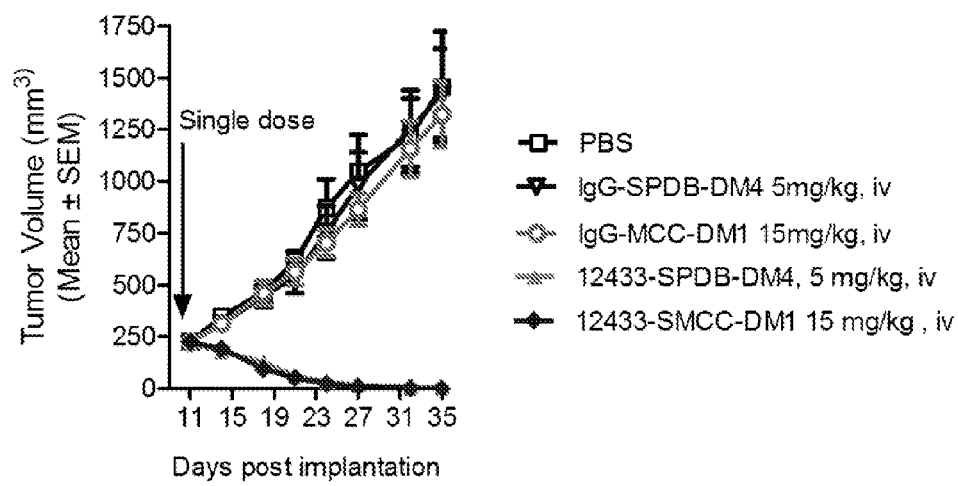
Figure 4:
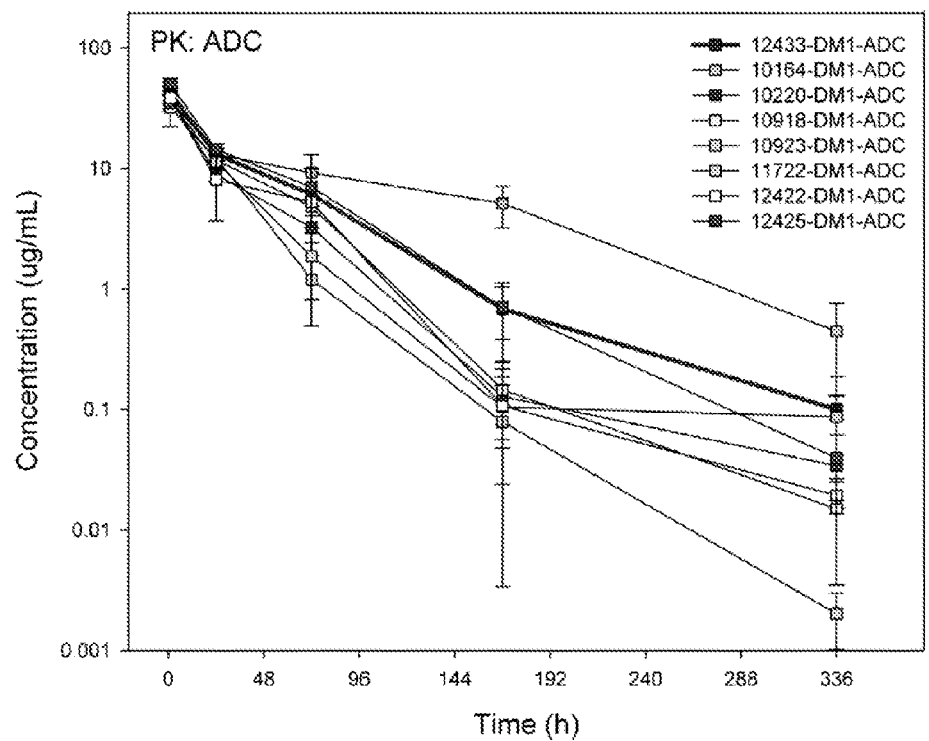
Figure 4:
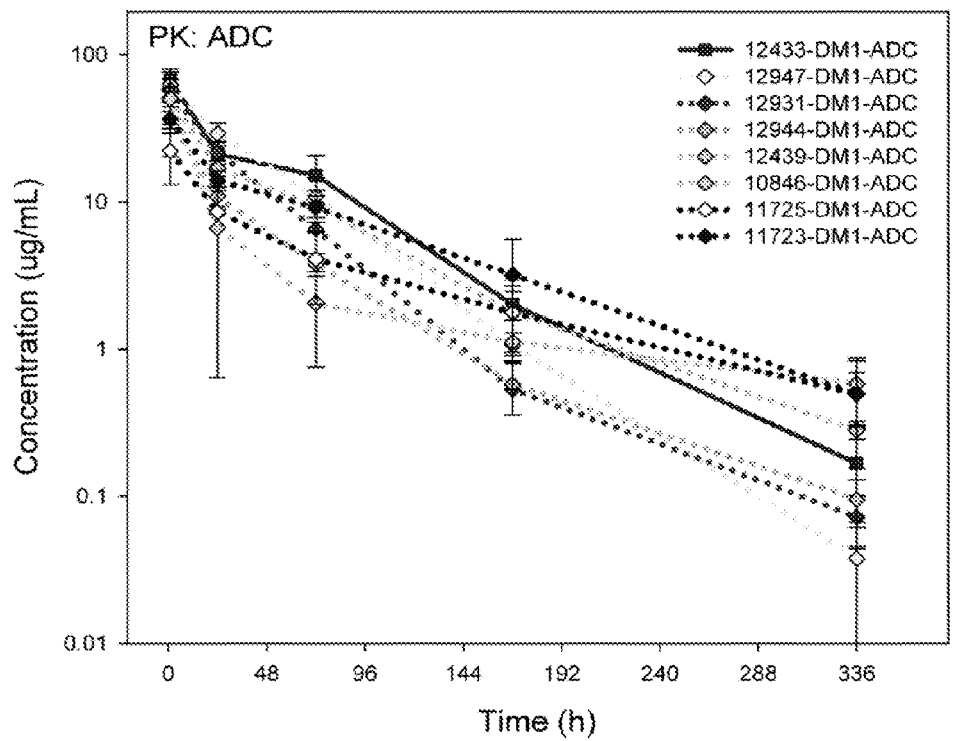
Figure 4:
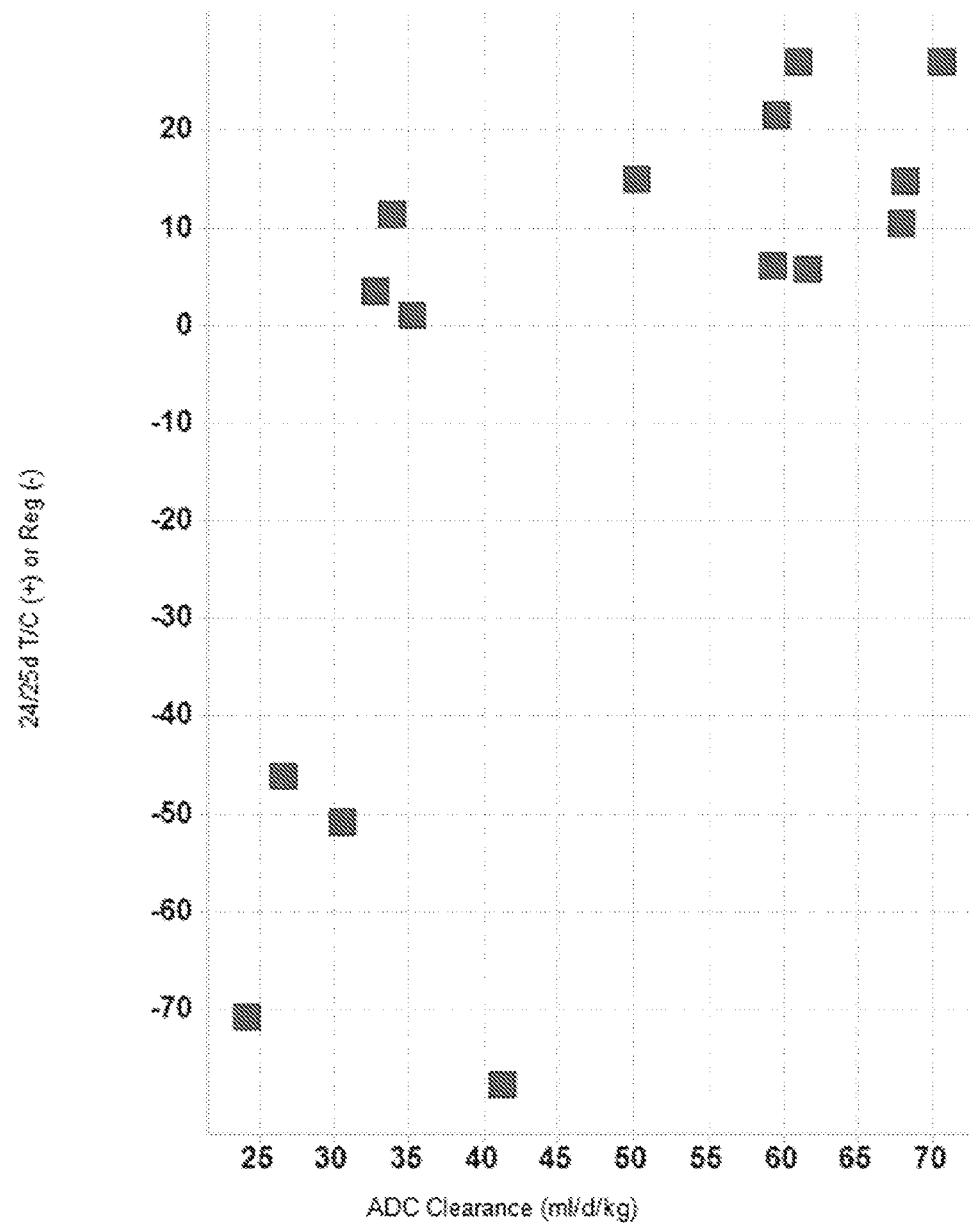

In another embodiment, one or more amino acid residues are altered to thereby alter the ability of the antibody to fix complement. This approach is described in, e.g., the PCT Publication WO 94/29351 by Bodmer et al. In a specific embodiment, one or more amino acids of an antibody or antigen binding fragment thereof of the present invention are replaced by one or more allotypic amino acid residues, such as those shown in FIG. 4 for the IgG1 subclass and the kappa isotype. Allotypic amino acid residues also include, but are not limited to, the constant region of the heavy chain of the IgG1, IgG2, and IgG3 subclasses as well as the constant region of the light chain of the kappa isotype as described by Jefferis et al., MAbs. 1:332-338 (2009).

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described in, e.g., the PCT Publication WO 00/42072 by Presta. Moreover, the binding sites on human IgG1 for FcγRI, FcγRII, FcγRIII and FcRn have been mapped and variants with improved binding have been described (see Shields et al., J. Biol. Chem. 276: 6591-6604, 2001).

In still another embodiment, the glycosylation of an antibody is modified. For example, an aglycosylated antibody can be made (i.e., the antibody lacks glycosylation). Glycosylation can be altered to, for example, increase the affinity of the antibody for "antigen." Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in, e.g., U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields et al., (2002) J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., Nat. Biotech. 17:176-180, 1999).

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

3. Production of the FGFR2 Antibodies

Anti-FGFR2 antibodies and antibody fragments (e.g., antigen binding fragments) thereof can be produced by any means known in the art, including but not limited to, recombinant expression, chemical synthesis, and enzymatic digestion of antibody tetramers, whereas full-length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc.

The invention further provides polynucleotides encoding the antibodies described herein, e.g., polynucleotides encoding heavy or light chain variable regions or segments comprising the complementarity determining regions as described herein. In some embodiments, the polynucleotide encoding the heavy chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 8, 28, 48, 68, 88, 108, 128, 148, 168, 188, 208, and 228. In some embodiments, the polynucleotide encoding the light chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 18, 38, 58, 78, 98, 118, 138, 158, 178, 198, 218, and 238.

In some embodiments, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO: 10, 30, 50, 70, 90, 110, 130, 150, 170, 190, 210, or 230. In some embodiments, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO: 20, 40, 60, 80, 100, 120, 140, 160, 180, 200, 220, or 240.

The polynucleotides of the invention can encode only the variable region sequence of an anti-FGFR2 antibody. They can also encode both a variable region and a constant region of the antibody. Some of the polynucleotide sequences encode a polypeptide that comprises variable regions of both the heavy chain and the light chain of one of the exemplified mouse anti-FGFR2 antibody. Some other polynucleotides encode two polypeptide segments that respectively are substantially identical to the variable regions of the heavy chain and the light chain of one of the mouse antibodies.

The polynucleotide sequences can be produced by de novo solid-phase DNA synthesis or by PCR mutagenesis of an existing sequence (e.g., sequences as described in the Examples below) encoding an anti-FGFR2 antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the invention are expression vectors and host cells for producing the anti-FGFR2 antibodies described above. Various expression vectors can be employed to express the polynucleotides encoding the anti-FGFR2 antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet. 15:345, 1997). For example, nonviral vectors useful for expression of the anti-FGFR2 polynucleotides and polypeptides in mammalian (e.g., human) cells include pThioHis A, B & C, pcDNA3.1/His, pEBVHis A, B & C (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an anti-FGFR2 antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an anti-FGFR2 antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted anti-FGFR2 antibody sequences. More often, the inserted anti-FGFR2 antibody sequences are linked to a signal sequences before inclusion in the vector. Vectors to be used to receive sequences encoding anti-FGFR2 antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the anti-FGFR2 antibody chains can be either prokaryotic or eukaryotic. E. coli is one prokaryotic host useful for cloning and expressing the polynucleotides of the present invention. Other microbial hosts suitable for use include bacilli, such as Bacillus subtilis, and other enterobacteriaceae, such as Salmonella, Serratia, and various Pseudomonas species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (tip) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express anti-FGFR2 polypeptides of the invention. Insect cells in combination with baculovirus vectors can also be used.

In some preferred embodiments, mammalian host cells are used to express and produce the anti-FGFR2 polypeptides of the present invention. For example, they can be either a hybridoma cell line expressing endogenous immunoglobulin genes (e.g., the myeloma hybridoma clones as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed, including the CHO cell lines, various Cos cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., Immunol Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express anti-FGFR2 antibody chains or binding fragments can be prepared using expression vectors of the invention which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Therapeutic and Diagnostic Uses

The antibodies, antibody fragments (e.g., antigen binding fragments), and antibody drug conjugates of the invention are useful in a variety of applications including, but not limited to, treatment of cancer, such as solid cancers. In certain embodiments, the antibodies, antibody fragments (e.g., antigen binding fragments), and antibody drug conjugates of the invention are useful for inhibiting tumor growth, inducing differentiation, reducing tumor volume, and/or reducing the tumorigenicity of a tumor. The methods of use can be in vitro, ex vivo, or in vivo methods.

In one aspect, the antibodies, antibody fragments (e.g., antigen binding fragments), and antibody drug conjugates of the invention are useful for detecting the presence of FGFR2 in a biological sample. The term "detecting" as used herein encompasses quantitative or qualitative detection. In certain embodiments, a biological sample comprises a cell or tissue. In certain embodiments, such tissues include normal and/or cancerous tissues that express FGFR2 at higher levels relative to other tissues.

In one aspect, the invention provides a method of detecting the presence of FGFR2 in a biological sample. In certain embodiments, the method comprises contacting the biological sample with an anti-FGFR2 antibody under conditions permissive for binding of the antibody to the antigen, and detecting whether a complex is formed between the antibody and the antigen.

In one aspect, the invention provides a method of diagnosing a disorder associated with increased expression of FGFR2. In certain embodiments, the method comprises contacting a test cell with an anti-FGFR2 antibody; determining the level of expression (either quantitatively or qualitatively) of FGFR2 on the test cell by detecting binding of the anti-FGFR2 antibody to the FGFR2 antigen; and comparing the level of expression of FGFR2 ib the test cell with the level of expression of FGFR2 on a control cell (e.g., a normal cell of the same tissue origin as the test cell or a cell that expresses FGFR2 at levels comparable to such a normal cell), wherein a higher level of expression of FGFR2 on the test cell as compared to the control cell indicates the presence of a disorder associated with increased expression of FGFR2. In certain embodiments, the test cell is obtained from an individual suspected of having a disorder associated with increased expression of FGFR2. In certain embodiments, the disorder is a cell proliferative disorder, such as a cancer or a tumor.

In certain embodiments, a method of diagnosis or detection, such as those described above, comprises detecting binding of an anti-FGFR2 antibody to FGFR2 expressed on the surface of a cell or in a membrane preparation obtained from a cell expressing FGFR2 on its surface. An exemplary assay for detecting binding of an anti-FGFR2 antibody to FGFR2 expressed on the surface of a cell is a "FACS" assay.

Certain other methods can be used to detect binding of anti-FGFR2 antibodies to FGFR2. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, anti-FGFR2 antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

In certain embodiments, anti-FGFR2 antibodies are immobilized on an insoluble matrix. Immobilization entails separating the anti-FGFR2 antibody from any FGFR2 proteins that remains free in solution. This conventionally is accomplished by either insolubilizing the anti-FGFR2 antibody before the assay procedure, as by adsorption to a water-insoluble matrix or surface (Bennich et al, U.S. Pat. No. 3,720,760), or by covalent coupling (for example, using glutaraldehyde cross-linking), or by insolubilizing the anti-FGFR2 antibody after formation of a complex between the anti-FGFR2 antibody and FGFR2 protein, e.g., by immunoprecipitation.

Any of the above embodiments of diagnosis or detection can be carried out using an immunoconjugate of the invention in place of or in addition to an anti-FGFR2 antibody.

In one embodiment, the invention provides a method of treating, preventing or ameliorating a disease comprising administering the antibodies, antibody fragments (e.g., antigen binding fragments), and antibody drug conjugates of the invention to a patient, thereby treating the disease. In certain embodiments, the disease treated with the antibodies, antibody fragments (e.g., antigen binding fragments), and antibody drug conjugates of the invention is a cancer. Examples of diseases which can be treated and/or prevented include, but are not limited to, adrenocortical carcinoma, bladder cancer, bone cancer, breast cancer, central nervous system atypical teratoid/rhabdoid tumors, colon cancer, colorectal cancer, embryonal tumors, endometrial cancer, gastric cancer, head and neck cancer, hepatocellular cancer, Kaposi sarcoma, liver cancer, non-small cell lung cancer, rectal cancer, rhabdomyosarcoma, small cell lung cancer, small intestine cancer, soft tissue sarcoma, squamous cell carcinoma, squamous neck cancer, stomach cancer, uterine cancer, vaginal cancer, vulvar cancer. In certain embodiments, the cancer is characterized by FGFR2 expressing cells to which the antibodies, antibody fragments (e.g., antigen binding fragments), and antibody drug conjugates of the invention binds.

The present invention provides for methods of treating cancer comprising administering a therapeutically effective amount of the antibodies, antibody fragments (e.g., antigen binding fragments), or antibody drug conjugates of the invention. In certain embodiments, the cancer is a solid cancer. In certain embodiments, the subject is a human.

In certain embodiments, the method of inhibiting tumor growth comprises administering to a subject a therapeutically effective amount of the antibodies, antibody fragments (e.g., antigen binding fragments), or antibody drug conjugates of the invention. In certain embodiments, the subject is a human. In certain embodiments, the subject has a tumor or has had a tumor removed.

In certain embodiments, the tumor expresses the FGFR2 to which the anti-FGFR2 antibody binds. In certain embodiments, the tumor overexpresses the human FGFR2.

For the treatment of the disease, the appropriate dosage of the antibodies, antibody fragments (e.g., antigen binding fragments), or antibody drug conjugates of the present invention depends on various factors, such as the type of disease to be treated, the severity and course of the disease, the responsiveness of the disease, previous therapy, patient's clinical history, and so on. The antibody or agent can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual antibody, antibody fragment (e.g., antigen binding fragment), or antibody drug conjugates. In certain embodiments, dosage is from 0.01 mg to 10 mg (e.g., 0.01 mg, 0.05 mg, 0.1 mg, 0.5 mg, 1 mg, 2 mg, 3 mg, 4 mg, 5 mg, 7 mg, 8 mg, 9 mg, or 10 mg) per kg of body weight, and can be given once or more daily, weekly, monthly or yearly. In certain embodiments, the antibody, antibody fragment (e.g., antigen binding fragment), or antibody drug conjugate of the present invention is given once every two weeks or once every three weeks. The treating physician can estimate repetition rates for dosing based on measured residence times and concentrations of the drug in bodily fluids or tissues.

Combination Therapy

In certain instances, an antibody, antibody fragment (e.g., antigen binding fragment), or antibody drug conjugate of the present invention is combined with other therapeutic agents, such as other anti-cancer agents, anti-allergic agents, anti-nausea agents (or anti-emetics), pain relievers, cytoprotective agents, and combinations thereof.

General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®)), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), *phoenix* (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

In one embodiment, an antibody, antibody fragment (e.g., antigen binding fragment), or antibody drug conjugate of the present invention is combined in a pharmaceutical combination formulation, or dosing regimen as combination therapy, with a second compound having anti-cancer properties. The second compound of the pharmaceutical combination formulation or dosing regimen can have complementary activities to the antibody or immunoconjugate of the combination such that they do not adversely affect each other. For example, an antibody, antibody fragment (e.g., antigen binding fragment), or antibody drug conjugate of the present invention can be administered in combination with, but not limited to, a chemotherapeutic agent, a tyrosine kinase inhibitor, a FGF downstream signaling pathway inhibitor, IAP inhibitors, Bcl2 inhibitors, Mcl1 inhibitors, and other FGFR2 inhibitors.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In one aspect, the present invention provides a method of treating cancer by administering to a subject in need thereof an antibody drug conjugate of the present invention in combination with one or more tyrosine kinase inhibitors, including but not limited to, EGFR inhibitors, Her2 inhibitors, Her3 inhibitors, IGFR inhibitors, and Met inhibitors.

For example, tyrosine kinase inhibitors include but are not limited to, Erlotinib hydrochloride (Tarceva®); Linifanib (N-[4-(3-amino-1H-indazol-4-yl)phenyl]-N'-(2-fluoro-5-methylphenyl)urea, also known as ABT 869, available from Genentech); Sunitinib malate (Sutent®); Bosutinib (4-[(2,4-dichloro-5-methoxyphenyl)amino]-6-methoxy-7-[3-(4-methylpiperazin-1-yl)propoxy]quinoline-3-carbonitrile, also known as SKI-606, and described in U.S. Pat. No. 6,780,996); Dasatinib (Sprycel®); Pazopanib (Votrient®); Sorafenib (Nexavar®); Zactima (ZD6474); and Imatinib or Imatinib mesylate (Gilvec® and Gleevec®).

Epidermal growth factor receptor (EGFR) inhibitors include but are not limited to, Erlotinib hydrochloride (Tarceva®), Gefitnib (Iressa®); N-[4-[(3-Chloro-4-fluorophenyl)amino]-7-[[(3"S")-tetrahydro-3-furanyl]oxy]-6-quinazolinyl]-4(dimethylamino)-2-butenamide, Tovok®); Vandetanib (Caprelsa®); Lapatinib (Tykerb®); (3R,4R)-4-Amino-1-((4-((3-methoxyphenyl)amino)pyrrolo[2,1-f][1,2,4]triazin-5-yl)methyl)piperidin-3-ol (BMS690514); Canertinib dihydrochloride (CI-1033); 6-[4-[(4-Ethyl-1-piperazinyl)methyl]phenyl]-N-[(1R)-1-phenylethyl]-7H-Pyrrolo[2,3-d]pyrimidin-4-amine (AEE788, CAS 497839-62-0); Mubritinib (TAK165); Pelitinib (EKB569); Afatinib (BIBW2992); Neratinib (HKI-272); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS599626); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); and 4-[4-[[(1R)-1-Phenylethyl]amino]-7H-pyrrolo[2,3-d]pyrimidin-6-yl]-phenol (PKI166, CAS 187724-61-4).

EGFR antibodies include but are not limited to, Cetuximab (Erbitux®); Panitumumab (Vectibix®); Matuzumab (EMD-72000); Trastuzumab (Herceptin®); Nimotuzumab (hR3); Zalutumumab; TheraCIM h-R3; MDX0447 (CAS 339151-96-1); and ch806 (mAb-806, CAS 946414-09-1).

Human Epidermal Growth Factor Receptor 2 (HER2 receptor) (also known as Neu, ErbB-2, CD340, or p185) inhibitors include but are not limited to, Trastuzumab (Herceptin®); Pertuzumab (Omnitarg®); Neratinib (HKI-272, (2E)-N-[4-[[3-chloro-4-[(pyridin-2-yl)methoxy]phenyl]amino]-3-cyano-7-ethoxyquinolin-6-yl]-4-(dimethylamino)but-2-enamide, and described PCT Publication No. WO 05/028443); Lapatinib or Lapatinib ditosylate (Tykerb®); (3R,4R)-4-amino-1-((4-((3-methoxyphenyl)amino)pyrrolo[2,1-f][1,2,4]triazin-5-yl)methyl)piperidin-3-ol (BMS690514); (2E)-N-[4-[(3-Chloro-4-fluorophenyl)amino]-7-[[(3S)-tetrahydro-3-furanyl]oxy]-6-quinazolinyl]-4-(dimethylamino)-2-butenamide (BIBW-2992, CAS 850140-72-6); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS 599626, CAS 714971-09-2); Canertinib dihydrochloride (PD183805 or CI-1033); and N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8).

HER3 inhibitors include but are not limited to, LJM716, MM-121, AMG-888, RG7116, REGN-1400, AV-203, MP-RM-1, MM-111, and MEHD-7945A.

MET inhibitors include but are not limited to, Cabozantinib (XL184, CAS 849217-68-1); Foretinib (GSK1363089, formerly XL880, CAS 849217-64-7); Tivantinib (ARQ197, CAS1000873-98-2); 1-(2-Hydroxy-2-methylpropyl)-N-(5-(7-methoxyquinolin-4-yloxy)pyridin-2-yl)-5-methyl-3-oxo-2-phenyl-2,3-dihydro-1H-pyrazole-4-carboxamide (AMG 458); Cryzotinib (Xalkori®, PF-02341066); (3Z)-5-(2,3-Dihydro-1H-indol-1-ylsulfonyl)-3-({3,5-dimethyl-4-[(4-methylpiperazin-1-yl)carbonyl]-1H-pyrrol-2-yl}methylene)-1,3-dihydro-2H-indol-2-one (SU11271); (3Z)—N-(3-Chlorophenyl)-3-({3,5-dimethyl-4-[(4-methylpiperazin-1-yl)carbonyl]-1H-pyrrol-2-yl}methylene)-N-methyl-2-oxoindoline-5-sulfonamide (SU11274); (3Z)—N-(3-Chlorophenyl)-3-{[3,5-dimethyl-4-(3-morpholin-4-ylpropyl)-1H-pyrrol-2-yl]methylene}-N-methyl-2-oxoindoline-5-sulfonamide (SU11606); 6-[Difluoro[6-(1-methyl-1H-pyrazol-4-yl)-1,2,4-triazolo[4,3-b]pyridazin-3-yl]methyl]-quinoline (JNJ38877605, CAS 943540-75-8); 2-[4-[1-(Quinolin-6-ylmethyl)-1H-[1,2,3]triazolo[4,5-b]pyrazin-6-yl]-1H-pyrazol-1-yl]ethanol (PF04217903, CAS 956905-27-4); N-((2R)-1,4-Dioxan-2-ylmethyl)-N-methyl-N'-[3-(1-methyl-1H-pyrazol-4-yl)-5-oxo-5H-benzo[4,5]cyclohepta[1,2-b]pyridin-7-yl]sulfamide (MK2461, CAS 917879-39-1); 6-[[6-(1-Methyl-1H-pyrazol-4-yl)-1,2,4-triazolo[4,3-b]pyridazin-3-yl]thio]-quinoline (SGX523, CAS1022150-57-7); and (3Z)-5-[[(2,6-Dichlorophenyl)methyl]sulfonyl]-3-[[3,5-dimethyl-4-[[(2R)-2-(1-pyrrolidinylmethyl)-1-pyrrolidinyl]carbonyl]-1H-pyrrol-2-yl]methylene]-1,3-dihydro-2H-indol-2-one (PHA665752, CAS 477575-56-7).

IGF1R inhibitors include but are not limited to, BMS-754807, XL-228, OSI-906, GSK0904529A, A-928605, AXL1717, KW-2450, MK0646, AMG479, IMCA12, MEDI-573, and BI836845. See e.g., Yee, JNCI, 104; 975 (2012) for review.

In another aspect, the present invention provides a method of treating cancer by administering to a subject in need thereof an antibody drug conjugate of the present invention in combination with one or more FGF downstream signaling pathway inhibitors, including but not limited to, MEK inhibitors, Braf inhibitors, PI3K/Akt inhibitors, SHP2 inhibitors, and also mTor.

For example, mitogen-activated protein kinase (MEK) inhibitors include but are not limited to, XL-518 (also known as GDC-0973, Cas No. 1029872-29-4, available from ACC Corp.); 2-[(2-Chloro-4-iodophenyl)amino]-N-(cyclopropylmethoxy)-3,4-difluoro-benzamide (also known as CI-1040 or PD184352 and described in PCT Publication No. WO2000035436); N-[(2R)-2,3-Dihydroxypropoxy]-3,4-difluoro-2-[(2-fluoro-4-iodophenyl)amino]-benzamide (also known as PD0325901 and described in PCT Publication No. WO2002006213); 2,3-Bis[amino[(2-aminophenyl)thio]methylene]-butanedinitrile (also known as U0126 and described in U.S. Pat. No. 2,779,780); N-[3,4-Difluoro-2-[(2-fluoro-4-iodophenyl)amino]-6-methoxyphenyl]-1-[(2R)-2,3-dihydroxypropyl]-cyclopropanesulfonamide (also known as RDEA119 or BAY869766 and described in PCT Publication No. WO2007014011); (3S,4R,5Z,8S,9S,11E)-14-(Ethylamino)-8,9,16-trihydroxy-3,4-dimethyl-3,4,9,19-tetrahydro-1H-2-benzoxacyclotetradecine-1,7(8H)-dione (also known as E6201 and described in PCT Publication No. WO2003076424); 2'-Amino-3'-methoxyflavone (also known as PD98059 available from Biaffin GmbH & Co., KG, Germany); Vemurafenib (PLX-4032, CAS 918504-65-1); (R)-3-(2,3-Dihydroxypropyl)-6-fluoro-5-(2-fluoro-4-iodophenylamino)-8-methylpyrido[2,3-d]pyrimidine-4,7(3H,8H)-dione (TAK-733, CAS1035555-63-5); Pimasertib (AS-703026, CAS1204531-26-9); and Trametinib dimethyl sulfoxide (GSK-1120212, CAS1204531-25-80).

Phosphoinositide 3-kinase (PI3K) inhibitors include but are not limited to, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036,082 and WO 09/055,730); 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806); 4-(trifluoromethyl)-5-(2,6-dimorpholinopyrimidin-4-yl)pyridin-2-amine (also known as BKM120 or NVP-BKM120, and described in PCT Publication No. WO2007/084786); Tozasertib (VX680 or MK-0457, CAS 639089-54-6); (5Z)-5-[[4-(4-Pyridinyl)-6-quinolinyl]methylene]-2,4-thiazolidinedione (GSK1059615, CAS 958852-01-2); (1E,4S,4aR,5R,6aS,9aR)-5-(Acetyloxy)-1-[(di-2-propenylamino)methylene]-4,4-a,5,6,6a,8,9,9a-octahydro-11-hydroxy-4-(methoxymethyl)-4-a,6a-dimethyl-cyclopenta[5,6]naphtho[1,2-c]pyran-2,7,10(1H)-trione (PX866, CAS 502632-66-8); and 8-Phenyl-2-(morpholin-4-yl)-chromen-4-one (LY294002, CAS154447-36-6).

mTor include but are not limited to, Temsirolimus (Torisel®); Ridaforolimus (formally known as deferolimus, (1R,2R,4S)-4-[(2R)-2[(1R,9S,12S,15R,16E,18R,19R,21R,23S,24E,26E,28Z,30S,32S,35R)-1,18-dihydroxy-19,30-dimethoxy-15,17,21,23, 29,35-hexamethyl-2,3,10,14,20-pentaoxo-11,36-dioxa-4-azatricyclo[30.3.1.0$^{4,9}$]hexatriaconta-16,24,26,28-tetraen-12-yl]propyl]-2-methoxycyclohexyl dimethylphosphinate, also known as AP23573 and MK8669, and described in PCT Publication No. WO 03/064383); Everolimus (Afinitor® or RAD001); Rapamycin (AY22989, Sirolimus®); Simapimod (CAS164301-51-3); (5-{2,4-Bis[(3S)-3-methylmorpholin-4-yl]pyrido[2,3-d]pyrimidin-7-yl}-2-methoxyphenyl) methanol (AZD8055); 2-Amino-8-[trans-4-(2-hydroxyethoxy)cyclohexyl]-6-(6-methoxy-3-pyridinyl)-4-methylpyrido[2,3-d]pyrimidin-7(8H)-one (PF04691502, CAS1013101-36-4); and N$^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-, inner salt (SF1126, CAS 936487-67-1).

In yet another aspect, the present invention provides a method of treating cancer by administering to a subject in need thereof an antibody drug conjugate of the present invention in combination with one or more pro-apoptotics, including but not limited to, IAP inhibitors, Bcl2 inhibitors, MCl1 inhibitors, Trail agents, Chk inhibitors.

For examples, IAP inhibitors include but are not limited to, LCL161, GDC-0917, AEG-35156, AT406, and TL32711. Other examples of IAP inhibitors include but are not limited to those disclosed in WO04/005284, WO 04/007529, WO05/097791, WO 05/069894, WO 05/069888, WO 05/094818, US2006/0014700, US2006/0025347, WO 06/069063, WO 06/010118, WO 06/017295, and WO08/134,679, all of which are incorporated herein by reference.

BCL-2 inhibitors include but are not limited to, 4-[4-[[2-(4-Chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide (also known as ABT-263 and described in PCT Publication No. WO 09/155,386); Tetrocarcin A; Antimycin; Gossypol ((−)BL-193); Obatoclax; Ethyl-2-amino-6-cyclopentyl-4-(1-cyano-2-ethoxy-2-oxoethyl)-4Hchromone-3-carboxylate (HA14-1); Oblimersen (G3139, Genasense®); Bak BH3 peptide; (−)-Gossypol acetic acid (AT-101); 4-[4-[(4'-Chloro[1,1'-biphenyl]-2-yl)methyl]-1-piperazinyl]-N—[[4-[[(1R)-3-(dimethylamino)-1-[(phenylthio)methyl]propyl]amino]-3-nitrophenyl]sulfonyl]-benzamide (ABT-737, CAS 852808-04-9); and Navitoclax (ABT-263, CAS 923564-51-6).

Proapoptotic receptor agonists (PARAs) including DR4 (TRAILR1) and DR5 (TRAILR2), including but are not limited to, Dulanermin (AMG-951, RhApo2L/TRAIL); Mapatumumab (HRS-ETR1, CAS 658052-09-6); Lexatumumab (HGS-ETR2, CAS 845816-02-6); Apomab (Apomab0); Conatumumab (AMG655, CAS 896731-82-1); and Tigatuzumab (CS1008, CAS 946415-34-5, available from Daiichi Sankyo).

Checkpoint Kinase (CHK) inhibitors include but are not limited to, 7-Hydroxystaurosporine (UCN-01); 6-Bromo-3-(1-methyl-1H-pyrazol-4-yl)-5-(3R)-3-piperidinyl-pyrazolo[1,5-a]pyrimidin-7-amine (SCH900776, CAS 891494-63-6); 5-(3-Fluorophenyl)-3-ureidothiophene-2-carboxylic acid N-[(S)-piperidin-3-yl]amide (AZD7762, CAS 860352-01-8); 4-[((3S)-1-Azabicyclo[2.2.2]oct-3-yl)amino]-3-(1H-benzimidazol-2-yl)-6-chloroquinolin-2(1H)-one (CHIR 124, CAS 405168-58-3); 7-Aminodactinomycin (7-AAD), Isogranulatimide, debromohymenialdisine; N-[5-Bromo-4-methyl-2-[(2S)-2-morpholinylmethoxy]-phenyl]-N'-(5-methyl-2-pyrazinyl)urea (LY2603618, CAS 911222-45-2); Sulforaphane (CAS 4478-93-7, 4-Methylsulfinylbutyl isothiocyanate); 9,10,11,12-Tetrahydro-9,12-epoxy-1H-diindolo[1,2,3-fg:3',2',1'-kl]pyrrolo[3,4-i][1,6]benzodiazocine-1,3(2H)-dione (SB-218078, CAS 135897-06-2); and TAT-S216A (YGRKKRRQRRRLYRSPAMPENL) (SEQ ID NO: 262), and CBP501 ((d-Bpa)sws(d-Phe-F5)(d-Cha) rrrqrr).

In one aspect, the present invention provides a method of treating cancer by administering to a subject in need thereof an antibody drug conjugate of the present invention in combination with one or more FGFR inhibitors. For example, FGFR inhibitors include but are not limited to, Brivanib alaninate (BMS-582664, (S)-((R)-1-(4-(4-Fluoro-2-methyl-1H-indol-5-yloxy)-5-methylpyrrolo[2,1-f][1,2,4]triazin-6-yloxy)propan-2-yl)2-aminopropanoate); Vargatef (BIBF1120, CAS 928326-83-4); Dovitinib dilactic acid (TKI258, CAS 852433-84-2); 3-(2,6-Dichloro-3,5-dimethoxy-phenyl)-1-{6-[4-(4-ethyl-piperazin-1-yl)-phenylamino]-pyrimidin-4-yl}-1-methyl-urea (BGJ398, CAS 872511-34-7); Danusertib (PHA-739358); and N-[2-[[4-(Diethylamino)butyl]amino]-6-(3,5-dimethoxyphenyl)pyrido[2,3-d]pyrimidin-7-yl]-N'-(1,1-dimethylethyl)-urea (PD173074, CAS 219580-11-7). In a specific embodiment, the present invention provides a method of treating cancer by administering to a subject in need thereof an antibody drug conjugate of the present invention in combination another FGFR2 inhibitor, such as 3-(2,6-dichloro-3,5-dimethoxyphenyl)-1-(6((4-(4-ethylpiperazin-1-yl)phenyl)amino)pyrimidin-4-yl)-1-methylurea (also known as BGJ-398); or 4-amino-5-fluoro-3-(5-(4-methylpiperazinl-yl)-1H-benzo

[d]imidazole-2-yl)quinolin-2(1H)-one (also known as dovitinib or TKI-258). AZD4547 (Gavine et al., 2012, Cancer Research 72, 2045-56, N-[5-[2-(3,5-Dimethoxyphenyl)ethyl]-2H-pyrazol-3-yl]-4-(3R,5S)-diemthylpiperazin-1-yl)benzamide), Ponatinib (AP24534; Gozgit et al., 2012, Mol Cancer Ther., 11; 690-99; 3-[2-(imidazo[1,2-b]pyridazin-3-yl)ethynyl]-4-methyl-N-{4-[(4-methylpiperazin-1-yl)methyl]-3-(trifluoromethyl)phenyl}benzamide, CAS 943319-70-8)

Pharmaceutical Compositions

To prepare pharmaceutical or sterile compositions including immunoconjugates, the immunoconjugates of the invention are mixed with a pharmaceutically acceptable carrier or excipient. The compositions can additionally contain one or more other therapeutic agents that are suitable for treating or preventing cancer (breast cancer, colorectal cancer, lung cancer, multiple myeloma, ovarian cancer, liver cancer, gastric cancer, pancreatic cancer, acute myeloid leukemia, chronic myeloid leukemia, osteosarcoma, squamous cell carcinoma, peripheral nerve sheath tumors schwannoma, head and neck cancer, bladder cancer, esophageal cancer, Barretts esophageal cancer, glioblastoma, clear cell sarcoma of soft tissue, malignant mesothelioma, neurofibromatosis, renal cancer, melanoma, prostate cancer, benign prostatic hyperplasia (BPH), gynacomastica, and endometriosis).

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., Goodman and Gilman's The Pharmacological Basis of Therapeutics, McGraw-Hill, New York, N.Y., 2001; Gennaro, Remington: The Science and Practice of Pharmacy, Lippincott, Williams, and Wilkins, New York, N.Y., 2000; Avis, et al. (eds.), Pharmaceutical Dosage Forms: Parenteral Medications, Marcel Dekker, NY, 1993; Lieberman, et al. (eds.), Pharmaceutical Dosage Forms: Tablets, Marcel Dekker, NY, 1990; Lieberman, et al. (eds.) Pharmaceutical Dosage Forms: Disperse Systems, Marcel Dekker, NY, 1990; Weiner and Kotkoskie, Excipient Toxicity and Safety, Marcel Dekker, Inc., New York, N.Y., 2000).

In a specific embodiment, The clinical service form (CSF) of the antibody drug conjugates of the present invention is a lyophilisate in vial containing the ADC, sodium succinate, and polysorbate 20. The lyophilisate can be reconstitute with water for injection, the solution comprises the ADC, sodium succinate, sucrose, and polysorbate 20 at a pH of about 5.0. For subsequent intravenous administration, the obtained solution will usually be further diluted into a carrier solution.

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, Antibody Therapy, Bios Scientific Pub. Ltd, Oxfordshire, UK, 1996; Kresina (ed.), Monoclonal Antibodies, Cytokines and Arthritis, Marcel Dekker, New York, N.Y., 1991; Bach (ed.), Monoclonal Antibodies and Peptide Therapy in Autoimmune Diseases, Marcel Dekker, New York, N.Y., 1993; Baert et al., New Engl. J. Med. 348:601-608, 2003; Milgrom et al., New Engl. J. Med. 341:1966-1973, 1999; Slamon et al., New Engl. J. Med. 344:783-792, 2001; Beniaminovitz et al., New Engl. J. Med. 342:613-619, 2000; Ghosh et al., New Engl. J. Med. 348:24-32, 2003; Lipsky et al., New Engl. J. Med. 343:1594-1602, 2000).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts.

Compositions comprising antibodies or fragments thereof of the invention can be provided by continuous infusion, or by doses at intervals of, e.g., one day, one week, or 1-7 times per week, once every other week, once every three weeks, once every four weeks, once every five weeks, once every six weeks, once every seven weeks, or once very eight weeks. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects.

For the immunoconjugates of the invention, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. The dosage of the antibodies or fragments thereof of the invention may be calculated using the patient's weight in kilograms (kg) multiplied by the dose to be administered in mg/kg.

Doses of the immunoconjugates the invention may be repeated and the administrations may be separated by at least 1 day, 2 days, 3 days, 5 days, 10 days, 15 days, 30 days, 45 days, 2 months, 75 days, 3 months, or at least 6 months. In a specific embodiment, doses of the immunoconjugates of the invention are repeated every 3 weeks.

An effective amount for a particular patient may vary depending on factors such as the condition being treated, the overall health of the patient, the method, route and dose of administration and the severity of side effects (see, e.g., Maynard et al., A Handbook of SOPs for Good Clinical Practice, Interpharm Press, Boca Raton, Fla., 1996; Dent, Good Laboratory and Good Clinical Practice, Urch Publ., London, UK, 2001).

The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al., Biopolymers 22:547-556, 1983; Langer et al., J. Biomed. Mater. Res. 15:167-277, 1981; Langer, Chem. Tech. 12:98-105, 1982; Epstein et al., Proc. Natl. Acad. Sci. USA 82:3688-3692, 1985; Hwang et al., Proc. Natl. Acad. Sci. USA 77:4030-4034, 1980; U.S. Pat. Nos. 6,350,466 and 6,316,024). Where necessary, the composition may also include a solubilizing agent or a local anesthetic such as lidocaine to ease pain at the site of the injection, or both. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

A composition of the present invention may also be administered via one or more routes of administration using one or more of a variety of methods known in the art. As will be appreciated by the skilled artisan, the route and/or mode of administration will vary depending upon the desired results. Selected routes of administration for the immunoconjugates of the invention include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the invention can be administered via a non-parenteral route, such as a topical, epidermal or mucosal route of administration, for example, intranasally, orally, vaginally, rectally, sublingually or topically. In one embodiment, the immunoconjugates of the invention is administered by infusion. In another embodiment, the immunoconjugates of the invention is administered subcutaneously.

If the immunoconjugates of the invention are administered in a controlled release or sustained release system, a pump may be used to achieve controlled or sustained release (see Langer, supra; Sefton, CRC Crit. Ref Biomed. Eng. 14:20, 1987; Buchwald et al., Surgery 88:507, 1980; Saudek et al., N. Engl. J. Med. 321:574, 1989). Polymeric materials can be used to achieve controlled or sustained release of the therapies of the invention (see e.g., Medical Applications of Controlled Release, Langer and Wise (eds.), CRC Pres., Boca Raton, Fla., 1974; Controlled Drug Bioavailability, Drug Product Design and Performance, Smolen and Ball (eds.), Wiley, New York, 1984; Ranger and Peppas, J. Macromol. Sci. Rev. Macromol. Chem. 23:61, 1983; see also Levy et al., Science 228:190, 1985; During et al., Ann. Neurol. 25:351, 1989; Howard et al., J. Neurosurg. 7 1:105, 1989; U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138, 1984).

Controlled release systems are discussed in the review by Langer, Science 249:1527-1533, 1990). Any technique known to one of skill in the art can be used to produce sustained release formulations comprising one or more immunoconjugates of the invention. See, e.g., U.S. Pat. No. 4,526,938, PCT publication WO 91/05548, PCT publication WO 96/20698, Ning et al., Radiotherapy & Oncology 39:179-189, 1996; Song et al., PDA Journal of Pharmaceutical Science & Technology 50:372-397, 1995; Cleek et al., Pro. Int'l. Symp. Control. Rel. Bioact. Mater. 24:853-854, 1997; and Lam et al., Proc. Int'l. Symp. Control Rel. Bioact. Mater. 24:759-760, 1997, each of which is incorporated herein by reference in their entirety.

If the immunoconjugates of the invention are administered topically, they can be formulated in the form of an ointment, cream, transdermal patch, lotion, gel, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising the immunoconjugates are administered intranasally, it can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., a cytokine, steroid, chemotherapeutic agent, antibiotic, or radiation, are known in the art (see, e.g., Hardman et al., (eds.) (2001) Goodman and Gilman's The Pharmacological Basis of Therapeutics, 10.sup.th ed., McGraw-Hill, New York, N.Y.; Poole and Peterson (eds.) (2001) Pharmacotherapeutics for Advanced Practice:A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%; at least 40%, or at least 50%.

Additional therapies (e.g., prophylactic or therapeutic agents), which can be administered in combination with the immunoconjugates of the invention may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the immunoconjugates of the invention. The two or more therapies may be administered within one same patient visit.

In certain embodiments, the immunoconjugates of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade, (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (Bloeman et al., (1995) FEBS Lett. 357:140; Owais et al., (1995) Antimicrob. Agents Chemother. 39:180); surfactant protein A receptor (Briscoe et al., (1995) Am. J. Physiol. 1233:134); p 120 (Schreier et al, (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The invention provides protocols for the administration of pharmaceutical composition comprising immunoconjugates of the invention alone or in combination with other therapies to a subject in need thereof. The therapies (e.g., prophylactic or therapeutic agents) of the combination therapies of the present invention can be administered concomitantly or sequentially to a subject. The therapy (e.g., prophylactic or therapeutic agents) of the combination therapies of the present invention can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the invention can be administered to a subject concurrently.

The term "concurrently" is not limited to the administration of therapies (e.g., prophylactic or therapeutic agents) at exactly the same time, but rather it is meant that a pharmaceutical composition comprising antibodies or fragments thereof the invention are administered to a subject in a sequence and within a time interval such that the antibodies of the invention can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

EXAMPLES

The following examples and intermediates serve to illustrate the invention without limiting the scope thereof.

Example 1

Screening for anti-FGFR2 Antibodies

Cell Lines

Ba/F3 cells were purchased from DSMZ, KatoIII, SNU16, SNU5 and HCI-H716 cells were purchased from the American Type Culture Collection (ATCC) and NUGC3 cells were obtained from the Japanese Collection of Research Bioresources (JCRB) Cell Bank. All cell lines were routinely cultured in appropriate growth medium supplemented with fetal bovine serum (FBS) as recommended by their respective suppliers.

Generation of Recombinant Human, Cyno, Mouse and Rat FGFR Vectors

Human, mouse and rat FGFR extracellular domains were gene synthesized based on amino acid sequences from the GenBank or Uniprot databases (see Table 2). The cynomolgus monkey FGFR2 cDNA template was gene synthesized based on amino acid sequences information generated using mRNA from various cynomolgus monkey tissues (e.g.

Zyagen Laboratories; Table 3). All synthesized DNA fragments were cloned into appropriate expression vectors e.g. CMV based vectors or pcDNA3.1. with C-terminal tags to allow for purification.

gravity flow. After base-line washing with PBS, bound material was eluted with 100 mM glycine (pH 2.7) and immediately dialyzed against PBS overnight and then sterile filtered. Protein concentrations were determined by measuring the

TABLE 2

Generation of FGFR expression vectors. Amino acid numbering is based on the accession numbers or seq IDs provided in the table

| Name | Description | Accession Number | SEQ ID NO |
|---|---|---|---|
| Human FGFR1 IIIb D1-3 | Human FGFR1 isoform IIIb, residues 22-373-TAG | NM 015850 | 243 |
| Human FGFR2 IIIb D1-3 | Human FGFR2 isoform IIIb, residues 22-378-TAG | NM_022970/P21802-3 | 244 |
| Human FGFR3 IIIb D1-3 | Human FGFR3 isoform IIIb, residues 23-377-TAG | NM_000142 | 245 |
| Human FGFR4 ECD | Human FGFR4 extracellular domain, residues 22-369-TAG | NM_002011; P22455 | 246 |
| Human FGFR2 IIIc D1-3 | Human FGFR2 isoform IIIc, residues 22-378-TAG | NM_022970/P21802-1 | 247 |
| Cynomolgus monkey FGFR2 IIIb D1-3 | Cynomolgus monkey FGFR2 isoform IIIb, residues 22-378-TAG | Not applicable. | 248 |
| Mouse FGFR2 IIIb D1-3 | Mouse FGFR2 isoform IIIb, residues 22-378-TAG | NM_010207 | 249 |
| Rat FGFR2 IIIb D1-3 | Rat FGFR2 isoform IIIb, residues 41-397-TAG | XM_001079450 | 250 |

TABLE 3

Sequences of cynomolgus FGFR2 proteins

| Construct | Amino acid sequence in one letter code | SEQ ID NO |
|---|---|---|
| Cynomolgus monkey FGFR2 IIIb D1-3 | METDTLLLWVLLLWVPGSTGRPSFSLVEDTTLEPEEPPTKYQIS QPEVYVAAPGESLEVRCLLKDAAVISWTKDGVHLGPNNRTVLI GEYLQIKGATPRDSGLYACTATRTVDSETWYFMVNVTDAISSG DDEDDTDGAEDFVSENGNNKRAPYWTNTEKMEKRLHAVPAA NTVKFRCPAGGNPTPTMRWLKNGKEFKQEHRIGGYKVRNQH WSLIMESVVPSDKGNYTCVVENEYGSINHTYHLDVVERSPHRP ILQAGLPANASTVVGGDVEFVCKVYSDAQPHIQWIKHVEKNG SKYGPDGLPYLKVLKHSGINSSNAEVLALFNVTEADAGEYICK VSNYIGQANQSAWLTVLPKQQAPGREKEITASPDYLEKLEFRH DSGLNDIFEAQKIEWHE | 248 |

Expression of Recombinant FGFR Proteins

The desired FGFR recombinant proteins were expressed in HEK293 derived cell lines (293T) previously adapted to suspension culture and grown in a mix of serum-free medium, 50% HyClone SFM4Transfx-293 without L-glutamine (HyClone) and 50% FreeStyle-293 (Gibco). Both small scale and large scale protein production were via transient transfection and was performed in multiple shaker flasks (Nalgene), up to 1 L each, with Polyethylenimine (PEI, 25K, AlfaAesar) as a plasmid carrier. When biotinylated proteins were to be expressed via the C-terminal Avi tag, a plasmid carrying the gene for BirA enzyme were included at the ratio of 1:2 to the ECD protein plasmid. Total DNA and Polyethylenimine was used at a ratio of 1:3 (w:w). DNA to culture ratio was 1 mg/L. The cell culture supernatants were harvested 6 days post transfection, centrifuged and sterile filtered prior to purification.

Tagged Protein Purification

Recombinant tagged FGFRECD proteins were purified by collecting the cell culture supernatant. An anti-APP column was prepared by coupling an anti-APP monoclonal antibody to CNBr activated Sepharose 4B at a final ratio of 10 mg antibody per mL of resin. Expression supernatant was applied to an anti-APP column at a flow rate of 1-2 mL/minute or by absorbance at 280 nm and converting using the protein extinction coefficient calculated based on individual protein's amino acid sequences. The purified protein was then characterized by SDS-PAGE, analytical size exclusion chromatography (HPLC-SEC). For those that had more than >10% aggregates in the affinity purified preparation, a second step SEC purification were performed followed by confirmation characterizations.

Generation of Ba/F3 FGFR2 Cell Lines

To generate these cells, human FRGR2-IIIb-C3 (NM_022970) was cloned into a pENTR TOPOD vector (Invitrogen catalog #K2400-20) and then into a pLenti6 DEST vector (Invitrogen catalog #V49610) under a CMV promoter. Virus was then packaged and Ba/F3 cells (DSMZ catalog #ACC300) were spin infected with the lentivirus, followed by treatment with 20 µg blasticidin (e.g. Invitrogen, catalog #A11139-03 or Cellgro, catalog #30-100-RB) and selection with IL3 (R&D systems catalog #403-m1-010) for 5 days in a tissue culture incubator at 37° C. and 5% $CO_2$. Surviving cells were then grown in medium (RPMI (Invitrogen catalog #11875-093) supplemented with 10% FBS (Clontech catalog #631101, 2 µg/ml heparin (Sigma, catalog #H3149) and 20 µg/ml blasticidin (e.g. Invitrogen, catalog #A11139-03 or Cellgro, catalog #30-100-RB)) but without IL3 for 1 month. Surviving cells were then dilution cloned to generate clonal cell populations which were then used for subsequent studies.

HuCAL PLATINUM® Pannings

For the selection of antibodies recognizing human FGFR2, multiple panning strategies were utilized. Therapeutic antibodies against human FGFR proteins were generated by the selection of clones that bound to FGFR2 using as a source of antibody variant proteins a commercially available phage display library, the Morphosys HuCAL PLATINUM® library. The phagemid library is based on the HuCAL® concept (Knappik et al., 2000, J Mol Biol 296: 57-86) and employs the CysDisplay™ technology for displaying the Fab on the phage surface (WO01/05950).

For the isolation of anti-FGFR2 antibodies, several different panning strategies were employed, using solid phase, solution, whole cell and differential whole cell approaches Solid Phase Panning on Recombinant FGFR2

Prior to the antigen selection process a coating check ELISA was performed to determine the optimal coating concentration for the antigen. Different recombinant FGFR2 proteins with various tags were used in the solid phase panning approach by coating on Maxisorp™ plates (Nunc) either via passive adsorption or via capture antibodies targeting the respective tag of the antigen. Alternatively Reacti-Bind™ NeutrAvidin™-coated Polystyrene Strip Plates (Pierce) were used to capture biotinylated FGFR2 antigen. An appropriate number (dependent on the number of sub-library pools) of wells of a 96-well Maxisorp™ plate (Nunc) were coated with 300 µl of antigen overnight at 4° C. The coated wells were blocked with PBS (phosphate buffered saline)/5% milk powder. For each panning, HuCAL PLATINUM® phage-antibodies were blocked. After the blocking procedure, 300 µl of pre-blocked phage mix was added to each antigen coated and blocked well and incubated for 2 hours (h) at room temperature (RT) on a microtiter plate (MTP) shaker. Afterwards, unspecific bound phage was washed off by several washing steps. For elution of specifically bound phage, 25 mM DTT (Dithiothreitol) was added for 10 minutes (min) at RT. The DTT eluates were used for infection of E. coli (Escherichia coli) TG-1 cells. After infection, the bacteria were. plated on LB (lysogeny broth)/Cam (chloramphenicol) agar plates and incubated overnight at 30° C. Colonies were scraped off the plates and were used for phage rescue, polyclonal amplification of selected clones, and phage production. Each FGFR2 solid phase panning strategy comprised individual rounds of panning and contained unique antigens, antigen concentrations, buffer compositions and washing stringencies.

Solution Panning on Recombinant FGFR2 with Streptavidin-Coupled Magnetic Beads

A prerequisite for solution panning approaches was the biotinylation of the antigen and confirmation of retained activity of biotinylated antigen. During solution panning, the Fab displaying phage and the biotinylated antigen were incubated in solution which facilitated the accessibility of the antigen by the phage For each phage pool, Streptavidin beads (Dynabeads M-280 Streptavidin; Invitrogen) were blocked in 1× Chemiblocker. In parallel, for each panning, HuCAL PLATINUM® phage-antibodies were blocked with an equal volume of 2× Chemiblocker/0.1% Tween20. Then, a certain concentration of biotinylated antigen (e.g. 100 nM) was added to the pre-adsorbed and blocked phage particles and incubated for 1-2 h at RT on a rotator. The phage-antigen complexes were captured using blocked Streptavidin beads and phage particles bound to the Streptavidin beads were collected with a magnetic separator. Unspecific bound phages were washed off by several washing steps. For elution of specifically bound phage from Streptavidin beads, 25 mM DTT were added for 10 min at RT. The DTT eluate was processed as described for the solid phase pannings. Each FGFR2 solution phase panning strategy comprised individual rounds of panning and contained unique antigens, antigen concentrations and washing stringencies.

Whole Cell Panning on FGFR2 Overexpressing Cells

For each cell panning, HuCAL PLATINUM® phage-antibodies were pre-blocked in PBS/FCS In parallel, 0.5–1.0× $10^7$ target cells per phage pool (Ba/F3 cells stably transfected with FGFR2,Kato-III, SNU16, H716) showing overexpression of FGFR2 were resuspended in PBS/FCS on ice.

The blocked target cells were spun down, re-suspended in the pre-blocked phage particles and incubated for 2 h at 4° C. on a rotator. The phage-cell complexes were washed in PBS/FCS. Elution of specifically bound phage from target cells was performed by acidic elution with glycine buffer, pH 2.2. After centrifugation, the supernatant (eluate) was neutralized by adding unbuffered Tris. The final phage containing supernatant was used for infection of E. coli TG1 culture. The following steps were done as described under the section solid phase pannings.

In more detail, either whole cell pannings were performed, where each panning round was performed with cells or, alternatively, differential whole cell pannings were performed, meaning either cells or recombinant protein was used in consecutive panning rounds. The selection rounds on recombinant antigen were performed as described for solid phase or solution pannings.

Maturation Pannings

In order to obtain FGFR2 specific antibodies with increased affinities, maturation pannings were performed (Prassler et al., 2009, Immunotherapy, 1: 571-583). For this purpose, standard pannings (solid phase and solution phase panning) were performed with different FGFR2 antigens as described above.

After the panning, Fab-encoding fragments of phage derived pMORPH30® vector DNA were digested with distinct specific restriction enzymes to generate either LCDR3 or HCDR2 matured libraries. The insertes were replaced using TRIM™ technology (Virnekas et al., 1994, Nucleic Acids Research 22: 5600-5607).

The generated libraries were amplified and subjected to two more rounds of panning with increased washing stringency and reduced antigen concentrations.

Subcloning and Microexpression of Selected Fab Fragments

To facilitate rapid expression of soluble Fab, the Fab encoding inserts of the selected HuCAL PLATINUM® phage were subcloned from pMORPH®30 display vector into pMORPH®x11 expression vector pMORPH®x11_FH.

After transformation of E. coli TG1-F⁻ single clone expression and preparation of periplasmic extracts containing HuCAL®-Fab fragments were performed as described previously (Rauchenberger et al., 2003 J Biol Chem 278: 38194-38205).

ELISA Screening

Using ELISA screening, single Fab clones are identified from panning output for binding to the target antigen. Fabs are tested using Fab containing crude E. coli lysates.

Maxisorp™ (Nunc) 384 well plates were coated with FGFR antigens of interest (either via passive adsoption or via capure antibodies targeting the respective tag of the antigen) in PBS at their previous determined saturation concentration. Alternatively Reacti-Bind™ NeutrAvidin™-coated Polystyrene Strip Plates (Pierce) were used to capture biotinylated FGFR2 antigen. After blocking of plates with 5% skim milk powder in PBS, Fab-containing E. coli lysates were added. Binding of Fabs was detected by F(ab)$_2$ specific goat anti-human IgG conjugated to alkaline phosphatase (diluted 1:5000) using Attophos fluorescence substrate (Roche, catalog #11681982001). Fluorescence emission at 535 nm was recorded with excitation at 430 nm.

FACS Screening (Fluorescence Activated Cell Sorting)

In FACS screening, single Fab clones binding to cell surface expressed antigen are identified from the panning output. Fabs are tested for cell binding using Fab containing crude E. coli lysates.

In these studies, 100 µl of cell-suspension was transferred into a fresh 96-well plate (resulting in 1×10$^5$ cells/well). Target cell suspension containing plates were centrifuged and the supernatant was discarded. The remaining cell pellets were re-suspended and 50 µl of Fab containing bacterial extracts was added to the corresponding wells.

Alternatively, the cell pellet was re-suspended and 50 µl FACS buffer (PBS, 3% FCS) and same volume of Fab containing bacterial extracts was added to the corresponding wells.

The cell-antibody suspensions were then incubated on ice for 1 hour. Following incubation, cells were spun down and washed three times with 200 µl FACS buffer. After each washing step, cells were centrifuged and carefully re-suspended.

Secondary detection antibody (PE conjugated goat anti human IgG; Dianova) was added and samples were incubate on ice and subsequently washed according to Fab incubation Fluorescence intensity was determined in a FACSArray™ instrument.

Expression and Purification of HuCAL® Fab Fragments

Expression of Fab fragments was performed in E. coli TG1 F-cells. Cultures were shaken at 30° C. for 18 h. Cells were harvested and disrupted using a combination of lysozyme and BugBuster Protein Extraction Reagent (Novagen, Germany). His6-tagged (SEQ ID NO: 261) Fab fragments were isolated via IMAC (Qiagen, Germany) and protein concentrations were determined by UV-spectrophotometry. The purity of representatively selected samples was analyzed in denaturing, reducing 15% SDS-PAGE (sodium dodecyl sulfate polyacrylamide gel electrophoresis).

The homogeneity of Fab preparations was determined in native state by size exclusion chromatography (HP-SEC) with calibration standards.

Conversion to IgG and IgG Expression

In order to express full length IgG, variable domain fragments of heavy (VH) and light chains (VL) were subcloned from Fab expression vectors into appropriate pMorph®_hIg vectors for human IgG1. Alternatively, eukaryotic HKB11 cells were transfected with pMORPH®4 expression vector DNA. The cell culture supernatant was harvested 3 or 7 days post transfection. After sterile filtration, the solution was subjected to Protein A affinity chromatography (MabSelect SURE, GE Healthcare) using a liquid handling station. If not otherwise stated, buffer exchange was performed to 1× Dulbecco's PBS (pH 7.2, Invitrogen) and samples were sterile filtered (0.2 µm pore size). Protein concentrations were determined by UV-spectrophotometry and purity of IgGs was analyzed under denaturing, reducing conditions using a Caliper Labchip System or in SDS-PAGE.

Bioassays

Anti-FGFR antibodies obtained following the panning processes described above were evaluated in the assays exemplified below:

BaF3/CMV-FGFRIIIB-C3 Cell Proliferation Assay

To determine the capacity of anti-FGFR2 antibodies to inhibit FGF1-dependent cell proliferation, a proliferation assay using an engineered Ba/F3 cell line (BaF3/CMV-FGFRIIIB-C3), which was stably transduced with a chimera of full-length FGFR2 IIIb receptor ECD and FGFR1-intracellular domain harboring the respective kinase domains. Addition of human FGF1 promoted cell proliferation in this cell line.

Cells were re-suspended in full-growth medium (RPMI+10% FCS+30 ng/ml FGF1+2 µg/ml Heparin+20 µg/ml Blasticidin) and seeded into flat-bottomed white 96-well assay plates (Corning Costar, #3903) at a cell density of 8×10$^3$ cells/well in 80 µl and incubated at 37° C. and 5% CO$_2$ overnight.

The next day, the HuCAL® antibodies (Fab or IgG) were diluted in full-growth medium to the desired concentrations (5 fold concentrated). 20 µl of the antibody solutions were added to the seeded cells of the previous day and the cells were cultivated for 72 hr. After 72 hr, 100 µl Cell Titer-Glo Luminescent Cell Viability Assay Reagent (#G7571; Promega) was added to each well and incubated for 15 min at RT slightly shaking with subsequent read-out of the luminescence in a illuminometer (GeniosPro, Tecan). For determination of the half maximal inhibitory concentration (IC$_{50}$ values), Fab/IgG titration was performed and IC$_{50}$ was calculated using GraphPad Prism.

For the evaluation of a potential agonistic activity of the HuCAL® IgGs, as determined by the ability of the antibodies to promote proliferation of the engineered BaF/3 cells in the absence of exogenous FGF1, the cells and IgGs were diluted in dilution medium (full-growth medium without FGF1). Seeding of the cells and the addition of the IgGs was done at the same day.

Affinity Determination

For K$_D$ determinations, monomer fractions of antibody protein were used (at least 90% monomer content, analyzed by analytical SEC; Superdex75 (Amersham Pharmacia) for Fab, or Tosoh G3000SWXL (Tosoh Bioscience) for IgG, respectively).

(a) Solution Equilibrium Titration (SET) Method for KD Determination Using Sector Imager 6000 (Mesoscale Discovery)

Affinity determination in solution was basically performed as described in the literature (Friguet et al., 1985 J Immunol Methods 77: 305-319). In order to improve the sensitivity and accuracy of the SET method, it was transferred from classical ELISA to ECL based technology (Haenel et al., 2005 Anal Biochem 339: 182-184). K$_D$ determination of HuCAL®_IgG was performed as described using the following reagents: biotinylated hFGFR2. was coated at 0.5 µg/ml in PBS overnight at 4° C. on standard MSD plates.

After washing the MSD plate and adding 30 µl/well MSD Read Buffer T with surfactant, electrochemiluminescence signals were detected using a Sector Imager 6000 (MesoScale Discovery, Gaithersburg, Md., USA).

The data was evaluated with XLfit (IDBS) software applying customized fitting models. For K$_D$ determination of Fab molecules the following fit model was used (according to (Haenel et al., 2005 Anal Biochem 339: 182-184):

$$y = B_{max} - \left( \frac{B_{max}}{2[Fab]_t} \left( [Fab]_t + x + K_D - \sqrt{([Fab]_t + x + K_D)^2 - 4x[Fab]_t} \right) \right)$$

[Fab]$_t$: applied total Fab concentration
x: applied total soluble antigen concentration (binding sites)
B$_{max}$: maximal signal of Fab without antigen
K$_D$: affinity For K$_D$ determination of IgG molecules the following fit model for IgG was used (modified according to (Piehler et al., 1997 J Immunol Methods 201: 189-206)) and a summary of the data is presented in FIG. 1:

$$y = \frac{2B_{max}}{[IgG]}\left([IgG]}{2} - \frac{\left(\frac{x+[IgG]+K_D}{2} - \sqrt{\frac{(x+[IgG]+K_D)^2}{4} - x[IgG]}\right)^2}{2[IgG]}\right)$$

[IgG]: applied total IgG concentration
x: applied total soluble antigen concentration (binding sites)
$B_{max}$: maximal signal of IgG without antigen
$K_D$: affinity Summary of Panning Strategies and Screening In total, 28 different panning strategies were employed using recombinant antigen material as well as cell lines as outlined above. Using the assays described above, panning outputs were screened for specificity and cross-reactivity and 935 clones were selected for sequencing. Following the screening process described, 15 antibodies were selected for further characterization as described in the examples below. Of these antibodies, 12433, 12947, 10846 and 12931 were found to bind to the FGFR2 IIIb isoform (Uniprot Accession # P21802-3), 10164, 11725, 10220, 11723, and 12944 were found to bind to both human FGFR2 IIIb (Uniprot Accession # P21802-3) and IIIc isoforms (Uniprot Accession # P21802-1), and 12425, 12422, 12439, 10918, 10923 and 11722 were found to bind to both human FGFR2 IIIb (Uniprot Accession # P21802-3) and IIIc isoforms (Uniprot Accession # P21802-1) and also human FGFR4 (Uniprot Accession # P22455).

Example 2

Affinity Determination

Affinity of the antibodies to FGFR2 species orthologues was determined using Biacore technology using a Biacore T100 instrument (GE Systems) and with CM5 sensor chips.

Briefly, HBS-EP+ (0.01 M HEPES, pH 7.4, 0.15 M NaCl, 0.005% Surfactant P20) supplemented with 0.5 mg/ml of BSA and 10 µg/ml heparin was used as running buffer for all experiments. The immobilization level and analyte interactions were measured by response unit (RU). Pilot experiments were performed to test and confirm the feasibility of the immobilization of anti-human Fc antibody and the capture of the test antibodies.

For kinetic measurements, experiments were performed in which the antibodies were immobilized to the sensor chip surface and the ability of the FGFR proteins described above listed in Table 1 to bind in free solution was determined Briefly, 50 µg/ml of anti-human Fc antibody at pH 4.75 was immobilized on a CM5 sensor chip through amine coupling at flow rate of 10 µl/minute on all four flow cells to reach 6000 RUs. 3 µg/ml of test antibodies were then injected at 10 µl/min for 10 s Immobilization levels of antibodies were generally kept below 250 RUs. Subsequently, 0.078-100 nM of FGFR receptors, diluted in a 2-fold series, were injected at a flow rate of 80 µl/min for 7 min over both reference and test flow cells. Dissociation of the binding was followed for 10 min using HBS-EP+ supplemented with 0.5 mg/ml of BSA and 10 µg/ml heparin as running buffer. After each injection cycle, the chip surface was regenerated with 10 mM glycine, pH 2.0 at 60 µl/min for 70 s. All experiments were performed at 25° C. and the response data were globally fitted with a simple 1:1 interaction model (using evaluation software version 1.1 (GE Systems)) to obtain estimates of on rate ($k_a$), off-rate ($k_d$) and affinity ($K_D$).

A summary of the affinity estimates obtained against FGFR2 IIIb species orthologues is presented in Table 4. It was found that all of the antibodies bound to the species orthologues of FGFR2 evaluated and that a subset of the antibodies also bound to human FGFR4. In addition, some of the antibodies (10846, 12433, 12931 and 12947) were unable to bind to the IIIc isoform of human FGFR2 (Uniprot Accession # P21802). All of the antibodies were specific to FGFR2 or bound to both FGFR2 and FGFR4 and none of the antibodies were found to bind appreciably to FGFR1 or FGFR3.

TABLE 4

| | Affinity estimates (M) obtained against FGFR2 IIIb species orthologues | | | |
|---|---|---|---|---|
| Antibody ID | Human FGFR2 IIIb | Mouse FGFR2 IIIb | Rat FGFR2 IIIb | Cyno FGFR2 IIIb |
| 10164 | 1.9E−08 | 3.3E−08 | 3.5E−08 | 1.6E−08 |
| 10220 | 1.6E−08 | 2.6E−08 | 2.6E−08 | 2.6E−08 |
| 10846 | 1.4E−12 | 1.5E−08 | 1.3E−08 | 2.3E−08 |
| 10918 | 7.7E−10 | 1.1E−09 | 1.3E−09 | 1.3E−09 |
| 10923 | 3.7E−09 | 4.0E−09 | 5.5E−09 | 4.5E−09 |
| 11722 | 1.3E−08 | 1.8E−08 | 2.1E−08 | 1.3E−08 |
| 11723 | 1.8E−08 | 2.8E−08 | 5.3E−08 | 1.7E−08 |
| 11725 | 2.6E−08 | 1.3E−07 | 1.4E−07 | 7.3E−09 |
| 12422 | 5.1E−09 | 7.7E−09 | 9.7E−09 | 7.4E−09 |
| 12425 | 1.4E−08 | 1.6E−08 | 2.2E−08 | 1.2E−08 |
| 12433 | 5.6E−09 | 8.0E−09 | 1.2E−08 | 1.2E−08 |
| 12439 | 1.5E−08 | 1.5E−08 | 1.6E−08 | 5.6E−09 |
| 12931 | 3.4E−09 | 1.2E−09 | 2.9E−09 | 2.4E−09 |
| 12944 | 9.4E−09 | 6.9E−09 | 1.1E−08 | 1.0E−08 |
| 12947 | 2.7E−09 | 3.1E−09 | 5.1E−09 | 2.4E−09 |

Example 3

Assessment of Functional Activity of Anti-FGFR Antibodies

The ability of the purified antibodies to act as either agonists or antagonists of FGFR2 was evaluated using a Baf cell system in which Baf cells were transduced to overexpress FGFR2.

To evaluate potential agonistic properties of the antibodies, Baf-FGFR2 cells were washed twice in PBS and re-suspended in dilution medium (RPMI supplemented with 10% FBS, 2 µg/ml heparin (Sigma, catalog #H3149) and 20 µg/ml blasticidin (e.g. Invitrogen, catalog #A11139-03 or Cellgro, catalog #30-100-RB) prior to seeding in 96 well plates (Costar catalog #3904) at 8000 cells/well in 90 µl dilution medium. In each assay, one plate was designated a "day 0" plate: to each well of these plates, an additional 10 µl of dilution medium was added, followed 80 µl/well of Cell titer Glo reagent (Promega #G7573). Assay plates were shaken gently for 10 min and the resulting luminescence intensity was measured using a Perkin Elmer EnVision 2101 plate reader. Serial dilutions were prepared for each antibody as 10× solutions in dilution medium and 10 µl was added to the appropriate wells. In addition to the test antibodies, FGF1 (Peprotech, catalog #100-17A; final assay concentration 0-30 nM) a commercially available anti-FGFR2 antibody (R&D systems, catalog #MAB6841) and a non-FGFR2 binding antibody were included as control reagents. Assay plates were incubated for 3 days at 37° C. with 5% $CO_2$. Following this incubation, the plates were brought to room temperature for around 30 min and 80 µl/well of Cell titer Glo reagent (Promega #G7573) was added. Plates were then shaken gently for 10 min and the resulting luminescence intensity was measured using a Perkin Elmer EnVision 2101 plate reader.

Figure 2:
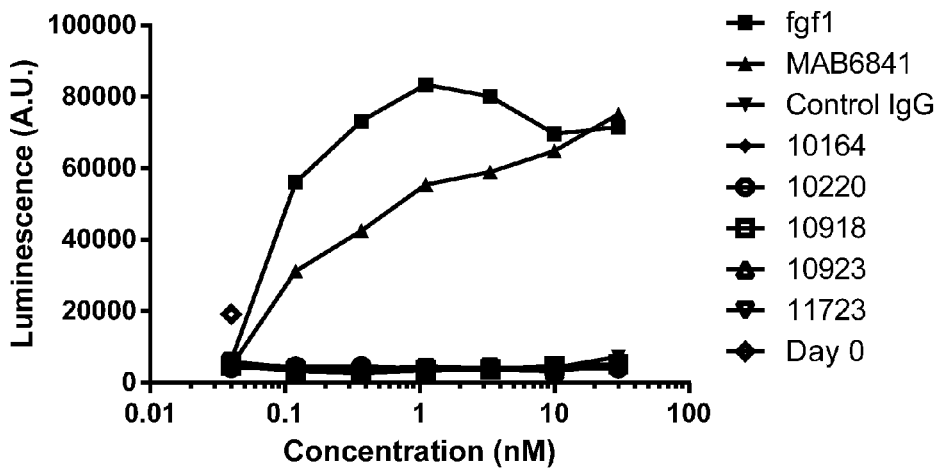
FIG. 2 (A)-(B) show the ability of anti-FGFR antibodies to act as agonists in a Baf-FGFR2 receptor system.
Figure 2:
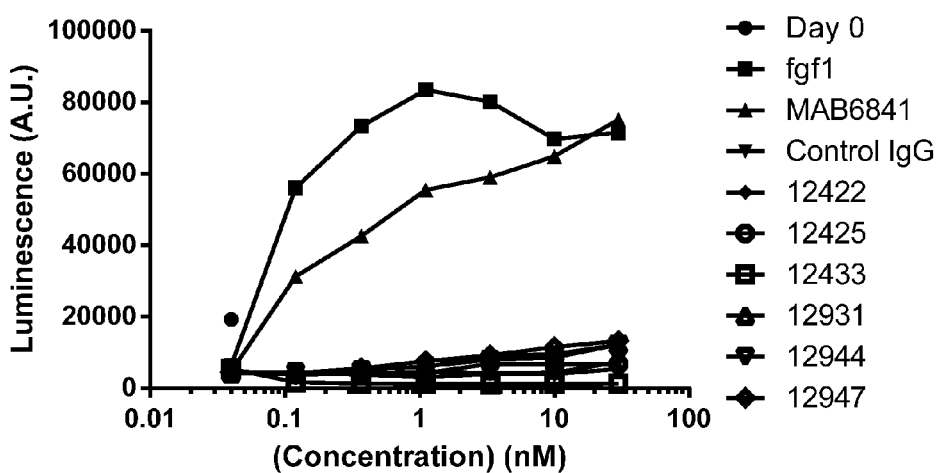

To determine the effect of the antibodies on cell proliferation, raw luminescence values were averaged across replicates and compared to day 0 controls. 10846, 11725 and 12439 were not evaluated in these studies but none of the other antibodies tested were able to substitute for FGF1 and maintain cell growth. A summary of the data is presented in FIG. 2 (A)/(B).

Figure 3:
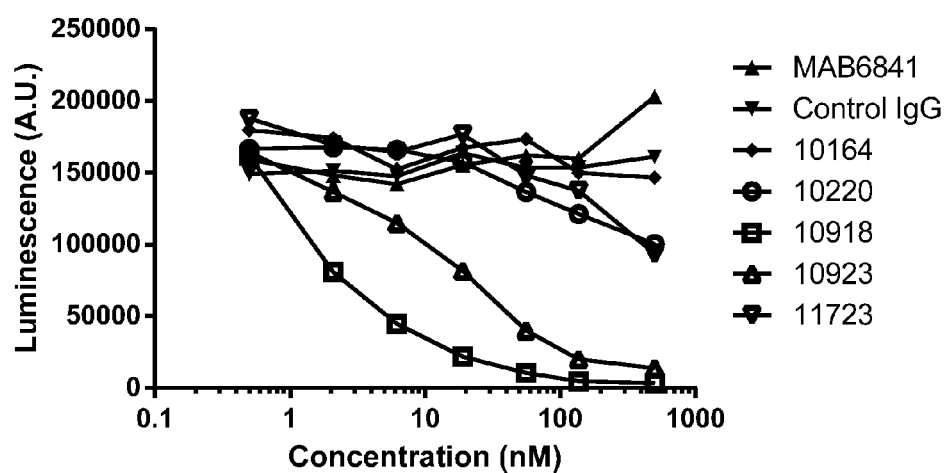
FIG. 3 (A)-(B) show the ability of anti-FGFR antibodies to act as antagonists in a Baf-FGFR2 receptor system.
Figure 3:
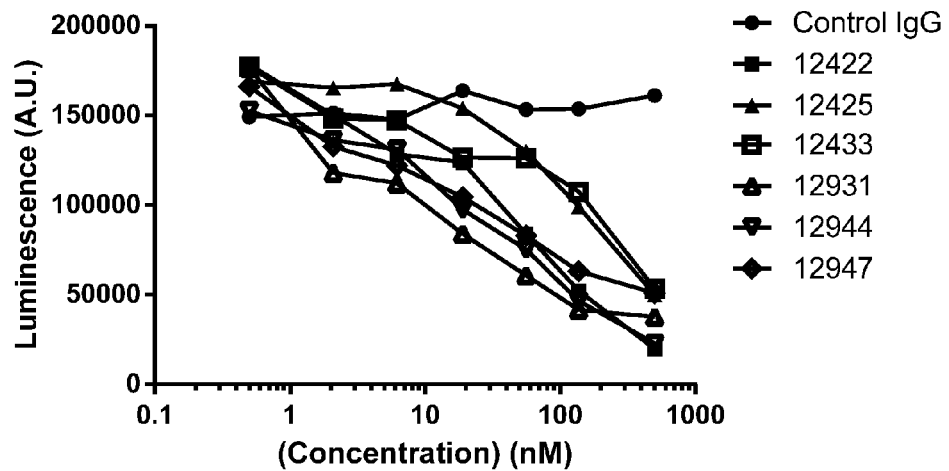

The Baf cell system was also used to assess the potential of the antibodies to act as antagonists of FGFR2 receptor signaling. In these studies, Baf-FGFR2 cells were plated as described in the agonism studies above with the addition of 30 µg/ml FGF1 (Peprotech, catalog #100-17A) to the dilution medium. Serial dilutions were prepared for each antibody as 4× solutions in dilution medium with 30 µg/ml FGF1 and 25 µl was added to the appropriate wells. In addition to the test antibodies, a commercially available anti-FGFR2 antibody (R&D systems, catalog #MAB6841) and a non-FGFR2 binding antibody were included as control reagents. Assay plates were incubated for 3 days at 37° C. with 5% $CO_2$. Following this incubation, the plates were brought to room temperature for around 30 min and 80 µl/well of Cell titer Glo reagent (Promega #G7573) was added. Plates were then shaken gently for 10 min and the resulting luminescence intensity was measured using a Perkin Elmer EnVision 2101 plate reader. To determine the effect of the antibodies on relative cell proliferation, raw luminescence values were averaged across replicates and compared. 10846, 11725 and 12439 were not evaluated in these studies. The effects of the other antibodies tested are presented in FIG. 3(A)/(B) and demonstrate that of the clones evaluated 10918, 10923, 12931, 12944, 12947 and 12422 inhibited the proliferation of the engineered Baf cells by greater than 50% at concentrations of less than 100 nM.

Example 4

Preparation of ADCs

Preparation of the DM1 Conjugates by One-Step Process

Antibody 12425 was diafiltered into a reaction buffer (15 mM potassium phosphate, 2 mM EDTA, pH 7.6) via Tangential Flow Filtration (TFF#1) prior to the start of the conjugation reaction. Subsequently, antibody 12425 (5.0 mg/mL) was mixed with DM1 (5.6-fold molar excess relative to the amount of antibody) and then with SMCC (4.7 fold excess relative to the amount of antibody). The reaction was performed at 20° C. in 15 mM potassium phosphate buffer (pH 7.6) containing 2 mM EDTA and 10% DMA for approximately 16 hours. The reaction was quenched by adding 1 M acetic acid to adjust the pH to 5.50. After pH adjustment, the reaction mixture was filtered through a multi-layer (0.45/0.22 µm) PVDF filter and purified and diafiltered into a 20 mM succinate buffer (pH 5.0) containing 8.22% sucrose using Tangential Flow Filtration (TFF#2). The instrument parameters for the Tangential Flow Filtration are listed in Table 5 below.

TABLE 5

Instrument parameters for the Tangential Flow Filtration

| TFF Parameter | TFF#1 Set Point | TFF#2 Set Point |
|---|---|---|
| Bulk Concentration (Cb - g/L) | 20 | 20 |
| TMP (psi) | 12-18 | 12-18 |
| Feed Flow rate (LMH) | 324 | 324 |
| Membrane Load (g/m2) | 110-150 | 110-150 |

TABLE 5-continued

Instrument parameters for the Tangential Flow Filtration

| TFF Parameter | TFF#1 Set Point | TFF#2 Set Point |
|---|---|---|
| Diavolumes | 10 | 14 |
| Diafiltration Buffer | 15 mM potassium phosphate, 2 mM EDTA, pH 7.6 | 20 mM Succinate, 8.22% Sucrose, pH 5.0 |
| Temperature (° C.) | RT (20-25) | RT (20-25) |

Conjugates obtained from the process described above was analyzed by: UV spectroscopy for cytotoxic agent loading (Maytansinoid to Antibody Ratio, MAR); SEC-HPLC for determination of conjugate monomer; and reverse-phase HPLC or hydrophobic shielded phase (Hisep)-HPLC for free maytansinoid percentage. The data is shown in Table 6.

TABLE 6

Properties of 12425-MCC-DM1

| Sample | MAR | Monomer (%) | Total Free Maytansinoid (%) |
|---|---|---|---|
| 12425-MCC-DM1 | 3.6 | 98.0 | 1.0 |

Preparation of DM1 Conjugates by In Situ Process

The conjugates of the present invention can also be prepared by in situ process according to the following procedures. Antibodies (21 clones) were conjugated to DM1 using the sulfosuccinimidyl 4-(N-maleimidomethyl)cyclohexane-1-carboxylate (sulfo-SMCC) linker Stock solutions of DM1 and sulfo-SMCC heterobifunctional linker were prepared in DMA. Sulfo-SMCC and DM1 thiol were mixed together to react for 10 minutes at 25° C. in DMA containing 40% v/v of aqueous 50 mM succinate buffer, 2 mM EDTA, pH 5.0, at the ratio of DM1 to linker of 1.3:1 mole equivalent and a final concentration of DM1 of 1.95 mM. The antibody was then reacted with an aliquot of the reaction to give a mole equivalent ratio of SMCC to Ab of around 6.5:1 under final conjugation conditions of 2.5 mg/mL of Ab in 50 mM EPPS, pH 8.0 and 10% DMA (v/v). After approximately 18 hours at 25° C., the conjugation reaction mixture was purified using a SEPHADEX™ G25 column equilibrated with 10 mM succinate, 250 mM glycine, 0.5% sucrose, 0.01% Tween 20, pH 5.5.

TABLE 7

Properties of DM1-conjugated antibodies

| Clone name | Linker excess | MAR | Monomer (%) | Yield (%) | Free drug (%) |
|---|---|---|---|---|---|
| 10164 | 6.8 | 3.5 | 98 | 88 | <0.5 |
| 10220 | 7.5 | 3.55 | 98 | 96 | 0.5 |
| 10553 | 6.4 | 3.7 | 100 | 64 | <0.5 |
| 10554 | 6.3 | 3.5 | 100 | 79 | <0.5 |
| 10846 | 6.3 | 3.4 | 99 | 71 | <0.5 |
| 10918 | 6.4 | 3.6 | 98 | 99 | 0.5 |
| 10923 | 6.2 | 3.5 | 100 | 95 | 0.7 |
| 10925 | 7.9 | 3.5 | 99 | 70 | <0.5 |
| 11722 | 9.5 | 3.5 | 99 | 84 | 3.7 |
| 11723 | 7.3 | 3.3 | 99 | 64 | <0.5 |
| 11725 | 8.2 | 3.4 | 99 | 74 | <0.5 |
| 11729 | 9.5 | 3.2 | 93 | 30 | 0.7 |
| 12422 | 6.2 | 4.0 | 99 | 60 | <0.5 |
| 12425 | 6.1 | 3.5 | 99 | 70 | <0.5 |
| 12433 | 6.1 | 3.4 | 99 | 82 | <0.5 |
| 12435 | 7.0 | 3.4 | 99 | 75 | <0.5 |

TABLE 7-continued

Properties of DM1-conjugated antibodies

| Clone name | Linker excess | MAR | Monomer (%) | Yield (%) | Free drug (%) |
|---|---|---|---|---|---|
| 12438 | 7.7 | 3.4 | 99 | 75 | <0.5 |
| 12439 | 6.4 | 3.5 | 99 | 99 | 0.5 |
| 12931 | 6.4 | 3.8 | 99 | 80 | 0.5 |
| 12944 | 7.8 | 3.5 | 99 | 38 | 1.6 |
| 12947 | 6.7 | 3.8 | 99 | 99 | <0.5 |

Preparation of ADCs with the SPDB Linker

Antibodies 12422, 12425 and 12433 (8 mg/me was modified with N-succinimidyl 4-(2-pyridyldithio)butanoate (SPDB, 5.0, 5.5 and 4.9 fold molar excess respectively) for 120 minutes at 25° C. in 50 mM potassium phosphate buffer (pH 7.5) containing 50 mM NaCl, 2 mM EDTA, and 5% DMA. The modified Ab without purification was subsequently conjugated to DM4 (1.7 fold molar excess over the unbound linker) at a final modified antibody concentration of 4 mg/mL in 50 mM potassium phosphate buffer (pH 7.5) containing 50 mM NaCl, 2 mM EDTA, and 5% DMA for 18 hours at 25° C. The conjugation reaction mixture was purified using a SEPHADEX™ G25 column equilibrated and eluted with 10 mM succinate, 250 mM glycine, 0.5% sucrose, 0.01% Tween 20, pH 5.5.

TABLE 8

Properties of DM4-conjugated antibodies

| Clone name | Linker excess | MAR | Monomer (%) | Yield (%) | Free drug (%) |
|---|---|---|---|---|---|
| 12422 | 5.0 | 3.6 | 99 | 85 | 0.5 |
| 12425 | 5.5 | 3.6 | 98 | >90 | <0.5 |
| 12433 | 4.9 | 4.0 | 99 | 75 | 0.5 |

Preparation of ADCs with the CX1-1 Linker

Antibody 12425 (5.0 mg/mL) was mixed with DM1 (7.15-fold molar excess relative to the amount of antibody) and then with CX1-1 (5.5-fold excess relative to the amount of antibody). The reaction was performed at 25° C. in 60 mM EPPS [4-(2-Hydroxyethyl)-1-piperazinepropanesulfonic acid] buffer (pH 8.5) containing 2 mM EDTA and 5% DMA for approximately 16 hours. The reaction mixture was then purified using a SEPHADEX™ G25 column equilibrated and eluted in 10 mM succinate, 250 mM glycine, 0.5% sucrose, 0.01% Tween 20, pH 5.5.

TABLE 9

Properties of CX1-1/DM1 conjugated 12425

| Clone name | Linker excess | MAR | Monomer (%) | Yield (%) | Free drug (%) |
|---|---|---|---|---|---|
| 12425 | 5.5 X | 3.4 | 97 | >90 | 0.1 |

Example 5

Affinity of ADCs Relative to Parental Antibodies

The affinity of the antibodies to FGFR2 following conjugation to SMCC-DM1 was determined using Biacore technology using a Biacore T100 instrument (GE Systems) and CM5 sensor chips using similar methodology to that described in example 2 above.

For the antibodies assessed, similar affinity estimates for binding to human FGFR2 IIIb were obtained for SMCC-DM1 conjugated antibodies relative to parental unconjugated antibodies, suggesting that conjugation does not appreciably impact antibody binding (Table 10).

TABLE 10

Affinity estimates for unconjugated and SMCC-DM1 conjugated antibodies

| | Human FGFR2 IIIb affinity ($K_D$) (nM) | |
|---|---|---|
| Antibody ID | Unconjugated antibody | Antibody-MCC-DM1 |
| 10164 | 2 | 2.6 |
| 10220 | 17 | 7.8 |
| 10846 | 3.5 | 3.8 |
| 10918 | 2.2 | 2.1 |
| 10923 | 2.2 | 2.3 |
| 11722 | 4.3 | 8.8 |
| 11723 | 6.6 | 5.9 |
| 11725 | 3.3 | 2.9 |
| 12422 | 5.1 | N.D. |
| 12425 | 2.1 | 2.3 |
| 12433 | 5.6 | 4.9 |
| 12439 | 15 | N.D. |
| 12931 | 3.4 | N.D. |
| 12944 | 9.4 | N.D. |
| 12947 | 2.7 | N.D. |

N.D. = not determined

In addition, the affinities of several SMCC-DM1 conjugated antibodies to FGFR2 species orthologues was determined In these studies, no appreciable differences in affinity were found between the conjugated and unconjugated antibodies (Table 11).

TABLE 11

Affinities of SMCC-DM1 conjugated antibodies to FGFR2 species orthologues

| | Affinity ($K_D$) (nM) | | | | | |
|---|---|---|---|---|---|---|
| Protein | 12433 | 12433-MCC-DM1 | 10164 | 10164-MCC-DM1 | 12425 | 12425-MCC-DM1 |
| Human FGFR 2IIIb | 5.6 | 4.9 | 2 | 2.6 | 2.1 | 2.3 |
| Mouse FGFR2 IIIb | 2.2 | 1.2 | 10 | 10 | 3.2 | 3.6 |
| Rat FGFR2 IIIb | 3.7 | 2.8 | 2.8 | 3.5 | 3.1 | 3.5 |
| Cynomolgus monkey FGFR2 IIIb | 1.7 | 1.5 | 9 | 3.8 | 1.6 | 1.9 |

Example 6

In Vitro Activity of ADCs in SNU16 and Kato-III Cells

Following conjugation to the SMCC-DM1 linker-payload, the ability of the antibody drug conjugates (ADCs) to inhibit the proliferation of FGFR2-amplified cell lines, SNU16 (ATCC catalog #CRL-5974) and Kato-III (ATCC catalog #HTB-103) was determined. Briefly, cells were cultured in a tissue culture incubator at 37° C. with 5% $CO_2$ in culture medium as recommended by the supplier. On the day of the assay, cells were washed twice with PBS (Lonza, catalog #17516C), prior to being treated with 0.25% trypsin-EDTA (Gibco catalog #25300) for 5 min and resuspension in the recommended culture medium. Cells were then counted and seeded in 96 well plates (Costar catalog #3940 or Corning catalog #3340) at densities of 2600-3600 cells/well in 100 µl of cell culture medium. A duplicate plate was generated for a day 0 measurement and all plates were incubated in a tissue culture incubator at 37° C. with 5% $CO_2$ overnight. Medium only wells were also generated to act as negative controls. Following this incubation, 50 µl/well of Cell titer Glo reagent (Promega catalog #G7573) was added to the day 0 plates, which were then shaken gently for 10 min and the resulting luminescence intensity was measured using a Perkin Elmer EnVision 2101 plate reader. Test ADCs were serially diluted in duplicate to a 2× stock solution in the appropriate cell culture medium and, following the removal of 50 µl of medium from each of rest of the assay plates, 50 µl of 2× serially diluted ADCs were added (final assay concentration 0.2-50 nM DM1 equivalents) prior to incubation in a tissue culture incubator at 37° C. with 5% $CO_2$ for 5 days. Following this incubation period, relative cell viability was determined via the addition of Cell titer Glo reagent as described above. The effect of the ADCs on cell proliferation was calculated using the average of the duplicates as follows:

% Inhibition=(ADC treated−untreated)/(untreated−Day 0)*100

The % inhibition data was fitted to a 4-parameter logistic equation and $IC_{50}$ values were determined Unlike the IgG control ADC, the tested ADCs were found to be potent inhibitors of the proliferation of both Kato-III and SNU16 cells with $IC_{50}$'s of less than 3 nM (Table 12).

TABLE 12

Antibody potency as MCC-DM1 ADCs

| Antibody ID | Cell proliferation IC50 (nM) | |
| --- | --- | --- |
| | Kato-III | SNU16 |
| 10164 | 1.6 | 0.5 |
| 10220 | 0.33 | <0.2 |
| 10846 | 0.43 | <0.2 |
| 10918 | 0.61 | <0.2 |
| 10923 | 0.45 | <0.2 |
| 11722 | 0.59 | <0.2 |
| 11723 | 0.91 | <0.2 |
| 11725 | 5.2 | 5 |
| 12422 | <3 | <3 |
| 12425 | 0.15 | <0.2 |
| 12433 | <3 | <3 |
| 12439 | <3 | <3 |
| 12931 | <3 | <3 |
| 12944 | <3 | <3 |
| 12947 | <3 | <3 |
| IgG control ADC | >50 | >25 |

The ability of several anti-FGFR antibodies conjugated via the SPDB-DM4 linker-payload was also evaluated. These studies, which were conducted as described above, revealed that the antibodies evaluated were also potent inhibitors of cell proliferation as SPDB-DM4 ADCs, suggesting that their ability to successfully deliver payloads to kill cells is not limited to SMCC-DM1. Data for the SNU16 cell line is summarized in Table 13.

TABLE 13

Antibody potency as SPDB-DM4 ADCs

| Antibody ID | Cell proliferation IC50 (nM) |
| --- | --- |
| 12422 | 0.07 |
| 12425 | 0.04 |
| 12433 | 0.8 |
| IgG control ADC | >25 |

Example 7

Assessment of In Vivo Activity of Anti-FGFR2 ADCs

The antitumor activity of 15 anti-FGFR2 or anti-FGFR2/FGFR4 cross-reactive ADCs was evaluated in the gastric, FGFR2 amplified (CN=31), FGFR2 IIIb isoform expressing SNU16 xenograft tumor model. In two independent studies, female nude mice were implanted subcutaneously with $10\times10^6$ cells in a suspension containing 50% phenol red-free matrigel (BD Biosciences) in Hank's balanced salt solution. The total injection volume containing cells in suspension was 200 µl. Mice were enrolled in the first study eight days post implantation with average tumor volume of 192.9 mm³. After being randomly assigned to one of nine groups (n=8/group), mice were administered PBS or a single 3 mg/kg intravenous (i.v.) injection of one of the following antibody drug conjugates: 12433-MCC-DM1, 10164-MCC-DM1, 10220-MCC-DM1, 10918-MCC-DM1, 10923-MCC-DM1, 11722-MCC-DM1, 12422-MCC-DM1, or 12425-MCC-DM1. Mice were enrolled in the second study seven days post implantation with average tumor volume of 223.4 mm³. After being randomly assigned to one of nine groups (n=8/group), mice were administered PBS or a single 3 mg/kg i.v. injection of one of the following antibody drug conjugates: 12433-MCC-DM1, 12947-MCC-DM1, 12931-MCC-DM1, 12944-MCC-DM1, 12439-MCC-DM1, 10846-MCC-DM1, 11725-MCC-DM1, or 11723-MCC-DM1. 12433-MCC-DM1 was included as a bridge between the two studies to facilitate direct comparison of antibody drug conjugates in both studies. Tumors were calipered twice per week. ADCs evaluated in these studies exhibited a broad spectrum of anti-tumor activity 23 to 24 days post dose (ranging from 33.2% T/C to 77.8% regression) (FIGS. 4 (A) and (B)).

The antitumor activity of cleavable disulfide linker based SPDB-DM4 FGFR2 ADCs was evaluated in the SNU16 xenograft tumor model. In these studies, female nude mice were implanted subcutaneously with $10\times10^6$ cells in a suspension containing 50% phenol red-free matrigel (BD Biosciences) in Hank's balanced salt solution. The total injection volume containing cells in suspension was 200 µl Mice were enrolled onto study 11 days post implantation with average tumor volume of 223 mm³. After being randomly assigned to one of five groups (n=7/group), mice were administered PBS (10 ml/kg), a single 15 mg/kg intravenous injection of 12433-MCC-DM1 or control IgG-MCC-DM1, or a single 5 mg/kg intraveneous injection of 12433-SPDB-DM4 or IgG-SPDB-DM4. Tumors were calipered twice per week. Neither control ADCs exhibited antitumor activity in this study (FIG. 4(C)). However, in contrast, both 12433-MCC-DM1 and 12433-SPDB-DM4 were highly active against the SNU16 xenograft model at the doses administered, suggesting that anti-tumor effects of anti-FGFR ADCs can be obtained with different linkers.

The pharmacokinetics (PK) of anti-FGFR ADCs was evaluated in SNU16 tumor-bearing mice following a single IV dose of 3 mg/kg. PK samples were collected at 1 h, 24 h, 72 h, 168 h, and 336 h post dose. In all studies, serum concentrations of both "total" antibody and "antibody drug conjugate (ADC)" were measured in all animal species using validated ELISA methods. The "total" fraction refers to the measurement of the antibody with or without the conjugated DM1, whereas the ADC fraction refers to the measurement of DM1 conjugated antibody only (≥1 DM1 molecule). In all studies, no appreciable differences were observed between clearance of the ADC and total antibody fractions. A summary of the PK properties of the ADCs is presented in FIG. 4 (D)-(E). When the ADC clearance following a single 3 mg/kg dose in SNU16 tumor bearing mice was compared to the observed anti-tumor effect, it was found that the ADCs with the greatest anti-tumor activity (>40% tumor regression) were all cleared at a rate of less than 45 ml/d/kg (FIG. 4 (F)).

Example 8

Figure 5:
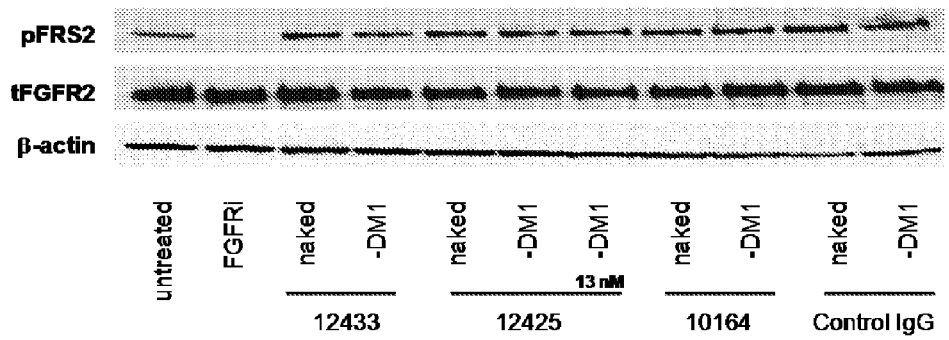
FIG. 5 (A)-(C) are western blots showing the ability of anti-FGFR antibodies or ADCs to modulate FGFR signaling and total receptor expression in FGFR2-amplified cell lines, SNU16 after 2 hours (A), 2-72 hours (B) or Kato-III cells (C).
Figure 5:
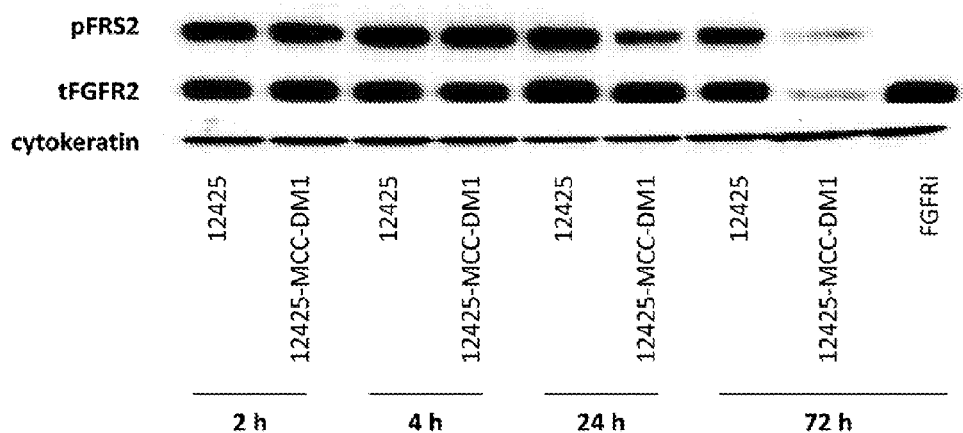
Figure 5:

Assessment of Signaling Activity of Unconjugated and Conjugated Antibodies In Vitro Using FGFR2-Amplified Cell Lines The ability of the unconjugated and SMCC-DM1 conjugated anti-FGFR2 antibodies to modulate FGFR signaling in FGFR2-amplified cell lines was evaluated. In initial studies, the effect of the 12433, 12425 and 10164 antibodies in SNU16 (ATCC catalog #CRL-5974) cells was determined. Briefly, cells were seeded in RPMI supplemented with 10% FBS in 12 well CellBind plates (Costar catalog #3336) and incubated overnight in a tissue culture incubator at 37° C. with 5% $CO_2$. On the day of the experiment, the cell culture medium was aspirated and replaced with either test antibodies or the small molecule FGFR inhibitor, BGJ398, all diluted in RPMI supplemented with 10% FBS at final concentrations of (13-130 nM, antibodies/ADCs; 500 nM, BGJ398). Cells were then incubated in a tissue culture incubator at 37° C. with 5% $CO_2$ for 2 h. Following this incubation, cells were washed twice with cold PBS (Lonza, catalog #17516C), placed on ice and 300 ml of lysis buffer (CST catalog #9803 with PhosphoSTOP Roche catalog #04 906237001) was added. Protein concentration was determined by BCA assay (Pierce catalog #23228). 60 mg of protein was then resolved by SDS-PAGE, transferred onto nitrocellulose membranes and probed with antibodies to pFRS2 (Cell Signaling Technology, catalog #3861), total FGFR2 (e.g. Santa Cruz Biotechnology, catalog #SC-122 or R&D systems catalog #6841) and β-actin (Bethyl, catalog #A300-485A) or cytokeratin (Dako catalog #M3515). Results are presented in FIG. 5 (A) and it was found that none of the antibodies, either unconjugated or as SMCC-DM1 ADCs were able to modulate pFRS2 signal at 2 h. Further experiments were conducted with the 12425 antibody (4.3 nM) and 12425-MCC-DM1 ADC (4.3 nM antibody, 13 nM DM1 equivalents) in which additional time points (4, 24 and 72 h) were evaluated in both SNU16 and also Kato-III (ATCC catalog #HTB-103) cells. Results are presented in FIG. 5 (B) (SNU16) and 5 (C) (Kato-III). No effects of either the naked antibody or ADC were observed up to 48 h in SNU16 cells or up to 72 h in Kato-III cells. A reduction in both pFRS2 and tFGFR2 signal was observed at 72 h in SNU16 cells relative to cytokeratin following 12425-MCC-DM1 treatment. As described in example 9 below, 12425-MCC-DM1 is a potent inhibitor of SNU16 proliferation at the 72 h timepoint and this decrease likely reflects heterogeneity of FGFR2 expression in the SNU16 cell population.

Example 9

Assessment of ADC and Unconjugated Antibodies on Cellular Proliferation

The ability of the unconjugated and SMCC-DM1 conjugated anti-FGFR antibodies to inhibit the proliferation of a panel of FGFR2-amplified, over-expressing and null cell lines was evaluated. In these studies, cells were cultured in a tissue culture incubator at 37° C. with 5% $CO_2$ in culture medium as recommended by the supplier. On the day of the assay, cells were washed twice with PBS (Lonza, catalog #17516C), prior to being treated with 0.25% trypsin-EDTA (Gibco catalog #25300) for 5 min and resuspension in the recommended culture medium. Cells were then counted and seeded in either 96 or 384 well plates (e.g. Costar catalog #3940, Corning catalog #3340, Costar catalog #3707) at densities of 800-3600 cells/well in 55-100 ml of cell culture medium. A duplicate plate was generated for a day 0 measurement and all plates were incubated in a tissue culture incubator at 37° C. with 5% $CO_2$ overnight. Medium only wells were also generated to act as negative controls. Following this incubation, 30-50 µl/well of Cell titer Glo reagent (Promega catalog #G7573) was added to the day 0 plates, which were then shaken gently for 10 min and the resulting luminescence intensity was measured using a Perkin Elmer EnVision 2101 plate reader. Test ADCs were serially diluted in duplicate to either a 2× or 10× stock solution in the appropriate cell culture medium. For assays in which a 2×ADC stock solution was used, half of the assay media was removed and replaced with an equal volume of the 2× serially diluted ADCs. Where a 10×ADC stock solution was employed, this was diluted 1:10 into the assay plates (e.g. 5 µl to 55 µl) prior to incubation in a tissue culture incubator at 37° C. with 5% $CO_2$ for 5 or 6 days. Final assay concentration of the ADCs ranged from 0.005-100 nM DM1 equivalents. Following this incubation period, relative cell viability was determined via the addition of Cell titer Glo reagent as described above. The effect of the ADCs on cell proliferation was calculated using the average of the duplicates as follows:

% Inhibition=(ADC treated−untreated)/(untreated−Day 0)*100

Figure 6:
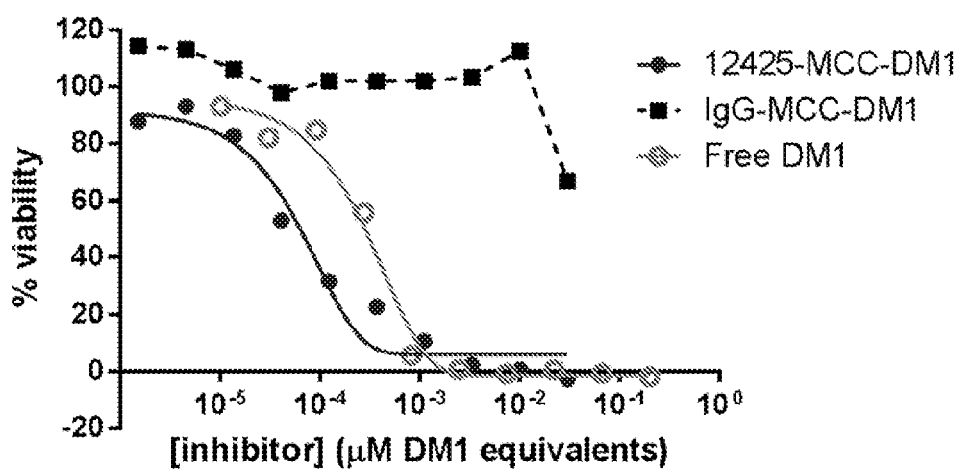
FIG. 6 (A)-(D) show the ability of 12425-MCC-DM1 to inhibit the proliferation of SNU-16 (A), Kato-III (B) or NUGC3 (C) cells relative to IgG and free payload controls; (D) is shows that the unconjugated antibody, 12425, did not have any appreciable anti-proliferative effect.
Figure 6:
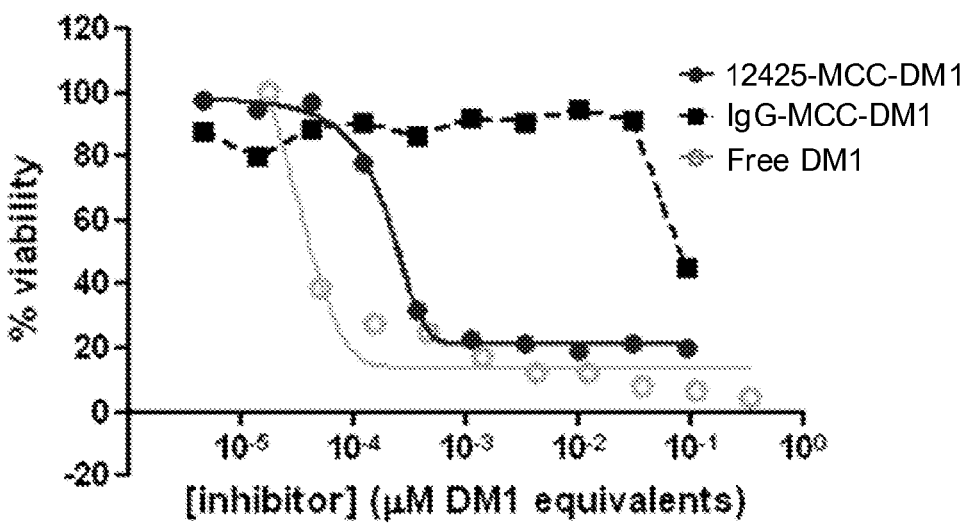
Figure 6:
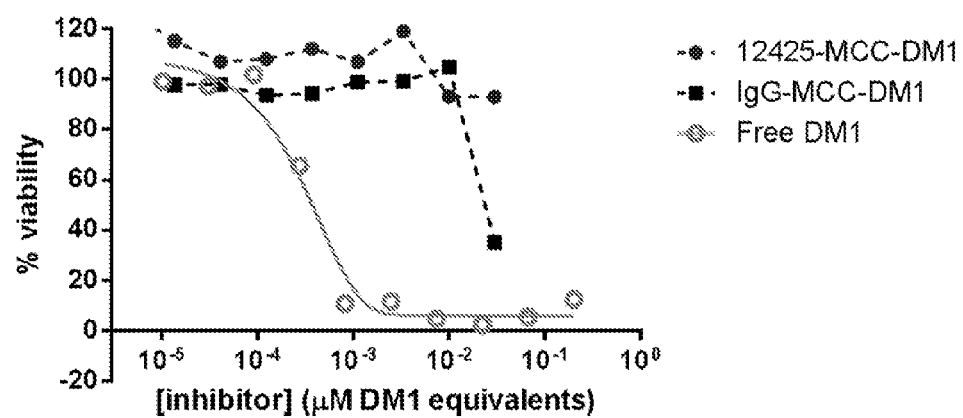
Figure 6:
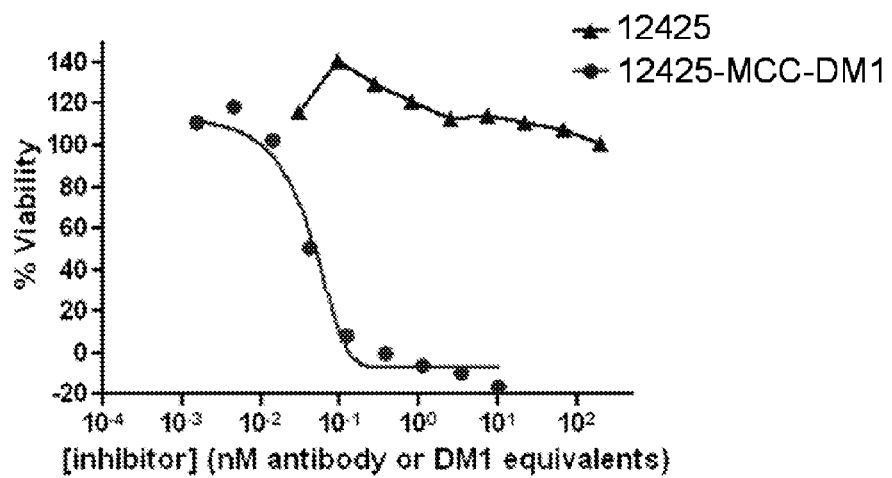

The % inhibition data was fitted to a 4-parameter logistic equation and $IC_{50}$ values were determined. Representative data for 12425-MCC-DM1 is presented in FIG. 6 (A). This ADC was found to be a potent inhibitor of cell proliferation in both the SNU16 (FIG. 6 (A)) and Kato-III FGFR2-amplified cell lines (FIG. 6 (B)). These cell lines were both confirmed to be sensitive to the maytansinoid payload (L-Me-DM1; free DM1 in FIG. 6 (A)-(C)) but not to a non-targeting ADC (directed to chicken lysozyme) conjugated via SMCC-DM1 at a similar maytansinoid antibody ratio. 12425-MCC-DM1 was also not active against a gastric cancer cell line, NUGC3, that is devoid of appreciable FGFR2 expression but that is sensitive to the maytansinoid payload (FIG. 6 (C)). In addition, the unconjugated antibody, 12425, was found to lack anti-proliferative activity in both SNU16 (FIG. 6 (D)) and Kato-III cells (data not shown). A summary of the anti-proliferative activity of several anti-FGFR-MCC-DM1 ADCs in FGFR2 amplified cell lines, including SNU16, Kato-III, SUM-52, MFM223 and H716 cells (Kunii et al., 2008 Cancer Res 68: 2340-2348; Turner et al., 2010 29: 2013-2023;

Mathur et al., 2010. Proceedings of the 101$^{st}$ Annual Meeting of the American Association for Cancer Research, poster #284) is shown in Table 14. In addition, none of the ADCs were found to be active against a panel of tumor cell lines, including AZ521, CAL-51, KYSE-150, TE-6, SNU-1041, TT, CHL-1, G401 and HEC59.

TABLE 14

Anti-proliferative activity of several anti-FGFR-MCC-DM1 ADCs in FGFR2 gene amplified & non-amplified cell lines

| Cell Line | Lineage | FGFR2 amplification? | In vitro potency (IC$_{50}$, nM free DM1 equivalents) | | | |
|---|---|---|---|---|---|---|
| | | | 12433-DM1 | 10164-DM1 | 12425-DM1 | IgG-DM1 |
| SNU16 | Gastric | Yes (IIIb) | 0.08 | 0.04 | 0.03 | 11 |
| Kato-III | Gastric | Yes (IIIb) | 0.28 | 0.32 | 0.34 | 30 |
| SUM-52 | Breast | Yes (IIIb) | 0.29 | 0.14 | 0.17 | >30 |
| MFM223 | Breast | Yes (IIIb) | 24 | 3.5 | 1 | >30 |
| H716 | Colon | Yes (IIIc) | >30 | 1.7 | 0.1-0.7 | >30 |
| NUGC3 | Gastric | No (IIIb) | >30 | >30 | >30 | >30 |

Example 10

In Vivo PK-PD of FGFR ADCs

Studies were conducted to assess the ability of 12425-MCC-DM1 to modulate pharmacodynamic markers in vivo. The goal of these studies was to evaluate the relationship between FGFR2 or FGFR4 expression and G2/M cell cycle arrest. Accumulation of pHH3 positive nuclei, as assessed by immunohistochemistry, was used as a marker of G2/M arrest.

A rabbit polyclonal antibody produced by immunizing animals with a synthetic phosphopeptide corresponding to residues surrounding Ser10 of human histone H3 was obtained from Cell Signaling Technology (Danvers, Mass.). Briefly, the IHC protocol included heat and standard exposure to Ventana Cell Conditioning #1 antigen retrieval reagent for approximately 48 minutes at a temperature ranging from 93° C. to 95° C. The primary antibody was diluted to 1:100 and incubated for 60 min at room temperature. Subsequently, incubation with Ventana OmniMap pre-diluted HRP-conjugated anti-rabbit antibody (Cat #760-4311) was performed for 4 min.

Figure 7:
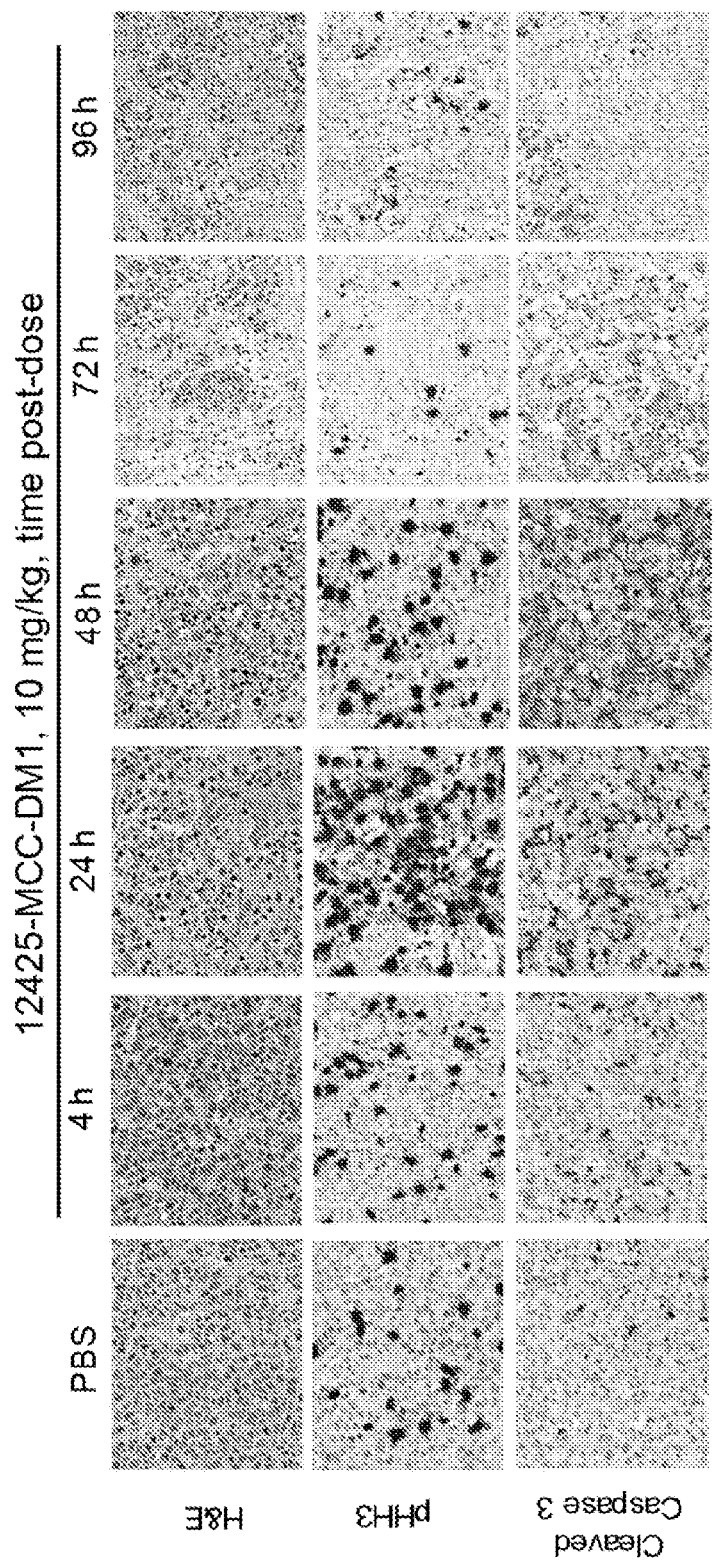
FIG. 7 (A)-(B) are images of SNU-16 (A) or NUGC3 (B) tumor xenografts following treatment with 12425-MCC-DM1 that show the assessment of pHH3 and cleaved caspase 3 expression.
Figure 7:
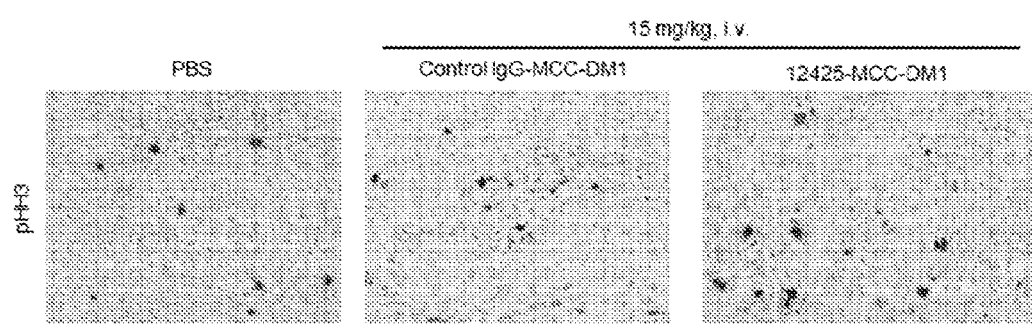

To assess PD in the FGFR2 amplified SNU16 xenograft model, female nude mice were implanted subcutaneously with 10×10$^6$ cells in a suspension containing 50% phenol red-free matrigel (BD Biosciences) in Hank's balanced salt solution. The total injection volume containing cells in suspension was 200 μl. Six mice were randomly assigned to receive an i.v. dose of either 12425-MCC-DM1 (10 mg/kg) or PBS (10 ml/kg) once tumors reached between 300 and 500 mm$^3$ (n=3/group). Consistent with the expected mechanism of action of the maytansinoid payload, 12425-MCC-DM1 yielded a marked, time-dependent increase in nuclear pHH3 positivity 24 h post dose relative to PBS treated controls (representative images shown in FIG. 7 (A)). Time dependent changes in cleaved caspase 3 were also evaluated. In these studies, a rabbit polyclonal antibody produced by immunizing animals with a synthetic peptide corresponding to amino-terminal residues adjacent to (Asp175) in human caspase-3 was obtained from Cell Signaling Technology (Danvers, Mass.). The IHC protocol included No Heat and Standard exposure to Ventana Cell Conditioning #1 antigen retrieval reagent for approximately 48 minutes at a temperature ranging from 93° C. to 95° C. The primary antibody was diluted to 1:300 and incubated for 60 minutes at room temperature. Subsequently, incubation with Ventana OmniMap prediluted HRP-conjugated anti-rabbit antibody (Cat #760-4311) was performed for 4 minutes. Similar to pHH3, time dependent changes in cleaved caspase 3 were also observed (FIG. 7(A)). Similar data was also obtained for other anti-FGFR2ADCs e.g. 12433-MCC-DM1.

To assess ADC specificity, PD was evaluated in the FGFR2 negative NUGC3 xenograft model. In these studies, female nude mice were injected subcutaneously with 1×10$^6$ cells in a suspension containing 50% phenol red-free matrigel (BD Biosciences) in Hank's balanced salt solution. The total injection volume containing cells in suspension was 200 μl. Nine mice were randomly assigned to receive a single intravenous 15 mg/kg dose of 12425-MCC-DM1, control IgG-MCC-DM1 or PBS (10 ml/kg) once tumors reached between 300 and 500 mm$^3$ (n=3/group). 12425-MCC-DM1 failed to modulate pHH3 levels relative to a 15 mg/kg i.v. dose of control IgG-MCC-DM1 in FGFR2 and FGFR4 negative NUGC3 xenografts (representative images shown in FIG. 7(B)). Similar data was also obtained for other anti-FGFR2ADCs e.g. 12433-MCC-DM1.

Taken together, these data demonstrate that 12425-MCC-DM1 is capable of eliciting robust in vivo cellular PD effects that are dependent upon FGFR2 expression and consistent with the mechanism of action of the maytansinoid payload.

Example 11

In Vivo Efficacy of Anti-FGFR ADCs

The anti-tumor activity of anti-FGFR2ADCs was evaluated in several tumor xenograft models.

The antitumor activity of three anti-FGFR-targeting ADCs was evaluated in the gastric, FGFR2 amplified (copy number=31, SNP6.0), FGFR2 IIIc isoform expressing NCI-H716 colorectal xenograft tumor model. Female nude mice were implanted subcutaneously with 5×10$^6$ cells containing 50% phenol red-free matrigel (BD Biosciences) in Hank's balanced salt solution. The total injection volume containing cells in suspension was 200 μl.

Figure 8:
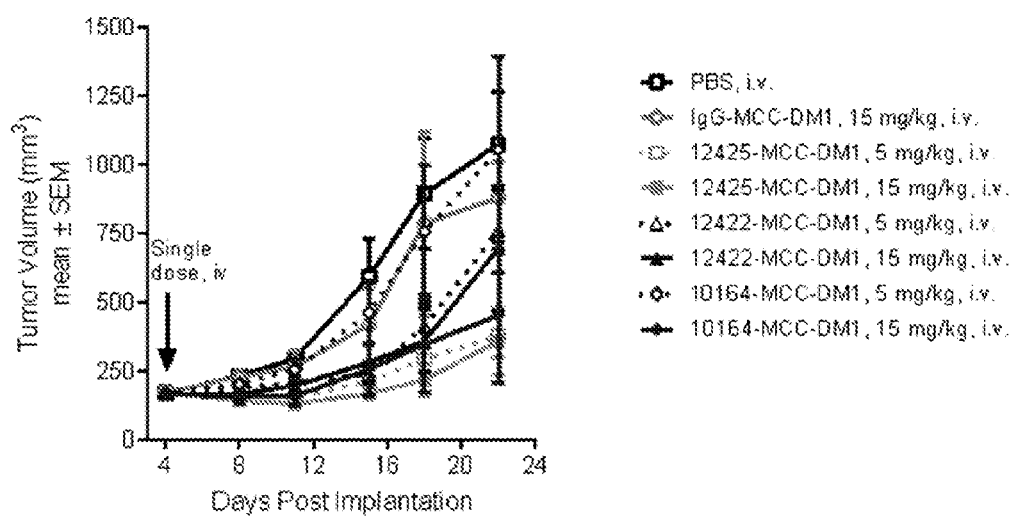
FIG. 8 (A)-(C) show the anti-tumor activity of anti-FGFR2-MCC-DM1 ADCs in H716 (A), MFM223 (B) and CHGA-010 (C) tumor xenograft mouse models.
Figure 8:
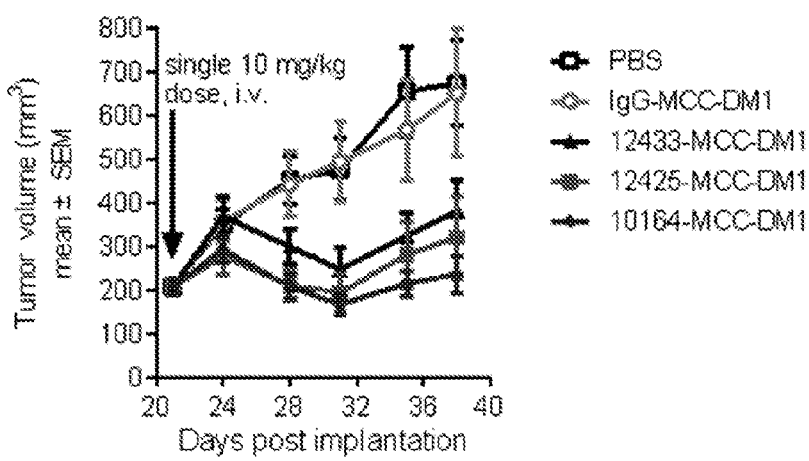
Figure 8:
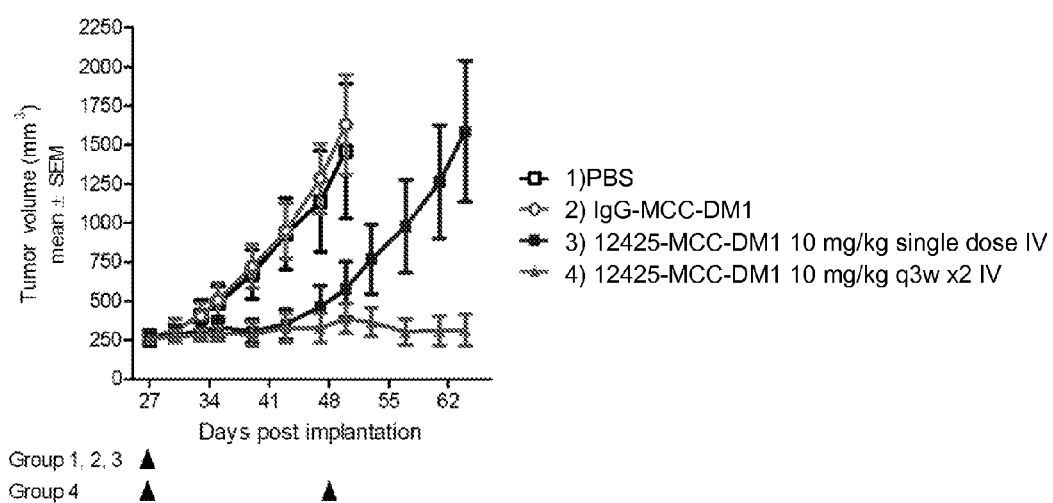

Mice were enrolled in the study four days post implantation with average tumor volume of 171.7 mm$^3$ (FIG. 8 (A)). After being randomly assigned to one of eight groups (n=6/group), mice were administered PBS (10 ml/kg), a single i.v. dose of control IgG-MCC-DM1 (15 mg/kg), 12433-MCC-DM1 (5 or 15 mg/kg), 12425-MCC-DM1 (5 or 15 mg/kg), or 10164-MCC-DM1 (5 or 15 mg/kg). Tumors were calipered twice per week. The control IgG-MCC-DM1 was not active at 15 mg/kg. 10164-MCC-DM1 was not active at 5 mg/kg. 10164-MCC-DM1 (15 mg/kg), 12422-MCC-DM1 (5 and 15 mg/kg) and 12425-MCC-DM1 (5 and 15 mg/kg) had exhibited similar activity through 14 d post dose. 12425-MCC-DM1 (5 mg/kg and 15 mg/kg) and 10164-MCC-DM1 (15 mg/kg only) yielded the most durable response through 18 d post dose (23, 21, and 31% T/C, respectively).

The dose response antitumor activity of three anti-FGFR-targeting c ADCs was also evaluated in the gastric, FGFR2 amplified, FGFR2 IIIb isoform expressing MFM223 ER/PR/HER2 negative breast xenograft tumor model. The MFM223 model was established as a fragment based model. One day before fragment implantation, female nude mice were implanted subcutaneously with 0.72 mg, 60 day sustained release 17β-estradiol pellet (Innovative Research of America) to maintain serum estrogen levels. One day after 17β-estradiol pellet implantation, xenografts harvested from donor mice were cut into 3 by 3 mm³ fragments subcutaneously implanted into recipient nude female mice. Mice were enrolled in the study 21 days post implantation with an average tumor volume of 208.4 mm³ (FIG. 8 (B)). After being randomly assigned to one of five groups (n=8/group), mice were administered PBS (10 ml/kg) or a single 10 mg/kg i.v. dose of control IgG-MCC-DM1, 12433-MCC-DM1, 10164-MCC-DM1, or 12425-MCC-DM1. Tumors were calipered twice per week. IgG-MCC-DM1 was not active in this model. A single 10 mg/kg i.v. dose of 12433-MCC-DM1, 12425-MCC-DM1, and 10164-DM1 yielded 37, 24, and 7% T/C 18 d post administration.

The activity of 12425-MCC-DM1 as a single agent was also evaluated in an FGFR2-amplified patient-derived primary gastric tumor xenograft model, CHGA-010 (FGFR2 copy number=48, (SNP6.0)). In these studies, female nu/nu athymic mice were implanted subcutaneously with 3×3×3 mm tumor fragments containing 50% phenol red-free matrigel (BD Biosciences) in DMEM. The tumor take rate was >50% and reached approximately 250 mm³ at 4 weeks post implantation. Following a single dose of 10 mg/kg IV 12425-MCC-DM1, tumor stasis as achieved through approximately 16 to 20 days post-dose (FIG. 8 (C)). Similar single dose data was also obtained for the FGFR2 specific ADC, 12433-MCC-DM1 (data not shown). In addition, a group receiving 10 mg/kg q3w*2 IV maintained roughly tumor stasis through 37 d post initial dose while tumors in the group receiving a single 10 mg/kg dose averaged 1588 mm³ by 37 d post initial dose. These data demonstrate that the CHGA010 xenografts are able to respond to a second dose of 12425-MCC-DM1.

Example 12

Improved Anti-Tumor Activity of FGFR ADC with Small Molecule FGFR Inhibitor, BGJ398

Figure 9:
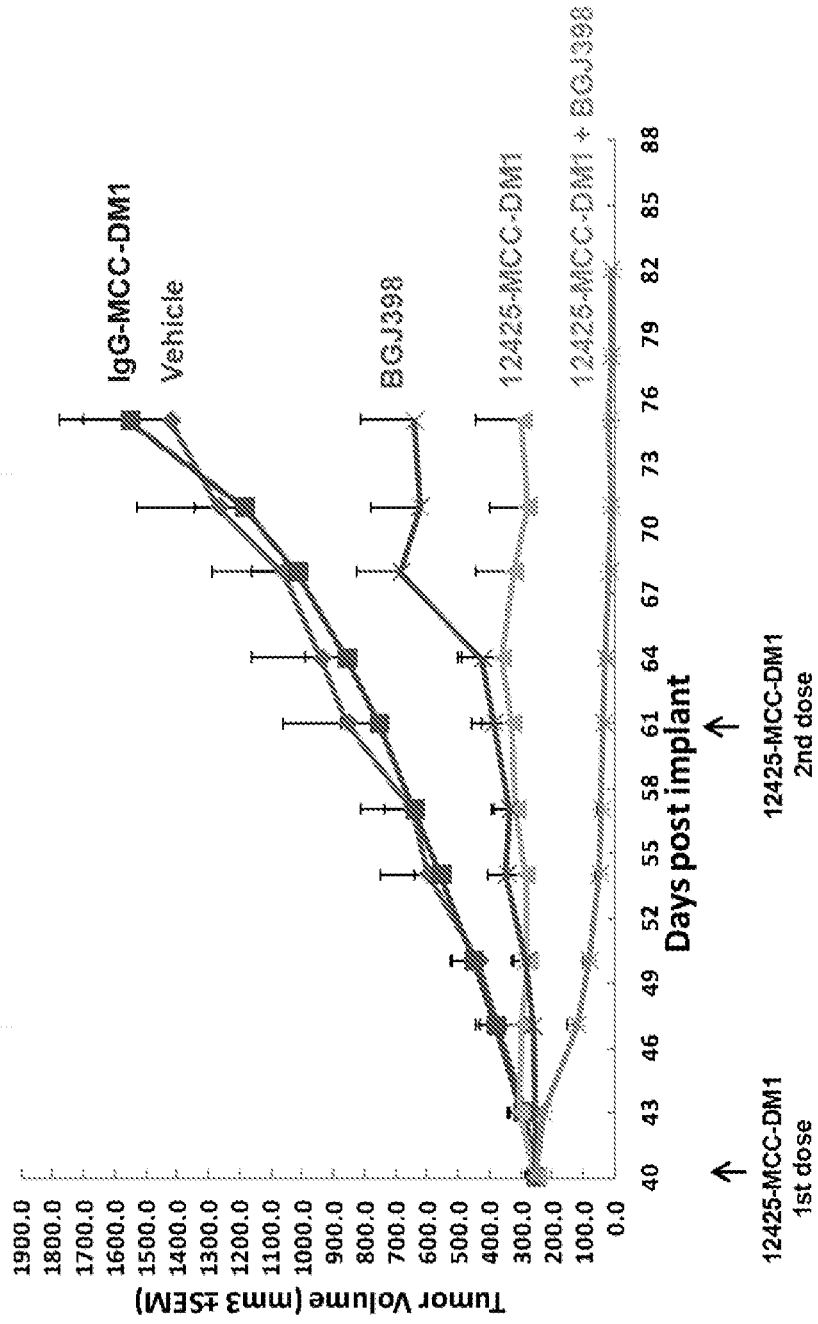
FIG. 9 shows the anti-tumor activity of the anti FGFR2 ADC, 12425-MCC-DM1, alone and in combination with the FGFR tyrosine kinase inhibitor, BGJ398 in the CHGA-119 tumor xenograft model.

Anti-tumor activity of FGFR2 antibody drug conjugate 12425-MCC-DM1 alone and in combination with the FGFR small molecule tyrosine kinase inhibitor, BGJ398 (Guagnano et al., 2011 J Med Chem 54: 7066-7083) was evaluated in the FGFR2-amplified CHGA119 patient-derived primary gastric tumor xenograft model (FGFR2 copy number=22 (SNP6.0)). In these studies, CHGA119 tumor fragments in size of 2 mm×2 mm×2 mm were implanted subcutaneously (s.c.) into female nu/nu athymic mice. Forty days after implantation, mice carrying CHGA119 tumors (n=8, average 251 mm³; range: 104-382 mm³) were treated with vehicle (50% PEG300 in acetic acid/acetate buffer) orally via gavage (pH4.6, 10 ml/kg, p.o., qd), control IgG-3207-DM1 (10 mg/kg, i.v., q2 wk), 12425-MCC-DM1 (10 mg/kg, i.v., q2 wk), NVP-BGJ398-AZ-3 (10 mg/kg, p.o., qd), or the combination of 12425-MCC-DM1 and NVP-BGJ398-AZ-3, respectively. Tumors were calipered twice a week. 12425-MCC-DM1 and BGJ398 each as single agent resulted in tumor stasis or partial response (T/C=4% or 33%, respectively, p<0.05), while the treatment in combination of 12425-MCC-DM1 and BGJ398 induced near complete tumor regression after 5 weeks of treatment (Regression=-94%, p<0.05) (see FIG. 9 and Table 15). Less than 10% body weight loss was observed following either the single agent or combination treatments (Table 15). These data suggest that combining FGFR ADCS with small molecule inhibitors of FGFR signaling (e.g. BGJ398, TKI258, ponatinib, AZD4547) can improve anti-tumor responses.

TABLE 15

Effect of anti-FGFR agents on tumor and host parameters in CHGA119-tumor bearing mice

| Treatment | Tumor response | | | Host response | | |
|---|---|---|---|---|---|---|
| | T/C (%) | Regression (%) | Mean tumor volume change (mm³ ± SEM) | Mean body weight change (g ± SEM) | % body weight change (mean ± SEM) | Survival (survivors/total) |
| Vehicle | 100 | — | 1168 ± 204 | −1.3 ± 0.3 | −5.7 ± 1.4 | 8/8 |
| IgG-MCC-DM1 | 111 | — | 1301 ± 243 | −1.7 ± 0.6 | −7.6 ± 2.7 | 8/8 |
| 12425-MCC-DM1 | 4 | — | 43 ± 35 | 0.6 ± 0.2 | 2.5 ± 1.0 | 8/8 |
| BGJ398 | 33 | — | 386 ± 169 | −0.8 ± 0.7 | −3.7 ± 3 | 8/8 |
| 12425-MCC-DM1 + BGJ398 | — | 94 | −223 ± 32 | −3.7 ± 3.8 | −4.3 ± 3.8 | 7/8 |

Example 13

Effect of Dose Fractionation on In Vivo Efficacy of FGFR ADC

To better understand the role 12425-MCC-DM1 $C_{max}$ (peak exposure) or $C_{avg}$ (average exposure over a dosing interval) play in its antitumor activity, a time-dose fractionation experiment was conducted using the SNU16 xenograft model. A range of dose schedule intervals and dose levels yielding a predicted fixed total exposure over a fixed treatment duration were studied. At certain dose levels, FGFR2ADCs exhibit nonlinear PK due to TMDD (see example 19). Therefore, in order to maintain a fixed total exposure across all dose schedule intervals and dose levels, PK modeling predicted that a larger total dose of 12425-MCC-DM1 would be required when administered at a lower, more frequent dose schedule as TMDD would be more pronounced at lower doses. PK modeling predicted that 12425-MCC-DM1 administered at 3 mg/kg q3w*2, 2.5 mg/kg q2w*3, 1.5 mg/kg qw*6, and 0.7 mg/kg q3d*14 would achieve similar total exposure.

Female nude mice were implanted subcutaneously with $10 \times 10^6$ cells in a suspension containing 50% phenol red-free matrigel (BD Biosciences) in Hank's balanced salt solution. The total injection volume containing cells in suspension was 200 μl. Mice were enrolled in the first study ten days post implantation with average tumor volume of 181.7 mm³.

To assess PK parameters, serum was collected via tail nick or retro-orbital bleeds and analyzed via ELISA. The total antibody PK assay measures total antibody concentration, with/without DM1 by colorimetric ELISA. Plates are coated with anti-human IgG (Fc specific), and detection is with donkey anti-human IgG-HRP before being read on an appropriate plate-reader. The conjugate PK assay measures antibody that is bound to at least 1 DM1 molecule by colorimetric ELISA. In this format, plates are coated with anti-DM1 antibody, and detected with donkey anti-human IgG-HRP. Serum was collected at the following time points post initial dose: 3 mg/kg q3w*2 (2, 6, 24, 48, 96, 168, 240, 336, 503 h); 2.5 mg/kg q2w*3 (2, 6, 24, 48, 96, 168, 240, 335, 503 h); 1.5 mg/kg qw*6 (2, 6, 24, 48, 96, 167, 335, 503, 671, 839 h); 0.7 mg/kg q3d*14 (2, 6, 24, 48, 71, 143, 215, 287, 359, 431, 503, 575, 647, 719, 791, 863, 935 h).

Figure 10:
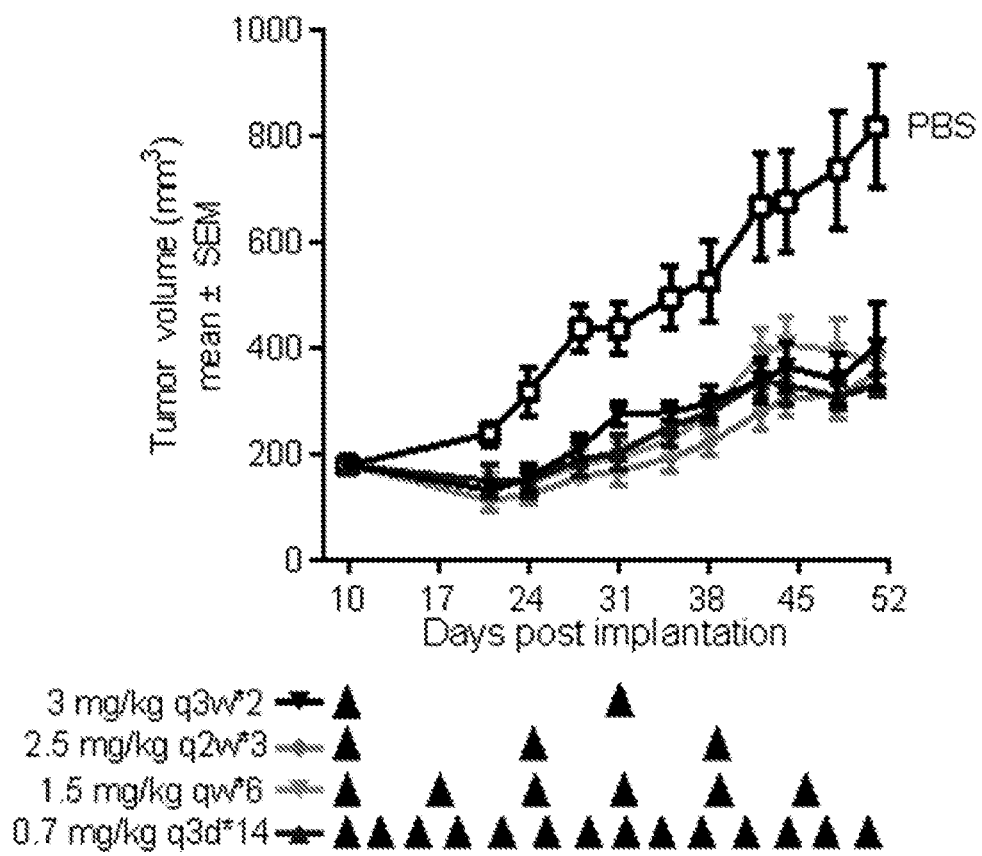
FIG. 10 shows the anti-tumor activity of the anti FGFR2 ADC, 12425-MCC-DM1 at different doses and schedules in the SNU-16 tumor xenograft mouse model.

After being randomly assigned to one of five groups (n=7/group), mice were administered PBS (10 ml/kg) or 12425-MCC-DM1 administered i.v. at 3 mg/kg q3w*2, 2.5 mg/kg q2w*3, 1.5 mg/kg qw*6, or 0.7 mg/kg q3d*14. As anticipated, $C_{max}$ varied across treatment regimens while $C_{avg}$ was static (Table 16). All treatment regimens were active and yielded similar tumor growth inhibition suggesting that average exposure of 12425-MCC-DM1 is the primary driver of antitumor activity (FIG. 10). These findings indicate that a variety of dose schedules could be employed in the clinic without compromising efficacy.

TABLE 16

PK parameters following administration of different doses and schedules of 12425- MCC-DM1 to SNU16 tumor-bearing mice

| Dosing Regimen | Total dose, mg | Cmax*, ug/ml | | Cavg$_{Tau}$, ug/ml | | Tau, h |
|---|---|---|---|---|---|---|
| | | Total† | Intact ADC‡ | Total† | Intact ADC‡ | |
| 3 mg/kg, iv, q3wx2 | 6 | 24.5 | 25.1 | 2.19 | 2.29 | 503 |
| 2.5 mg/kg, iv, q2wx3 | 7.5 | 21.2 | 21.6 | 2.59 | 2.30 | 335 |
| 1.5 mg/kg, iv, qwx6 | 9 | 11.0 | 11.0 | 2.56 | 2.50 | 167 |
| 0.72 mg/kg, iv, q3dx14 | 10 | 4.0 | 4.2 | 1.94 | 1.63 | 72 |

Example 14

Evaluation of ADCC Activity In Vitro and In Vivo

Figure 11:
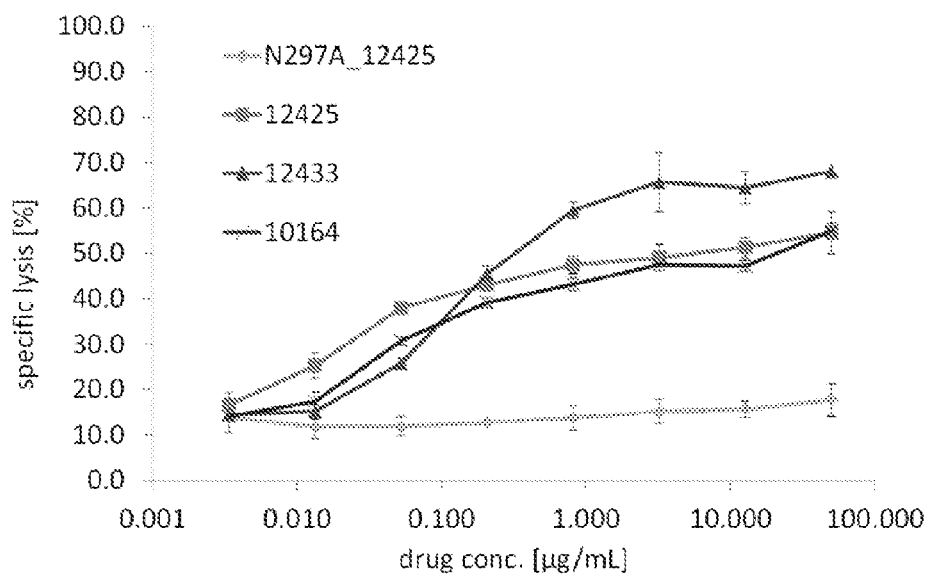
FIG. 11 (A)-(C) show the assessment of the ability of anti-FGFR2 antibodies to induce ADCC in vitro in Kato III cells (A), to bind to C1q (B), and induce CDC in Kato III cells (C). (D) shows the effect of an ADCC depleted variant as an unconjugated antibody or MCC-DM1 conjugated ADC in vivo.
Figure 11:
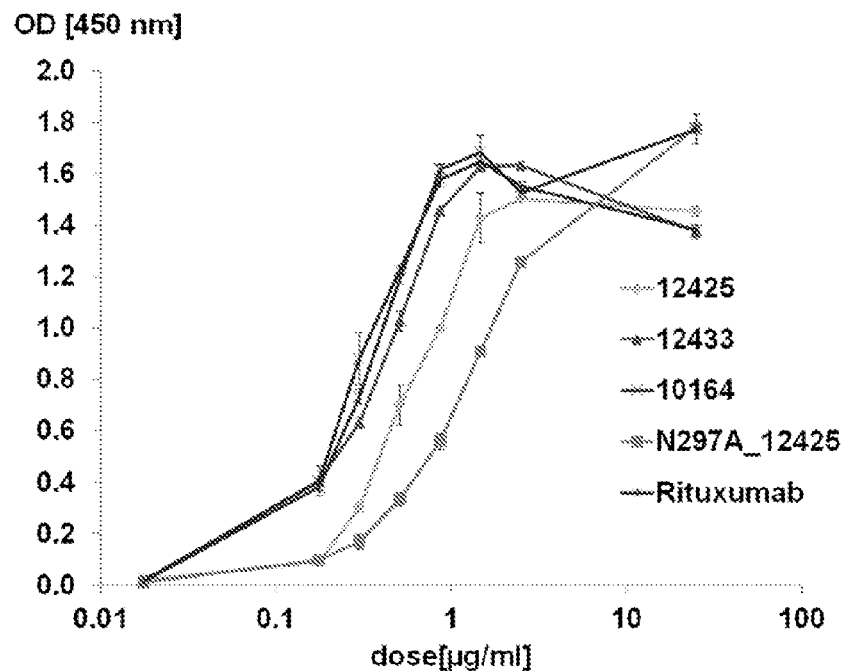
Figure 11:
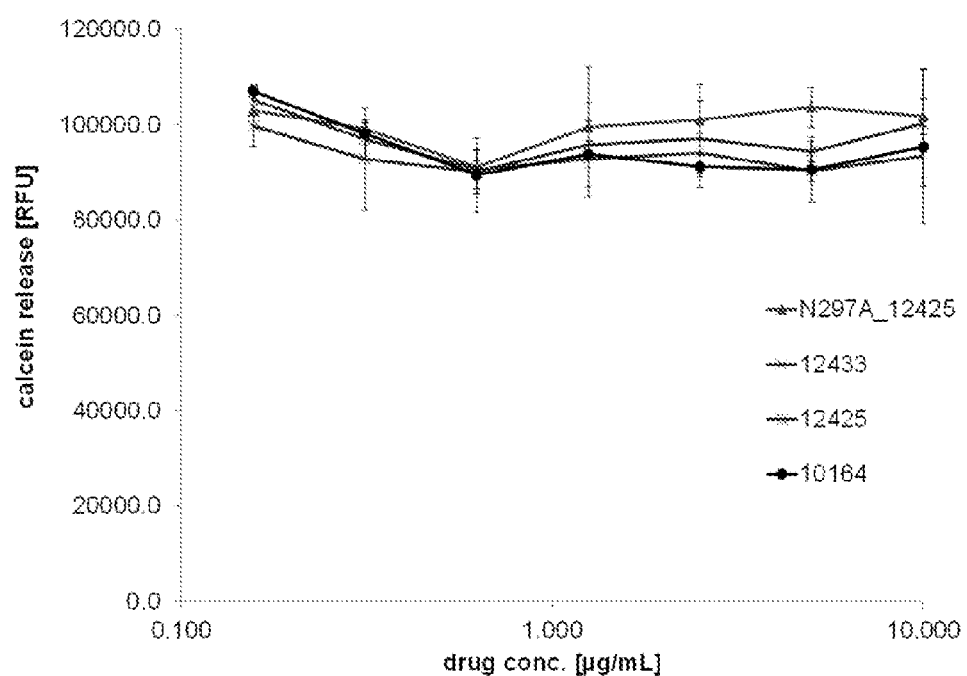
Figure 11:
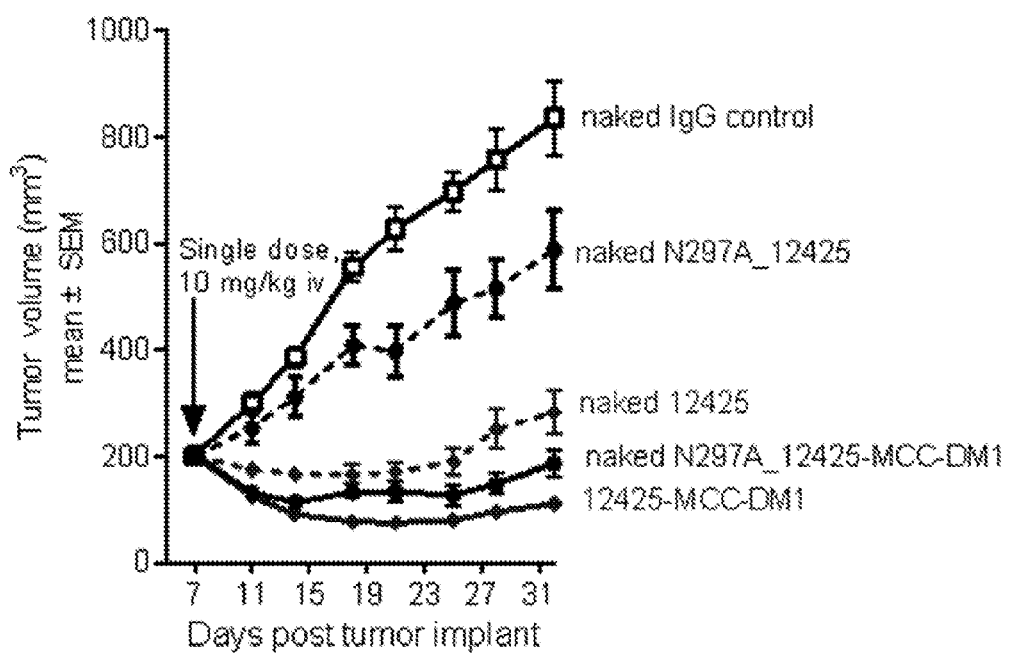

The ability of the unconjugated anti-FGFR2 antibodies (12433, 10164, 12425, N297A_12425 (an ADCC-depleted variant (Bolt et al., 2003 Eur J Immunol 23: 403-411))) to mediate antibody dependent cellular cytotoxicity was determined versus Kato-III cells (target cells; ATCC catalog #HTB-103) in co-incubation with NK3.3 cells (killer cells or effector cells; kindly provided by Jacky Kombluth from San Louis University). In brief, Kato-III cells were stained with Calcein acetoxy-methyl ester (Calcein-AM; Sigma-Aldrich catalog #17783-5MG), washed twice, pipetted into a 96-well microtiterplate (96 well, U-bottomed, clear plastic; Corning Costar, catalog #650 160) at a concentration of 5000 cells per well and pre-incubated for 10 min with a serial dilution of the above mentioned antibodies and proteins (from 50,000 to 0.003 μg per ml) before adding the effector cells. In order to calculate the antibody specific lysis of the target cells, a parallel incubation of target cells only without antibody or effector cells served as a baseline and negative control, whereas the positive control or maximal lysis or hundred percent specific lysis was determined by lysis of target cells only with a 1% Triton-X 100 solution. Following a co-incubation of target and effector cells in a ratio of one to five, the microtiterplate was centrifuged and an aliquot of the supernatant fluid was transferred to another microtiterplate (96 well, flat-bottomed, black with clear bottom; Corning Costar, catalog #3904) and the concentration of free Calcein in solution was determined with a fluorescence counter (Victor 3 multilabel counter, Perkin Elmer). Results are presented in FIG. 11 (A) and it was observed that all tested antibodies mediated ADCC to a varying extent. The N297A_12425, carrying no glycosylation in the Fc-part of the antibody and thus lacking the binding to the CD16a receptor of the effector cells, did not mediate any ADCC and served as a specific negative control. The constant and protein-concentration independent killing of target cells is due to a unspecific background, natural killing activity of the NK3.3 cells against the Kato-III cells. The antibody 12433 mediated the highest specific lysis of target cells with about sixty percent (signal deduced the background lysis of Kato-III cells by NK3.3 cells), whereas the antibodies 12425 and 10164 reached a specific lysis of about fifty-five percent (signal deduced the background lysis of Kato-III cells by NK3.3 cells). The potency (the concentration at the half maximal killing of each dose response curve; effective concentration 50, $EC_{50}$) of all three molecules was similar. In a similar series of experiments, the ability of the naked antibody 12425 to induce ADCC was compared 12425-MCC-DM1. No differences between the naked 12425 and 12425-MCC-DM1 were observed (data not shown) suggesting that DM1 conjugation does not appreciably impair the ability of the naked antibody to induce ADCC.

In additional studies, the ability of the unconjugated anti-FGFR2 antibodies to bind the complement factor C1q was evaluated. The binding of the complement factor C1q is the initial step leading to complement dependent cytotoxicity (CDC) and cell lysis in vivo. In these studies the surface of the wells of 96-well microtiterplates (Nunc, Maxisorp, catalog #439454) were coated with serial dilutions of the antibodies 12433, 12425, N297A_12425 and 10164 over night at 4° C. in the dark (all in a concentration range from 25 to 0.02 μg/ml). The commercially available antibody, Rituximab served as a positive control. In order to monitor the amount of bound antibody analyte on the microtiterplate, this procedure was performed twice per plate utilizing the second dilution (in triplicate) for determining the coating efficacy of the analyte to the plate. C1q binding was quantified by adding a constant concentration of C1q (Sigma; Complement component C1q catalog #C1740-1 mg) and detected using a polyclonal goat-anti-human C1q antibody conjugated to Horse Radish Peroxidase HRP (AbD Serotec; Sheep Anti-Human C1q:HRP; Catalogue number 2221-5004P). The control of the coating efficiency was determined in the second dilution series with a peroxidase-conjugated goat-anti-human IgG antibody fragment (Jackson ImmunoResearch; catalog #109-036-003; AffiniPure F(ab'2) fragment Goat Anti-Human IgG (H+L)). Both were visualized using the TMB substrate (TMB Peroxidase EIA Substrate Kit; Bio-Rad; catalog #172-1067) with subsequent measurement of optical density at 450 nm with a UV-Vis Spectroscope (Molecular Devices; SpectramaxPro 340). Results are presented in FIG. 11 (B). The maximal amount of C1q protein bound to the tested antibodies was the same for all analytes. The amount of antibody that was bound to the microtiterplate was the same for all analytes except for the 10164 antibody, which reached only around 50% of the other molecules. The potency (the concentration at the half maximal binding of each dose response curve; effective concentration 50, $EC_{50}$) of 12433, 10164 and Rituximab was about the same. The $EC_{50}$ of the 12425 antibody was a factor of 3 higher and the $EC_{50}$ of the N297A_12425 was a factor of about 8 higher. Given the result that 10164 did not coat equally well to the microtiterplate as the other antibodies did, the observed result in C1q binding implicates an approximate double capacity of 10164 in binding to the C1q protein.

Further to the assessment of C1q binding, the ability of unconjugated anti-FGFR2 antibodies 12433, 10164 12425 and N297A_12425 to trigger complement dependent cytotoxicity (CDC) was evaluated. Kato-III cells (target cells; ATCC catalogues number HTB-103) were equally distributed into the wells of a 96-well microtiterplate (Costar; sterile, white, 96-well flat bottomed cell culture plates, catalog #3610) at a concentration of 10000 cells per well and pre-incubated for 10 min with a serial dilution of the above mentioned antibodies before adding the effector reagent. The effector reagent used in this study was rabbit complement (PelFreez; catalog #31060-1), which was pipetted onto the Kato-III cells at a final dilution of one to six. Following a two hour incubation in a humidified cell culture incubator at 37° C., the microtiterplate was centrifuged, supernatant was discarded and the cell pellet was dissolved in reconstituted Cell-TiterGlo (Promega; CellTiterGlo Luminescence Kit, catalog #G7572) Luminescence was quantified in a multilabel reader (PerkinElmer; Victor 3). Results are presented in FIG. 11 (C) for all tested antibodies. No evidence of CDC was observed for the tested antibodies (FIG. 11 (C)) or additional controls (commercially available antibodies Erbitux & Herceptin, data not shown).

To assess the role of ADCC in 12425-MCC-DM1's in vivo activity, female nude mice were implanted subcutaneously with 10×10⁶ cells in a suspension containing 50% phenol red-free matrigel (BD Biosciences) in Hank's balanced salt solution. The total injection volume containing cells in suspension was 200 Mice were enrolled in the study seven days post implantation with average tumor volume of 201.4 mm³. After being randomly assigned to one of five groups (n=6/group), mice received a 10 mg/kg i.v. dose of naked control IgG, naked N297A_12425, naked 12425, N297A_12425-MCC-DM1, or 12425-MCC-DM1. Tumors were calipered twice per week (FIG. 11 (D)). The naked, ADCC-depleted 12425 variant (naked N297A_12425) exhibited less antitumor activity than the ADCC competent parental 12425 (61 and 13% T/C, respectively) at 25 d post dose. These data suggest that the parental 12425's effector cell function may play a role in the activity of the naked antibody's in vivo antitumor activity. The ADCC competent 12425-MCC-DM1 and ADCC depleted N297A_12425-MCC-DM1 exhibited similar ant-tumor activity at 25 d post dose (45 and 32% regression, respectively). These data suggest that while ADCC activity is expendable, that the maytansinoid payload is both required and sufficient for 12425-MCC-DMZ's robust in vivo antitumor activity.

Example 15

Evaluation of Pharmacokinetics of Anti-FGFR ADCs in Mouse, Rat and Cynomolgus Monkey The pharmacokinetics (PK) of anti-FGFR ADCs was evaluated in tumor- and non-tumor-bearing mice at several dose levels ranging from 1-15 mg/kg, in non-tumor bearing rats at 1, 5 and 45 mg/kg and in cynomolgus monkey at 30 mg/kg. In all studies, serum concentrations of both "total" antibody and "antibody drug conjugate (ADC)" were measured in all animal species using validated ELISA methods. The "total" fraction refers to the measurement of the antibody with or without the conjugated DM1, whereas the ADC fraction refers to the measurement of DM1 conjugated antibody only (>1 DM1 molecule). In all studies, no appreciable differences were observed between clearance of the ADC and total antibody fractions.

Figure 12:
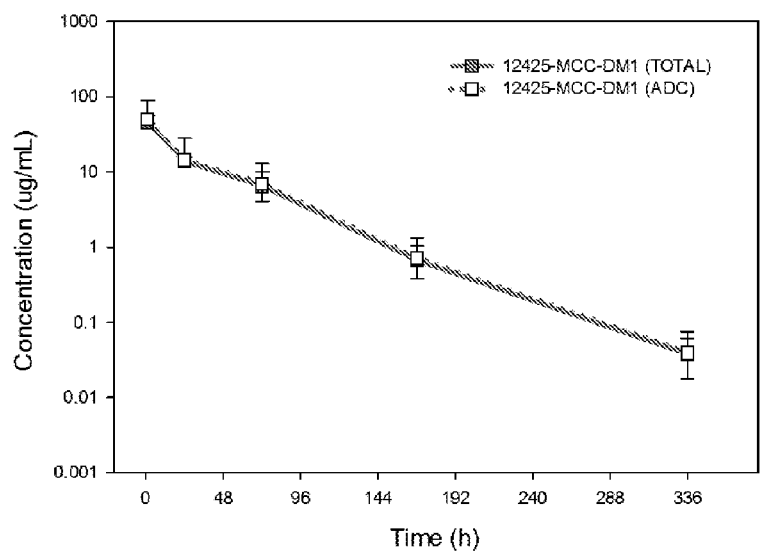
FIG. 12 (A)-(D) show the PK profiles of 12425-MCC-DM1 in mouse ((A)-(B)), rat (C), or cynomolgus monkey (D).
Figure 12:
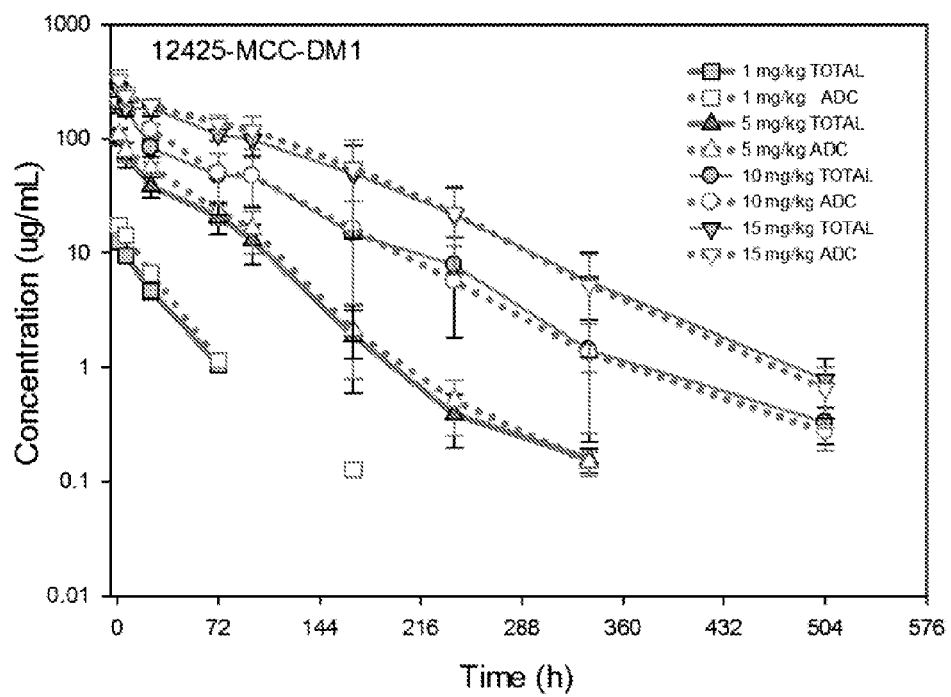
Figure 12:
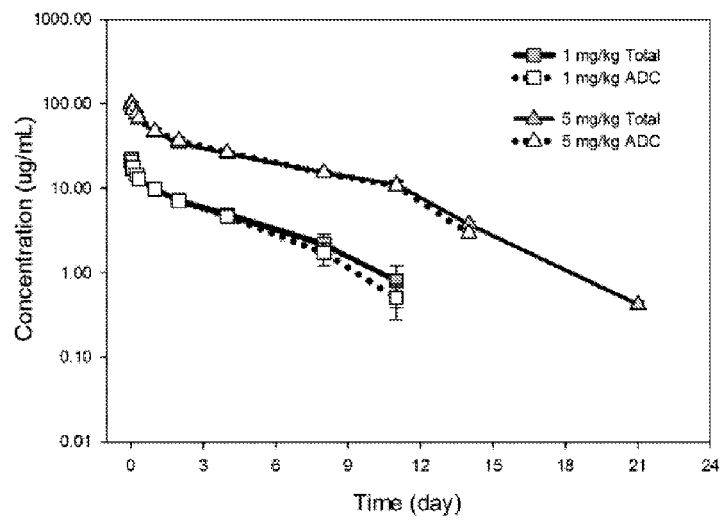
Figure 12:
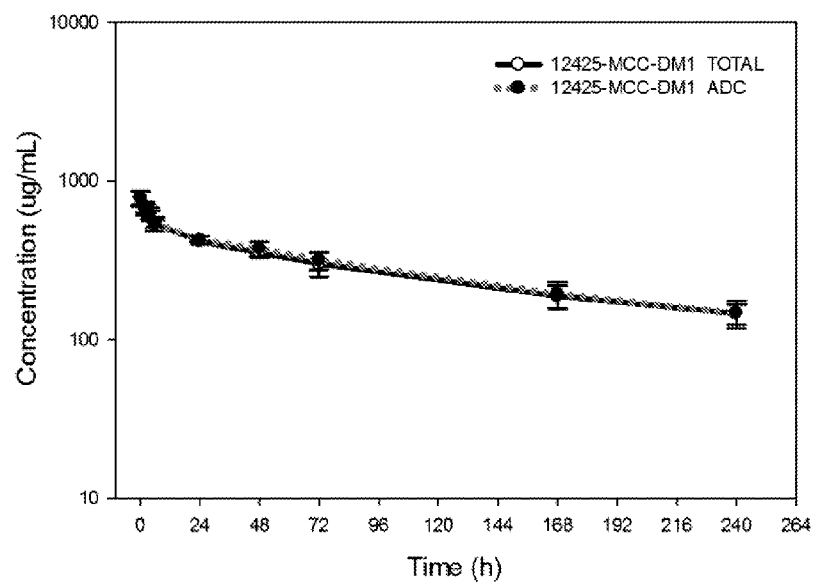

12425-MCC-DM1 PK was investigated in SNU16 tumor-bearing mice following a single IV dose of 3 mg/kg. PK samples were collected at 1 h, 24 h, 72 h, 168 h, and 336 h post dose and the serum concentrations of the total and ADC fraction were super-imposable at this dose (FIG. 12 (A)). 12425-MCC-DM1 half-life was about 1.5 days in the presence of the SNU16 xenograft.

12425-MCC-DM1 PK was also investigated in non-tumor bearing mice following a single IV dose of 1, 5, 10 or 15 mg/kg. PK samples were collected at 1 h, 6 h, 24 h, 72 h, 96 h, 168 h, 240 h. 336 h, and 540 h post dose. The serum concentrations of the total and ADC fraction were super-imposable at these doses (FIG. 12 (B)) and PK properties appeared similar in non-tumor bearing relative to tumor bearing animals.

The PK of 12433-MCC-DM1 and 10164-MCC-DM1 in SNU16 tumor-bearing mice was also determined. The overall PK profile of these ADCs was similar to that of 12425-MCC-DM1 and the data obtained is summarized in Table 17.

TABLE 17

Pharmacokinetic properties of 12433-, 12425- and 10164-MCC-DM1 in mice at 3 mg/kg dose

| Ab | Cmax (ug/mL) | | CL (mL/h/kg) | | V (mL/kg) | | t½ (h) | |
|---|---|---|---|---|---|---|---|---|
| | TOTAL | ADC | TOTAL | ADC | TOTAL | ADC | TOTAL | ADC |
| 12425-MCC-DM1 | 45.0 | 50.4 | 1.85 | 1.72 | 97.0 | 89.5 | 36.4 | 36.1 |
| 12433-MCC-DM1 | 52.4 | 42.7 | 1.61 | 1.95 | 101.0 | 122.9 | 43.5 | 43.8 |
| 10164-MCC-DM1 | 42.8 | 37.5 | 1.18 | 1.28 | 101.4 | 117.5 | 59.4 | 64.0 |

12425-MCC-DM1 PK was investigated in non-tumor bearing rats at two dose levels; 1 and 5 mg/kg administered IV. PK samples were collected at 0.5 h, 1 h, 2 h, 6 h, 8 h and on day 1, 2, 4, 8, 11, 14, 21 and 35. The concentration-time profiles for the "total" and "ADC" species were near super-imposable at both dose levels (FIG. 12 (C)). The terminal elimination phase was slightly steeper in the 1 mg/kg dose group, and this could be as a result of target-mediated drug disposition (TMD) at later time-points. Similarly, clearance values for the total and ADC fractions were 0.757±0.088 mL/h/kg and 0.813±0.041 mL/b/kg, respectively at the 1 mg/kg dose, while slightly lower values of 0.623±0.027 mL/h/kg and 0.607±0.019 mL/h/kg, respectively were noted at the 5 mg/kg dose. 12425-MCC-DM1 ADC species have a terminal half-life of around 3.9 days at the 5 mg/kg dose level. In additional studies, rat PK was also determined at 5 mg/kg and 45 mg/kg dose levels. Half-life at the 5 mg/kg dose was similar to the values noted above, while at the 45 mg/kg dose the half-life was 163.9 h, 121.3 h (~5 days) for the total and ADC fractions, respectively and these values were similar to observations for a non-FGFR2 cross-reactive control ADC, suggesting saturation of any possible TMD clearance pathways.

12433-MCC-DM1 and 10164-MCC-DM1 PK was also determined in similar studies and the PK parameters obtained are presented in Table 18. It was found that at the dose levels employed, similar estimates of total and ADC half-life and clearance were obtained for all 3 ADCs tested.

TABLE 18

Pharmacokinetic properties of 12433-, 12425- and 10164-MCC-DM1 in rats

| Dose (mg/kg) | Ab | t½ (h) TOTAL | t½ (h) ADC | AUCinf (ug · h/mL) TOTAL | AUCinf (ug · h/mL) ADC | CL (mL/h/kg) TOTAL | CL (mL/h/kg) ADC |
|---|---|---|---|---|---|---|---|
| 5 | 12433-MCC-DM1 | 71.1 | 59.0 | 388.8 | 374.0 | 0.536 | 0.557 |
| 45 | 12433-MCC-DM1 | 176.7 | 131.9 | 4399.3 | 3929.8 | 0.426 | 0.477 |
| 5 | 12425-MCC-DM1 | 77.0 | 64.0 | 12853 | 12874 | 0.389 | 0.388 |
| 45 | 12425-MCC-DM1 | 163.9 | 121.3 | 103265 | 103647 | 0.436 | 0.434 |
| 5 | 10164-MCC-DM1 | 88.0 | 78.0 | 12677 | 14644 | 0.394 | 0.341 |
| 45 | 10164-MCC-DM1 | 140.1 | 110.3 | 139842 | 150433 | 0.322 | 0.299 |

12425-MCC-DM1 PK was investigated following administration of a single 30 mg/kg IV dose to a group of three cynomolgus monkeys (1 male, 2 female). Serum samples were collected on Day 1-0 h (prior to dosing), and at 0.25 h, 2 h, 4 h, 6 h, 24 h, 48 h, 72 h, 168 h and 240 h post dose. The maximum exposure to 12425-MCC-DM1 was observed immediately following IV injection, i.e. at 0.25 h, which was the first sampling time-point. The time course was characterized by a long elimination phase, and the profiles for the total and ADC fractions were superimposable over the sampling time course (FIG. 12 (D)). The terminal half-life was around 6-7 days.

10164-MCC-DM1 PK was also investigated following administration of a single 30 mg/kg IV dose to a group of three cynomolgus monkeys. The time course for this reagent was also characterized by a long elimination phase (terminal half-life of 6-7 days) and PK parameters of both 10164-MCC-DM1 and 12425-MCC-DM1 are presented in Table 19.

TABLE 19

Pharmacokinetic properties of 12425- and 10164-MCC-DM1 in cynomolgus monkey following a 30 mg/kg IV dose

| Test article | | Cmax (µg/mL) | AUC0-240 h (µg · h/mL) | AUC0-inf (µg · h/mL) | CL (mL/h/kg) | t½ (h) |
|---|---|---|---|---|---|---|
| 12425 | Total | 785.6 ± 72.2 | 64612 ± 6477 | 99979 ± 12060 | 0.303 ± 0.038 | 166.5 ± 36.4 |
| | ADC | 780.6 ± 84.2 | 66656 ± 7577 | 99113 ± 16895 | 0.310 ± 0.052 | 151 ± 22.3 |
| 10164 | Total | 1032 ± 423 | 79535 ± 6506 | 124946 ± 11687 | 0.242 ± 0.0237 | 175.1 ± 44.1 |
| | ADC | 909.5 ± 224.3 | 81150 ± 4658 | 122061 ± 8615 | 0.247 ± 0.018 | 158.1 ± 33 |

Example 16

Assessment of the Activity of Sequence-Modified Anti-FGFR Antibodies and ADCs In Vitro and In Vivo It is recognized that potential structural liabilities can exist in the sequences of therapeutic antibodies that can affect the heterogeneity of the final protein and may impact, for example, antibody manufacturability and immunogenicity. Such liabilities can include glycosylation sites, up-paired cysteines, potential deamidation sites etc. To reduce the risk of such potential liabilities, mutations can be introduced to remove one or more of these liabilities. For example, potential deamidation sites can be replaced either alone or in conjunction with other structural changes. Examples of potential deamidation sites include DG in heavy chain CDR2 of 10164 and 12425 (see Table 1). These residues can be mutated to other appropriate amino acids. By way of non-limiting example, the aspartic acid (D) in 10164 HCDR2 can be mutated to glutamic acid (E) or threonine (T). In 12425, the HCDR2 glycine (G) can be mutated to another amino acid, such as alanine (A).

It should also be appreciated that where an antibody differs from its respective germline sequence at the amino acid level, the antibody can be mutated back to its germline sequence. Such corrective mutations can occur at one or more positions and be generated using standard molecular biology techniques or by gene synthesis. By way of non-limiting example, the heavy chain sequence of 10164 (SEQ ID NO: 29) differs from the corresponding germline sequence by an E to a Q at position 1, an A for a T at position 99 and an R for a T at position 100. The light chain sequence of 10164 (SEQ ID NO: 39) differs from the corresponding germline sequence by an S to an D at position 1, a Y to an I at position 2, an L to an P at position 8, an A to an S at position 13, an L to an P at position 14, an R to an S at position 19, an R to an G at position 76, an A to a T at position 77, and a G to an E at position 80. Thus the amino acids in 10164 can be modified at any or all of these sites. For 12425, the heavy chain sequence (SEQ ID NO:49, see Table 1) differs from the corresponding germline sequence by an E to a Q at position 1, and the light chain (SEQ ID NO: 59) differs from the corresponding germline by a T for a V at position 85. Thus the amino acids in 12425 can be modified at any or all of these sites.

The chemistry employed to generate the antibody drug conjugates described in this application relies on conjugation to lysine (K) residues in the antibody sequence. Where these lysine residues exist within regions involved in epitope recognition, for example, in CDR regions, if significant conjugation occurs at these sites, the ability of the antibody drug conjugate to bind to its intended target could be altered. To mitigate this potential risk, such lysine residues can be mutated to alternative appropriate amino acids, such as arginine, asparagine or glutamine. One lysine is present in both the heavy chain CDR2 and CDR3 regions of 12425. Either one or more of these lysines can be mutated to alternative residues, such as arginine, asparagine or glutamine.

Figure 13:
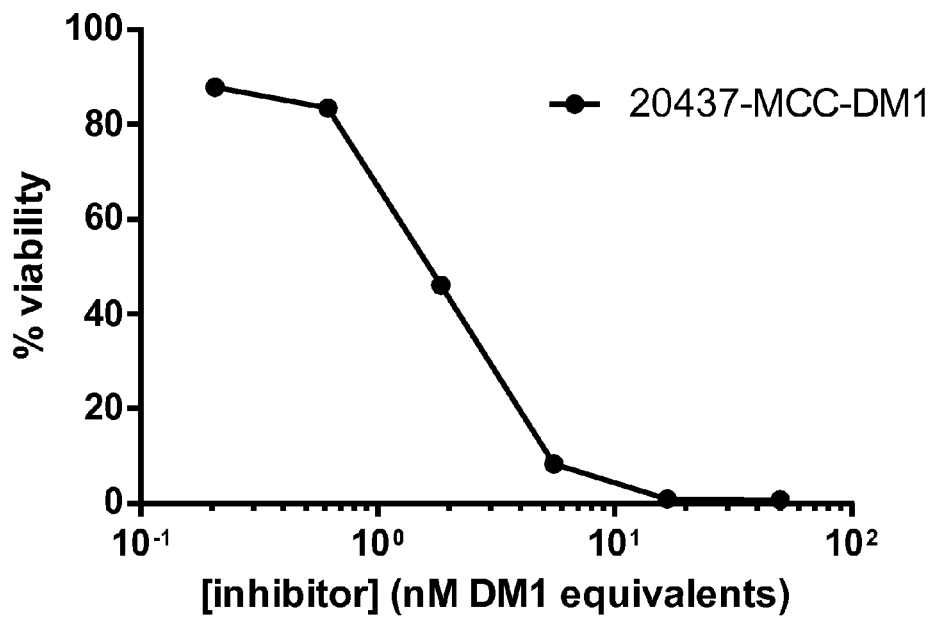
FIG. 13 (A)-(D) show the ability of the engineered variants of 10164 (20437-MCC-DM1) and 12425 (20562-MCC-DM1) to inhibit the proliferation of SNU-16 cells in vitro (13A/C) and in vivo (13B/D)
Figure 13:
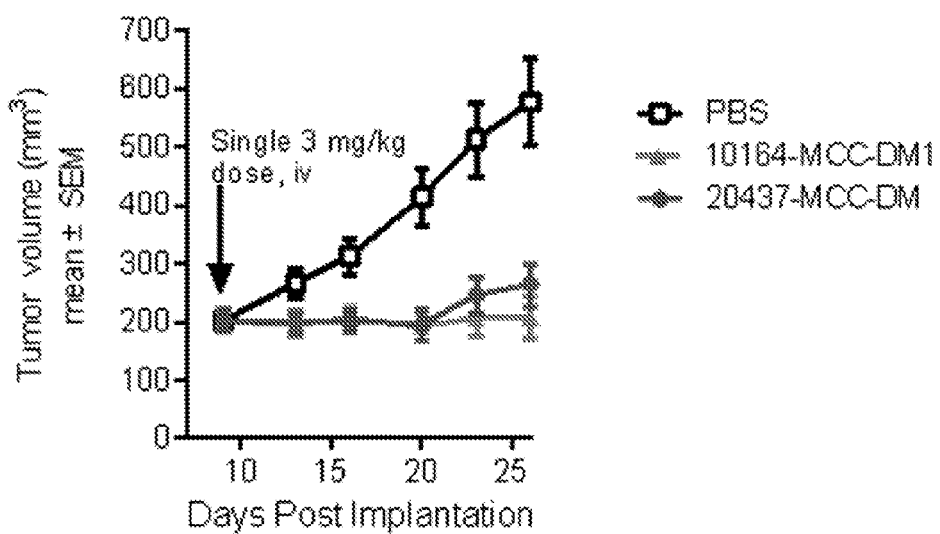
Figure 13:
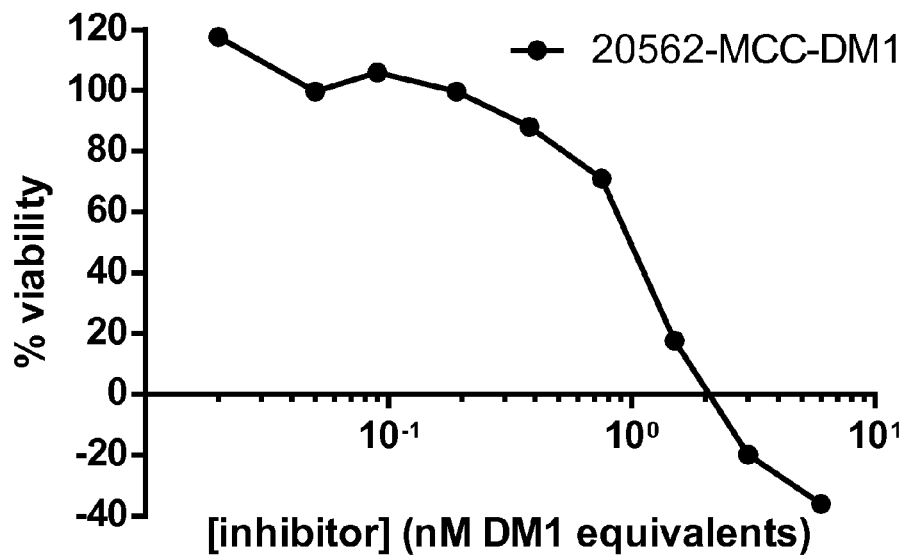
Figure 13:
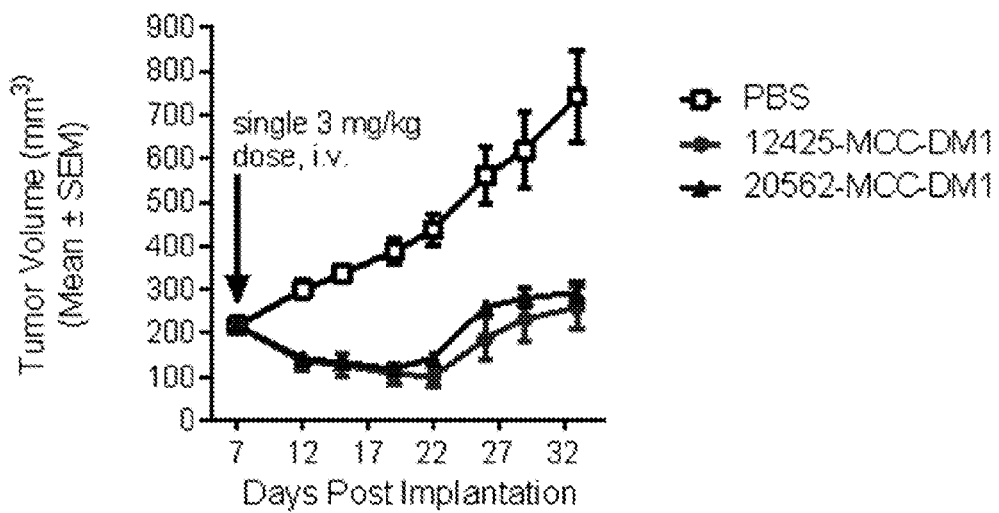

Several of the changes described above were introduced into the 10164 antibody to yield the antibody 20437 (Table 1). This antibody was compared to 10164 for its ability to bind to FGFR2, its ability to inhibit the proliferation of FGFR2-amplified cell lines, such as SNU16 and to cause an anti-tumor effect against SNU16 cells in vivo. Using the methodology as described in example 2, no differences in affinity between 10164 and 20437 were observed to human FGFR2 IIIb (20437 affinity estimate: 3.1 nM). Employing the methodology described in example 6, similar to 10164-MCC-DM1, 20437-MCC-DM1 was a potent inhibitor of the proliferation of SNU16 cells in vitro (FIG. 13(A)). To assess the potency of 20437-MCC-DM1 in vivo, female nude mice were implanted subcutaneously with $10 \times 10^6$ cells in a suspension containing 50% phenol red-free matrigel (BD Biosciences) in Hank's balanced salt solution. The total injection volume containing cells in suspension was 200 µl. Mice were enrolled in the study seven days post implantation with an average tumor volume of 202 mm$^3$. After being randomly assigned to a treatment group (n=7/group), mice received PBS (10 ml/kg) or a 3 mg/kg i.v. dose of 10164, 10164-MCC-DM1 or 20437-MCC-DM1. Tumors were calipered twice per week (FIG. 13(B)). Both 10164-MCC-DM1 and its variant 20437-MCC-DM1 had similar activity in vivo against the FGFR2-amplified SNU16 xenograft. These data suggest that it is possible to make several changes to the sequence of the 10164 parent antibody without impacting in vivo activity as an ADC.

Several of the changes described above were introduced into the 12425 antibody to yield the antibody 20562 (Table 1). This antibody was compared to 12425 for its ability to bind to FGFR2, its ability to inhibit the proliferation of FGFR2-amplified cell lines, such as SNU16 and to cause an anti-tumor effect against SNU16 cells in vivo. The affinity of 20562 to human FGFR2 IIIb was found to be similar to that of 12425 under similar assay conditions (20562 FGFR2 IIIb affinity estimate: 9 nM). Employing the methodology described in example 6, similar to 12425-MCC-DM1, 20562-MCC-DM1 was also a potent inhibitor of the proliferation of SNU16 cells in vitro (FIG. 13 (C)). To assess the potency of 20562-MCC-DM1 in vivo, female nude mice were implanted subcutaneously with $10 \times 10^6$ cells in a suspension containing 50% phenol red-free matrigel (BD Biosciences) in Hank's balanced salt solution. The total injection volume containing cells in suspension was 200 µl. Mice were enrolled in the study seven days post implantation with an average tumor volume of 217.1 mm$^3$. After being randomly assigned to one of five groups (n=6/group), mice received PBS (10 ml/kg) or a 3 mg/kg i.v. dose of 12425-MCC-DM1 or 20562-MCC-DM1. Tumors were calipered twice per week (FIG. 13(D)). Both 12425-MCC-DM1 and its variant 20562-MCC-DM1 had similar activity in vivo against the FGFR2 amplified SNU16 xenograft. These data suggest that it is possible to remove the DG site of the parent antibody without impacting in vivo activity as an ADC.

Example 17

Generation and Characterization of Affinity-Matured FGFR ADCs

To evaluate the effect of affinity on the biological activity of selected anti-FGFR antibodies, affinity optimization was performed on the 12433, 10164 and 12425 clones. In these studies, the L-CDR3 and H-CDR2 regions were optimized in parallel by cassette mutagenesis using trinucleotide directed mutagenesis (Virnekas et al., 1994 Nucleic Acids Research 22: 5600-5607), while the framework regions were kept constant. Prior to cloning for affinity maturation, parental Fab fragments were transferred from the corresponding expression vector pM®x11 into the CysDisplay™ vector pMORPH®30 via XbaI/EcoRI.

For optimizing L-CDR3 of parental Fab fragments the L-CDR3, framework and the constant region of the light chains (405 bp) of the binder pool were removed by BpiI/SphI and replaced by a repertoire of diversified L-CDR3s together with framework 4 and the constant domain. 250 ng of the antibody pool vector were ligated with a 3-fold molar excess of the insert fragment carrying the diversified L-CDR3s. In a second library set the H-CDR2 (XhoI/BssHII) was diversified, while the connecting framework regions were kept constant. In order to monitor the cloning efficiency the parental H-CDR2 was replaced by a dummy, before the diversified H-CDR2 cassette was cloned in. Ligation mixtures were electroporated in 200 µl E. coli MC106F' cells yielding from $10^8$ to $10^9$ independent colonies. This library size ensured coverage of the theoretical diversity. Amplification of the library was performed as described elsewhere (Rauchenberger et al., 2003 J Biol Chem 278: 38194-38205). For quality control single clones were randomly picked and sequenced.

For the selection of affinity improved binders phage derived from maturation libraries were subjected to three rounds of solution pannings using biotinylated human FGFR2. Stringency was increased by lowering the antigen concentration in each panning round (Low et al., 1996 J Mol Biol 260(3): 359-368). In addition to antigen reduction, off-rate selection (Hawkins et al., 1992 J Mol Biol 226: 889-896) was performed. This was combined with prolonged washing steps at RT.

For selected subcodes an "advanced maturation" was set-up where the $2^{nd}$ round panning output of a conducted H-CDR2 affinity maturation panning was diversified additionally in the L-CDR3. Library generation was exactly done as described above. For the selection of improved binders, the new generated libraries were subjected into two additional rounds of solution panning.

The sequence unique clones that were identified were expressed as IgGs and affinity to human FGFR2 was determined using either SET or Biacore methodologies similar to those described in examples 1 and 2. More than 80 clones were evaluated from the 3 parental antibodies and affinity improvements of 3-6 fold were obtained for clones derived from the 12433 antibody, 27-fold for 10164 derived clones and 68-fold for 12425 derived antibodies. The highest affinity clone derived from 10164 was designated 20809 (Table 1) and it's affinity for human FGFR2 was determined to be 450 µM. The highest affinity antibody derived from 12425 was designated 20811 (Table 1) and it's affinity for human FGFR2 was determined to be 110 pM.

Figure 14:
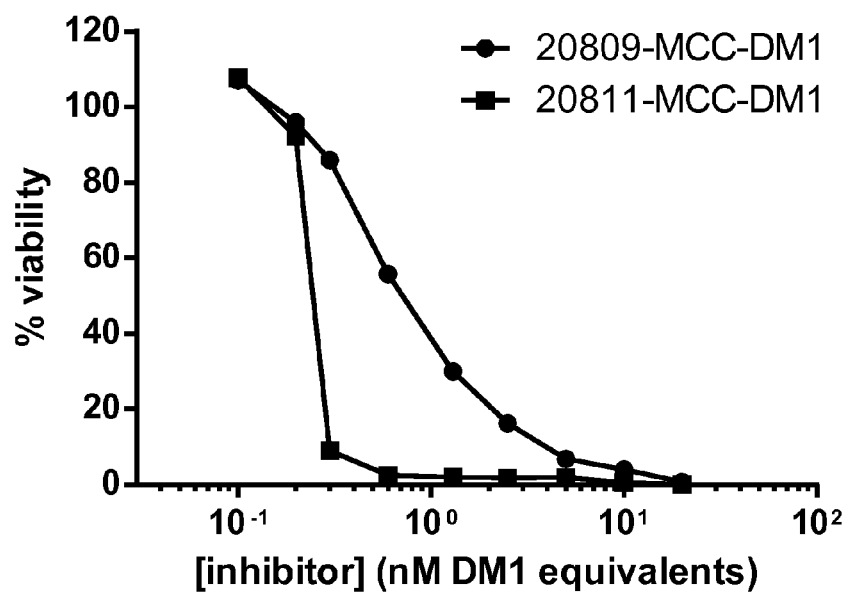
FIG. 14 (A)-(B) show the ability of the affinity-matured variants of 10164 (20809-MCC-DM1) and 12425 (20811-MCC-DM1) to inhibit the proliferation of SNU-16 cells in vitro (A) and in vivo (B).
Figure 14:
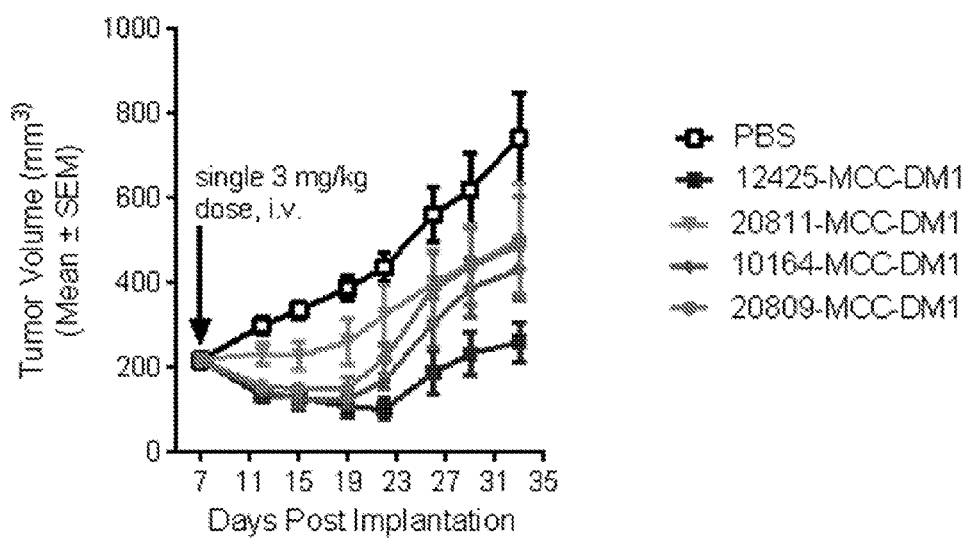

In additional studies, both 20809 and 20811 were directly conjugated to SMCC-DM1 to yield 20809-MCC-DM1 and 20811-MCC-DM1. The ability of these ADCs to inhibit the growth of SNU16 cells is shown in FIG. 14 (A). The impact of affinity on in vivo antitumor activity was assessed in the FGFR2 amplified SNU16 xenograft model. Female nude mice were implanted subcutaneously with 10×10⁶ cells in a suspension containing 50% phenol red-free matrigel (BD Biosciences) in Hank's balanced salt solution. The total injection volume containing cells in suspension was 200 µl Mice were enrolled in the study seven days post implantation with an average tumor volume of 217.6 mm³. After being randomly assigned to one of five groups (n=6/group), mice received PBS (10 ml/kg) or a 3 mg/kg i.v. dose of 12425-MCC-DM1, 20811-MCC-DM1, 10164-MCC-DM1, or 20809-MCC-DM1. Tumors were calipered twice per week (FIG. 14 (B)). 10164-MCC-DM1 and its affinity matured variant 20809-MCC-DM1 demonstrated similar activity against the SNU16 xenograft. 12425-MCC-DM1 demonstrated superiority over its affinity matured variant 20811-MCC-DM1 with regards to antitumor activity. These data suggest that affinity maturation did not yield improved activity in vivo as MCC-DM1 ADCs.

Example 18

Epitope Mapping of FGFR2 and its Antibody Complex by Deuterium Exchange Mass Spectrometry (HDx-MS)

Deuterium exchange mass spectrometry (HDx-MS) measures the deuterium uptake on the amide backbone of a protein. These measurements are sensitive to the amide's solvent accessibility and to changes in the hydrogen bonding network of the backbone amides. HDx-MS is often used to compare proteins in two different states, such as apo and ligand-bound, and coupled with rapid digestion with pepsin. In such experiments one can locate regions, typically of 10 to 15 amino acids, that show differential deuterium uptake between two different states. Regions that are protected are either directly involved in ligand binding or allosterically affected by binding of the ligand.

In these experiments, the deuterium uptake of *E. Coli.* derived FGFR2D2-D3 protein (SEQ ID NO:256, see below) was measured in the absence and presence of three therapeutic antibodies: 12425, 10164, and 12433. Regions in FGFR2 that show a decrease in deuterium uptake upon binding of the antibody are likely to be involved in the epitope; however, due to the nature of the measurement it is also possible to detect changes remote from the direct binding site (allosteric effects). Usually, the regions that have the greatest amount of protection are involved in direct binding although this may not always be the case. In order to delineate direct binding events from allosteric effects orthogonal measurements (e.g. X-ray crystallography, alanine mutagenesis) are required.

TABLE 20

FGFR2 D2-D3 Construct

SEQ ID NO: 256
LENGTH: 237 amino acids
TYPE: Protein
ORGANISM: Human

MAEDFVSENSNNKRAPYWTNTEKMEKRLHAVPAANTVKFRCPAGGNPMPT
MRWLKNGKEFKQEHRIGGYKVRNQHWSLIMESVVPSDKGNYTCVVENEYG
SINHTYHLDVVERSPHRPILQAGLPANASTVVGGDVEFVCKVYSDAQPHI
QWIKHVEKNGSKYGPDGLPYLKVLKHSGINSSNAEVLALFNVTEADAGEY
ICKVSNYIGQANQSAWLTVLPKQQAPGREKEHHHHHH

The epitope mapping experiments described in this example were performed on a Waters HDx-MS platform, which includes a LEAP autosampler, nanoACQUITY UPLC System, and Synapt G2 mass spectrometer. The studies were automated by a LEAP autosampler operated by the LeapShell software, which performed initiation of the deuterium exchange reaction, reaction time control, quench reaction, injection onto the UPLC system and digestion time control. The Leap autosampler was equipped with two temperature controlled stacks maintained at 25° C. for HDx reaction and maintained at 2° C. for storage of protein and quench solution, respectively. Triplicate control experiments were carried out on antigen at a deuterium exchange time of 25 minutes. HDX was quenched with quenching buffer (6 M urea and 1 M TCEP pH=2.5). After quenching, the antigen was injected into the UPLC system where it is subjected to on-line pepsin digestion at 12° C. followed by a rapid 8 min 2 to 35% acetonitrile gradient over a Waters BEH C18 1×100 mm column (maintained at 1° C.) at a flow rate of 40 µL/min. Triplicate experiments were carried out on antigen-mAb complex just as the control experiments except in these experiments the antigen in incubated for 30 min with the antibody at 25° C. prior to deuterium exchange.

Figure 15:
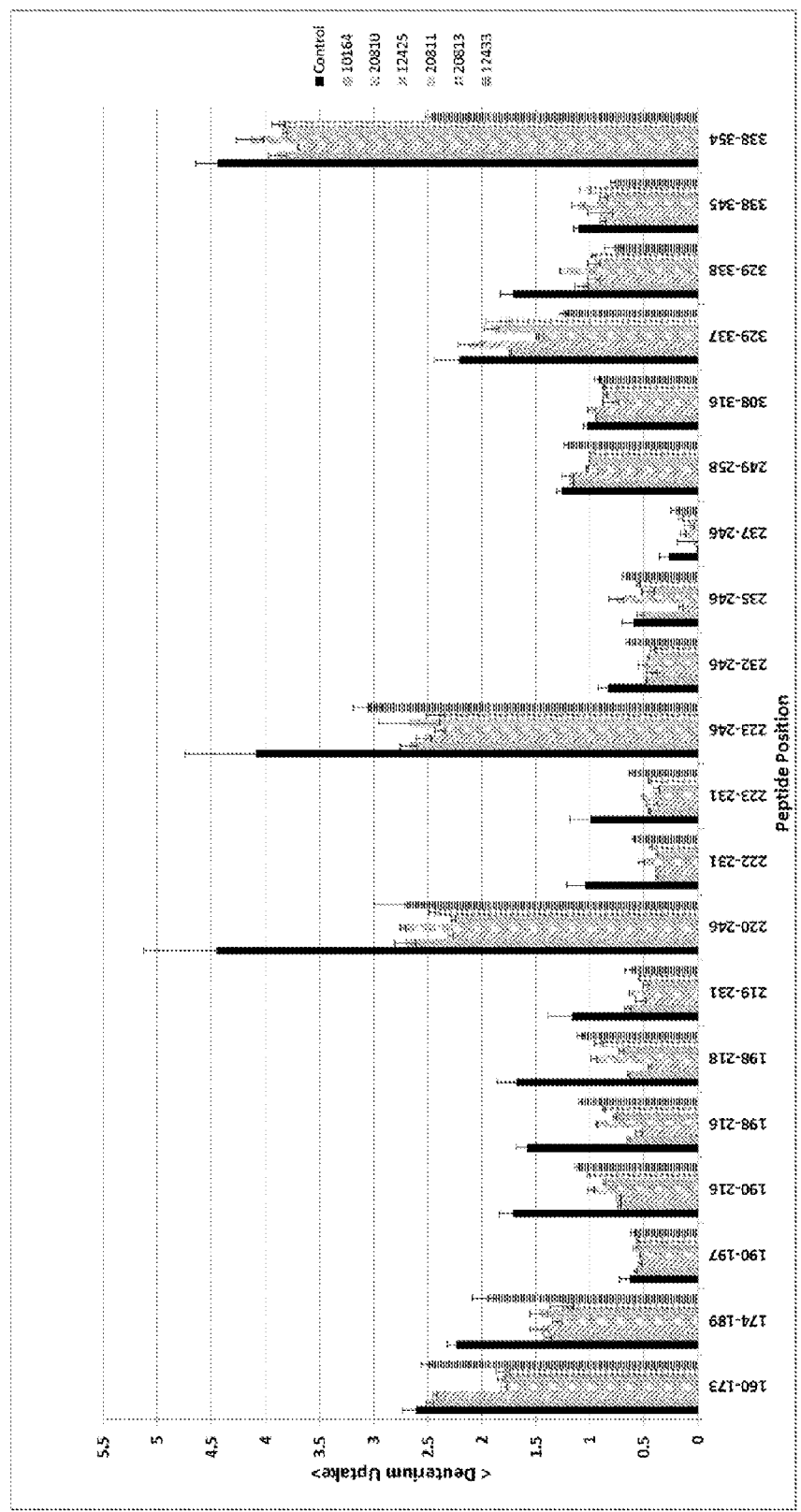
FIG. 15 shows the results of deuterium exchange experiments to FGFR2. (A) shows the absolute deuterium uptake for FGFR2 in the absence (control) and presence of six therapeutic mAb. The heights of the bars are the average of three measurements and the error bars are one standard deviation; (B) shows the difference in deuterium uptake between mAb bound and control FGFR2 divided by the standard error in the measurement; (C) shows regions of high protection upon binding of mAbs to FGFR2 mapped onto FGFR2 IIIc: FGFR2 crystal structure (PDB ID: 1EV2); and (D) shows regions of high protection upon binding of mAbs to FGFR2 mapped onto FGFR2 IIIb: FGFR1 crystal structure (PDB ID: 3OJM).
Figure 15:
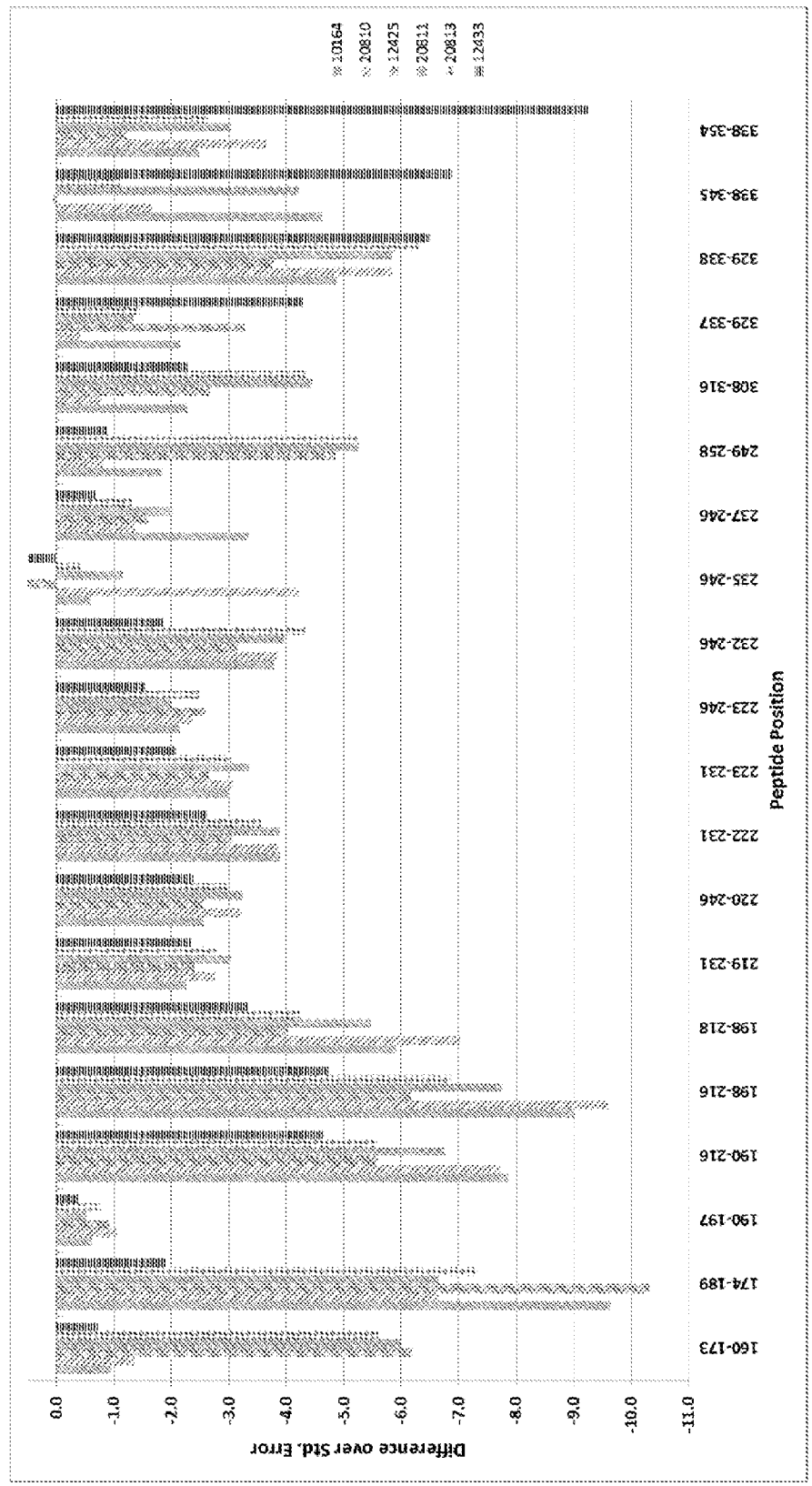
Figure 15:
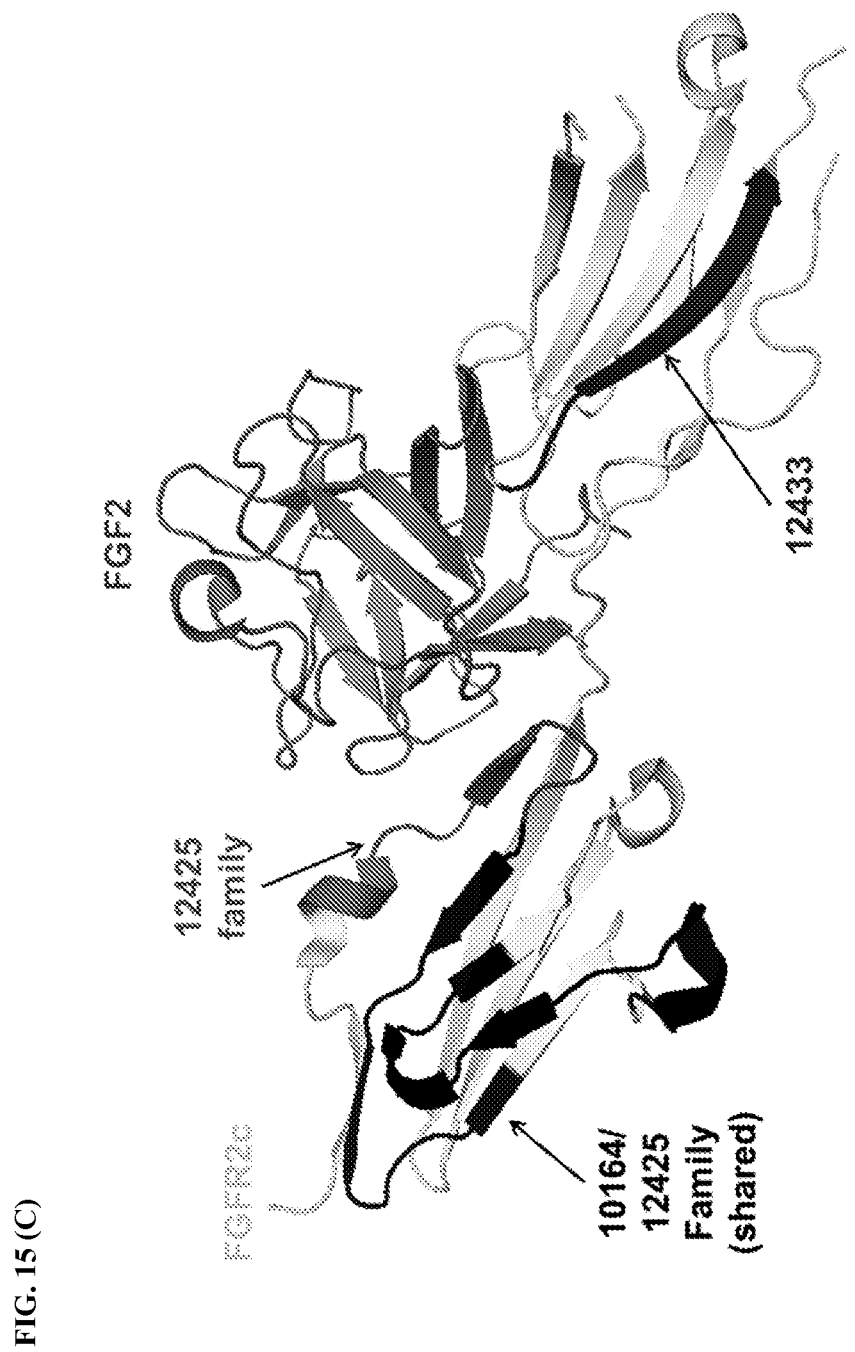
Figure 15:
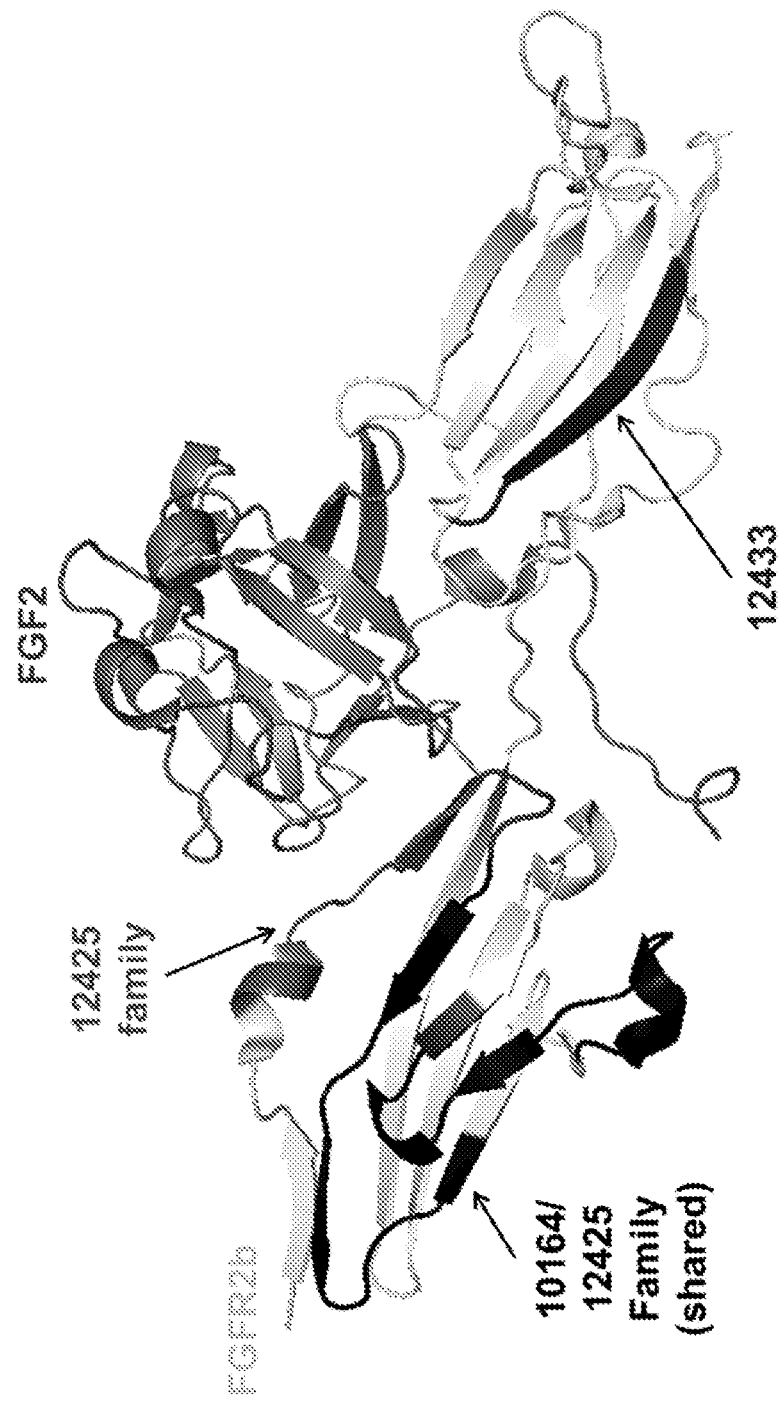

The results of these measurements are summarized in FIG. 15 (A) and FIG. 15 (B). In FIG. 15 (A) the average deuterium uptake for FGFR2 peptides in the absence (control) and presence of mAbs is indicated. In this Figure it is useful to examine two differences: differences between control and mAbs and differences among mAb groups. In FIG. 15 (B), the difference in the deuterium uptake between the mAb and control samples is divided by the standard error in the measurement. Differences are considered significant if they are greater than 0.5 Da in absolute scale (FIG. 15 (A)) and if the ratio of the difference divided by the standard error is less than or equal to −3.0 (FIG. 15 (B)). From this analysis we can rank order regions of the FGFR2 that are protected upon mAb binding into categories of high, medium, and low amounts of protection. FGFR2 regions of high protection are potentially involved in the formation of the epitope with a specific antibody although one cannot rule out other contributions for lesser protected regions.

Upon binding of 10164 to FGFR2 we observe high amounts of protection in the following two regions of FGFR2: 174-189 and 198-216. These regions are located in the D2 domain specifically consisting of βB to N-terminal side of βC and βC' loop to the βE (FIGS. 15 (C) and (D)). There is one region of low protection found in the regions 222-231. However, this region is protected upon binding of all studied antibodies; this observation suggests that this region undergoes a stabilization of its local hydrogen bonding network that may be non-specific and allosteric in nature. Binding of the antibody 12425 to FGFR2 also cause a high amount of protection in the regions 174-189 and 198-216. In addition, with 12425 family a high amount of protection in the region 160-173 (FIGS. 15 (A) and (B)) was also observed. These regions comprises a region of FGFR2 that is known to interact with FGF2 and FGF1 from published crystallography data (Plotnikov et al., M. Cell 2000, 101, 413-424; Beenken et. al., M. J. Biol. Chem. 2012, 287, 3067-3078). Protection in this region is unique to the 12425 family of antibodies. Of the antibodies studied, 12433 is unique in that it specifically targets the IIIb isoform of FGFR2 through interactions with the D3 domain of FGFR2. For 12433 high amounts of protection (~2 Da) in the peptide 338-354, and insignificant amounts of protection in a shorter N-terminal fragment from 338-345 were observed. This observation suggests that the portion of the 338-354 peptide that is protected upon 12433 binding is the region 346-354 (FIGS. 15 (A) and (B)). The region 346 to 354 contains four residues that are specific to IIIb isoform relative to the IIIc isoform; these residues include: Q348, A349, N350, and Q351. In additional studies, affinity matured versions of 10164 and 12425 (see Example 17) were evaluated and were found to be similar to their respective parental antibodies in terms of the protected regions observed.

Example 19

X-Ray Crystallographic Structure Determination of the Human FGFR2/12425 Fab Complex The crystal structure of a human FGFR2ECD fragment (domain 2, or D2, SEQ ID NO: 258, Table 21) bound to Fab fragment of 12425 (Table 19) are determined. As detailed below, FGFR2D2 is expressed, refolded, purified and mixed with 12425 Fab to form a complex. Protein crystallography was then employed to generate atomic resolution data for FGFR2D2 bound to 12425 Fab to define the epitope.

Protein Production of FGFR D2 and 12425 Fab for Crystallography

The sequences of FGFR2D2 and 12425 Fab produced for crystallography are shown in Table 21. Construct of FGFR2D2 comprises residues 146 to 249 (underlined) of human FGFR2 (UniProt identifier P21802-3, SEQ ID NO: 257), along with N- and C-terminal residues from recombinant expression vector (shown in lower case letters, SEQ ID NO: 258). For 12425 Fab, the sequences of heavy and light chains are shown (SEQ ID NO: 259 and 260, respectively).

FGFR2D2 was expressed in *E. coli* BL21 (DE3) (Novagen<sup>R</sup>, EMD Millipore). Following overnight induction with IPTG at 18° C., cells were harvested and lysed. The inclusion body was extracted by incubation with 20 mM sodium phosphate pH 7.5, 300 mM NaCl and 8 M urea, and loaded onto a Ni-NTA column pre-equilibrated in the same buffer. The column was washed with 20 mM sodium phosphate pH 7.5, 300 mM NaCl, 50 mM ammonium sulfate and 20 mM imidzole, followed by elution with 20 mM sodium phosphate pH 7.5, 300 mM NaCl, 50 mM ammonium sulfate and 300 mM imidazole. The eluted protein was then diluted 12-fold with 20 mM sodium phosphate pH 6.5 (buffer A), and loaded onto HiTrap S HP column (GE Healthcare), pre-equilibrated in buffer A plus 2% of 20 mM sodium phosphate pH 6.5, 1.5 M NaCl, 50 mM ammonium sulfate (buffer B). The S column was eluted by a gradient of 2%-100% buffer B. The major peak containing FGFR D2 was collected, concentrated, and loaded onto HiLoad 16/60 Superdex 75 (GE Healthcare) equilibrated in 20 mM Hepes pH 7.5, 150 mM NaCl. Peak fractions were analyzed by SDS-PAGE and LCMS and then pooled to form a complex with 12425 Fab.

12425 Fab is produced by cleavage of full-length 12425 IgG with immobilized papain (Pierce). 12425 IgG at 20 mg/ml in 20 mM sodium phosphate pH 7.0 and 10 mM EDTA was mixed with immobilized papain at a weight ratio of 80:1. The mixture was rotated in a 15 ml tube at 37° C. overnight. The next day the immobilized papain was removed by gravity

TABLE 21

Proteins used for crystal structure determination

| Construct | Amino acid sequence in one letter code | SEQ ID NO |
|---|---|---|
| Human FGFR2 (P21802-3) | MVSWGRFICLVVVTMATLSLARPSFSLVEDTTLEPEEPPTKYQ ISQPEVYVAAPGESLEVRCLLKDAAVISWTKDGVHLGPNNRT VLIGEYLQIKGATPRDSGLYACTASRTVDSETWYFMVNVTDA ISSGDDEDDTDGAEDFVSENSNNKRAPYWTNTEKMEKRLHA VPAANTVKFRCPAGGNPMPTMRWLKNGKEFKQEHRIGGYK VRNQHWSLIMESVVPSDKGNYTCVVENEYGSINHTYHLDVV ERSPHRPILQAGLPANASTVVGGDVEFVCKVYSDAQPHIQWI KHVEKNGSKYGPDGLPYLKVLKHSGINSSNAEVLALFNVTEA DAGEYICKVSNYIGQANQSAWLTVLPKQQAPGREKEITASPD YLEIAIYCIGVFLIACMVVTVILCRMKNTTKKPDFSSQPAVHK LTKRIPLRRQVTVSAESSSSMNSNTPLVRITTRLSSTADTPMLA GVSEYELPEDPKWEFPRDKLTLGKPLGEGCFGQVVMAEAVGI DKDKPKEAVTVAVKMLKDDATEKDLSDLVSEMEMMKMIGK HKNIINLLGACTQDGPLYVIVEYASKGNLREYLRARRPPGME YSYDINRVPEEQMTFKDLVSCTYQLARGMEYLASQKCIHRDL AARNVLVTENNVMKIADFGLARDINNIDYYKKTTNGRLPVK WMAPEALFDRVYTHQSDVWSFGVLMWEIFTLGGSPYPGIPV EELFKLLKEGHRMDKPANCTNELYMMMRDCWHAVPSQRPT FKQLVEDLDRILTLTTNEEYLDLSQPLEQYSPSYPDTRSSCSSG DDSVFSPDPMPYEPCLPQYPHINGSVKT | 257 |
| FGFR2 D2 | mNSNNKRAPYWTNTEKMEKRLHAVPAANTVKFRCPAGGNP MPTMRWLKNGKEFKQEHRIGGYKVRNQHWSLIMESVVPSD KGNYTCVVENEYGSINHTYHLDVVlvprgslehhhhhh | 258 |
| 12425 Fab heavy chain | QVQLLESGGGLVQPGGSLRLSCAASGFTFSDYAMSWVRQAP GKGLEWVSVIEGDGSYTHYADSVKGRFTISRDNSKNTLYLQ MNSLRAEDTAVYYCAREKTYSSAPFDYWGQGTLVTVSSASTK GPSVFPLAPSSKSTSGGTAALGCLVKDYFPEPVTVSWNSGAL TSGVHTFPAVLQSSGLYSLSSVVTVPSSSLGTQTYICNVNHKP SNTKVDKRVEPKSCDKTH | 259 |
| 12425 Fab light chain | DIQMTQSPSSLSASVGDRVTITCRASQDISSDLNWYQQKPGK APKLLIYDASNLQSGVPSRFSGSGSGTDFTLTISSLQPEDFAVY YCQQHYSPSHTFGQGTKVEIKRTVAAPSVFIFPPSDEQLKSGT ASVVCLLNNFYPREAKVQWKVDNALQSGNSQESVTEQDSKD STYSLSSTLTLSKADYEKHKVYACEVTHQGLSSPVTKSFNRG EC | 260 | flow column; the flow through, which contains both Fab and Fc segments, was collected and loaded onto HiTrap MabSelect SURE column (GE Healthcare) to remove the Fc segment. The flow through from this step, which contains only the Fab fragment, was concentrated and loaded onto HiLoad 16/60 Superdex 75 (GE Healthcare) equilibrated in 20 mM Hepes pH 7.5, 150 mM NaCl. Peak fractions were analyzed by SDS-PAGE and LCMS, and then pooled to form a complex with FGFR D2.

Crystallization and Structure Determination of FGFR2D2/12425 Fab Complex

A complex of FGFR2D2 with 12425 Fab was prepared by mixing the purified FGFR2D2 and 12425 Fab at a 2:1 molar ratio (concentration measured via LCUV), incubating on ice for 30 min, and purifying the complex on a HiLoad 16/60 Superdex 75 (GE Healthcare) equilibrated in 20 mM Hepes pH 7.5, 150 mM NaCl. Peak fractions were analyzed by SDS-PAGE and LCMS. Fractions containing FGFR2D2/12425 Fab complex were concentrated to about 30 mg/ml. Trypsin (dissolved in 1 mM HCl and 2 mM $CaCl_2$ at 1 mg/ml) was added into the complex at a volume ratio of 1:100 to facilitate crystallization (Wernimont et al., (2009) Plos One 4:e5095). The FGFR2D2/12425 Fab/trypsin mixture was immediately centrifuged and screened for crystallization.

Crystals were grown by sitting drop vapor diffusion. In detail, 0.1 μl of protein was mixed with 0.1 μl of reservoir solution which contains 0.1 M tri-sodium citrate dihydrate pH 5.0, 20% (w/v) PEG6000; and the drop was equilibrated against 45 μl of the same reservoir solution at 20° C.

Before data collection, the FGFR2D2/12425 Fab crystals was transferred to a reservoir solution containing an additional 22.5% glycerol and flash cooled in liquid nitrogen. Diffraction data were collected at beamline 17-ID at the Advanced Photon Source (Argonne National Laboratory, USA). Data were processed and scaled at 2.8 Å using HKL2000 (HKL Research) in space group C2 with cell dimensions a=228.79 Å, b=96.94 Å, c=200.66 Å, alpha=90°, beta=106.11°, gamma=90°. The FGFR2D2/12425 Fab complex structure was solved by molecular replacement using Phaser (McCoy et al., (2007) J. Appl. Cryst. 40:658-674) with FGFR2D2 structure (PDB ID: 3DAR) and an in-house Fab structure as search models. The final model was built in COOT (Emsley & Cowtan (2004) Acta Cryst. 60:2126-2132) and refined with Buster (Global Phasing, LTD) to $R_{work}$ and $R_{free}$ values of 22.6% and 24.9%, respectively, with an rmsd of 0.009 Å and 1.1° for bond lengths and bond angles, respectively. Residues of FGFR2D2 that contain atoms within 5 Å of any atom in 12425 Fab are identified by PyMOL (Schrödinger, LLC) and listed in Tables 20 and 21.

FGFR2 Epitope for 12425

The crystal structure of the FGFR2D2/12425 Fab complex was used to identify the FGFR2 epitope for 12425. There are six copies of 12425 Fab-FGFR2D2 complex in the asymmetric unit of the crystal (an asymmetric unit contains all the structural information needed to reproduce the whole crystal). All six copies share almost identical residues in contact with 12425 Fab except for small variations due to crystal packing. Only those 12425-contacting FGFR2 residues that are shared by all six copies were used to define epitope.

Figure 16:
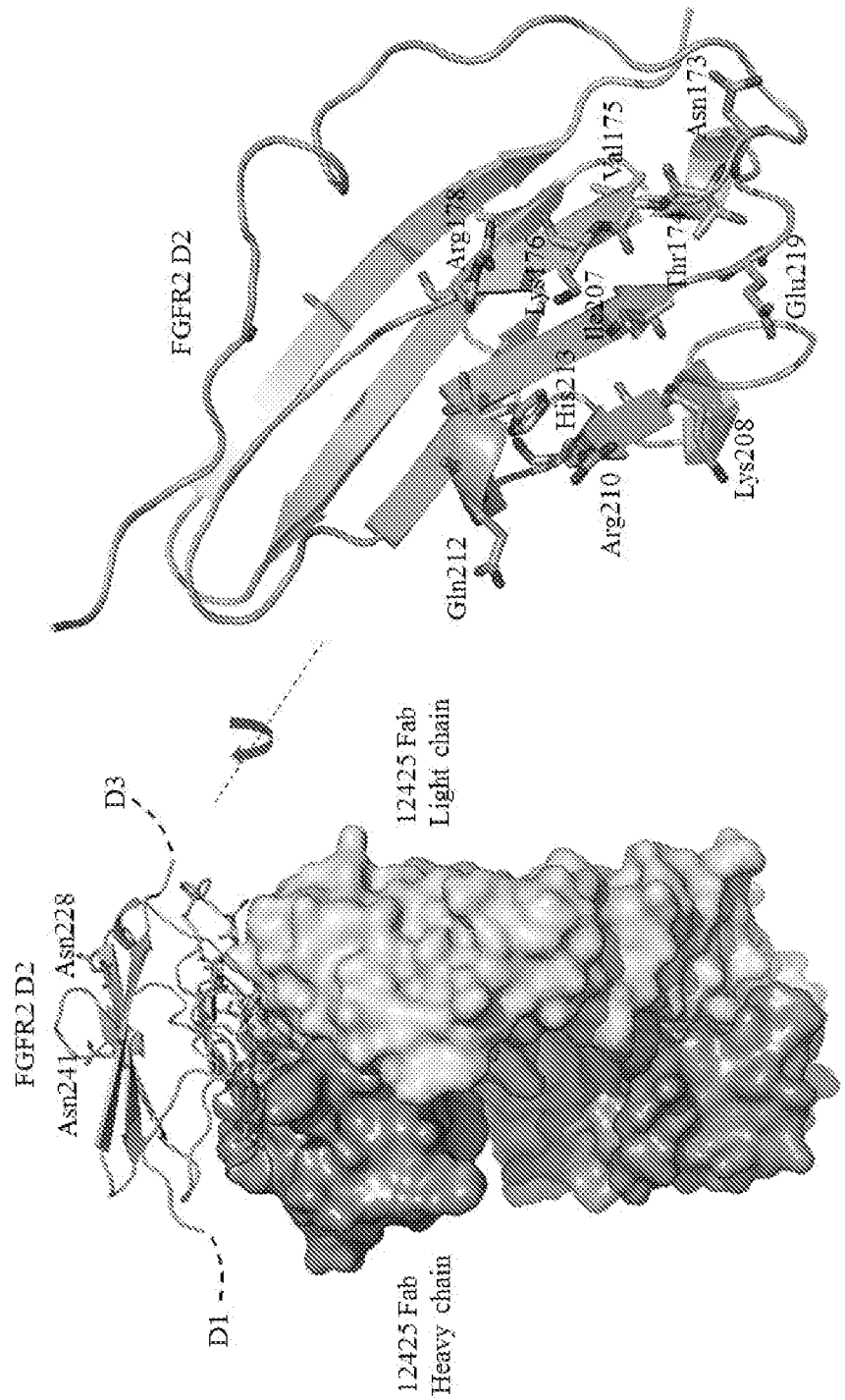
FIG. 16 shows the results from X-ray crystallography epitope mapping studies. (A) shows the overall structure of 12425 Fab binding to FGFR2 (left panel) and detailed interaction surface on FGFR2 with epitope residues labeled (right panel) (figure discloses residues at indicated positions of SEQ ID NO: 257); (B)-(C) show two dimerization models of FGFR-FGF-heparin signaling complex (upper panels) and the clash of 12425 Fab with both models (lower panels).
Figure 16:
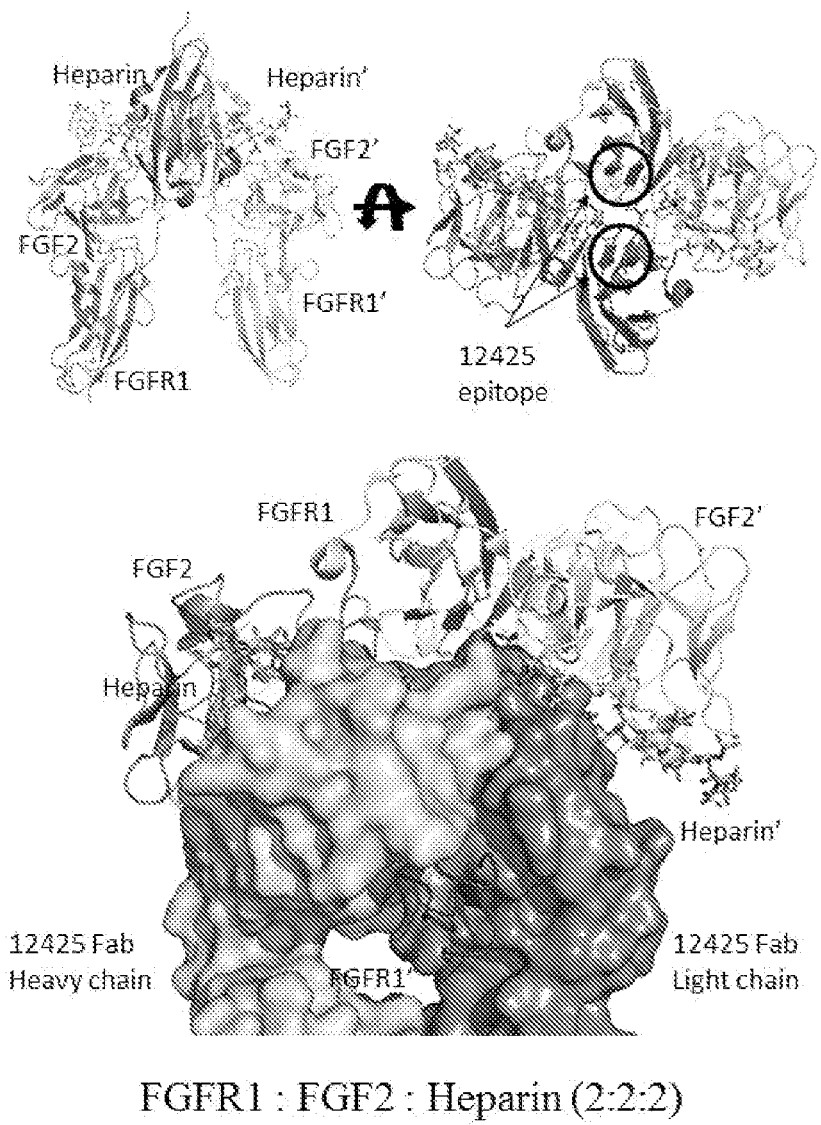
Figure 16:
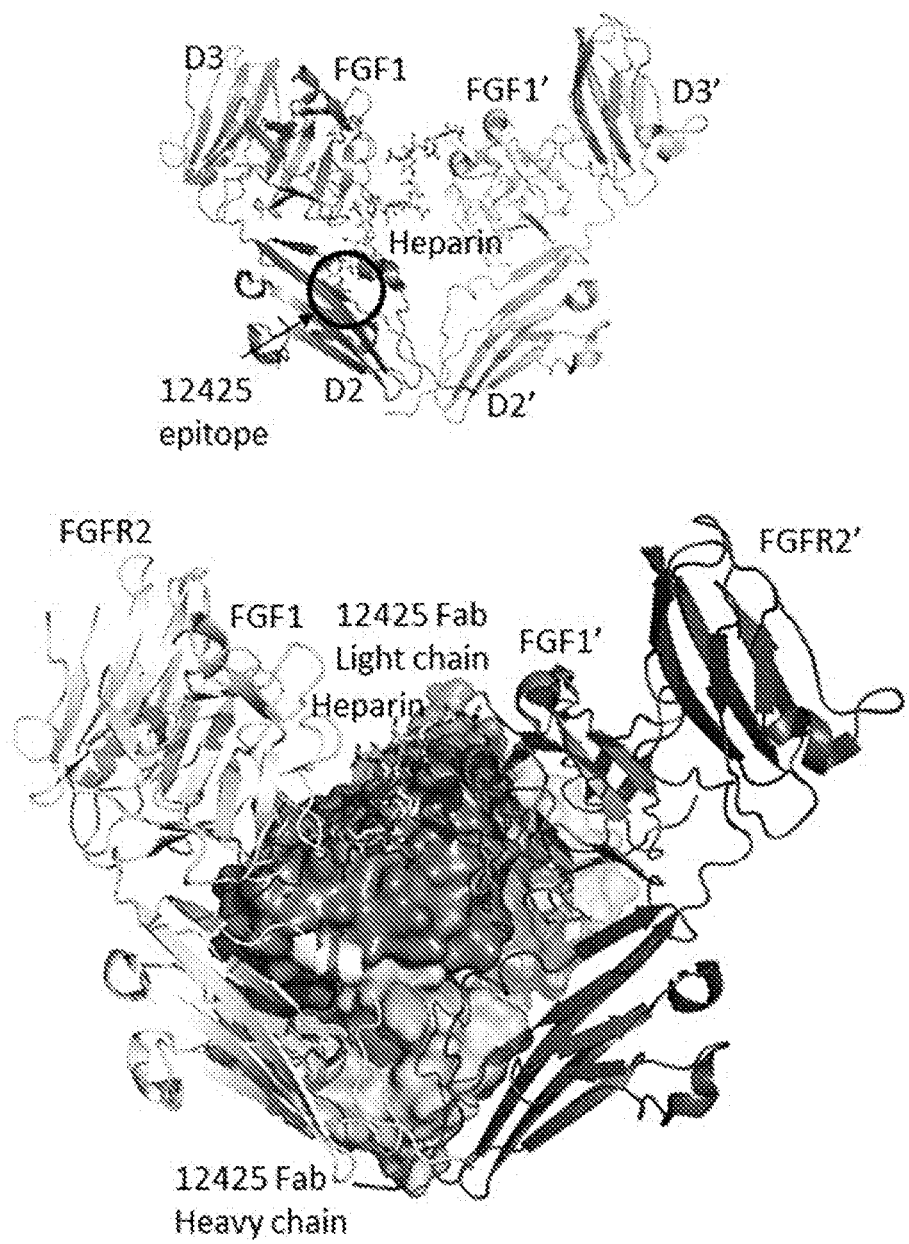

The interaction surface on FGFR2D2 by 12425 Fab is formed by several discontinuous (i.e., noncontiguous) sequences: namely residues 173 through 176, residue 178, residues 208 through 210, residues 212, 213, 217 and 219, as detailed in Table 22 and 23. These residues form the three-dimensional surface that is recognized by 12425 Fab (FIG. 16 (A)). This epitope defined by crystallography is in good agreement with that defined by deuterium exchange mass spectrometry (HDx-MS), which comprises residues 160-173, 174-189 and 198-216.

TABLE 22

Interactions between human FGFR2 D2 and 12425 Fab heavy chain (H). FGFR2 residues are numbered based upon P21802-3 (SEQ ID NO: 257). Fab heavy chain residues are numbered based upon their linear amino acid sequence (SEQ ID NO: 259). FGFR2 residues shown have at least one atom within 5 Å of an atom in the 12425 Fab, to account for potential water mediated interactions.

| Human FGFR2 | | 12425 Fab | | |
|---|---|---|---|---|
| Amino acid | Number | Amino acid | Number | Chain |
| LYS | 208 | HIS | 59 | H |
| VAL | 209 | TYR | 57 | H |
| ARG | 210 | ALA | 33 | H |
| | | VAL | 50 | H |
| | | TYR | 57 | H |
| | | GLU | 52 | H |
| | | GLU | 99 | H |
| | | SER | 104 | H |
| GLN | 212 | GLU | 52 | H |
| | | ASP | 54 | H |
| HIS | 213 | GLU | 52 | H |
| | | SER | 104 | H |

TABLE 23

Interactions between human FGFR D2 and 12425 Fab light chain (L). FGFR2 residues are numbered based upon P21802-3 (SEQ ID NO: 257). Fab light chain residues are numbered based upon their linear amino acid sequence (SEQ ID NO: 260). FGFR2 residues shown have at least one atom within 5 Å of an atom in the 12425 Fab, to account for potential water mediated interactions.

| Human FGFR2 | | 12425 Fab | | |
|---|---|---|---|---|
| Residue | Number | Residue | Number | Chain |
| ASN | 173 | GLN | 27 | L |
| THR | 174 | GLN | 27 | L |
| | | TYR | 92 | L |
| VAL | 175 | TYR | 92 | L |
| LYS | 176 | ASP | 32 | L |
| | | HIS | 91 | L |
| | | TYR | 92 | L |
| | | ASP | 32 | L |
| ARG | 178 | ASP | 32 | L |
| ARG | 210 | HIS | 96 | L |
| ILE | 217 | TYR | 92 | L |
| | | PRO | 94 | L |
| GLU | 219 | SER | 93 | L |
| | | PRO | 94 | L |

From the FGFR2D2/12425 Fab structure, the potential N-linked glycosylation sites on FGFR2, namely Asn241 and Asn288 (Duchesne et al., (2006) J. Biol. Chem. 281:27178-27189) are on the opposite surface of the protein away from the 12425 epitope (FIG. 16 (A)), indicating that 12425 binding to FGFR2 is independent of glycosylation. This is consistent with the finding that 12425 antibody binds E. coli-produced (no glycosylation) and mammalian cell-produced (glycosylated) FGFR2D2-D3 with similar affinity (data not shown).

Lys176 and Arg210 of FGFR2D2 are the two epitope residues making most contacts with 12425 Fab light and heavy chains, respectively. Interestingly, Arg210 has been demonstrated to bind heparin (Pellegrini et al., (2000) Nature 407:1029-1034), which can enhance FGFR2 binding to FGFs and subsequent dimerization and signaling. Meanwhile, Lys176 is also postulated to be in the heparin binding pocket (Pellegrini et al., (2000) Nature 407:1029-1034).

Two models have been reported for how FGFR-FGF-heparin complex dimerizes on the cell surface to activate downstream signaling, namely the 2:2:1 (FGFR:FGF:heparin) model (Pellegrini et al., (2000) Nature 407:1029-1034) and the 2:2:2 model (Schlessinger et al., (2000) Mol. Cell. 6:743-750). Based on the crystal structure of FGFR2D2/12425 Fab complex, the binding of 12425 antibody to FGFR2 clashes with and thus can block both dimerization models (FIGS. 16 (B) and (C)).

Example 20

Formulation

The clinical service form (CSF) of the ADC is a lyophilisate in vial containing 50 mg 12425-MCC-DM1, 16.2 mg sodium succinate, 410.8 mg sucrose and 1 mg polysorbate 20 (without considering the overfill of 10% to allow for withdrawal of the declared content). After reconstitution of the lyophilizate with 5 mL water for injection, a solution containing 10 mg/mL 12425-MCC-DM1, 20 mM sodium succinate, 240 mM Sucrose and 0.02% polysorbate 20 at a pH of 5.0 is obtained.

For subsequent intravenous administration, the obtained solution will usually be further diluted into a carrier solution to the ready-to-use ADC solution for infusion.

For the CSF, an ADC concentration of 10 mg/mL was chosen based on preliminary stability testing. A sucrose concentration of 240 mM was selected in order to create an isotonic formulation, to maintain an amorphous lyophilizate cake structure and to afford protein stabilization.

Important stability-indicating analytical methods to select the most stable formulation encompassed, amongst others, size-exclusion chromatography to determine aggregation levels, subvisible particulate matter testing, free Toxin determination and potency testing.

The pre-screening study showed that polysorbate 20 at a concentration of 0.02% provides sufficient stabilization against mechanical stress. The liquid and lyophilized stability studies at real-time and accelerated stability conditions (25° C. and 40° C.) demonstrated that a succinate pH 5.0 formulation provides the overall best storage stability. Most notably in this formulation the best balance of all tested formulations between aggregation and release of the free Toxin could be met. After three months at 40° C. no noteworthy increase in degradation products could be determined It is understood that the examples and embodiments described herein are for illustrative purposes only and that various modifications or changes in light thereof will be suggested to persons skilled in the art and are to be included within the spirit and purview of this application and scope of the appended claims.

We claim:

1. An antibody drug conjugate of the formula

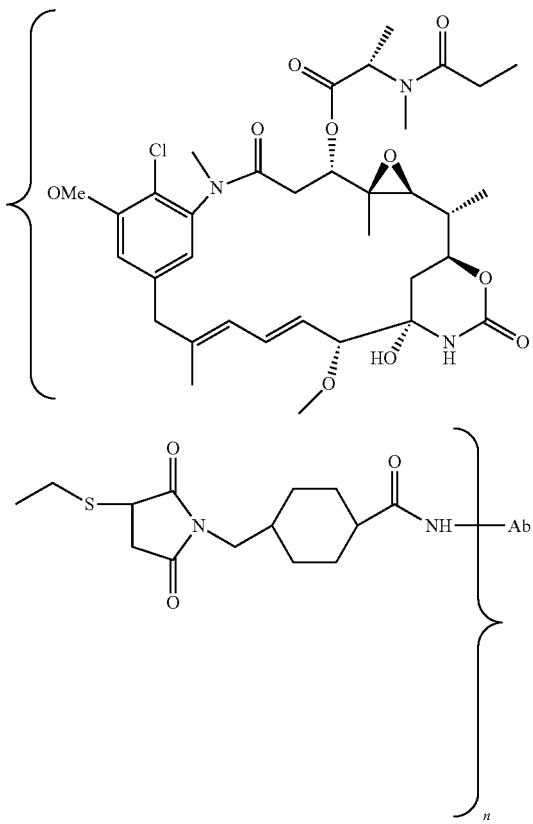

or a pharmaceutically acceptable salt thereof; wherein

Ab is an antibody or antigen binding fragment thereof that specifically binds to human FGFR2; wherein the antibody comprises a heavy chain variable region that comprises: (a) a VH CDR1 of SEQ ID NO: 21, (b) a VH CDR2 of SEQ ID NO: 22, (c) a VH CDR3 of SEQ ID NO: 23; and a light chain variable region that comprises: (d) a VL CDR1 of SEQ ID NO: 31, (e) a VL CDR2 of SEQ ID NO: 32, (f) a VL CDR3 of SEQ ID NO: 33, wherein the CDR is defined in accordance with the Kabat definition; and n is an integer from 1 to 10.

2. The antibody drug conjugate of claim 1, wherein said n is 3 or 4.

3. The antibody drug conjugate of claim 1, wherein said antibody or antigen binding fragment thereof specifically binds to all isoforms of human FGFR2.

4. The antibody drug conjugate of claim 3, wherein said antibody or antigen binding fragment specifically binds to an epitope of human FGFR2 comprising amino acids 174-189 and 198-216 of SEQ ID NO:257.

5. The antibody drug conjugate of claim 1, wherein said antibody or antigen binding fragment thereof specifically binds to the human FGFR2 IIIb isoform.

6. The antibody drug conjugate of claim 5, wherein said antibody or antigen binding fragment thereof specifically binds to an epitope of human FGFR2 comprising amino acids 346-354 of SEQ ID NO:257.

7. The antibody drug conjugate of claim 1, wherein said antibody or antigen binding fragment has enhanced ADCC activity as compared to an antibody consisting of a heavy chain of SEQ ID NO: 9 and a light chain of SEQ ID NO: 19.

8. The antibody drug conjugate of claim 1, wherein said antibody is a human antibody.

9. The antibody drug conjugate of claim 1, wherein said antibody is a monoclonal antibody.

10. The antibody drug conjugate of claim 1, wherein said linker is selected from the group consisting of a cleavable linker, a non-cleavable linker, a hydrophilic linker, a procharged linker and a dicarboxylic acid based linker.

11. The antibody drug conjugate of claim 10, wherein the linker is derived from a cross-linking reagent selected from the group consisting of N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)-2-sulfo-butanoate (sulfo-SPDB), N-succinimidyl iodoacetate (SIA), N-succinimidyl(4-iodoacetyl)aminobenzoate (SIAB), maleimide PEG NHS, N-succinimidyl 4-(maleimidomethyl) cyclohexanecarboxylate (SMCC), N-sulfosuccinimidyl 4-(maleimidomethyl) cyclohexanecarboxylate (sulfo-SMCC) or 2,5-dioxopyrrolidin-1-yl 17-(2,5-dioxo-2,5-dihydro-1H-pyrrol-1-yl)-5,8,11,14-tetraoxo-4,7,10,13-tetraaza-heptadecan-1-oate (CX1-1).

12. The antibody drug conjugate of claim 11, wherein said linker is N-succinimidyl 4-(maleimidomethyl) cyclohexanecarboxylate (SMCC).

13. The antibody drug conjugate of claim 1, wherein said drug moiety is selected from a group consisting of a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, proteasome inhibitors, inhibitors of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder and a DHFR inhibitor.

14. The antibody drug conjugate of claim 13, wherein the cytotoxic agent is a maytansinoid.

15. The antibody drug conjugate of claim 14, wherein the maytansinoid is N(2')-deacetyl-N(2')-(3-mercapto-1-oxopropyl)-maytansine (DM1) or N(2')-deacetyl-N2-(4-mercapto-4-methyl-1-oxopentyl)-maytansine (DM4).

16. A pharmaceutical composition comprising the antibody drug conjugate of claim 1 and a pharmaceutically acceptable carrier.

17. The pharmaceutical composition of claim 16 wherein said composition is prepared as a lyophilisate.

18. The pharmaceutical composition of claim 17, wherein said lyophilisate comprises said antibody drug conjugate, -sodium succinate, and polysorbate 20.

19. An antibody or antigen binding fragment thereof that specifically bind to human FGFR2 and comprises a heavy chain variable region that comprises: (a) a VH CDR1 of SEQ ID NO: 21, (b) a VH CDR2 of SEQ ID NO: 22, (c) a VH CDR3 of SEQ ID NO: 23; and a light chain variable region that comprises: (d) a VL CDR1 of SEQ ID NO: 31, (e) a VL CDR2 of SEQ ID NO: 32, (f) a VL CDR3 of SEQ ID NO: 33, wherein the CDR is defined in accordance with the Kabat definition.

20. The antibody or antigen binding fragment of claim 19, wherein said antibody is a human antibody.

21. The antibody or antigen binding fragment of claim 20, wherein said antibody is a monoclonal antibody.

22. The antibody or antigen binding fragment of claim 19, wherein said antibody or antigen binding fragment is a single chain antibody (scFv).

23. A diagnostic reagent comprising the antibody or antigen binding fragment thereof of claim 19 which is labeled.

24. The diagnostic reagent of claim 23, wherein the label is selected from the group consisting of a radiolabel, a fluorophore, a chromophore, an imaging agent, and a metal ion.

* * * * *